US012616753B2

(12) United States Patent
Murphy et al.

(10) Patent No.: US 12,616,753 B2
(45) Date of Patent: May 5, 2026

(54) HSP70 INHIBITORS AND METHODS OF USING SAME

(71) Applicants: THE WISTAR INSTITUTE, Philadelphia, PA (US); THE TRUSTEES OF THE UNIVERSITY OF PENNSYLVANIA, Philadelphia, PA (US)

(72) Inventors: Maureen E. Murphy, Philadelphia, PA (US); Joseph Salvino, Philadelphia, PA (US); Donna L. George, Philadelphia, PA (US); Julia Leu, Philadelphia, PA (US)

(73) Assignees: The Wistar Institute, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 747 days.

(21) Appl. No.: 17/914,659

(22) PCT Filed: Mar. 30, 2021

(86) PCT No.: PCT/US2021/024900

§ 371 (c)(1),
(2) Date: Sep. 26, 2022

(87) PCT Pub. No.: WO2021/202540

PCT Pub. Date: Oct. 7, 2021

(65) Prior Publication Data

US 2023/0158146 A1 May 25, 2023

Related U.S. Application Data

(60) Provisional application No. 63/002,847, filed on Mar. 31, 2020.

(51) Int. Cl.

| | |
|---|---|
| ***A61P 35/00*** | (2006.01) |
| ***A61K 45/06*** | (2006.01) |
| ***A61K 47/18*** | (2017.01) |
| ***A61K 47/20*** | (2006.01) |
| ***A61K 47/22*** | (2006.01) |
| ***A61K 47/24*** | (2006.01) |

(52) U.S. Cl.

CPC .............. *A61K 47/22* (2013.01); *A61K 45/06* (2013.01); *A61K 47/18* (2013.01); *A61K 47/20* (2013.01); *A61K 47/24* (2013.01); *A61P 35/00* (2018.01)

(58) Field of Classification Search

CPC ........ A61K 47/22; A61K 45/06; A61K 47/18; A61K 47/20; A61K 47/24; A61P 35/00

See application file for complete search history.

(56) References Cited

U.S. PATENT DOCUMENTS

| | | | | |
|---|---|---|---|---|
| 4,680,300 A * | 7/1987 | Nelson ................ | C07D 215/46 546/163 |
| 2017/0014434 A1 | 1/2017 | George et al. | |
| 2019/0119300 A1 | 4/2019 | Hamm et al. | |

OTHER PUBLICATIONS

Katritzky, Alan R., and Maria Szajda. "SN2' type substitution reactions of 1-diphenylamino-and 1-carbazol-9-ylpyridinium cations." Journal of the Chemical Society, Perkin Transactions 1 (1985): 2155-2157. (Year: 1985).*

International Search Report and Written Opinion, PCT/US21/24900, dated Jun. 8, 2021, 8 pages.

Balaburski, et al., "A Modified HSP70 Inhibitor Shows Broad Activity as an Anticancer Agent", Mol Cancer Res. Mar. 2013;11(3):219-29. doi: 10.1158/1541-7786.MCR-12-0547-T. Epub Jan. 9, 2013. PubMed PMID: 23303345; PubMed Central PMCID: PMC3606282.

Budina-Kolomets, et al., "Comparison of the activity of three different HSP70 inhibitors on apoptosis, cell cycle arrest, autophagy inhibition, and HSP90 inhibition", Cancer Biol Ther. Feb. 2014;15(2):194-9. doi: 10.4161/cbt.26720. Epub Nov. 1, 2013. PubMed PMID: 24100579; PubMed Central PMCID: PMC3928135.

Budina-Kolomets, et al., "HSP70 Inhibition Limits FAK-Dependent Invasion and Enhances the Response to Melanoma Treatment with BRAF Inhibitors", Cancer Res. May 1, 2016:76(9):2720-30. doi:10.1158/0008-5472.CAN-15-2137. Epub Mar. 16, 2016. PubMed PMID: 26984758; PubMed Central PMCID: PMC4939897.

Kang, et al., "Combinatorial Drug Design Targeting Multiple Cancer Signaling Networks Controlled By Mitochondrial HSP90", J Clin Invest. Mar. 2009:119(3):454-64.

Leu, et al., "A small molecule inhibitor of inducible heat shock protein 70", Mol Cell. Oct. 9, 2009;36(1):15-27.

Leu, et al., "HSP70 inhibition by the small-molecule 2-phenylethynesulfonamide impairs protein clearance pathways in tumor cells", Mol Cancer Res. Jul. 2011;9(7):936-47. doi: 10.1158/1541-7786.MCR-11-0019. Epub Jun. 2, 2011. PubMed PMID: 21636681; PubMed Central PMCID: PMC3140602.

(Continued)

*Primary Examiner* — Kamal A Saeed
*Assistant Examiner* — Quincy McKoy
(74) *Attorney, Agent, or Firm* — Saul Ewing LLP; Kathryn Doyle; Domingos J. Silva

(57) ABSTRACT

The disclosure provides in one aspect compounds, and compositions comprising such compounds, that can be used to treat, ameliorate, and/or prevent cancer, especially colorectal cancer (CRC). In certain embodiments, the compounds of the disclosure inhibit HSP70. In other embodiments, the compounds of the disclosure promote or increase immune cell recruitment to a cancer. In yet other embodiments, the compounds of the disclosure promote and/or increase immune cell infiltration in a cancer.

23 Claims, 60 Drawing Sheets

(56) References Cited

OTHER PUBLICATIONS

Leu, et al., "Inhibition of stress-inducible HSP70 impairs mitochondrial proteostasis and function", Oncotarget. Jul. 11, 2017;8(28):45656-45669. doi:10.18632/oncotarget.17321. PubMed PMID: 28484090; PubMed Central PMCID: PMC5542216.

Leu, et al., "Structural basis for the inhibition of HSP70 and Dnak chaperones by small-molecule targeting of a C-terminal allosteric pocket", ACS Chem Biol. Nov. 21, 2014;9(11):2508-16. doi:10.1021/cb500236y. Epub Aug. 28, 2014. PubMed PMID: 25148104; PubMed Central PMCID:PMC4241170.

Li, et al., "Analogues of the Allosteric Heat Shock Protein 70 (Hsp70) Inhibitor, MKT-077, As Anti-Cancer Agents", ACS Med Chem Lett. Nov. 14, 2013;4(11). doi: 10.1021/ml400204n. PubMed PMID: 24312699; PubMed Central PMCID: PMC3845967.

Murphy, Michael, "Targeting lipophilic cations to mitochondria", Biochim Biophys Acta . Jul.-Aug. 2008;1777(7-8):1028-31. doi: 10.1016/j.bbabio.2008.03.029. Epub Apr. 8, 2008.

Murphy, Maureen, "The HSP70 family and cancer", Carcinogenesis. Jun. 2013;34(6):1181-8. doi: 10.1093/carcin/bgt111. Epub Apr. 4, 2013. Review. PubMed PMID: 23563090; PubMed Central PMCID: PMC3670260.

Park, et al., "Subcellular Hsp70 Inhibitors Promote Cancer Cell Death via Different Mechanisms", Cell Chemical Biology, 2018, vol. 25, pp. 1242-1254.

Porteous, et al., "Rapid uptake of lipophilic triphenylphosphonium cations by mitochondria in vivo following intravenous injection: implications for mitochondria-specific therapies and probes", Blochim Biophys Acta. Sep. 2010;1800(9):1009-17.

Ross, et al., "Rapid and extensive uptake and activation of hydrophobic triphenylphosphonium cations within cells". Biochem J. May 1, 2008;411(3):633-45.

Taldone, et al., "Heat shock protein 70 inhibitors. 2. 2,5'-thiodipyrimidines, 5-(phenylthio)pyrimidines, 2-(pyridin-3-ylthio)pyrimidines, and 3-(phenylthio)pyridines as reversible binders to an allosteric site on heat shock protein 70", . J Med Chem. Feb. 27, 2014;57(4):1208-24. doi: 10.1021/jm401552y. Epub Feb. 18, 2014. PubMed PMID: 24548239; PubMed Central PMCID: PMC3983364.

Taldone, et al., "Selective targeting of the stress chaperome as a therapeutic strategy", Trends Pharmacol Sci. Nov. 2014;35(11):592-603. doi: 10.1016/j.tips.2014.09.001. Epub Sep. 25, 2014. Review. PubMed PMID: 25262919; PubMed Central PMCID: PMC4254259.

Williamson, et al., "Novel adenosine-derived inhibitors of 70 kDa heat shock protein, discovered through structure-based design", J Med Chem., Mar. 26, 2009;52(6):1510-3. doi: 10.1021/jm801627a.

* cited by examiner

| Comp. | $IC_{50}$, nmol/L |
|---|---|
| PET-16 | 3,085 |

AP-1-54
PET-16

| Comp. | $IC_{50}$, nmol/L |
|---|---|
| AP-3-97 | 670 |

AP-3-97

| Comp. | $IC_{50}$, nmol/L |
|---|---|
| AP-4-139B | 180 |

AP-4-139B

| Comp. | $IC_{50}$, nmol/L |
|---|---|
| VY-3-277 | >30,000 |

VY-3-277

Top Mitochondrial Proteins Affected by AP-4-139B

| AP-4-139B | | unt | | 139B | | |
|---|---|---|---|---|---|---|
| fold | FDR | 1 | 2 | 1 | 2 | Protein |
| -20.1 | 5.8% | | | | | NDUFS1 |
| -18.2 | 5.8% | | | | | NDUFV1 |
| -17.2 | 5.8% | | | | | NDUFS6 |
| -16.7 | 5.8% | | | | | MRPS14 |
| -16.2 | 5.8% | | | | | NDUFA9 |
| -16.0 | 7.6% | | | | | NDUFA6 |
| -14.6 | 5.8% | | | | | MRPL13 |
| -14.2 | 5.8% | | | | | NDUFS4 |
| -14.1 | 8.9% | | | | | NDUFA7 |
| -13.8 | 7.0% | | | | | NDUFA2 |
| -12.6 | 5.8% | | | | | MRPL28 |
| -11.6 | 5.8% | | | | | MRPL23 |
| -11.3 | 6.6% | | | | | NDUFA12 |
| -11.0 | 5.8% | | | | | MRPL21 |

| | SW620 | HT-29 | HCT116 | HCT116 p53 -/- | RKO | LS411N |
|---|---|---|---|---|---|---|
| IC50 | 8.199 | 39.81 | 22.31 | 28.56 | 32.21 | 11.64 |

| | SW620 | HT-29 | HCT116 | HCT116 p53 -/- | RKO | LS411N |
|---|---|---|---|---|---|---|
| IC50 | 1.961 | 2.449 | 3.114 | 2.196 | 2.014 | 1.478 |

| | SW620 | HT-29 | HCT116 | HCT116 p53 -/- | RKO | LS411N |
|---|---|---|---|---|---|---|
| IC50 | 83.84 | 3.125 | 3.512 | 5.249 | 2.090 | 5.285 |

| | SW620 | HT-29 | HCT116 | HCT116 p53 -/- | RKO | LS411N |
|---|---|---|---|---|---|---|
| IC50 | 36.75 | 0.3609 | 0.6450 | 5.888 | 0.3937 | 0.4284 |

| | VY-3-277 | PET-16 | AP-4-139B | 5-FU | Oxaliplatin |
|---|---|---|---|---|---|
| IC50 | 596.6 | 60.72 | 5.567 | 2.074 | 7.162 |

| | VY-3-277 | PET-16 | AP-4-139B | 5-FU | Oxaliplatin |
|---|---|---|---|---|---|
| IC50 | 182.9 | 11.88 | 3.259 | 0.5105 | 3.595 |

| PET-16 Analogs | |
|---|---|
| Compound | IC50, nM |
| PET-16* | 5,200 |
| AP-3-49 | 2,300 |
| AP-3-48 | 24,000 |
| AP-3-148 | >30,000 |
| AP-3-24 | 2,000 |
| AP-3-22 | >30,000 |
| AP-3-23 | >30,000 |
| AP-3-147 | >30,000 |
| AP-3-19 | 11,000 |
| AP-3-140 | 9,300 |
| AP-3-69 | >30,000 |
| * Geometric mean of 2 independent expts | |

PET-16

AP-3-49

AP-3-48

AP-3-148

AP-3-24

AP-3-22

AP-3-23

AP-3-147

AP-3-19

AP-3-140

AP-3-69

| AP-3-90 & -97 Series | |
|---|---|
| Compound | IC50, nM |
| AP-3-90 | 510 |
| AP-3-230 | >30,000 |
| AP-3-97 | 670 |
| AP-3-231 | >30,000 |
| AP-3-95 | 1,300 |
| AP-3-229 | >30,000 |
| AP-3-96 | 1,200 |
| AP-4-139B | 180 |
| AP-4-195 | 1,100 |
| AP-4-226 | 8,800 |
| AP-4-198 | 14,000 |
| AP-4-196 | 2,200 |

AP-3-90

AP-3-230

AP-3-97

AP-3-231

AP-3-95

AP-3-229

AP-3-96

AP-4-139B

AP-3-195

AP-4-226

AP-4-198

AP-4-196

Biotin-AP-4-139B

| AP-4-139B | | | |
|---|---|---|---|
| Parameter | Plasma | Brain | Liver |
| | IP/10 mg/kg | IP/10 mg/kg | IP/10 mg/kg |
| Cmax (ng/mL) | 1650 | 52 | 11755 |
| Tmax (h) | 0.25 | 1 | 0.25 |
| T1/2 (hr) | 5.52 | 3.54 | 2.48 |
| AUC 0-t, (ng *h/mL) | 3359 | 138.9 | 30370 |
| AUC 0-∞ (ng *h/ml) | 7951 | 279.4 | 48433 |
| Brain penetrance (%) | | 4.14 | 904.14 |
| Liver penetrance (%) | | | 609 |
| Mean, n=3/time point | | | |

RKO

Data: PLX+1398 plate 1&2 combined --- averaged at each dosage level:

difference = Observed inhibition rate - Bliss expected inhibition rate:

| Inhibition decimal | | Dose of 1398 | | | | | | | | | | |
|---|---|---|---|---|---|---|---|---|---|---|---|---|
| | | 110 | 170 | 270 | 430 | 670 | 1000 | 1600 | 2600 | 4100 | 6400 | 10000 |
| Dose of PLX | 36 | -0.050 | -0.073 | -0.055 | -0.076 | -0.183 | -0.194 | -0.044 | -0.036 | -0.021 | -0.025 | -0.004 |
| | 57 | -0.050 | -0.073 | -0.055 | -0.077 | -0.200 | -0.179 | -0.058 | -0.016 | -0.020 | -0.017 | -0.006 |
| | 89 | -0.050 | -0.073 | -0.055 | -0.043 | -0.155 | -0.180 | -0.051 | -0.003 | -0.006 | -0.007 | 0.006 |
| | 140 | -0.0408078 | -0.073 | -0.048 | -0.013 | -0.101 | -0.157 | -0.075 | 0.011 | -0.008 | -0.004 | 0.002 |
| | 320 | -0.050 | -0.0734341 | -0.038 | 0.021 | -0.060 | -0.143 | 0.008 | 0.027 | -0.009 | -0.006 | 0.016 |
| | 350 | -0.050 | -0.073 | -0.027 | 0.009 | -0.132 | -0.121 | -0.031 | 0.033 | -0.003 | 0.007 | 0.008 |
| | 540 | -0.050 | -0.073 | -0.055 | 0.001 | -0.087 | -0.122 | -0.030 | 0.026 | 0.005 | 0.003 | 0.018 |
| | 850 | -0.022 | -0.047 | 0.053 | 0.126 | 0.016 | 0.010 | 0.107 | 0.125 | 0.031 | 0.013 | 0.027 |
| | 1300 | -0.035 | 0.001 | 0.035 | 0.092 | 0.016 | 0.027 | 0.116 | 0.132 | 0.029 | 0.030 | 0.034 |
| | 2100 | 0.035 | -0.027 | 0.068 | 0.134 | 0.021 | 0.019 | 0.138 | 0.119 | 0.031 | 0.037 | 0.031 |
| | 3300 | -0.009 | -0.010 | 0.082 | 0.154 | 0.107 | 0.132 | 0.158 | 0.145 | 0.037 | 0.039 | 0.035 |
| | 5200 | 0.021 | 0.078 | 0.145 | 0.178 | 0.122 | 0.183 | 0.172 | 0.177 | 0.040 | 0.035 | 0.039 |
| | 8100 | 0.092 | 0.043 | 0.067 | 0.137 | 0.132 | 0.163 | 0.157 | 0.135 | 0.023 | 0.025 | 0.035 |
| | 13000 | 0.037 | -0.018 | 0.061 | 0.126 | 0.128 | 0.132 | 0.124 | 0.105 | 0.005 | 0.018 | 0.030 |
| | 20000 | -0.030 | -0.0449911 | -0.033 | 0.037 | 0.035 | 0.055 | 0.049 | 0.043 | -0.009 | 0.002 | 0.017 |

LS411N

Data: PLX+1398 plate 1 & 2 --- averaged at each dosage level:

Observed - Bliss expected:

| Inhibition % | | Dose of 1398 | | | | | | | | | | |
|---|---|---|---|---|---|---|---|---|---|---|---|---|
| | | 110 | 170 | 270 | 430 | 670 | 1000 | 1600 | 2600 | 4100 | 6400 | 10000 |
| Dose of PLX | 9 | [illegible] | [illegible] | 0.0980397 | 0.0534703 | 0.0205297 | -0.0112786 | 0.0264943 | 0.0198066 | -0.0034072 | 0.0011102 | -0.0002092 |
| | 14 | [illegible] | 0.1003517 | 0.1265677 | 0.001619 | 0.096365 | 0.0118213 | 0.0264068 | 0.0214888 | 0.0109417 | 0.0007973 | -4.859E-05 |
| | 22 | -0.0477862 | -0.0441661 | 0.0147622 | 0.0785548 | 0.1468865 | 0.0711297 | 0.0766041 | 0.0384216 | 0.0153261 | 0.0019305 | -0.0002596 |
| | 35 | 0.1732333 | 0.0750326 | 0.0018348 | 0.0954177 | 0.143035 | 0.0760204 | 0.0614441 | 0.0309129 | 0.0161188 | 0.0026527 | -0.0001362 |
| | 55 | 0.0892693 | 0.0501265 | 0.0540721 | 0.1062333 | 0.1768586 | 0.0633376 | 0.064591 | 0.0433292 | 0.0205883 | 0.0026735 | -6.935E-05 |
| | 86 | 0.1204689 | 0.0909998 | 0.0092268 | 0.0401224 | 0.1344633 | 0.050349 | 0.0549109 | 0.0403832 | 0.0157523 | 0.0009862 | -0.0001548 |
| | 140 | 0.1437064 | 0.1194552 | 0.0672575 | 0.0249733 | 0.1207708 | 0.0570744 | 0.047527 | 0.0339143 | 0.017635 | 0.0017096 | -2.187E-05 |
| | 210 | 0.1367127 | 0.0893715 | -0.018404 | 0.1170848 | 0.1408686 | 0.0556227 | 0.0474123 | 0.0321318 | 0.0157512 | 0.0016565 | -4.197E-05 |
| | 330 | 0.0868203 | 0.0346028 | 0.0380911 | 0.1458805 | 0.1564865 | 0.0683406 | 0.0446485 | 0.0299866 | 0.0143624 | 0.0019516 | -4.859E-05 |
| | 520 | 0.0953796 | 0.0335009 | 0.0344713 | 0.1156204 | 0.1302047 | 0.053428 | 0.0407468 | 0.0254394 | 0.0132392 | 0.0015984 | -5.15E-05 |
| | 820 | 0.0973421 | 0.0332877 | 0.071775 | 0.1233491 | 0.1519939 | 0.0546709 | 0.0359257 | 0.0221675 | 0.0138063 | 0.0016127 | -4.526E-05 |
| | 1300 | 0.1288615 | 0.0509253 | 0.0040996 | 0.1061149 | 0.1142386 | 0.0459683 | 0.0229081 | 0.0186489 | 0.0105242 | 0.0013424 | 8.261E-06 |
| | 2000 | -0.0380462 | 0.0382507 | 0.0718416 | 0.1435044 | 0.1407223 | 0.0446842 | 0.0374577 | 0.0229806 | 0.0111158 | 0.0012025 | 7.759E-06 |
| | 3100 | -0.055535 | -0.0162398 | 0.0674426 | 0.1377263 | 0.1263299 | 0.0448779 | 0.0374067 | 0.021357 | 0.0105296 | 0.0011388 | -2.649E-05 |
| | 5000 | -0.0195863 | 0.0344195 | 0.1084614 | 0.1181464 | 0.1031841 | 0.0313034 | 0.0216317 | 0.0180629 | 0.0078203 | 0.0004771 | 6.546E-05 |

FIG. 20A

Proteins Upregulated Less Than 1.2 Fold by AP-4-139B

| mw kDA | pept N | intens /bg | fold /unt | unt 1 | unt 2 | 139B 1 | 139B 2 | Protein |
|---|---|---|---|---|---|---|---|---|
| 51.4 | 5 | 51 | 1.02 | | | | | PACSIN2 |
| 15.5 | 7 | 964 | 1.02 | | | | | TOMM22 |
| 16.5 | 6 | 232 | 1.02 | | | | | MGST3 |
| 51.5 | 14 | 246 | 1.03 | | | | | MTX1 |
| 47.1 | 11 | 215 | 1.03 | | | | | PAICS |
| 24.2 | 8 | 38 | 1.03 | | | | | DCAKD |
| 25.0 | 17 | 464 | 1.03 | | | | | PRDX6 |
| 88.3 | 19 | 419 | 1.04 | | | | | CPT1A |
| 102.0 | 57 | 10099 | 1.04 | | | | | SND1 |
| 17.6 | 5 | 365 | 1.05 | | | | | MGST1 |
| 90.2 | 15 | 114 | 1.05 | | | | | ATXN2 |
| 41.3 | 6 | 91 | 1.05 | | | | | GDAP1 |
| 79.2 | 20 | 551 | 1.06 | | | | | ACSL4 |
| 41.9 | 16 | 395 | 1.06 | | | | | PTGES2 |
| 50.4 | 7 | 192 | 1.07 | | | | | TUBB3 |
| 75.4 | 25 | 618 | 1.08 | | | | | RARS |
| 52.1 | 10 | 245 | 1.10 | | | | | RMDN3 |
| 36.1 | 29 | 21134 | 1.10 | | | | | GAPDH |
| 37.5 | 10 | 108 | 1.11 | | | | | ARMC10 |
| 19.3 | 4 | 337 | 1.12 | | | | | TMEM205 |

| | | | | | | | | |
|---|---|---|---|---|---|---|---|---|
| 54.8 | 10 | 84 | 1.12 | | | | | ALDH3A2 |
| 40.7 | 7 | 153 | 1.12 | | | | | ATAD1 |
| 67.5 | 26 | 2158 | 1.12 | | | | | TOMM70 |
| 25.0 | 9 | 205 | 1.12 | | | | | RAB32 |
| 84.2 | 11 | 211 | 1.13 | | | | | MFN1 |
| 15.3 | 5 | 16 | 1.13 | | | | | BID |
| 16.7 | 7 | 480 | 1.13 | | | | | CYB5B |
| 79.7 | 38 | 1093 | 1.14 | | | | | HSD17B4 |
| 35.4 | 10 | 173 | 1.15 | | | | | RDH11 |
| 102.3 | 32 | 2085 | 1.15 | | | | | HK1 |
| 119.8 | 18 | 468 | 1.16 | | | | | ACLY |
| 101.6 | 33 | 788 | 1.16 | | | | | MTHFD1 |
| 62.7 | 7 | 12 | 1.17 | | | | | PGS1 |
| 23.4 | 8 | 93 | 1.17 | | | | | BAK1 |
| 20.1 | 7 | 138 | 1.17 | | | | | PRDX2 |
| 19.2 | 6 | 236 | 1.18 | | | | | PTRH2 |
| 34.8 | 12 | 367 | 1.18 | | | | | EMC2 |
| 34.6 | 11 | 109 | 1.19 | | | | | TOMM34 |
| 15.3 | 6 | 161 | 1.19 | | | | | CISD2 |

MW: Molecular Weight
Pept: N peptides detected
Intens: Intensity vs. Background
Fold: Fold vs. Untreated Intensity vs mean

FIG. 20C

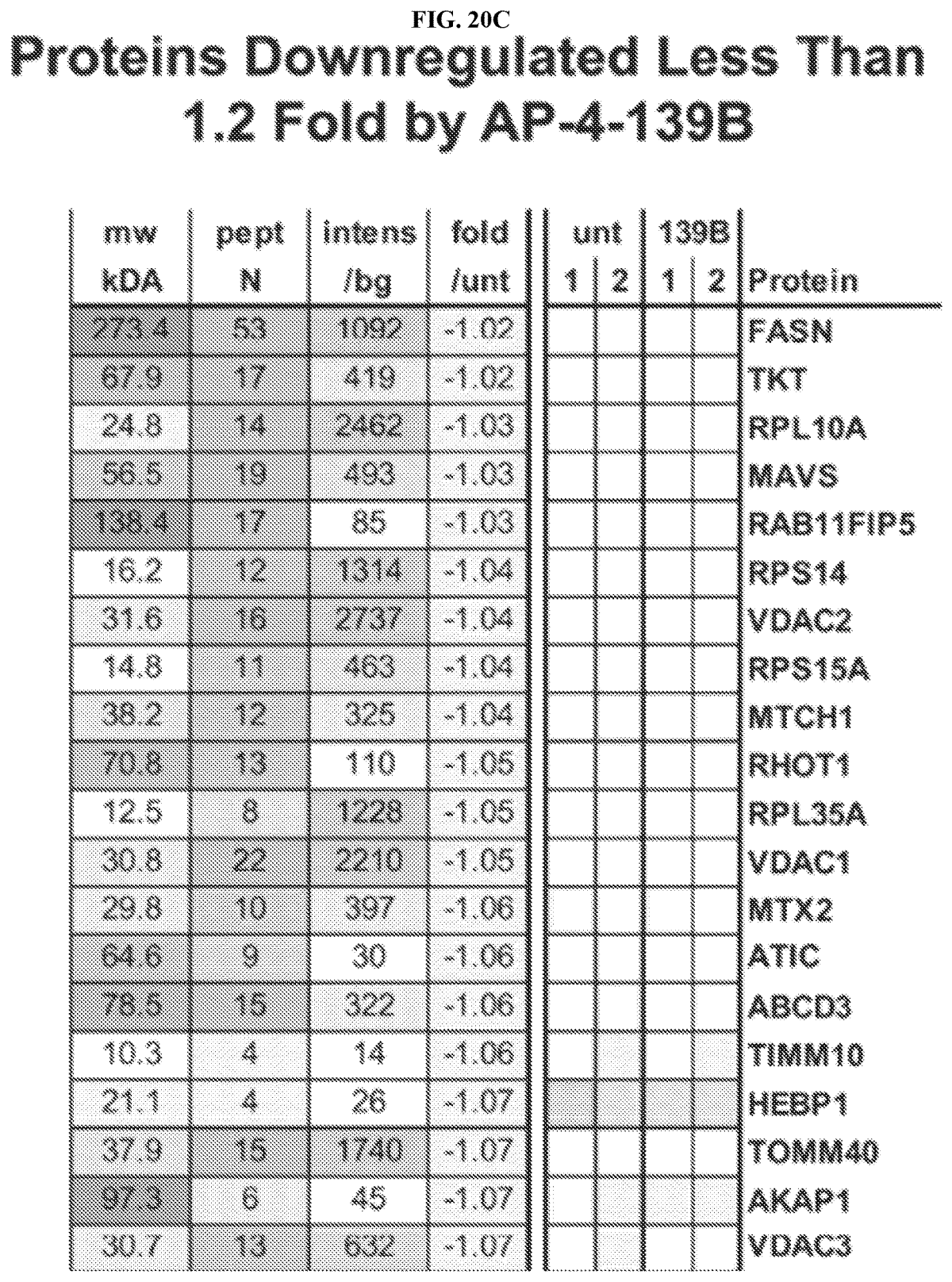

Proteins Downregulated Less Than 1.2 Fold by AP-4-139B

| mw kDA | pept N | intens /bg | fold /unt | unt 1 | unt 2 | 139B 1 | 139B 2 | Protein |
|---|---|---|---|---|---|---|---|---|
| 273.4 | 53 | 1092 | -1.02 | | | | | FASN |
| 67.9 | 17 | 419 | -1.02 | | | | | TKT |
| 24.8 | 14 | 2462 | -1.03 | | | | | RPL10A |
| 56.5 | 19 | 493 | -1.03 | | | | | MAVS |
| 138.4 | 17 | 85 | -1.03 | | | | | RAB11FIP5 |
| 16.2 | 12 | 1314 | -1.04 | | | | | RPS14 |
| 31.6 | 16 | 2737 | -1.04 | | | | | VDAC2 |
| 14.8 | 11 | 463 | -1.04 | | | | | RPS15A |
| 38.2 | 12 | 325 | -1.04 | | | | | MTCH1 |
| 70.8 | 13 | 110 | -1.05 | | | | | RHOT1 |
| 12.5 | 8 | 1228 | -1.05 | | | | | RPL35A |
| 30.8 | 22 | 2210 | -1.05 | | | | | VDAC1 |
| 29.8 | 10 | 397 | -1.06 | | | | | MTX2 |
| 64.6 | 9 | 30 | -1.06 | | | | | ATIC |
| 78.5 | 15 | 322 | -1.06 | | | | | ABCD3 |
| 10.3 | 4 | 14 | -1.06 | | | | | TIMM10 |
| 21.1 | 4 | 26 | -1.07 | | | | | HEBP1 |
| 37.9 | 15 | 1740 | -1.07 | | | | | TOMM40 |
| 97.3 | 6 | 45 | -1.07 | | | | | AKAP1 |
| 30.7 | 13 | 632 | -1.07 | | | | | VDAC3 |

FIG. 20D

| | | | | | | | | |
|---|---|---|---|---|---|---|---|---|
| 174.0 | 6 | 78 | -1.07 | | | | | LAMC1 |
| 68.1 | 9 | 134 | -1.07 | | | | | RHOT2 |
| 16.3 | 4 | 142 | -1.08 | | | | | TOMM20 |
| 31.2 | 7 | 106 | -1.08 | | | | | MARCH5 |
| 13.3 | 7 | 1191 | -1.08 | | | | | RPL34 |
| 84.4 | 26 | 661 | -1.08 | | | | | AFG3L2 |
| 54.9 | 4 | 12 | -1.09 | | | | | POLG2 |
| 74.3 | 4 | 38 | -1.09 | | | | | ACSL1 |
| 82.9 | 7 | 34 | -1.10 | | | | | ABCD1 |
| 17.7 | 18 | 4373 | -1.10 | | | | | RPS18 |
| 35.8 | 9 | 282 | -1.11 | | | | | GHITM |
| 63.3 | 17 | 328 | -1.12 | | | | | DNAJC11 |
| 29.1 | 9 | 122 | -1.13 | | | | | TFAM |
| 33.3 | 13 | 205 | -1.14 | | | | | MTCH2 |
| 13.3 | 5 | 188 | -1.14 | | | | | COX20 |
| 63.5 | 6 | 36 | -1.14 | | | | | SLC30A9 |
| 23.0 | 5 | 85 | -1.15 | | | | | RAB35 |
| 29.2 | 9 | 170 | -1.15 | | | | | APOOL |
| 21.2 | 9 | 77 | -1.15 | | | | | BAX |
| 6.2 | 4 | 13 | -1.15 | | | | | TOMM7 |
| 27.7 | 4 | 42 | -1.15 | | | | | LETMD1 |
| 29.5 | 5 | 46 | -1.16 | | | | | CCDC90B |
| 11.5 | 4 | 96 | -1.16 | | | | | HIGD2A |
| 33.2 | 19 | 5027 | -1.16 | | | | | PHB2 |
| 25.1 | 5 | 92 | -1.17 | | | | | SLC25A20 |
| 47.1 | 15 | 761 | -1.17 | | | | | AGK |
| 29.8 | 25 | 3833 | -1.19 | | | | | PHB |
| 81.9 | 27 | 235 | -1.19 | | | | | DNM1L |
| 56.6 | 31 | 15708 | -1.19 | | | | | ATP5F1B |

MW: Molecular Weight
Pept: N peptides detected
Intens: Intensity vs. Background
Fold: Fold vs. Untreated

Intensity vs mean

≤-4 -3 -2 -1.5 ±1 1.5 2 3 ≥4

HSP70 INHIBITORS AND METHODS OF USING SAME

CROSS-REFERENCE TO RELATED APPLICATIONS

This application is a 35 U.S.C. § 371 national phase application from, and claiming priority to, International Application No. PCT/US2021/024900, filed Mar. 30, 2021, which claims priority under 35 U.S.C. § 119(e) to U.S. Provisional Patent Application No. 63/002,847, filed Mar. 31, 2020, all of which are incorporated herein by reference in their entireties.

STATEMENT REGARDING FEDERALLY SPONSORED RESEARCH OR DEVELOPMENT

This invention was made with government support under grant numbers R01 CA139319 and P01 CA114046 awarded by the National Institutes of Health. The government has certain rights in the invention.

BACKGROUND

The chaperone heat shock protein 70 (HSP70, also HSPA1A) is the founding member of a family of proteins that function in the control of protein homeostasis, or proteostasis. There are over ten members of this family. Of these, HSP70 is the primary stress-induced member, while other family members like Hsc70, BiP and GRP75 are constitutively expressed and are not appreciably induced by stress.

Unlike these other constitutively expressed family members, HSP70 is not required for life: HSP70 knockout mice are viable and fertile. In cancer cells HSP70 serves a cytoprotective role, protecting tumor cells from proteotoxicity induced by stresses such as oxidative stress and aneuploidy. Consistent with this, this protein is markedly overexpressed in human tumors, but is marginally or undetectably expressed in normal, non-transformed cells. In colorectal cancer, HSP70 overexpression is a significant marker of poor prognosis, particularly in late stage cancer. Along these lines, this chaperone plays a significant role in CRC incidence, as crossing APC-Min mice to HSP70 knockout mice dramatically reduces adenoma formation and improves survival.

There is a need in the art for novel compounds and/or compositions that can be used to treat cancer, especially cancers overexpressing HSP70. The present disclosure addresses these unmet needs.

SUMMARY OF THE DISCLOSURE

In one aspect, the present disclosure related to a compound of formula (I), or a salt, solvate, enantiomer, and/or tautomer thereof:

$$\text{BINDER-X}—(Z_1)_{m1}—\text{Y}—(Z_2)_{m2}\text{-L} \quad (I),$$

wherein: BINDER, L, X, Y, $Z_1$, $Z_2$, $m_1$, and $m_2$ are described elsewhere herein. In certain embodiments, the compound of formula (I) is selected from the group consisting of:

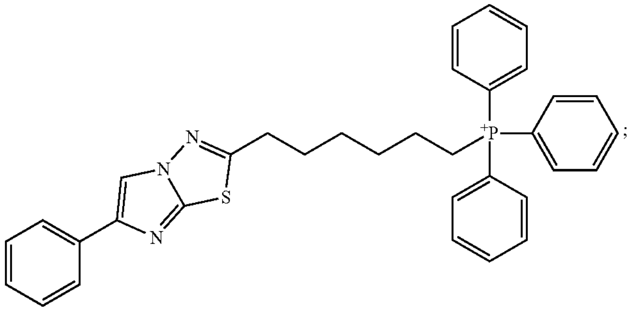
;

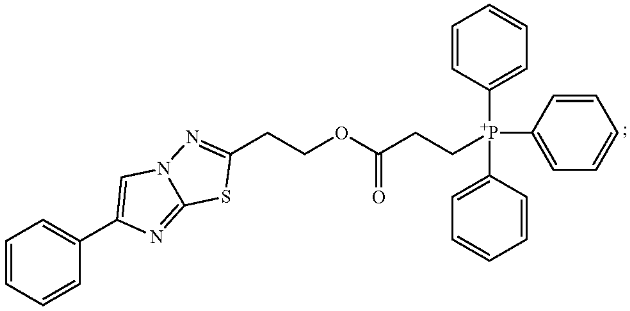
;

-continued
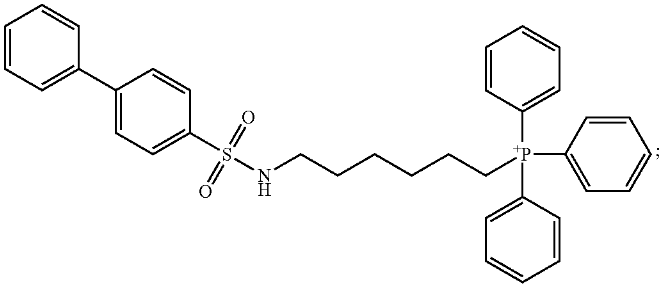
;
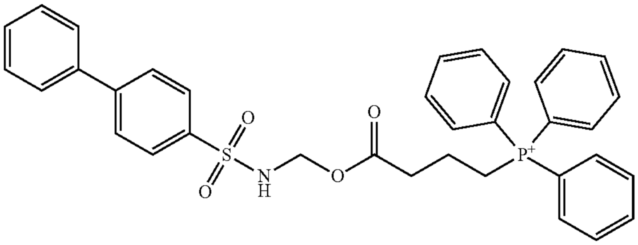
;
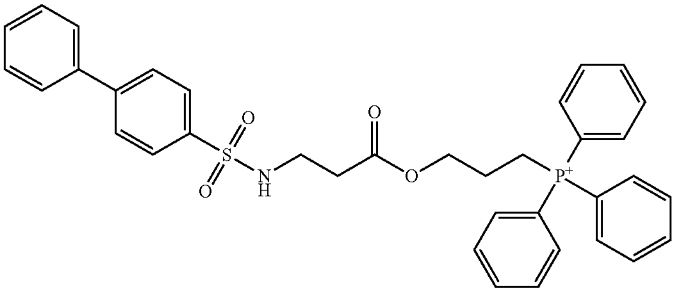
;
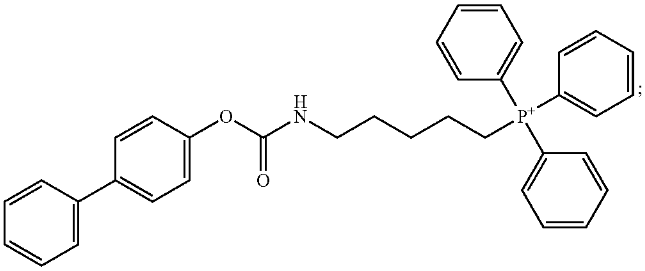
;
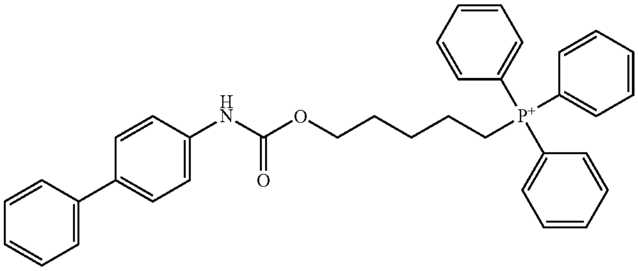
;
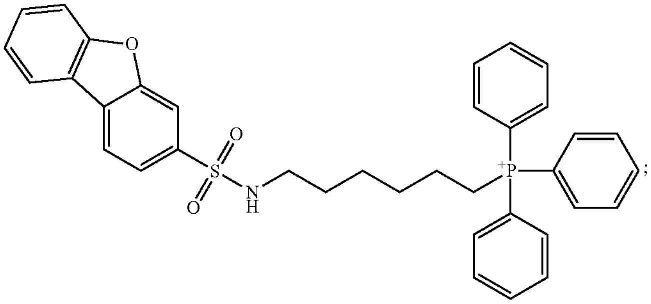
;

-continued
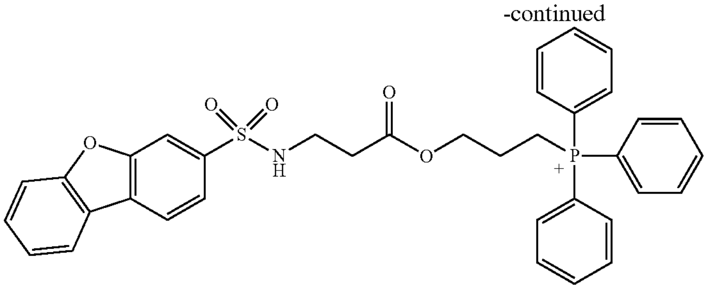
;
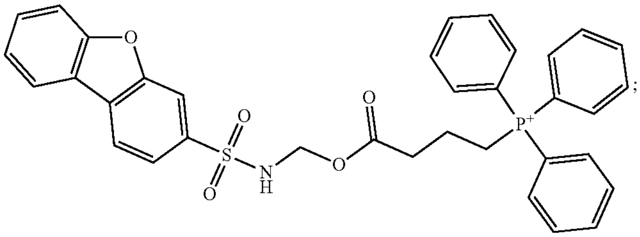
;
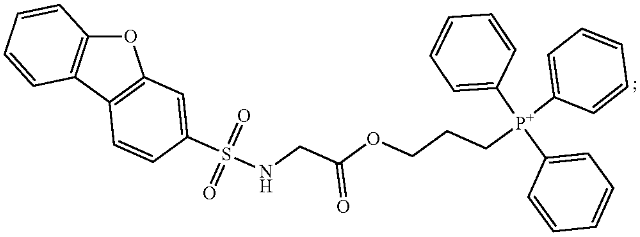
;
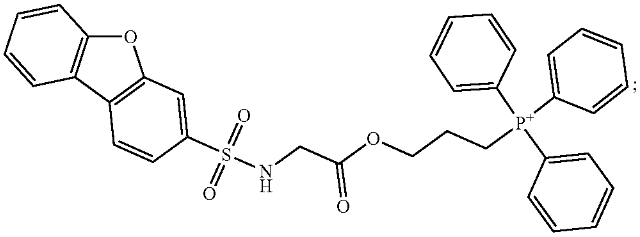
;
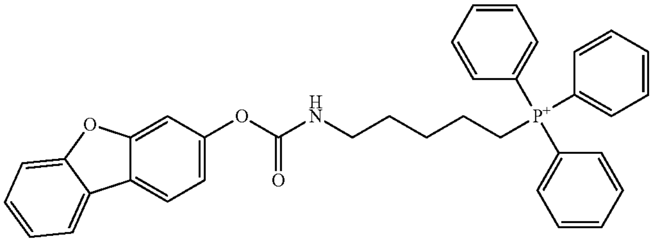
;
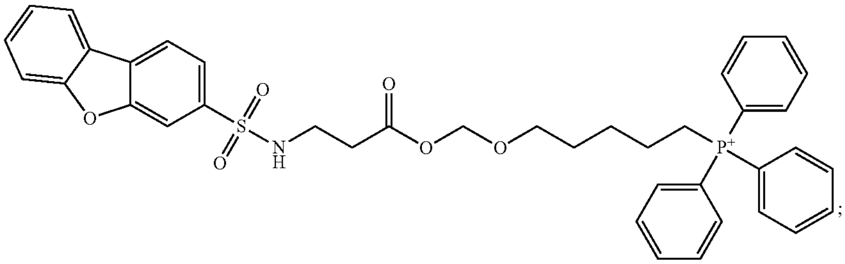
;
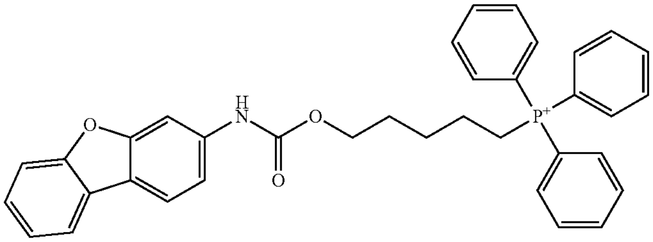
;

-continued

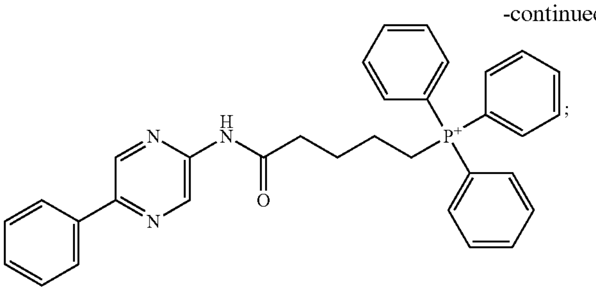
;

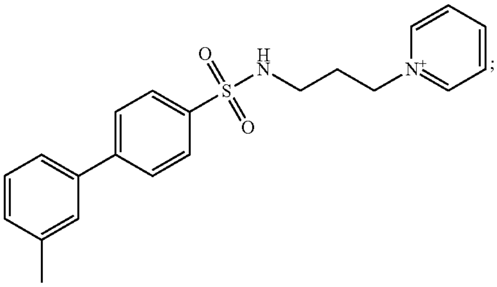
;

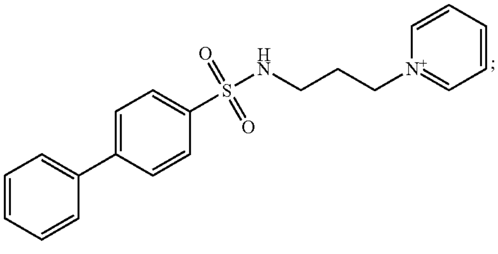
;

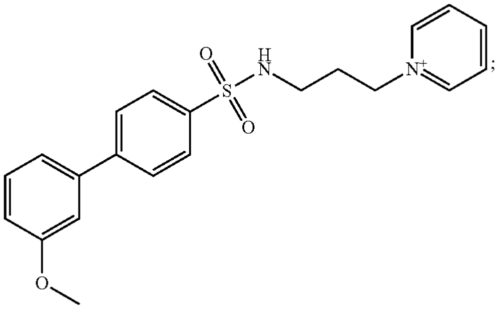
;

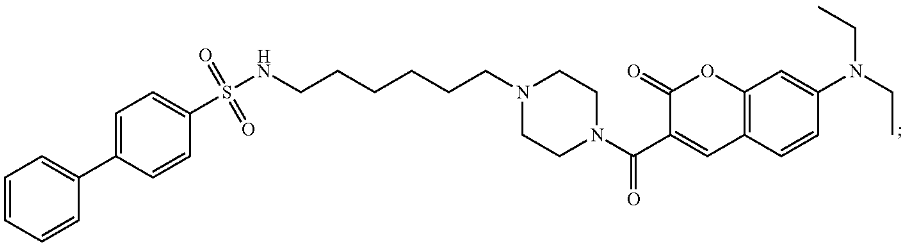
; and

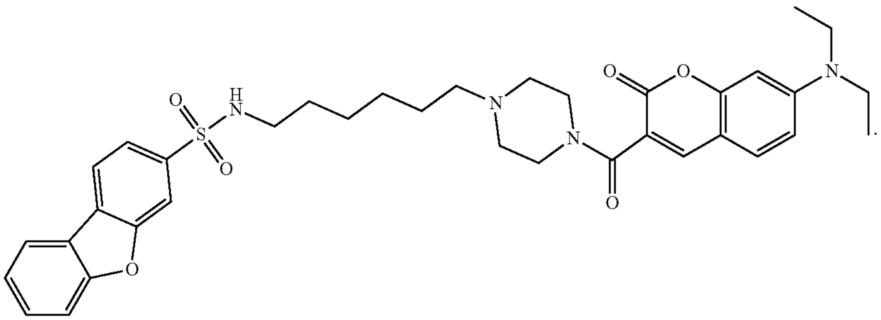 [SMILES: CCN(CC)c1ccc2cc(C(=O)N3CCN(CCCCCCNS(=O)(=O)c4ccc5c(c4)oc4ccccc45)CC3)c(=O)oc2c1]
.

In another aspect, the present disclosure relates to a pharmaceutical composition comprising a compound of formula (I) and at least one pharmaceutically acceptable carrier. In certain embodiments, the pharmaceutical composition further comprises at least one additional agent that treats, ameliorates, and/or prevents a cancer. In certain embodiments, the at least one additional agent comprises a MEK inhibitor, a BRAF inhibitor, or an immune checkpoint inhibitor. In certain embodiments, the cancer is at least one selected from the group consisting of colorectal cancer, melanoma, drug-resistant BRAF mutant melanoma and non-small-cell lung cancer (NSCLC).

In another aspect, the present disclosure relates to a method of treating, ameliorating, and/or preventing a cancer in a subject, wherein the method comprises administering to the subject a therapeutically effective amount of the compound of a compound of formula (I) and/or a pharmaceutical composition comprising a compound of formula (I) and at least one pharmaceutically acceptable carrier. In certain embodiments, the compound is administered as a pharmaceutical composition comprising at least one pharmaceutically acceptable carrier. In certain embodiments, the compound is the only therapeutically effective agent administered to the subject. In certain embodiments, the compound is the only therapeutically effective agent administered to the subject in an amount that treats, ameliorates, and/or prevents the cancer in the subject. In certain embodiments, the cancer is at least one selected from the group consisting of epithelial cancer, Merkel cell carcinoma, liver cancer, cervical cancer, anal cancer, penile cancer, vulvar cancer, vaginal cancer, breast cancer, ovarian cancer, uterine cancer, skin cancer, melanoma, oral cancer, colon cancer, neck cancer, head cancer, eye cancer, Kaposi's sarcoma, leukemia, nasopharyngeal carcinoma, mesothelioma, bone cancer, brain cancer, prostate cancer, testicular cancer, pancreatic cancer, hepatocellular carcinoma, lung cancer, and lymphoma. In certain embodiments, cancer is at least one selected from the group consisting of colorectal cancer, melanoma, drug-resistant BRAF mutant melanoma and non-small-cell lung cancer (NSCLC). In certain embodiments, the subject is a mammal. In certain embodiments, the compound is administered by an administration route selected from the group consisting of inhalational, oral, rectal, vaginal, parenteral, intracranial, topical, transdermal, pulmonary, intranasal, buccal, ophthalmic, intrathecal, and intravenous. In certain embodiments, the subject is further administered at least one additional agent that treats the cancer. In certain embodiments, the at least one additional agent comprises a MEK inhibitor, a BRAF inhibitor, or an immune checkpoint inhibitor. In certain embodiments, the compound and the at least one additional agent are co-administered. In certain embodiments, the compound and the at least one additional agent are co-formulated.

In yet another aspect, the present disclosure relates to a method of increasing and/or promoting immune cell infiltration and/or immune cell recruitment to a cancerous tumor in a subject, wherein the method comprises administering to the subject a therapeutically effective amount of a compound of formula (I) and/or a pharmaceutical composition comprising a compound of formula (I) and at least one pharmaceutically acceptable carrier. In certain embodiments, the compound is administered as a pharmaceutical composition comprising at least one pharmaceutically acceptable carrier. In certain embodiments, the compound is the only therapeutically effective agent administered to the subject. In certain embodiments, the compound is the only therapeutically effective agent administered to the subject in an amount that treats, ameliorates, and/or prevents the cancer in the subject. In certain embodiments, the cancer is at least one selected from the group consisting of epithelial cancer, Merkel cell carcinoma, liver cancer, cervical cancer, anal cancer, penile cancer, vulvar cancer, vaginal cancer, breast cancer, ovarian cancer, uterine cancer, skin cancer, melanoma, oral cancer, colon cancer, neck cancer, head cancer, eye cancer, Kaposi's sarcoma, leukemia, nasopharyngeal carcinoma, mesothelioma, bone cancer, brain cancer, prostate cancer, testicular cancer, pancreatic cancer, hepatocellular carcinoma, lung cancer, and lymphoma. In certain embodiments, cancer is at least one selected from the group consisting of colorectal cancer, melanoma, drug-resistant BRAF mutant melanoma and non-small-cell lung cancer (NSCLC). In certain embodiments, the subject is a mammal. In certain embodiments, the compound is administered by an administration route selected from the group consisting of inhalational, oral, rectal, vaginal, parenteral, intracranial, topical, transdermal, pulmonary, intranasal, buccal, ophthalmic, intrathecal, and intravenous. In certain embodiments, the subject is further administered at least one additional agent that treats the cancer. In certain embodiments, the at least one additional agent comprises a MEK inhibitor, a BRAF inhibitor, or an immune checkpoint inhibitor. In certain embodiments, the compound and the at least one additional agent are co-administered. In certain embodiments, the compound and the at least one additional agent are co-formulated.

BRIEF DESCRIPTION OF THE DRAWINGS

For the purpose of illustrating the disclosure, there are depicted in the drawings certain embodiments of the disclosure. However, the disclosure is not limited to the precise arrangements and instrumentalities of the embodiments depicted in the drawings.

FIG. 1A: Compounds AP-3-97 and AP-4-139B are direct inhibitors of HSP70. HSP70 mediated ATPase activity was assessed using the TRANSCREENER® ADP-FI assay. Five microliters of 30 nM purified human HSP70 in assay buffer was added to test compounds for 30 minutes, followed by addition of excess ATP. After 15 minutes, reactions were stopped and fluorescence was assessed on a plate reader. Data are normalized to percent inhibition, where 100% is the value in the absence of HSP70, and 0% is the value in the presence of HSP70. Compounds shown include PET-16 (positive control) and the novel HSP70 inhibitors AP-3-97 and AP-4-139B. VY-3-277 was used as a negative control. FIG. 1B: Compound AP-4-139B binds HSP70. Whole cell extracts (WCE) from H1299 cells were incubated with 10 μM Biotin or with a Biotin-labeled variant of AP-4-139B (Biotin-AP-4-139B) for 5 hours. Biotin-AP-4-139B containing complexes were captured using NeutrAvidin resins and separated by SDS-PAGE. The Coomassie-stained protein band of approximately 70 kDa was excised and subjected to tryptic digestion and liquid chromatography-tandem mass spectrometry, and identified to be HSP70. FIG. 1C: H1299 cells were pre-treated with 10 μM of VY-3-277, PET-16, or AP-4-139B for 1 hour prior to the addition of 10 μM Biotin-AP-4-139B for 5 hours. Biotin-AP-4-139B containing complexes were captured by NeutrAvidin resins and immunoblotted using the indicated antibodies following SDS-PAGE. Whole cell extracts (WCE) were examined for the expression of HSP70 (input) and GRP75 (input) by Western blot analysis. FIG. 1D: Compound AP-4-139B directly binds purified human HSP70. Surface Plasmon Resonance experiments were conducted using a Biacore T200. Approximately 20,000 RU of N-terminal HIS tagged Hsp70 was immobilized on a multidentate NTA derivatized linear carboxylate sensor chip. Flow rate was 30 μL/min, contact time for each sample concentration was 30 seconds, followed by a 60 second dissociation time. Data were analyzed using the evaluation software from Biacore and the resulting sensograms were exported and re-plotted in GraphPad Prism.

FIG. 2A: IMR90 cells (non-transformed fibroblasts), 1205Lu (melanoma), and HT-29 (CRC) cancer cells were treated with sub-lethal doses (500 nM) of the HSP70 inhibitors PET-16 (positive control) or AP-4-139B for 24 hours. Cells were then subjected to the Seahorse Mito Stress Test Assay. Injections were Oligomycin (1 μM, line A), FCPP (0.5-1 μM, line B), and Rotenone/Antimycin A (1 μM, line C). Each graphical representation indicates the mean±standard deviation of a minimum of 5 technical replicates. VY-3-277 was used as a negative control compound that does not inhibit HSP70 function. Each experiment was performed in triplicate and independently repeated twice. FIGS. 2B-2D: Basal Oxygen Consumption Rate (ORC) (FIG. 2B), Maximal OCR (FIG. 2C), and ATP production (FIG. 2D) were analyzed in IMR90 fibroblasts, non-transformed colonic epithelial cells (CCD 841 CoN), 1205Lu melanoma cells and HT-29 CRC cells, in the presence or absence of 500 nM HSP70 inhibitors or negative control (VY-3-277). All experiments were performed in triplicate, with each group containing 5-6 technical replicates.  $p<0.01$, * $p<0.001$, n.s. not significant.

FIG. 3A: Volcano plot showing the top up- and down-regulated proteins from isolated mitochondria of treated (1 μM AP-4-139B) and vehicle-treated 1205Lu melanoma cells. FIG. 3B: Heatmap of the top 10 down-regulated mitochondrial proteins after treatment with AP-4-139B. Proteins were identified using False Discovery Rate (FDR) values less than 10% and p values less than 0.05. FIG. 3C: Three different melanoma cell lines (WM983B, WM4265, and 1205Lu) were treated with the indicated concentrations of AP-4-139B for 24 hours. Cell lysates were subjected to Western blot analysis, and immunoblotted for NDUFA6, MRPS14, and GAPDH (loading control). FIGS. 3D-3E: HT-29 (FIG. 3D) and LS411N (FIG. 3E) CRC cell lines were treated with the indicated concentrations of PET-16 or AP-4-139B for 48 hours. Cell lysates were subjected to Western blot analysis, and immunoblotted for EGFR, MRPS14, AKT, Cleaved Lamin A (CLA), Cleaved Caspase 3 (CC3), HSP70, HSP90 and GAPDH (loading control). FIG. 3F: HT-29 cells were treated with the indicated concentration of AP-4-139B, Gamitrinib (G-TPP), or VY-3-277 (negative control) for 48 hours. Cell lysates were subjected to Western blot analysis, and immunoblotted for HSP90, AKT, p53, and MRPS14.

FIG. 4A: Three CRC cell lines (HT-29, LS411N, and SW620) were treated with 10 μM of PET-16 or AP-4-139B for 48 hours. Cell were then subjected to viability assays using Trypan Blue exclusion. * $p<0.001$. Note that non-transformed colonic epithelial cells, CCD 841 CoN, are far less sensitive to AP-4-139B compared to transformed cells. FIGS. 4B-4C: A panel of six CRC cell lines (SW620, HT-29, HCT 116+/− p53, RKO, and LS411N) were plated at a density of 1,000 cells per well in 96-well plates. The next day, cells were treated with the indicated inhibitors for 72 hours. Cells were then subjected to the Alamar Blue cell viability assays. Shown are representative $IC_{50}$ values of an average of six technical replicates and two biological replicates. FIG. 4D: $2.5\times10^6$ HT-29 cells were injected subcutaneously into the right flank of NSG mice. Once tumors reached an approximate volume of 100 $mm^3$, mice were separated randomly into two groups: control vs. AP-4-139B. Mice were treated with 12.5 mg/kg AP-4-139B three times a week. All mice were euthanized 22 days after the start of treatment. Tumor volumes were recorded using digital calipers and using the formula $v=\text{length}\times\text{width}^2\times0.52$. * $p<0.001$. n=10 mice per group. FIG. 4E: Immunohistochemistry (IHC) analysis of HT-29 xenograft tumors treated with AP-4-139B. Shown are representative images (4-6 random fields of view per condition) of Ki67 (proliferation) and Cleaved Lamin A (cell death). n=4 mice per group. Scale bar=100 μm. Respective IgG antibody was used as the negative control. FIG. 4F: Shows a quantification of FIG. 4E.  $p<0.01$; * $p<0.001$.

FIGS. 5A-5B: Mouse CRC cell lines, MC38 (FIG. 5A) and CT26 (FIG. 5B), were plated at a density of 1,000 cells per well in 96-well plates. The next day, cells were treated with the indicated inhibitors for 72 hours. Cells were then subjected to the Alamar Blue cell viability assays. Shown are representative $IC_{50}$ values of an average of six technical replicates and two biological replicates. FIG. 5C: Mouse CRC cell lines MC38 and CT26 were treated with 10 μM AP-4-139B for 24 or 48 hours and immunoblotted for HSP70, p53, AKT, Cleaved Lamin A (CLA), Cleaved Caspase 3, MRPS14, and GAPDH (loading control). The doublet detected for HSP70 is seen in other murine cell lines, and may represent a degradation product or post-translational modification. FIG. 5D: $1\times10^6$ MC38 cells were injected subcutaneously into the right flank of 6-8 week old male C57Bl/6 mice. Once tumors reached an approximate volume of 50 $mm^3$, mice were separated randomly into two groups: vehicle vs. AP-4-139B. Mice were treated with 10 mg/kg AP-4-139B every 48 hours. All mice were euthanized 20 days after the start of treatment. Tumor volumes were recorded using digital calipers and using the formula $v=\text{length}\times\text{width}^2\times0.52$. *** $p<0.001$. n=15 mice per group.

FIG. 5E: Immunohistochemistry (IHC) analysis of MC38 tumors treated with AP-4-139B. Shown are representative images (4-6 random fields of view per condition from four independent tumors) of $CD8^+$ T cells and Granzyme B (marker for activated immune cells). Respective IgG antibody was used as the negative control. Scale bars=100 μm. FIG. 5F: Quantification of FIG. 5E * $p<0.05$; ** $p<0.01$.

FIG. 6A: $1\times10^6$ MC38 cells were injected subcutaneously into the right flank of 6-8-week-old male C57Bl/6 mice. Once tumors reached an approximate volume of 100 $mm^3$, mice were treated with AP-4-139B (10 mg/kg) every 48 hours. 20 days after the start of treatment, tumors were excised, weighed, minced and digested. Tumor-infiltrating and splenic conventional CD4 (cCD4) (Live $CD45^+$ $DUMP^-$ $CD3^+CD4^+Foxp3^-$), Tregs (Live $CD45^+$ $DUMP^-$ $CD3^+$ $CD4^+Foxp3^+$), CD8 (Live $CD45^+$ $DUMP^-$ $CD3^+CD8^+$) T-cells, and Dendritic Cells (Live $CD45^+$ $DUMP^-$ $CD3^-$ $CD11c^+MHCII^+$) numbers were assessed by flow cytometry. * $p<0.05$, n.s. not significant. n=8 mice per group. FIG. 6B: MC38 and HT-29 cells were treated with the indicated concentrations of AP-4-139B for either 8 or 24 hours; media was collected and subjected to WB for HMGB1. Data shown are representative of three technical replicates. FIG. 6C: MC38 and HT-29 cells were treated with the indicated concentrations of AP-4-139B for three hours and then assayed for extracellular ATP release. Each graphical representation indicates the mean±the standard deviation of three independent experiments relative to control (DMSO-treated) cells.

FIG. 6D: MC38 cells were treated with 5 μM AP-4-139B for 24 hours and subjected to flow cytometry, using Alexa488-tagged calreticulin antibody. *** $p<0.001$, n=4 biological replicates performed in duplicate. FIG. 6E: MC38 cells were treated with increasing concentrations of AP-4-139B, G-TPP, 17-AAG or Metformin for 3 hours and then assayed for extracellular ATP release. Three independent cultures were assayed for each treatment, and DMSO-treated cells were used as internal controls. Error bars represent standard deviation (SD).

FIGS. 7A-7B: HSP70 inhibitors generated as derivatives of PET-16. Shown are the structures of 22 different HSP70 inhibitors and their respective ATPase $IC_{50}$ values. Data are representative means of two independent experiments. FIG. 7C: Structure of Biotin-AP-4-139B (BAP-4-139B). FIG. 7D: Surface Plasmon Resonance (SPR) profiling of the HSP70 inhibitor VER-15508, used as a positive control.

FIG. 8A: Association of HSPA1A gene expression and survival rate of patients with colorectal adenocarcinoma (COAD). Patient data was gathered from USCS Xena platform (GDC-TCGA COAD; n=435). Log-rank test was used to determine significance. p=0.0004. FIG. 8B: Association of HSPA1A gene expression and stage of COAD (n=440). Wilcoxon rank sum test was used to determine significance. * $p<0.05$, * $p<0.001$. FIG. 8C: Body weights of mice injected with HT-29 tumor xenografts. Weights were measured at the start of the treatment to determine mouse toxicity. n.s. not significant, n=10 mice per group. FIG. 8D: H&E staining of livers and colons of mice injected with HT-29 tumor xenografts. Tissues were collected at the end of the study. FIG. 8**E. Pharmacokinetic values of AP-4-139B in the liver, plasma, and brain from three CDI mice treated with 10 mg/kg of compound.

FIG. 9A: Body weights of mice injected with HT-29 tumor xenografts. Weights were measured at the start of the treatment to determine mouse toxicity. n.s. not significant, n=15 mice per group. FIG. 9B: Immunohistochemistry (IHC) analysis of MC38 tumors treated with AP-4-139B. Shown are representative images (4-6 random fields of view per condition from four independent tumors) of $CD4^+$ T cells. Respective IgG antibody was used as the negative control. Scale bars=100 μm. FIG. 9C: Quantification of FIG. 9B.

FIG. 10A: Gating strategy for immune cell populations in the liver and spleen of C57Bl/6 mice injected with MC38 tumor xenografts. FIG. 10B: CT26 cells were treated with 1 μM Doxorubicin (positive control) or 10 uM AP-4-139B and 24 hours later, cells were subjected to flow cytometry using Alexa488 fluorochrome-linked antibody to calreticulin. * $p<0.001$,  $p<0.01$, n=3 biological replicates.

FIGS. 20A-20D show that HSP70 inhibition does not affect global expression of mitochondrial proteins. FIG. 20A: First portion of a heatmap of the mitochondrial proteins that are up-regulated by less than 1.2 fold after treatment with AP-4-139B. FIG. 20B: Second portion of a heatmap of the mitochondrial proteins that are up-regulated by less than 1.2 fold after treatment with AP-4-139B. FIG. 20C: First portion of a heatmap of the mitochondrial proteins that are down-regulated by less than 1.2 fold after treatment with AP-4-139B. FIG. 20D: Second portion of a heatmap of the mitochondrial proteins that are down-regulated by less than 1.2 fold after treatment with AP-4-139B.

FIG. 22A: The contour plot of bliss combination effect and interaction index plot for HT-29. FIG. 22B: The interaction index plot for HT-29. FIG. 22C: The contour plot of bliss combination effect plot for RKO. FIG. 22D: The interaction index plots for RKO. FIG. 22E: The contour plot of bliss combination effect and interaction index plot for LS411N. FIG. 22F: The interaction index plot for LS411N.

FIG. 24A: MC38 cells were subjected to invasion assays using BioCoat Matrigel transwells in the presence of the indicated concentrations of AP-4-139B. 24 hours later, cells were fixed and stained with Crystal Violet. Shown are representative images taken from 8 random fields of view per well. Scale bar=100 μm. FIG. 24B: Quantification of FIG. 24A * $p<0.001$. FIG. 24C: Schematic representation of the metastasis assay. $4\times10^5$ MC38 cells were injected into the tail vein of 8-10 week old male C57Bl/6 mice. Mice were treated with i.p. injection of 10 mg/kg AP-4-139B every 48 hours. After 3 weeks, the lungs of mice were formalin fixed and H&E stained, and assessed for the presence of metastatic nodules. FIG. 24D: Representative images of lung metastases (black arrows) from C57Bl/6 mice injected with MC38 cells in the tail vein, followed by treatment with vehicle or AP-4-139B. Scale bar=250 μm. FIG. 24E: Quantification of FIG. 24**D. n=5 mice per group. * $p<0.05$.

FIG. 25A: C57Bl/6 mice were injected with either PBS or AP-4-139B pre-treated MC38 cells into the left flank. 10 days later, the same mice were injected with untreated MC38 cells in the right flank. Tumor incidence was measured as mice who displayed tumors on the right flank. n=15 mice per group. Log rank test $p<0.0001$. FIG. 25B: Tumor growth measured in mice in FIG. 25A over 25 days. n=15 mice per group. Wilcox rank-sum test $p<0.0001$.

FIG. 27A: MC38 tumors untreated with AP-4-139B. FIG. 27B: MC38 tumors untreated with AP-4-139B. FIG. 27C: MC38 tumors treated with AP-4-139B. FIG. 27D: MC38 tumors treated with AP-4-139B.

DETAILED DESCRIPTION OF THE DISCLOSURE

Figure 1A:
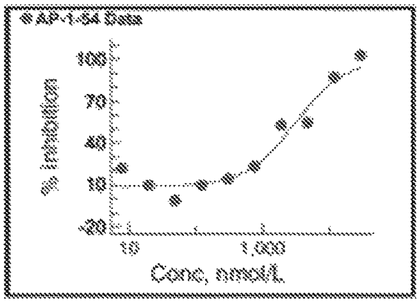
FIGS. 1A-1D show ATPase inhibition and direct binding of a novel HSP70 inhibitor.
Figure 1A:
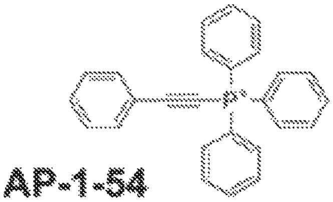
Figure 1A:
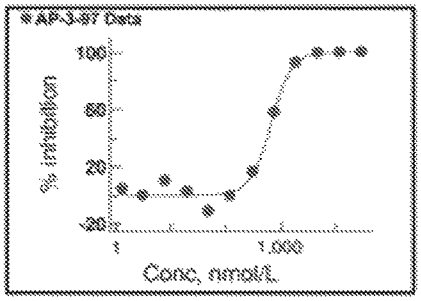
Figure 1A:
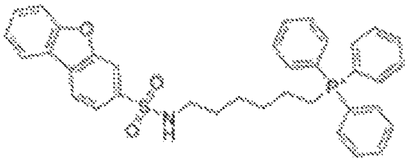
Figure 1A:
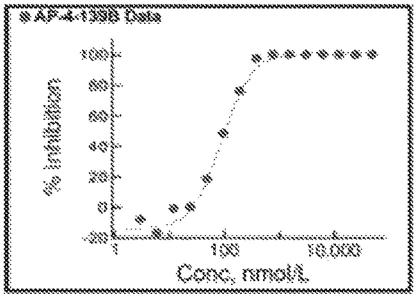
Figure 1A:
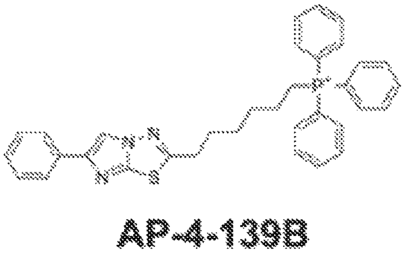
Figure 1A:
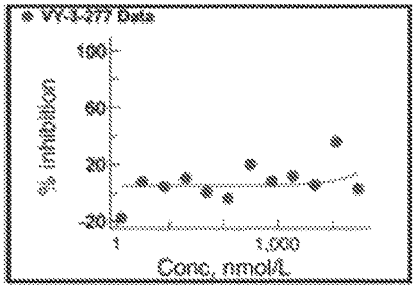
Figure 1A:
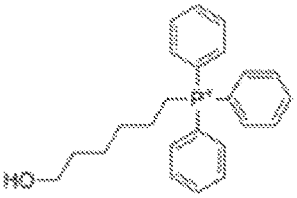

The disclosure relates in one aspect to compounds, and compositions comprising such compounds, that can be used to treat cancer, especially cancers that overexpress HSP70, such as but not limited to colorectal cancer (CRC) and melanoma. In certain embodiments, the compounds of the disclosure can be used in combination with inhibitors of BRAF. In certain embodiments, the combination of a compound of the disclosure and an inhibitor of BRAF is synergistic. In certain embodiments, the compounds of the disclosure can be used in combination with inhibitors of MEK. In certain embodiments, the combination of a compound of the disclosure and an inhibitor of MEK is synergistic. In certain embodiments, the compounds of the disclosure can be used in combination with immune checkpoint inhibitors. In certain embodiments, the combination of a compound of the disclosure and an immune checkpoint inhibitor is synergistic.

The disclosure is based, at least in part, on the identification of novel HSP70 inhibitors that target multiple compartments in the cancer cell, such as but not limited to mitochondria. As described elsewhere herein, the inhibitors are mitochondrio-toxic, and are cytotoxic to CRC cells but not normal colon epithelial cells. The inhibitors are shown to be efficacious in xenograft models of CRC, and that treatment leads to reduced level of mitochondrial and other client proteins. In a syngeneic CRC model, the inhibitors cause increased immune cell recruitment into tumors. Mechanistically, it was shown that cells treated with the inhibitors cause immunogenic cell death, and they recruit immune cells to tumors by causing tumors to secrete danger-associated molecular patterns (DAMPs), including ATP and HMGB1. The unique properties of these HSP70 inhibitors, in the disruption of mitochondrial health, the inhibition of cellular proteostasis, and the induction of DAMP release, all contribute to the efficacy of these compounds against cancer.

The compound pifithrin-mu (phenylethynesulfonamide, hereafter PES) was first identified as an inhibitor of mitochondrial trafficking of p53: PES was cytotoxic to tumor but not normal cells, and the target of PES was identified as stress-induced HSP70 (HSPA1A), but not other HSP70 family members. Silencing HSP70 markedly alleviates PES-mediated cytotoxicity, and PES significantly delays lymphoma progression in the Eu-MYC model of lymphoma, with no evidence of toxicity or weight loss. Silencing or inhibition of HSP70 is cytotoxic to tumor cells, with little toxicity to normal cells.

Since first described in 2009, over twenty different groups have confirmed the finding that PES functions as an HSP70 inhibitor. In subsequent studies, PES was coupled to a triphenylphosphonium (TPP) group, in order to target this compound to the mitochondria and inhibit the significant fraction of HSP70 that localizes to the mitochondria in tumor, but not normal, cells. This compound, PET-16, interacts with mitochondrially-localized HSP70 in tumor cells, but not with the family member GRP75. PET-16 binds to an allosteric pocket within the substrate binding domain, thus freezing the protein in the ADP bound form and preventing cycles of substrate binding and release that are required for protein unfolding. Despite these promising data, there were two concerning liabilities of PET-16. The first was the existence of a potentially reactive ethynyl group in the compound, which may be responsible for a <30 minute half-life of the compound in plasma. The second was somewhat modest (low micromolar) potency in vivo. Both of these deficiencies were sought be corrected in the work described herein.

Cancer cells tend to be more highly sensitive than normal cells to inhibitors of chaperones like HSP70 and HSP90 due to their genetic instability, nutrient and oxygen deprivation, and abundance of mutated and misfolded proteins. The studies described herein have identified active (AP-4-139B) and inactive (VY-3-277) analogs, established affinity reagents (BAP-4-139B), shown a direct interaction by surface plasmon resonance, developed a reliable high throughput ATPase assay in which to test derivatives, and identified and shown measurable effects on client proteins in cancer cells and tumors. The compounds described herein are mitochondria-directed by virtue of the triphenylphosphonium (TPP) group, and also uniquely cause insolubility of client proteins at the mitochondria, cytosol and nucleus. Data that the HSP70 inhibitors of the disclosure induce DAMP release and immune cell infiltration are provided herein.

Demonstrated herein is a high throughput ATPase assay for HSP70, which was used to identify more potent derivatives of PET-16. One of these derivatives, AP-4-139B, is significantly more potent and interacts directly with purified HSP70. This compound is cytotoxic and mitochondrio-toxic to cancer cells, but is much less so in normal non-transformed cells. This inhibitor is efficacious against colorectal cancer xenografts, and that it has a significantly extended (>5 hour) half-life in plasma. Interestingly, this inhibitor induces significant immune cell infiltration into tumors, including $CD8^+$ and $CD4^+$ T cells and dendritic cells. Finally, treatment of tumor cells with AP-4-139B causes secretion of DAMPs from tumor cells, including ATP and HMGB1, thus explaining at least one role of this compound as an anti-cancer agent, in the activation of the immune system.

Figure 6A:
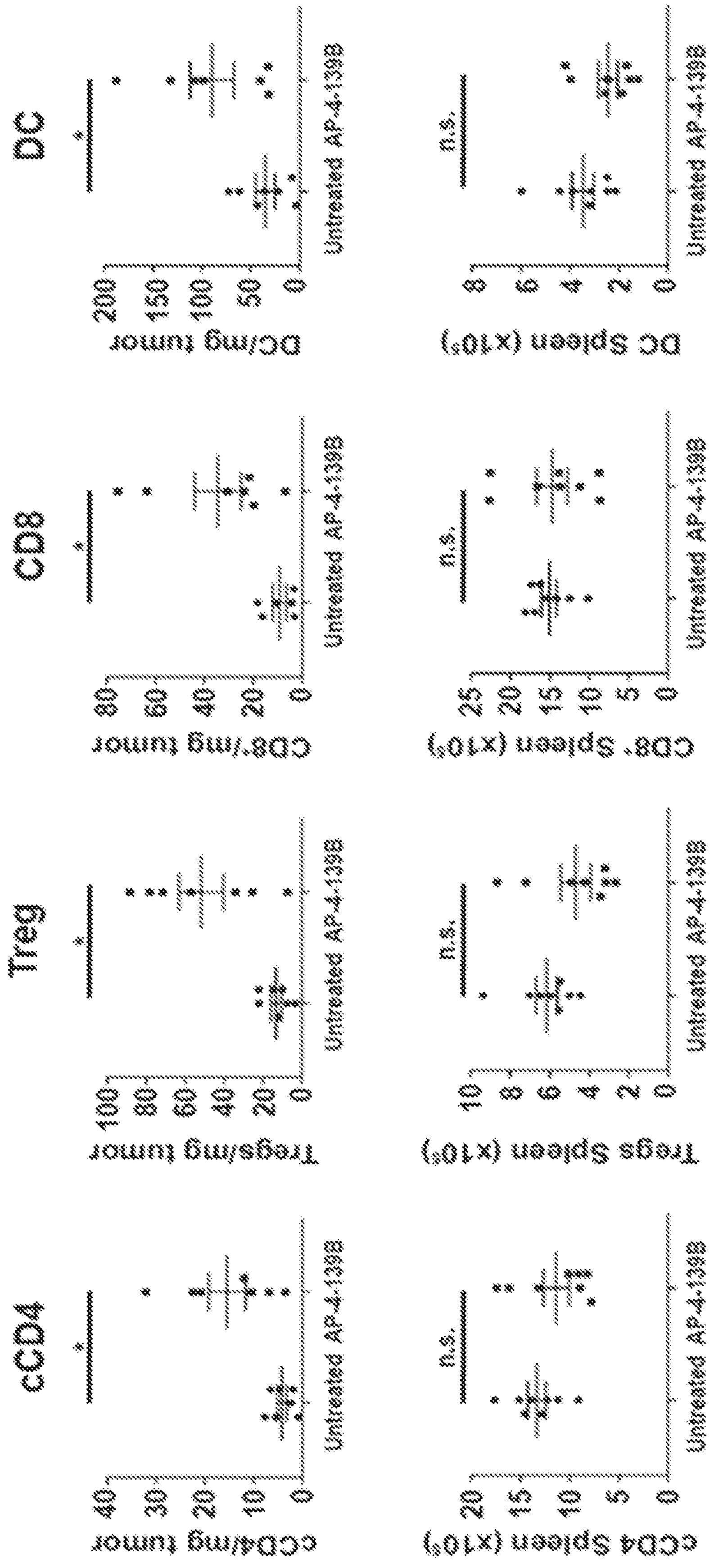
FIGS. 6A-6E show that AP-4-139B treatment leads to increased immune cell infiltration in CRC tumors and increased markers of immunogenic cell death.
Figure 6B:
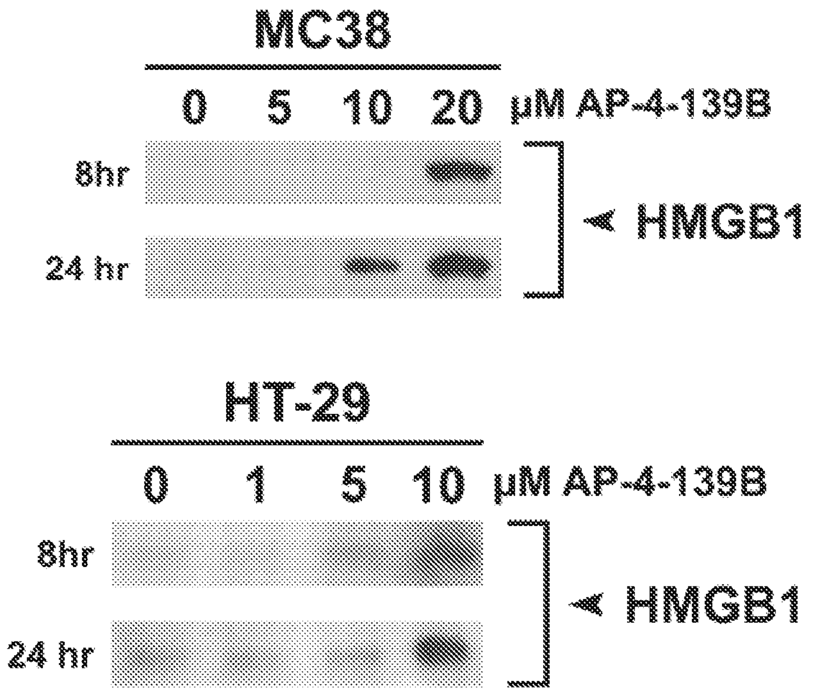
Figure 6C:
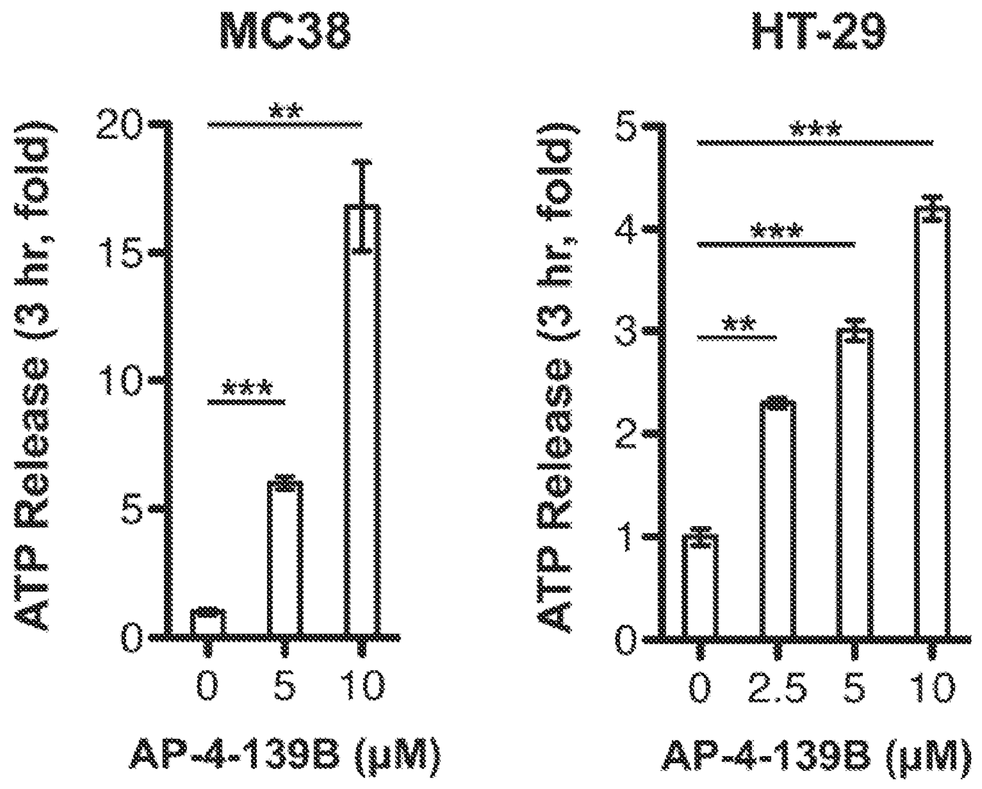
Figure 6D:
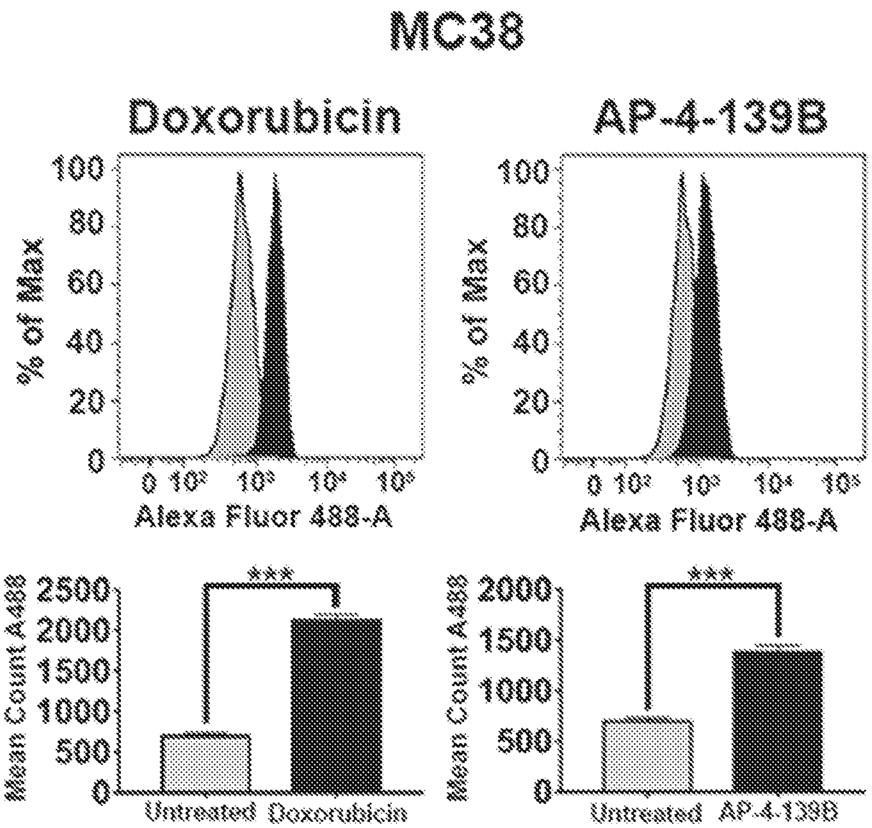
Figure 6E:
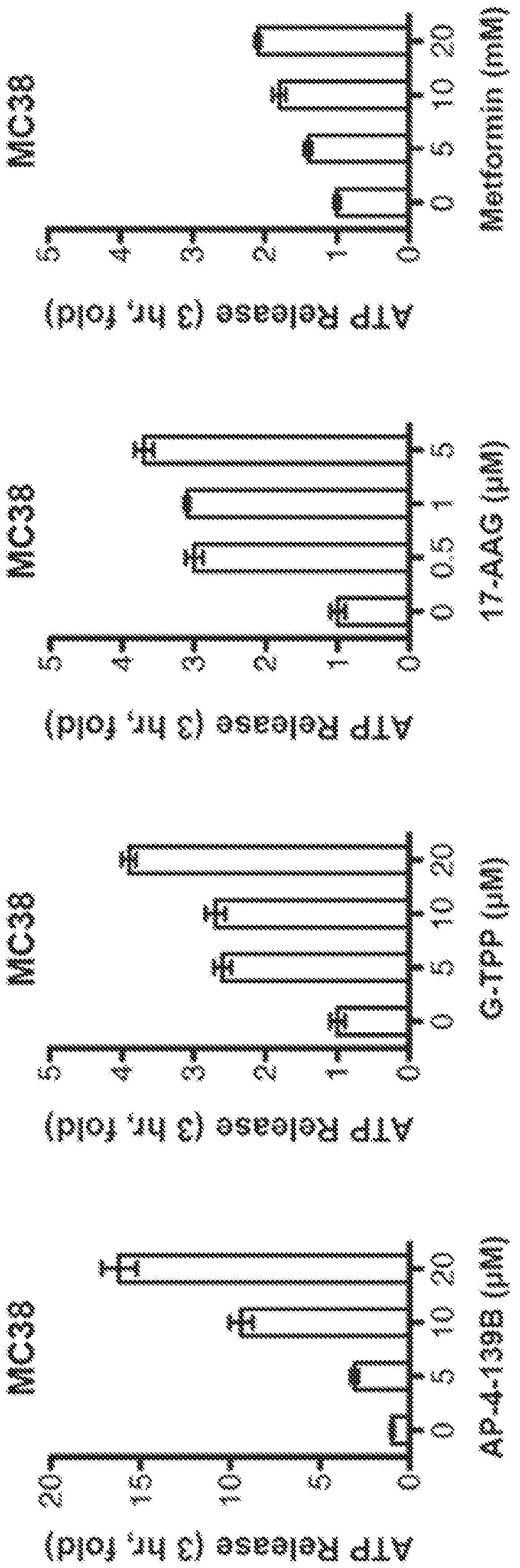

Release of DAMPs like HMGB1 and ATP, and localization of calreticulin to the plasma membrane, are three hallmarks of a putative pathway of cell death known as immunogenic cell death. It was shown herein that the HSP70 inhibitor herein induces all three markers of immunogenic cell death. The finding herein that AP-4-139B also induces $CD8^+$ T and other immune cell recruitment lends support to this premise that HSP70 inhibitors may function by enhancing immune cell recruitment. Without wishing to be limited by any theory, there are two consistent causes of immunogenic cell death: proteostatic stress, and the accumulation of reactive oxygen species. Inhibitors of HSP70 consistently lead to the accumulation of misfolded proteins, and concomitant proteostatic stress. Further, by designing the compound described herein to traffic to the mitochondria, the studies herein show that it disrupts mitochondrial function. This leads to the accumulation of significant mitochondrial reactive oxygen species. Without wishing to be limited by any theory, these facts together may explain the particular ability of AP-4-139B to induce markers of immunogenic cell death like ATP release, beyond what is observed for either the HSP90 inhibitor 17-AAG or the mitochondrial inhibitor metformin (FIG. 6E). It is important to note that AP-4-139B exhibited significant anti-cancer activity in immune-compromised mice as well, so the ability to induce immune cell activation is only part of the anti-cancer properties of this compound. In sum, the novel and diverse mechanisms of action of AP-4-139B, combined with the importance of HSP70 in late stage colorectal cancer, support the promise for the use of this compound for CRC therapy. Because HSP70 is overexpressed in many other cancers, without wishing to be limited by theory, it is believed the findings described herein have broad relevance to other cancers as well.

Definitions

As used herein, each of the following terms has the meaning associated with it in this section.

Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, separation science, and organic chemistry are those well-known and commonly employed in the art.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

In one aspect, the terms "co-administered" and "co-administration" as relating to a subject refer to administering to the subject a compound of the disclosure or salt thereof along with a compound that may also treat any disease or disorder contemplated herein and/or with a compound that is useful in treating other medical conditions but which in themselves may cause or facilitate any disease or disorder contemplated herein. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "$ED_{50}$" refers to the effective dose of a formulation that produces 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the disclosure in a kit. The instructional material of the kit may, for example, be affixed to a container that contains the compound and/or composition of the disclosure or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term “pharmaceutical composition” or “composition” refers to a mixture of at least one compound useful within the disclosure with a pharmaceutically acceptable carrier. The pharmaceutical composition facilitates administration of the compound to a subject.

As used herein, the term “pharmaceutically acceptable” refers to a material, such as a carrier or diluent, which does not abrogate the biological activity or properties of the compound useful within the disclosure, and is relatively non-toxic, i.e., the material may be administered to a subject without causing undesirable biological effects or interacting in a deleterious manner with any of the components of the composition in which it is contained.

As used herein, the term “pharmaceutically acceptable carrier” means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the subject such that it may perform its intended function. Typically, such constructs are carried or transported from one organ, or portion of the body, to another organ, or portion of the body. Each carrier must be “acceptable” in the sense of being compatible with the other ingredients of the formulation, including the compound useful within the disclosure, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer’s solution; ethyl alcohol; phosphate buffer solutions; and other non-toxic compatible substances employed in pharmaceutical formulations. As used herein, “pharmaceutically acceptable carrier” also includes any and all coatings, antibacterial and antifungal agents, and absorption delaying agents, and the like that are compatible with the activity of the compound useful within the disclosure, and are physiologically acceptable to the subject. Supplementary active compounds may also be incorporated into the compositions. The “pharmaceutically acceptable carrier” may further include a pharmaceutically acceptable salt of the compound useful within the disclosure. Other additional ingredients that may be included in the pharmaceutical compositions used in the practice of the disclosure are known in the art and described, for example in Remington’s Pharmaceutical Sciences (Genaro, Ed., Mack Publishing Co., 1985, Easton, PA), which is incorporated herein by reference.

As used herein, the language “pharmaceutically acceptable salt” refers to a salt of the administered compound prepared from pharmaceutically acceptable non-toxic acids and bases, including inorganic acids, inorganic bases, organic acids, inorganic bases, solvates, hydrates, and clathrates thereof.

The term “prevent,” “preventing” or “prevention,” as used herein, means avoiding or delaying the onset of symptoms associated with a disease or condition in a subject that has not developed such symptoms at the time the administering of an agent or compound commences. Disease, condition and disorder are used interchangeably herein.

By the term “specifically bind” or “specifically binds,” as used herein, is meant that a first molecule preferentially binds to a second molecule (e.g., a particular receptor or enzyme), but does not necessarily bind only to that second molecule.

As used herein, a “subject” may be a human or non-human mammal or a bird. Non-human mammals include, for example, livestock and pets, such as ovine, bovine, porcine, canine, feline and murine mammals. In certain embodiments, the subject is human.

The term “treat,” “treating” or “treatment,” as used herein, means reducing the frequency or severity with which symptoms of a disease or condition are experienced by a subject by virtue of administering an agent or compound to the subject.

As used herein, the term “alkyl,” by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term “alkylene” by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term “cycloalkyl,” by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$) cycloalkyl, such as, but not limited to, cyclopropyl, cyclobutyl, cyclopentyl and cyclohexyl.

As used herein, the term “alkenyl,” employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by $—CH_2—CH═CH_2$.

As used herein, the term “alkynyl,” employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term “propargylic” refers to a group exemplified by $—CH_2—C≡CH$. The term “homopropargylic” refers to a group exemplified by $—CH_2CH_2—C≡CH$. The term “substituted propargylic” refers to a group exemplified by $—CR_2—C≡CR$, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(═O)OH, trifluoromethyl, —C≡N, —C(═O)O($C_1$-$C_4$)alkyl, —C(═O)$NH_2$, —C(═O)NH($C_1$-$C_4$)alkyl, —C(═O)N(($C_1$-$C_4$)alkyl)$_2$, —$SO_2NH_2$, —C(═NH)$NH_2$, and —$NO_2$, preferably containing one or two substituents selected from halogen, —OH, alkoxy, —$NH_2$, trifluoromethyl, —$N(CH_3)_2$, and —C(═O)OH, more preferably selected from halogen, alkoxy and —OH. Examples of substituted alkyls include, but are not limited to, 2,2-difluoropropyl, 2-carboxycyclopentyl and 3-chloropropyl. In certain embodiments, the substituted alkyl is not substituted with a hydroxy group.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(═O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—$CH_3$, —CH—CH—$CH_2$—OH, —$CH_2$—CH═N—$OCH_3$, —CH—CH—N($CH_3$)—$CH_3$, and —$CH_2$—CH═CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-CH ($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

Throughout this disclosure, various aspects of the disclosure may be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

The disclosure includes a compound of formula (I), or a composition containing the same, or a salt, solvate, racemate (if applicable), enantiomer (if applicable), and/or tautomer (if applicable) thereof:

$$\text{BINDER-X—}(Z_1)_{m1}\text{—Y—}(Z_2)_{m2}\text{-L} \quad \text{(I)},$$

wherein:

BINDER is selected from the group consisting of:

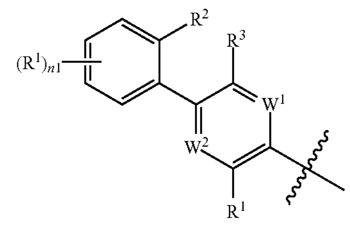

and

-continued

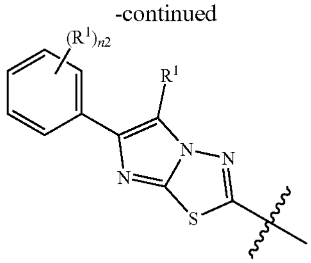

;

wherein:

$R^2$ and $R^3$ are each independently $R^1$, or $R^2$ and $R^3$ combine to form —O—, —S—, —NH—, or —N($C_1$-$C_6$ alkyl)-;

$W^1$ is C($R^1$) or N;

$W^2$ is C($R^1$) or N;

each occurrence of $R^1$ is independently selected from the group consisting of H, $C_1$-$C_6$ alkyl, $C_1$-$C_6$ haloalkyl, $C_1$-$C_6$ alkoxy, $C_1$-$C_6$ haloalkoxy, fluoro, chloro, bromo, iodo, cyano, nitro, —N(R')(R'), —C(=O)OR', and —C(=O)NR'R', wherein each occurrence of R' is independently H or $C_1$-$C_6$ alkyl;

n1 is an integer selected from the group consisting of 0, 1, 2, 3, and 4;

n2 is an integer selected from the group consisting of 0, 1, 2, 3, 4, and 5;

X is selected from the group consisting of a chemical bond, —$(CH_2)_{1-5}$, —$(CH_2CH_2O)_{1-5}$, —$(OCH_2CH_2)_{1-5}$, —NHS(=O)$_2$—*, —S(=O)$_2$NH—*, —OC(=O)NH—*, and —NHC(=O)O—*, wherein the bond marked with * is formed with Y;

Y is selected from the group consisting of a chemical bond, *—OC(=O)—, and *—C(=O)O—, wherein the bond marked with * is formed with X;

each occurrence of $Z_1$ is independently selected from the group consisting of bond, —$CH_2$—, —$OCH_2CH_2$—, and —$CH_2CH_2O$—;

each occurrence of $Z_2$ is independently selected from the group consisting of bond, —$CH_2$—, —$OCH_2CH_2$—, and —$CH_2CH_2O$—;

m1 is an integer selected from the group consisting of 1-10;

m2 is an integer selected from the group consisting of 1-10;

with the proviso that X—$(Z_1)_{m1}$—Y—$(Z_2)_{m2}$-L does not comprise a O—O bond;

L is a group selected from the group consisting of:

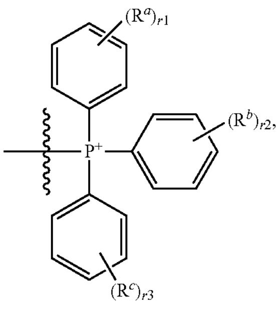

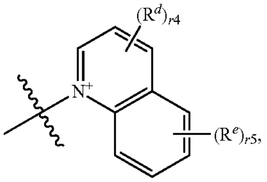

-continued

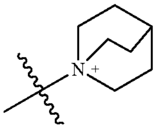,

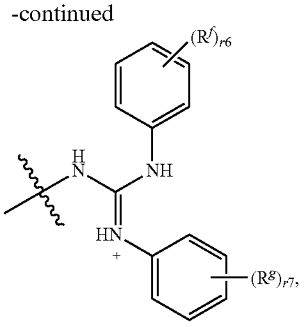

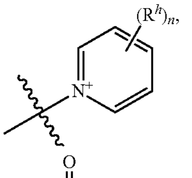 and

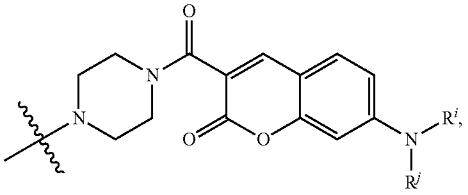

wherein:

each occurrence of $R^a$, $R^b$, $R^c$, $R^d$, $R^e$, $R^f$, $R^g$, and $R^h$ is independently selected from the group consisting of H, $C_1$-$C_6$ alkyl, $C_1$-$C_6$ haloalkyl, $C_1$-$C_6$ alkoxy, $C_1$-$C_6$ haloalkoxy, fluoro, chloro, bromo, iodo, cyano, nitro, —N(R")(R"), —C(═O)OR", and —C(═O)NR"R", wherein each occurrence of R" is independently H or $C_1$-$C_6$ alkyl;

$R^i$ and $R^j$ are independently H or optionally substituted $C_1$-$C_6$ alkyl;

each occurrence of r1, r2, r3, r6, and r7 is independently an integer selected from the group consisting of 1-5;

each occurrence of r4 is an integer selected from the group consisting of 1-3; and each occurrence of r5 is an integer selected from the group consisting of 1-4;

In certain embodiments, the BINDER is selected from the group consisting of:

(Ia)

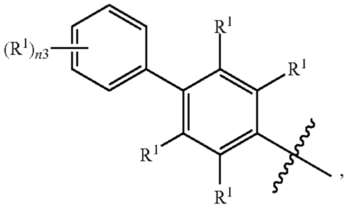

(Ib)

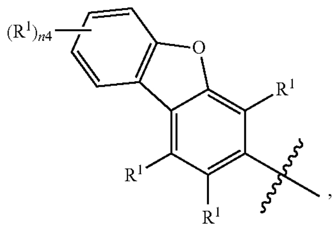

-continued (Ic)

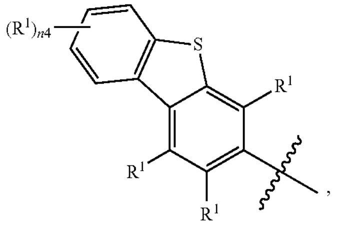

(Id)

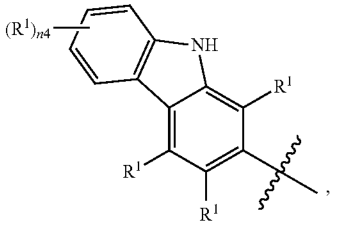

(Ie)

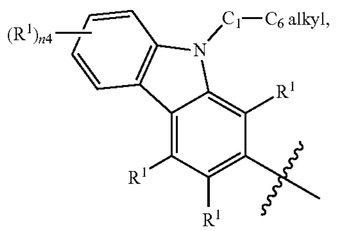 and (If)

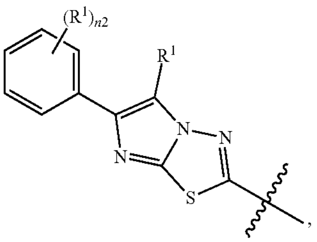

wherein n3 is selected from the group consisting of 0, 1, 2, 3, 4, and 5; and n4 is selected from the group consisting of 0, 1, 2, 3, and 4.

In certain embodiments, m1 is 1. In other embodiments, m1 is 2. In yet other embodiments, m1 is 3. In yet other embodiments, m1 is 4. In yet other embodiments, m1 is 5. In yet other embodiments, m1 is 6. In yet other embodiments, m1 is 7. In yet other embodiments, m1 is 8. In yet other embodiments, m1 is 9. In yet other embodiments, m1 is 10.

In certain embodiments, m2 is 1. In other embodiments, m2 is 2. In yet other embodiments, m2 is 3. In yet other embodiments, m2 is 4. In yet other embodiments, m2 is 5. In yet other embodiments, m2 is 6. In yet other embodiments, m2 is 7. In yet other embodiments, m2 is 8. In yet other embodiments, m2 is 9. In yet other embodiments, m2 is 10.

In certain embodiments, L is
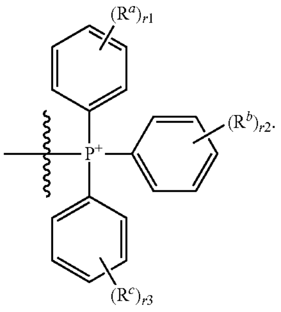
In other embodiments, L is
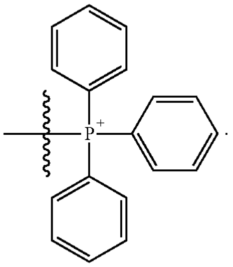
In certain embodiments, L is
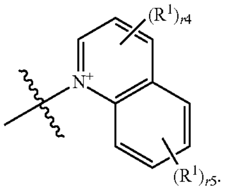
In other embodiments, L is
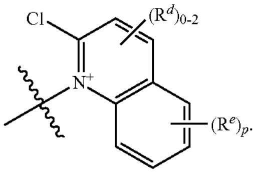
In yet other embodiments, L is
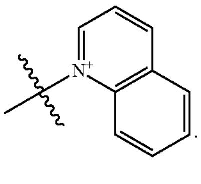 [SMILES: *[n+]1cccc2ccccc21]
In yet other embodiments, L is
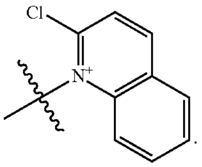 [SMILES: *[n+]1c(Cl)ccc2ccccc21]
In certain embodiments, L is
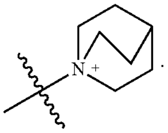
In certain embodiments, L is
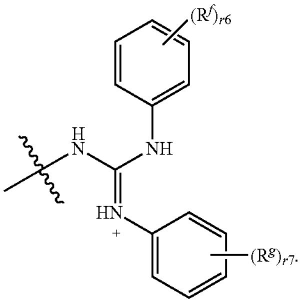
In other embodiments, L is
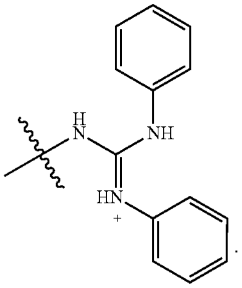 [SMILES: *N/C(=N/c1ccccc1)Nc1ccccc1]
In certain embodiments, L is
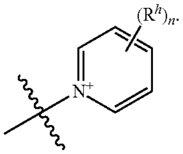

In other embodiments, L is
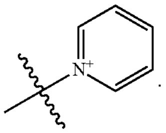 [SMILES: *[n+]1ccccc1]
In certain embodiments, L is
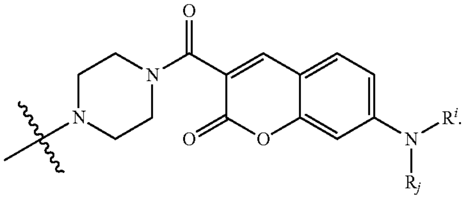
In other embodiments, L is
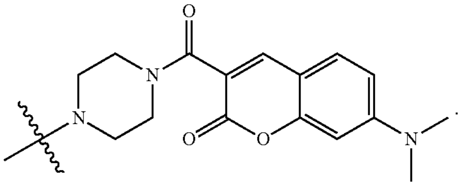 [SMILES: *N1CCN(C(=O)c2cc3ccc(N(C)C)cc3oc2=O)CC1]
In yet other embodiments, L is
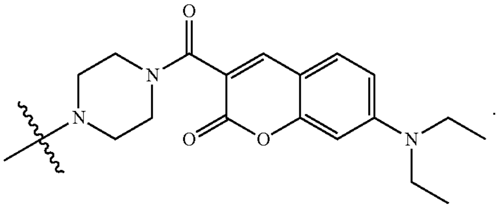 [SMILES: *N1CCN(C(=O)c2cc3ccc(N(CC)CC)cc3oc2=O)CC1]
In certain embodiments, the compound is selected from the group consisting of:
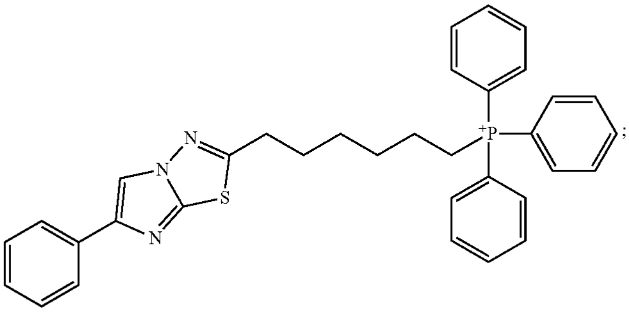
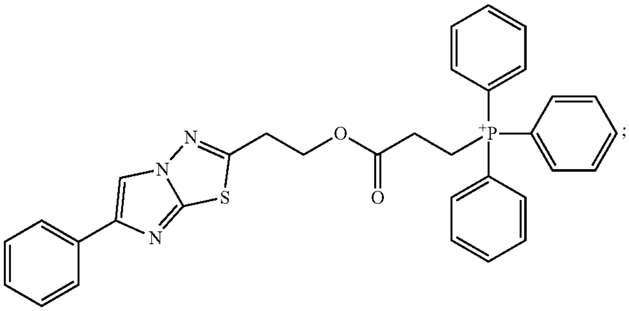
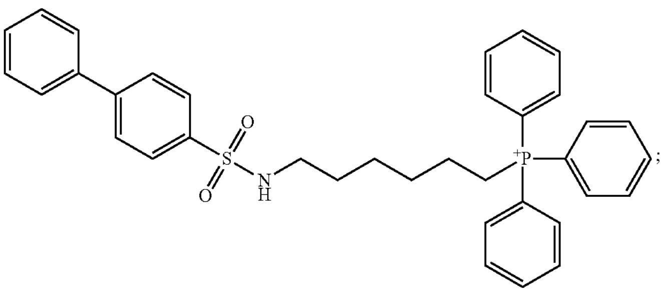

-continued
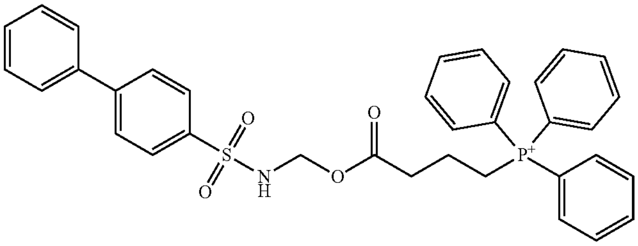
;
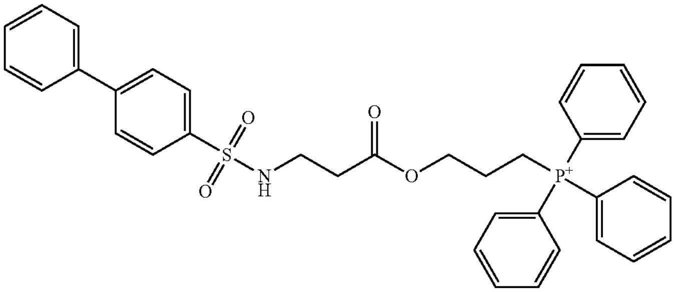
;
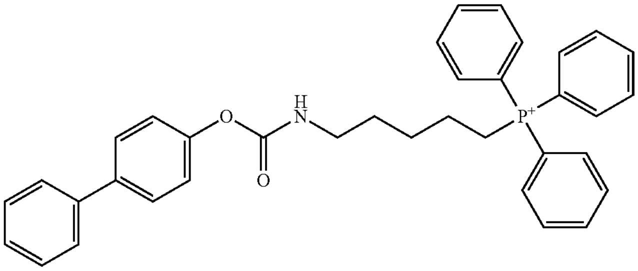
;
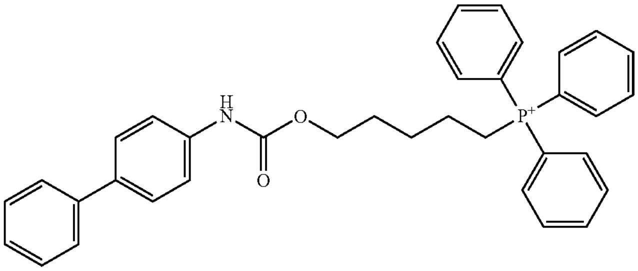
;
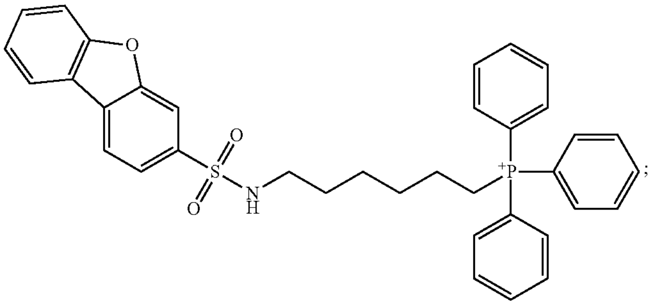
;
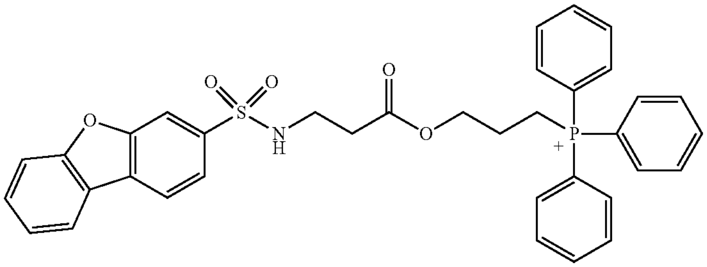
;

-continued
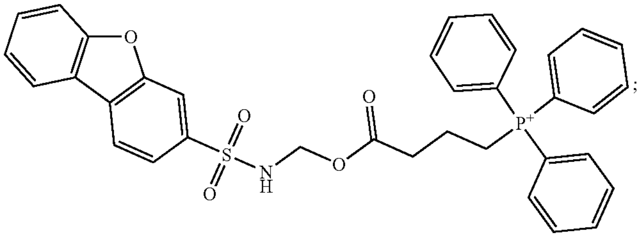
;
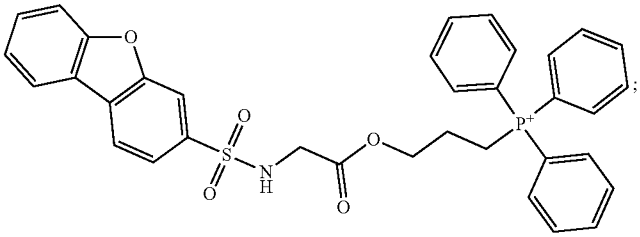
;
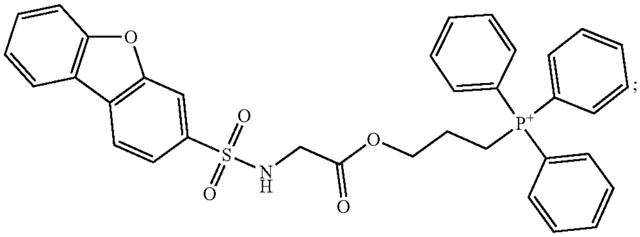
;
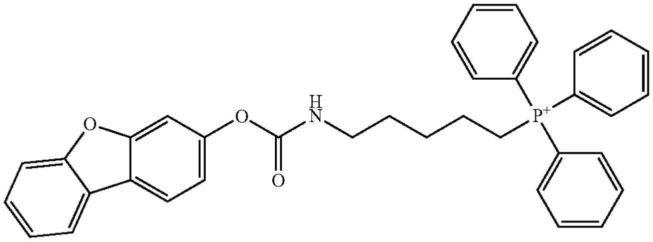
;
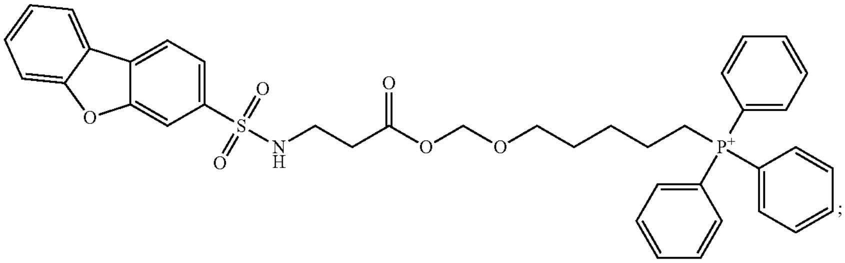
;
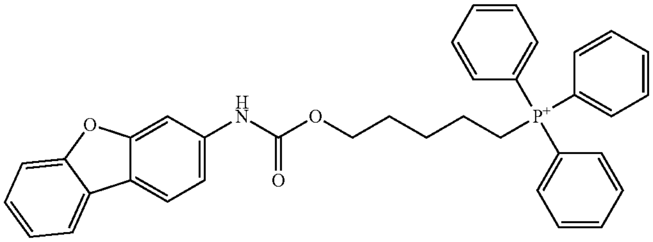
;

-continued

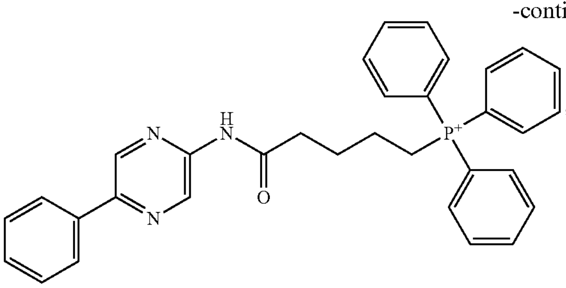

;

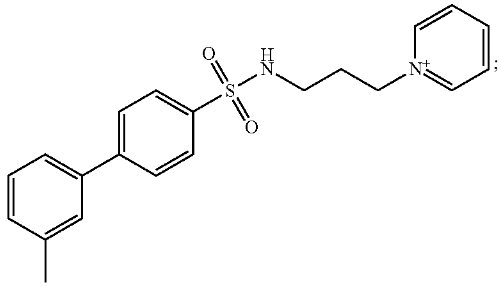

;

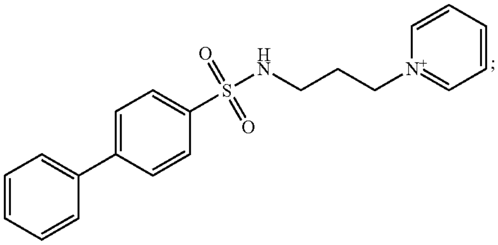

;

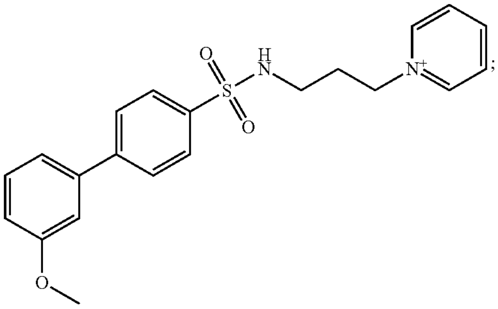

;

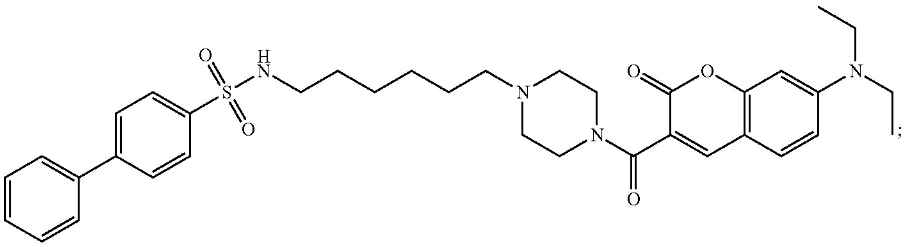

; and

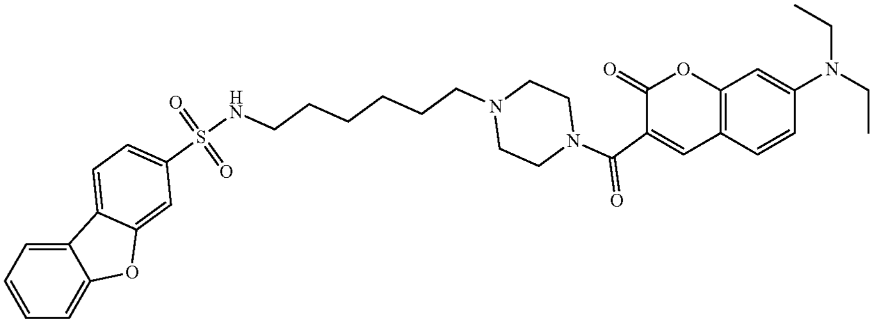 [SMILES: CCN(CC)c1ccc2cc(C(=O)N3CCN(CCCCCCNS(=O)(=O)c4ccc5c(c4)oc4ccccc45)CC3)c(=O)oc2c1]

.

In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography. All possible stereochemical configurations of a given compound containing chiral center(s) are contemplated. All possible mixtures enriched with a particular enantiomer or diastereoisomer(s) are contemplated. All pure individual enantiomers or diastereoisomers are contemplated.

The methods and formulations described herein include the use of N-oxides (if appropriate), crystalline forms (also known as polymorphs), solvates, amorphous phases, and/or pharmaceutically acceptable salts of compounds having the structure of any compound of the disclosure, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the disclosure may exist as tautomers. "Tautomerization" is a form of isomerization involving the migration of a proton accompanied by changes in bond order, often the interchange of a single bond with an adjacent double bond. Where tautomerization is possible, (e.g., in solution), a chemical equilibrium of tautomers can be reached. One well known example of tautomerization is between a ketone and its corresponding enol. Heterocycles may form tautomers such as the interconversion of pyrrolidinone and hydroxypyrrole. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the disclosure is susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Compounds of the disclosure can in certain embodiments form acids or bases. In certain embodiments, the disclosure contemplates acid addition salts. In other embodiments, the disclosure contemplates base addition salts. In yet other embodiments, the disclosure contemplates pharmaceutically acceptable acid addition salts. In yet other embodiments, the disclosure contemplates pharmaceutically acceptable base addition salts. Pharmaceutically acceptable salts refer to salts of those bases or acids that are not toxic or otherwise biologically undesirable.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the disclosure include, for example, metallic salts including alkali metal, alkaline earth metal and transition metal salts such as, for example, calcium, magnesium, potassium, sodium, lithium and copper, iron and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

Protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Combination Therapies

In certain embodiments, the compounds of the disclosure are useful in the methods of the disclosure in combination with at least one additional agent useful for treating or preventing a disease or disorder contemplated herein. This additional agent can comprise compounds identified herein or compounds, e.g., commercially available compounds, known to treat, prevent or reduce the symptoms of the disease or disorder contemplated herein.

In certain embodiments, the at least one additional agent is a genotoxic agent. In certain embodiments, the at least one additional agent is a chemotherapeutic agent. In some embodiments, the at least one additional agent is an anti-cancer agent. In certain embodiments, the at least one additional agent is radiation. In certain embodiments, the at least one additional agent is a HSP90 inhibitor. In certain embodiments, the at least one additional agent is a BRAF inhibitor, such as but not limited to sorafenib or vemurafenib. In certain embodiments, the at least one additional agent is a MEK inhibitor, such as but not limited to Trametinib or binimetinib. In certain embodiments, the at least one additional agent is an immune checkpoint blockade inhibitor.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the compounds of the disclosure in prevention of the occurrence of tumor in the first place. The term "anti-tumor agent" or "anti-cancer agent" as used herein, refers to an agent that has an "anti-tumor effect."

The term "genotoxic agent" as used herein refers to a chemical compound, environmental agent, and/or external stimulation that is damaging to DNA. In certain embodiments, the genotoxic agent causes mutations in DNA. In certain embodiments, the genotoxic agent treats preferentially kills cancer over healthy cells of a patient. In certain embodiments, the genotoxic agent enhances the effectiveness of a compound described herein.

In certain embodiments, the anti-cancer agent includes an HSP90 inhibitor. Examples of HSP90 inhibitors that can be utilized as described herein include, without limitation, a geldanamycin (GA)-derived mitochondrial matrix inhibitor, Gamintrinib, Gamitrinib-G4, Gamitrinib-G3, Gamitrinib-G2, Gamitrinib-G1, Gamitrinib-TPP Gamitrinib-TPP-OH, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090. See the HSP90 inhibitors described in International Patent Publication No. WO 2013/123151, which is incorporated by reference herein.

In certain embodiments, the anti-cancer agent is a BRAF inhibitor. Examples of BRAF inhibitor that can be utilized as described herein include, without limitation, sorafenib, vemurafenib, dabrafenib, RAF-265, XL281, BMS-908662, LGX818, PLX3603, PLX4720, and RO5185426.

In certain embodiments, the anti-cancer agent is a MEK inhibitor. Examples of MEK inhibitor that can be utilized as described herein include, without limitation, Trametinib, Binimetinib, 5-((4-bromo-2-fluorophenyl)amino)-4-fluoro-N-(2-hydroxyethoxy)-1-methyl-1H-benzo[d]imidazole-6-carboxamide (MEK162), and N-[(2R)-2,3-Dihydroxy-propoxy]-3,4-difluoro-2-[(2-fluoro-4-iodophenyl)amino]-benzamide (PD0325901).

In certain embodiments, the anti-cancer agent is an immune checkpoint blockade inhibitor. Examples of immune checkpoint blockade inhibitors that can be utilized as described herein include, without limitation, an anti-PD1, PDL1, or CTLA4 immune checkpoint blockade inhibitor. In certain embodiments, the immune checkpoint blockade inhibitor is ipilimumab.

In certain embodiments, the chemotherapeutic is selected from the group consisting of cisplatin, carboplatin, 5-fluorouracil, cyclophosphamide, oncovin, vincristine, prednisone, or rituximab, mechlorethamine, cyclophosphamide, ifosfamide, melphalan, chlorambucil, carmustine, lomustine, semustine, thriethylenemelamine, triethylene thiophosphoramide, hexamethylmelamine altretamine, busulfan, triazines dacarbazine, methotrexate, trimetrexate, fluorodeoxyuridine, gemcitabine, cytosine arabinoside, 5-azacytidine, 2,2'-difluorodeoxycytidine, 6-mercaptopurine, azathioprine, 2'-deoxycoformycin, erythrohydroxynonyladenine, fludarabine phosphate, 2-chlorodeoxyadenosine, camptothecin, topotecan, irinotecan, paclitaxel, vinblastine, vincristine, vinorelbine, docetaxel, estramustine, estramustine phosphate, etoposide, teniposide, mitoxantrone, mitotane, and aminoglutethimide.

In certain embodiments, the at least one additional agent is selected from the group consisting of dabrafenib, vemurafenib, cobimetinib, trametinib, ipilimumab, nivolumab, and pembrolizumab.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Methods

The disclosure provides a method of treating, ameliorating, and/or preventing a cancer in a subject in need thereof. In another aspect, the disclosure provides a method of treating, ameliorating, and/or preventing a HSP70 mediated disease, disorder or condition in a subject in need thereof. In another aspect, the disclosure provides a method of increasing immune cell infiltration or immune cell recruitment to a tumor in a subject in need thereof.

In certain embodiments, the method comprises administering to the subject a therapeutically effective amount of at least one compound of the disclosure. In other embodiments, the at least one compound of the disclosure is administered as a pharmaceutical composition comprising at least one pharmaceutically acceptable carrier. In other embodiments, the at least one compound of the disclosure is the only therapeutically effective agent administered to the subject. In yet other embodiments, the at least one compound of the disclosure is the only therapeutically effective agent administered to the subject in an amount that treats, ameliorates, and/or prevents the cancer in the subject.

In another aspect, the disclosure provides a method of inhibiting HSP70 in a cell. In another aspect, the disclosure provides a method of inhibiting mitochondrial function or activity in a cell. In yet another aspect, the disclosure provides a method of inhibiting proteostasis in a cell. In some embodiments, the cell is a cancer or tumor cell. In still another aspect, the disclosure provides a method of inhibiting proliferation of a cancer or tumor cell. In certain embodiments, the method comprises contacting the cell with an effective amount of at least one compound of the disclosure.

In certain embodiments, the cancer is at least one selected from the group consisting of epithelial cancer, Merkel cell carcinoma, liver cancer, cervical cancer, anal cancer, penile cancer, vulvar cancer, vaginal cancer, breast cancer, ovarian cancer, uterine cancer, skin cancer, melanoma, oral cancer, colon cancer, colorectal cancer (CRC), neck cancer, head cancer, eye cancer, Kaposi's sarcoma, leukemia, nasopharyngeal carcinoma, mesothelioma, bone cancer, brain cancer, prostate cancer, testicular cancer, pancreatic cancer, hepatocellular carcinoma, lung cancer, and lymphoma. In some embodiments, the cancer is identified as overexpressing HSP70. In certain embodiments, the cancer is colorectal cancer (CRC).

In certain embodiments, the subject is a mammal. In other embodiments, the mammal is human.

In some embodiments, the subject is identified as having a cancer that has increased level of HSP70 relative to a reference level. In some embodiments, the reference level is the level of HSP70 in healthy tissue. In some embodiments, the method of treatment comprises measuring the level of HSP70 in a sample comprising a cancer cell from the subject, and administering a therapeutically effective amount of at least one compound of the disclosure to the subject if the level of HSP70 is increased relative to a reference level or a control. A person of skill in the art will appreciate that a variety of methods of measuring the level of HSP70 and controls are possible. For example, levels of HSP70 expression can be measured by measuring levels of HSP70 polynucleotide (e.g., mRNA) or HSP70 protein in the sample using methods known in the art. The reference level or control can be, by way of non-limiting example, a predetermined reference or may be a level of HSP70 measured in non-cancer tissue (e.g., healthy tissue).

In yet other embodiments, the at least one compound is administered by an administration route selected from the group consisting of inhalational, oral, rectal, vaginal, parenteral, intracranial, topical, transdermal, pulmonary, intranasal, buccal, ophthalmic, intrathecal, and intravenous.

In certain embodiments, the subject is further administered at least one additional agent that treats the disease and/or disorder. In other embodiments, the compound and the at least one additional agent are co-administered. In yet other embodiments, the compound and the at least one additional agent are co-formulated.

Method of Screening Compounds as HSP70 Inhibitors

In one aspect, the disclosure provides a method of identifying a compound that inhibits HSP70. In certain embodiments, the method comprises contacting a putative inhibitor compound with (i) a HSP70 or a catalytically active fragment thereof and (ii) ATP, thus forming a composition. In other embodiments, the method comprises measuring HSP70 ATPase activity in the composition. In some embodiments, the composition does not contain HSP40. In yet other embodiments, the method comprises comparing the HSP70 ATPase activity in the composition to a reference level; thereby identifying the putative inhibitor compound as a compound that inhibits HSP70. In some embodiments, the putative inhibitor compound is identified as a compound that inhibits HSP70 is the HSP70 ATPase activity in the composition is decreased relative to a reference level.

In some embodiments, the HSP70 ATPase activity in the composition is measured by measuring level of ADP in the composition. In some embodiments, the level of ADP is measured using a TRANSCREENER® ADP-FI assay. In some embodiments, the level of ADP is compared to a reference level of ADP. In some embodiments, the reference level of ADP is the level of ADP of the composition without HSP70. In some embodiments, the putative inhibitor compound is identified as a compound that inhibits HSP70 if the level of ADP in the composition is decreased relative to a reference level (e.g., the level of ADP of the composition with HSP70 and without any HSP70 inhibitor).

In some embodiments, the HSP70 is human HSP70. In some embodiments, the HSP70 is purified HSP70. In some embodiments, the composition does not comprise HSP40.

In certain embodiments, the method is practiced as a high-throughput screen by which a plurality of compounds (putative inhibitors) are contacted with HSP70 and ATP, and inhibitors are identified from among the plurality of compounds by comparing their individual activities to a reference level. In some embodiments, the reference level is the activity of HSP70 in the absence of an HSP70 inhibitor.

A person of skill in the art will recognize that activity can be measured by combining the substrate (ATP) and HSP70 or any catalytically active fragment thereof, i.e. the ATP binding domain of HSP70 or an active fragment thereof. A person of skill in the art will appreciate that a variety of methods of measuring HSP70 ATPase activity and reference levels or controls are possible and will be familiar with the same by analogy to activity assays. The reference level or control can be, by way of non-limiting example, a predetermined reference or may be a reaction performed without a HSP70 inhibitor.

Kits

The disclosure includes a kit comprising at least one compound of the disclosure, optionally an applicator, and instructional material for use thereof.

The instructional material included in the kit comprises instructions for preventing or treating a HSP70 modulated disease (e.g., cancer) in a subject. The instructional material recites the amount of, and frequency with which, the compound should be administered to the mammal. In certain embodiments, the kit further comprises at least one additional agent that prevents or treats an HSP70 modulated disease (e.g., cancer) in a subject. In other embodiments, the kit further comprises at least one additional anti-cancer agent.

Administration/Dosage/Formulations

The disclosure also encompasses pharmaceutical compositions and methods of their use. These pharmaceutical compositions may comprise an active ingredient (which can be one or more compounds of the disclosure, or pharmaceutically acceptable salts thereof) optionally in combination with one or more pharmaceutically acceptable agents. The compositions set forth herein can be used alone or in combination with additional compounds to produce additive, complementary, or synergistic effects.

The regimen of administration may affect what constitutes an effective amount. The therapeutic formulations may be administered to the subject either prior to or after the onset of a disease or disorder contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, preferably a mammal, more preferably a human, may be carried out using known procedures, at dosages and for periods of time effective to treat a disease or disorder contemplated herein. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated herein. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect, and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated herein.

In certain embodiments, the compositions of the disclosure are formulated using one or more pharmaceutically acceptable excipients or carriers. In certain embodiments, the pharmaceutical compositions of the disclosure comprise a therapeutically effective amount of a compound of the disclosure and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

In certain embodiments, the compositions of the disclosure are administered to the patient in dosages that range from one to five times per day or more. In other embodiments, the compositions of the disclosure are administered to the patient in range of dosages that include, but are not limited to, once every day, every two, days, every three days to once a week, and once every two weeks. It is readily apparent to one skilled in the art that the frequency of administration of the various combination compositions of the disclosure varies from individual to individual depending on many factors including, but not limited to, age, disease or disorder to be treated, gender, overall health, and other factors. Thus, the disclosure should not be construed to be limited to any particular dosage regime and the precise dosage and composition to be administered to any patient is determined by the attending physical taking all other factors about the patient into account.

Compounds of the disclosure for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In certain embodiments, the dose of a compound of the disclosure is from about 1 mg and about 2,500 mg. In other embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in other embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of a disease or disorder contemplated herein.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the disclosure include oral, nasal, rectal, intravaginal, parenteral, buccal, sublingual or topical. The compounds for use in the disclosure may be formulated for administration by any suitable route, such as for oral or parenteral, for example, transdermal, transmucosal (e.g., sublingual, lingual, (trans) buccal, (trans) urethral, vaginal (e.g., trans- and perivaginally), (intra) nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the disclosure may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY—P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present disclosure also includes a multi-layer tablet comprising a layer providing for the delayed release of one or more compounds of the disclosure, and a further layer providing for the immediate release of a medication for treatment of diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the disclosure may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 20030147952; 20030104062; 20030104053; 20030044466; 20030039688; and 20020051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the disclosure may be administered in the form of microparticles, for example, by injection or in the form of wafers or discs by implantation.

In certain embodiments, the compounds of the disclosure are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present disclosure depends on the age, sex and weight of the patient, the current medical condition of the patient and the progression of a disease or disorder contemplated herein in the patient being treated. The skilled artisan is able to determine appropriate dosages depending on these and other factors.

A suitable dose of a compound of the present disclosure may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the disclosure is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the disclosure may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents are considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

EXPERIMENTAL EXAMPLES

The disclosure is now described with reference to the following Examples. These Examples are provided for the purpose of illustration only and the disclosure should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, point out specific embodiments of the present disclosure, and are not to be construed as limiting in any way the remainder of the disclosure.

The materials and methods employed in these experiments are now described.

Cell Lines and Culture Conditions

HT-29 and SW620 colorectal cancer (CRC) cell lines, and the non-transformed CCD 841 CoN cell line, were obtained from the Fox Chase Cancer Center Cell Culture Facility (Philadelphia, PA, USA). RKO cells were a gift from Margie Clapper (Fox Chase Cancer Center). HCT116+/−p53 CRC cell lines were provided by Bert Vogelstein (Johns Hopkins School of Medicine). CT26 and LS411N cells were purchased from the ATCC. MC38 cells were provided by Dmitry Gabrilovich (Wistar Institute) or I. Turkova (University of Pittsburgh, Pittsburgh, PA). IMR90, 1205Lu, WM983B, and WM4265 cells were provided by Meenhard Herlyn and Qing Chen (Wistar Institute, Philadelphia, PA). Cells were grown in their respective media as advised by the ATCC; all media was supplemented with 10% Fetal Bovine Serum (Hyclone™, GE Healthcare Life Sciences) and 1% penicillin/streptomycin (Corning Cellgro™). Cells were grown in a 5% $CO_2$ humidified incubator at 37° C. Cell lines were authenticated using short tandem repeat (STR) profiling (ATCC) and were tested for mycoplasma every 6 months.

Antibodies, Reagents, Western Blot and IHC Analysis

Antibodies used were purchased from: p53 (Ab-6) (DO-1, Millipore Sigma), p53 (1C12) (2524S), Cleaved Caspase 3 (9661S), Cleaved Lamin A (2035S), HSP90 (4877S), EGFR (4267S), HMGB1 (6893S), HSP70 (4873S), AKT (9272S), and GAPDH (2218S) (Cell Signaling, Danvers, MA, USA), MRPS14 (ab151118) (Abcam, Cambridge, MA, USA), NDUFA6 (GTX65550) (GeneTex, Irvine, CA, USA), BAK (H-211, sc-7873; Santa Cruz Biotechnology, Inc., Dallas, TX, USA), and HSP70 (C92F3A-5) (Enzo Life Sciences, Farmingdale, NY, USA). 17-AAG (Item No. 11039) and Metformin (Item No. 13118) were purchased from Cayman Chemical (Ann Arbor, MI, USA). Gamitrinib (G-TPP, HY-102007A) was purchased from MedChemExpress (Monmouth Junction, NJ, USA). All HSP70 inhibitors used were generated and confirmed by NMR. PLX-4720 was purchased from Chemietek (Catalog No. CT-P4720; Indianapolis, IN, USA). For in vitro studies, AP-4-139B was dissolved in DMSO. For in vivo studies AP-4-139B was made as a stock solution of 100 mg/mL in DMSO and diluted to 2 mg/mL in 0.9% saline solution (Sigma Aldrich, S8776). Western blot analysis and IHC were performed. The following antibodies were used for IHC: CD8 (4SM15) and CD4 (4SM95, Thermo Fisher Scientific), Cleaved Lamin A (2035S), COXIV (4850S), α-Smooth Muscle Actin (19245T) and Ki67 (9449S, Cell Signaling Technologies), p53 FL-393 (sc-6243 rabbit) (Santa Cruz Biotechnology, Inc.), NDUFA6 (GTX65550) (GeneTex), and Granzyme B (ab4059, Abcam). All secondary antibodies used for IHC were purchased from Vector Laboratories (Burlingame, CA, USA).

Identification of Biotin-AP-4-139B Interacting Proteins

H1299 human lung carcinoma cells were treated with 10 μM Biotin or the biotin-labeled variant of AP-4-139B (Biotin-AP-4-139B; BAP-4-139B) for 5 hours. Cells were harvested and centrifuged at 500 g for 5 minutes at 4° C., and the cell pellets were resuspended in 1×DPBS (Thermo Fisher Scientific catalogue number 14190144) supplemented with 0.5% IGEPAL CA-630 and protease inhibitors at 4° C. Cell disruption was performed by passing the cells through a 23-gauge needle, and the homogenates were gently rocked at 4° C. for 30 minutes. The homogenates were spun at 11,000 g for 10 minutes at 4° C. The supernatants were removed and spun at 11,000 g for 10 minutes at 4° C. twice. After adding 100 μL of pre-washed NeutrAvidin Resin (Thermo Fisher Scientific catalogue number 29202) to 15 mg of whole cell extracts (WCE), the mixtures were gently rocked at 4° C. for 1 hour. The Biotin-AP-4-139B-immunocomplex-NeutrAvidin Resin was washed five times using the 1×DPBS (Thermo Fisher Scientific #14190144) supplemented with 0.5% IGEPAL CA-630 and protease inhibitors at 4° C. The captured Biotin-AP-4-139B-immunocomplexes bound to the NeutrAvidin Resin were treated with 50 mM DTT, which cleaves the disulfide bond in the spacer arm of the biotin label. The associated proteins in the eluates were resolved by SDS-PAGE in a 4%-20% gradient gel (Thermo Fisher Scientific catalogue number XP04200BOX) and visualized by Coomassie staining (Bio-Rad catalogue number 1610786). The Coomassie-stained band of ~70 kDa was excised from the gel and subjected to trypsin digestion, and the resulting peptides were analyzed by liquid chromatography-tandem mass spectrometry.

HSP70 Competition Assays

For the competition experiments, H1299 cells were pretreated with 10 UM of VY-3-277, PET-16 or AP-4-139B for 1 hour prior to the addition of 10 μM Biotin-AP-4-139B for 5 hours. Protein extracts were prepared as described elsewhere herein. After adding 25 μL of pre-washed NeutrAvidin Resin (Thermo Fisher Scientific catalog number 29202) to 5 mg of WCE, the mixtures were incubated at 4° C. for 1 hour on a rocker. The Biotin-AP-4-139B-immunocomplex-NeutrAvidin Resin were washed as described above, and the protein samples were size fractionated on Novex 4-20% Tris-Glycine Mini Gels (Thermo Fisher Scientific catalog number XP04200BOX) at room temperature and subsequently transferred overnight onto Immuno-Blot PVDF membranes (BioRad catalog number 1620177) at 4° C. The membranes were blocked with 3% nonfat dry milk (BioRad catalog number 1706404) in 1×PBST for 30 minutes at room temperature and incubated with antibody to GRP75 (Cell Signaling Technology catalog number 3593) or HSP70 (Enzo Life Sciences catalog number ADI-SPA-812) overnight with rotation at 4° C. After washing the blots in 1×PBST, the membranes were incubated with Donkey anti-Rabbit (Jackson ImmunoResearch 711-036-152) for 2 hours at room temperature. Membrane-immobilized protein detection was carried out using ECL Western Blotting Detection Reagents (GE Healthcare catalog number RPN2106; Millipore Sigma catalog number GERPN2106).

HSP70 Mediated ATPase Assay and Cell Viability Assays

HSP70 mediated ATPase activity was measured using the Transcreener® ADP-FI assay (BellBrook Labs). Five μL of 30 nM full length human HSP70 in assay buffer (25 mM HEPES-KOH, pH 7.2, 100 mM KOAc, 10 mM MgOAc, 5 mM DTT, 0.05% CHAPS) was dispensed into a black, small volume 384-well plate. Test compounds were diluted in 100% DMSO and 0.1 μL were added to the assay using the Janus Nanohead, resulting in a final DMSP concentration of 1% for all wells. After a 30 minute pre-incubation with test compound, 5 μL of 6 μM ATP in assay buffer was added to each well. After 15 minutes, the reactions were stopped by adding 10 μL of stop buffer containing the recommended concentrations of ADP-FI tracer and IR-dye conjugated ADP antibody. After 30 minutes, fluorescence at 560/620 nm was measured using the Envision plate reader. Data were normalized to % inhibition, where 100% is the counts in the absence of HSP70, and 0% is the counts in the presence of HSP70. Cell viability assays were performed. For synergy assays, cells were plated in 50 μL of complete media at 500 cells per well in 384 well plates. Serial dilutions of AP-4-139B and PLX4720 at 1000× final concentration in 100% DMSO were prepared as follows. For AP-4-139B, 12×1:1.57 serial dilutions from 0 to 50 mM in duplicate plated across an entire 384 well plate. For PLX4720, 16×1:2 serial dilutions from 0 to 20 mM plated down an entire 384 well plate. After the cells had incubated for 18-24 hrs at 37 C, 50 nL from both 384 well plates were transferred to the cell culture plate using the Janus MDT Nanohead. As a result, each cell plate received all concentrations of both compounds in a matrix format and the final concentration of DMSO in the cell culture plate was 0.2%. Four replicate plates were prepared for each cell line. After 72 hr, the media was removed and 20 μL of Cell Titer Glo reagent was added to each well and the resulting luminescence was measured on the Envision plate reader. For in vitro drug combination experiments, interaction indexes were calculated to determine the synergistic effect.

Small Molecule Binding to HSP70 Using SPR

SPR experiments were conducted using the Biacore T200. Approximately 20,000 RU of N-terminal HIS tagged HSP70 was immobilized on a multi-dentate NTA derivatized linear carboxylate sensor chip (NICH1500M, Xantec Bioanalytics). The running buffer was PBS containing 2 mM MgCl2, 0.05% Tween, and 5% DMSO. Test compounds were diluted at 20× final concentration in 100% DMSO and then diluted into running buffer without DMSO so that the DMSO concentrations in both the sample and the running buffer were similar. Flow rate was 30 μL/min, contact time for each sample concentration was 30 seconds, followed by a 60 second dissociation time. Data were analyzed using the Biacore evaluation software and the resulting sensograms exported and re-plotted in GraphPad Prism.

Proteomics

1205Lu cells treated with vehicle control and AP-4-139B (1 μM) were cultured in light and heavy complete media (Silantes) respectively for 6 passages. Cells from light and heavy media were mixed at a ratio of 1:1 and collected for mitochondrial isolation. Mitochondria were isolated using the Thermo Fisher's Mitochondria isolation kit (#89874) using Dounce homogenization. Following mitochondria isolation, 30 μg of protein was isolated and subjected to analysis for mitochondrial client proteins. SILAC samples (12 μg per sample) were run into a NuPAGE 10% Bis-Tris gel (Thermo Fisher Scientific), and the entire gel lanes were excised and digested with trypsin. Liquid chromatography tandem mass spectrometry (LC-MS/MS) analysis was performed using a Q Exactive HF mass spectrometer (ThermoFisher Scientific) coupled with a Nano-ACQUITY UPLC system (Waters). Samples were injected onto a UPLC Symmetry trap column (180 μm i.d.×2 cm packed with 5 μm C18 resin; Waters), and peptides were separated by reversed phase HPLC on a BEH C18 nanocapillary analytical column (75 μm i.d.×25 cm, 1.7 μm particle size; Waters) using a 4-h gradient formed by solvent A (0.1% formic acid in water) and solvent B (0.1% formic acid in acetonitrile). Eluted peptides were analyzed by the mass spectrometer set to repetitively scan m/z from 400 to 2000 in positive ion mode. The full MS scan was collected at 60,000 resolution followed by data-dependent MS/MS scans at 15,000 resolution on the 20 most abundant ions exceeding a minimum threshold of 10,000. Peptide match was set as preferred, exclude isotope option and charge-state screening were enabled to reject unassigned and single charged ions. Peptide sequences were identified using MaxQuant 1.6.2.3. MS/MS spectra were searched against a UniProt human protein database (October 2018) and a common contaminants database using full tryptic specificity with up to two missed cleavages, static carboxamidomethylation of Cys, variable oxidation of Met, and variable protein N-terminal acetylation. Heavy $^{13}C_6$-lysine and $^{13}C_6 15N_4$-arginine were also considered in the search for SILAC samples. Consensus identification lists were generated with false discovery rates set at 1% for protein and peptide identifications. Undetected intensity levels were floored to value of minimum detected intensity across all proteins and sample (min intensity=$10^6$). Raw intensities were log 2-transformed and quantile normalized. Normalized intensities were used for differential expression analysis between two groups by unpaired t-test and nominal p-values were corrected for multiple testing with Benjamini-Hochberg method. FDR<10% results were considered significant unless stated otherwise. Proteins were considered mitochondrial if recorded in MitoCarta 2.0 database.

Mitochondrial Oxygen Consumption Rates (OCR), HMGB1 and ATP Release Assays

The XF Cell Mito Stress Test was performed. Briefly, HT-29 (10,000 cells/well), IMR90 (15,000 cells/well), and 1205Lu (15,000 cells/well) were plated in Seahorse 96-well cell culture microplates, treated with the respective inhibitors for 24 hours, and subjected to the Seahorse XF Cell Mito Stress Test, according to the manufacturer's protocol (Agilent Technologies). For extracellular HMGB1 release, $1\times10^6$ MC38 cells were plated in 10-cm dishes. The next day, cells were treated with the indicated concentrations of AP-4-139B for 8 or 24 hours in serum-free media. Media was collected and spun down at 2,000 rpm for 5 minutes to pellet any remaining cells or debris. Media was then transferred to Amicon Ultra 15, 10K tubes and spun down at 4,000 rpm for 45 minutes, according to the manufacturer's protocol. Concentrated media was then transferred to fresh Eppendorf tubes. Equal amounts of media (15 μL) were combined with equal volumes of 2× Laemmli sample buffer and subjected to Western blot analysis as described above. Western blots were probed for HMGB1 to determine extracellular HGMB1. For extracellular ATP release, ATP was measured using the CellTiter-Glo Kit (Promega catalog #G7570). Briefly, 10-15,000 MC38 cells were seeded in complete growth medium in 24 well plates. The next day, growth medium was replaced with Opti-MEM (ThermoFisher Scientific catalog #31985062), and the cells were then treated with various concentrations of the chemicals, as indicated. DMSO-treated cells were used as controls. At 3 hours, 15 μl of culture media was removed from each well and spun at 15,000 rpm for 2 minutes at 4° C. 10 μl of CellTiter-Glo Reaction Mix was then mixed with 10 μl of culture media; the luminescence signal was detected using a luminometer.

HSP70 Survival and Gene Expression Analysis

Human colorectal adenocarcinoma gene expression (n=512) and patient data (n=570) were downloaded from USCS Xena platform (GDC-TCGA COAD). Samples with available gene expression and overall survival were included in the survival analysis (n=435) and divided into high and low expression groups based on HSPA1A expression levels using mean expression threshold. Significance of difference in survival was tested using log-rank test and visualized by Kaplan-Meier curves generated by "survival" and "ggplot" R packages. For association of stage and expression (n=440), patients were stratified into 4 groups (stage I, II, III, and IV) and significance between group pairs was estimated using Wilcoxon rank sum test. Boxplots showing the median expression for HSPA1A across four stages were generated using ggplot R package. All analyses were completed using RStudio (R version 3.5.1 (2018 Jul. 2)).

Membrane Associated Calreticulin Analysis by Flow Cytometry

Flow cytometry was used to detect calreticulin localization after exposure to Doxorubicin (positive control) or AP-4-139B. MC38 cells were plated at a density of $3\times10^5$ cells per well in 6-well plates. The following day, cells were treated with 1 μM of doxorubicin, 15 μM of AP-4-139B (MC38), or 5 μM of AP-4-139B (CT26). After 24 hours, cells were collected and stained with anti-CRT antibody (ab196158) (Abcam) diluted in a solution of 1% FBS in PBS for 30 minutes on ice in the dark. Cells were then washed with PBS and stained with DAPI (1 μg/mL) for 5 minutes prior to analysis. Samples were analyzed using a FACSCelesta (Becton Dickinson) flow cytometer. Dead cells were removed from analysis using FSC/SSC profiles, and cell doublets were eliminated by comparing forward scatter signal height vs forward scatter signal area. Fluorescent intensity of DAPI negative cells was measured and at least 10,000 events in the analysis gate were obtained.

Pre-Clinical Analyses

All studies were carried out in accordance with the recommendations in the Guide for the Care and Use of Laboratory Animals of the National Institutes of Health (NIH). All protocols were approved by The Wistar Institute Institutional Animal Care and Use Committee (IACUC). Mice were housed in plastic cages with ad libitum diet and maintained with a 12-hour dark/12-hour light cycle at 22° C. For human xenograft studies, $2.5\times10^6$ HT-29 cells were injected subcutaneously into the right flanks of 6-8 week old male NSG (NOD.Cg-Prkdcscid Il2rgtm1 Wjl/SzJ) mice. For mouse xenograft studies, $1\times10^6$ MC38 cells were subcutaneously into the right flanks of 6-8 week old male C57Bl/6J mice. Tumor volumes were measured using digital calipers and tumor volume was calculated using the formula: volume=(length×width$^2$)×0.52. All mice were monitored daily for signs of pain or distress.

Flow Cytometric Immunophenotyping of MC38 Tumors

Tumors were excised, weighed with an electronic scale, minced and digested in 5 mL HBSS containing 1 mg/ml Type 1 Collagenase from *Clostridium histolyticum* (Sigma-Aldrich) for 30 minutes at 37° C. Spleens were crushed with a frosted glass slide to obtain a single cell suspension and red blood cells lysed with eBioscience RBC lysis buffer (Thermo Fisher Scientific) for 3 minutes at room temperature. Cells from tumors and spleens were washed and passed through a 70 μM filter. For the staining, cells were transferred to a 96 well plate, centrifuged at 1500 RPM for 5 minutes at 4° C., washed and incubated with Fc blocking reagent (anti-mouse CD16/CD32, clone 2.4 g2, BD bioscience) for 10 minutes at 4° C. A master mix containing all surface antibodies (CD45: clone 30-F11, BioLegend; CD8b: clone H35-17.2, eBioscience; CD3ε: clone 145-2c11, BioLegend; CD4: clone RM4-5, eBioscience; CD103: clone 2E7, BioLegend; CD11c: clone N418 (Thermo Fisher Scientific); PE anti-mouse I-A/I-E: Clone M5/114.15.2, BioLegend; FITC anti-mouse Ly-6G: clone 1A8, BioLegend; FITC anti-mouse CD19: clone 6D5, BioLegend; LIVE/DEAD, Thermo Fisher Scientific) were incubated for 20 minutes at 4° C. Fixation and intracellular staining were accomplished using the eBioscience Foxp3 fixation and permeabilization kit (Thermo Fisher Scientific) and stained with Foxp3 antibody (Foxp3 PE-Cy7: clone FJK-16s, Thermo Fisher Scientific). Absolute number of cells was obtained with Flow cytometry using 123count eBeads (Thermo Fisher Scientific). FITC was used as DUMP channel for CD19 and Ly6G. The number of tumor-infiltrating immune cells was normalized for mg of tumor tissue. Samples were analyzed using FACSymphony A3 (BD Biosciences) flow cytometer equipped with 5 lasers. Data were analyzed using FlowJo Version 10 and GraphPad Prism software.

Invasion, Metastasis, and Anti-Tumor Vaccination

Matrigel invasion assays were carried out using 24-well Corning® BioCoat™ Matrigel Invasion Chambers with an 8.0 μm PET membrane (#354480). Transwells were first rehydrated with serum free DMEM for 2 hours at 37° C. Then, the lower chamber was inserted into a 24-well filled with 750 μL of DMEM with 20% FBS, and 50,000 MC38 cells in 500 μL DMEM with 1% FBS were placed in the upper chamber in the presence of control (DMSO) or AP-4-139B. Cells were allowed to invade for 24 hours at 37° C. before the Matrigel was removed, inserts fixed with 100% methanol, and stained with 0.5% Crystal Violet. Transwells were imaged for analysis using a Nikon TE2000 Inverted Microscope. Number of invaded cells per field (n=8 random fields of view per transwell) were quantified with ImageJSoftware (NIH), normalized to live cells, and expressed as mean±SEM.

For in vivo metastasis assays, 8-10 week old male C57Bl/6 mice were injected with $4\times10^5$ MC38 cells. Mice were then treated with either vehicle or 10 mg/kg AP-4-

139B every 48 hours for 3 weeks. At the end of the study, mice were euthanized, lungs were harvested and fixed in formalin for analysis of lung tumor nodules by H&E. For anti-tumor vaccination studies, MC38 cells were treated with 10 μM AP-4-139B for 48 h, resulting in approximately 20% cell death (as assessed by Trypan Blue staining). $2\times10^6$ pre-treated MC38 cells or PBS was inoculated subcutaneously into the left flank of 8-10 week old male C57BL/6 mice. Ten days later, mice were challenged on the right flank with $5\times10^5$ live MC38 cells, and tumor growth and incidence were monitored 3 times per week. The absence of tumors was scored as an indication for efficient antitumor vaccination.

Soluble/Insoluble Fractionation

Proteins were extracted from cultured cells using the Lysis Buffer (50 mM Tris-HCl, pH 7.5; 150 mM NaCl; 2 mM EDTA; 1% IGEPAL CA-630; and 0.5% Triton X-100) supplemented with protease inhibitors at 4° C. The homogenates were spun at 11,000 g for 30 minutes at 4° C. The supernatants contained the detergent-soluble fractions. The pellets containing the detergent-insoluble fractions were resuspended using the Lysis Buffer. The detergent-soluble and detergent-insoluble protein samples were size fractionated on Novex 4-20% Tris-Glycine Mini Protein Gels (Thermo Fisher Scientific catalog #XP04200BOX) at room temperature and subsequently transferred overnight onto Immuno-Blot PVDF membranes at 4° C. The membranes were blocked with 3% Blotting-Grade Blocker in 1×PBST for 30 min at room temperature and incubated with the indicated antibodies overnight with rotation/nutation at 4° C. After washing the blots in 1×PBST, the membranes were incubated with the indicated secondary antibodies for 2 hours at room temperature. Membrane-immobilized protein detection used ECL Western blotting detection reagents.

Statistical Analysis of Data

Unless otherwise stated, all experiments were carried out in three biological replicates (n=3). All mouse experiments had a minimum of n=8-15 per experimental group except for tail vein injections, which had n=5 mice. The log-rank test was used to analyze time-to tumor growth data and survival data. The Student t test or Wilcoxon rank-sum test was used for analyzing continuous variables. For in vitro studies, the two-tailed unpaired Student t-test was performed. All in vitro data are reported as the mean±standard deviation unless stated otherwise, and all in vivo data are reported as the mean±standard error. Statistical analyses were performed using GraphPad Prism and R. p values are as indicated: * $p<0.05$,  $p<0.01$, * $p<0.001$, and n.s is not statistically significant. The results of the experiments are now described.

Figure 7A:
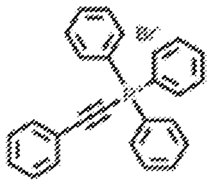
FIGS. 7A-7D show identification of a novel mitochondrial-targeting HSP70 inhibitor.
Figure 7A:
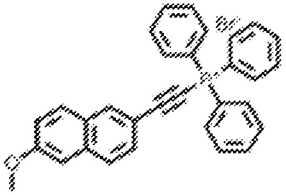
Figure 7A:
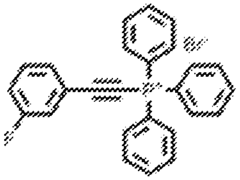
Figure 7A:
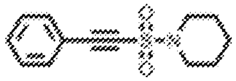
Figure 7A:
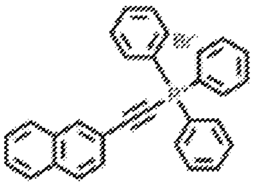
Figure 7A:
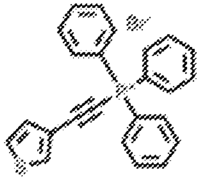
Figure 7A:
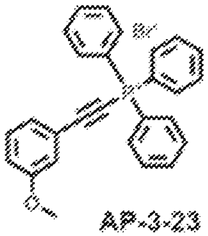
Figure 7A:
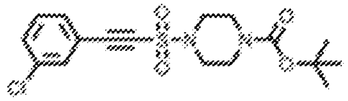
Figure 7A:
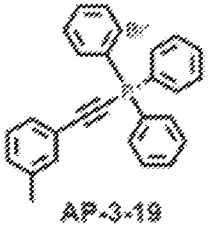
Figure 7A:
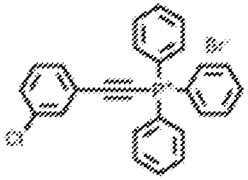
Figure 7A:
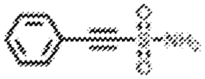
Figure 7B:
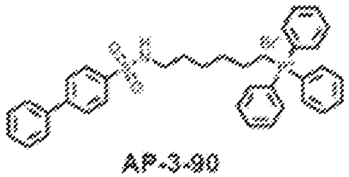
Figure 7B:
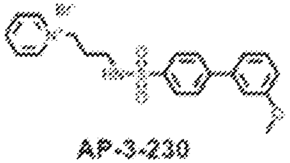
Figure 7B:
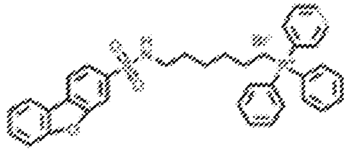
Figure 7B:
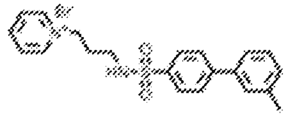
Figure 7B:
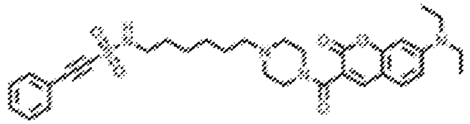
Figure 7B:
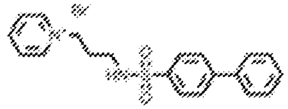
Figure 7B:
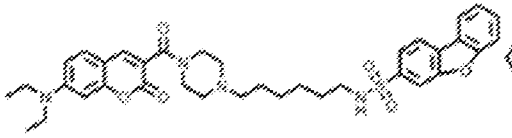
Figure 7B:
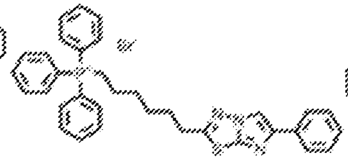
Figure 7B:
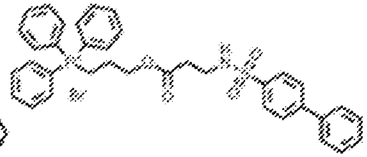
Figure 7B:
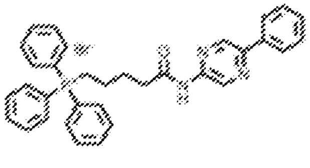
Figure 7B:
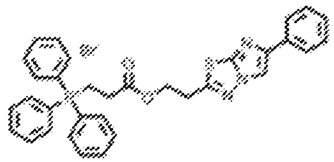
Figure 7B:
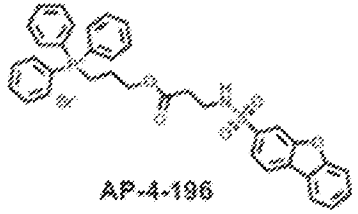

Example 1: AP-4-139B is a Novel Compound that Binds and Inhibits HSP70 in Cell-Based and Cell-Free Assays HSP70 inhibitors (HSP70i) PES and the related compound PET-16 were previously described. One predicted liability of PET-16 was a central ethynyl group between the active phenyl group and the triphenylphosphonium (TPP) group (FIG. 1A); this ethynyl made the compound potentially reactive as a Michael acceptor. Using guidance from the crystal structure, the ethynyl group was replaced with several different planar groups. The linker length between the phenyl group and the TPP was also altered, and modifications were made to the phenyl group (FIGS. 7A-7B). Each of these derivatives was analyzed in a novel high throughput ATPase assay designed as described herein; unlike other HSP70 ATPase assays, this one uses only purified HSP70 and does not require the nucleotide exchange factor HSP40 (see Methods). In this ATPase inhibition assay, PET-16 inhibits purified human HSP70 in a dose-dependent manner with an $IC_{50}$ of approximately 3 μM; this value is consistent with the cytotoxicity of this compound in tumor cells (Leu et al., Oncotarget. 2017 Jul. 11; 8(28):45656-45669). Several derivatives demonstrated markedly superior potency in this assay compared to PET-16, including the compounds AP-3-97 and AP-4-139B. In contrast the negative control consisting of the TPP group plus linker (VY-3-277) showed no inhibitory activity in this assay (FIG. 1A; FIGS. 7A-7B).

Figure 1B:
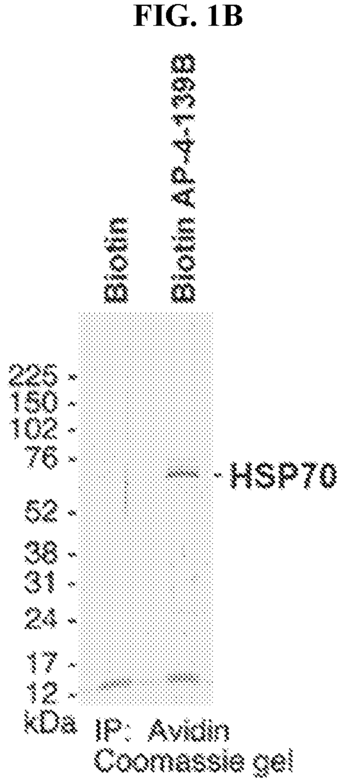
Figure 1C:
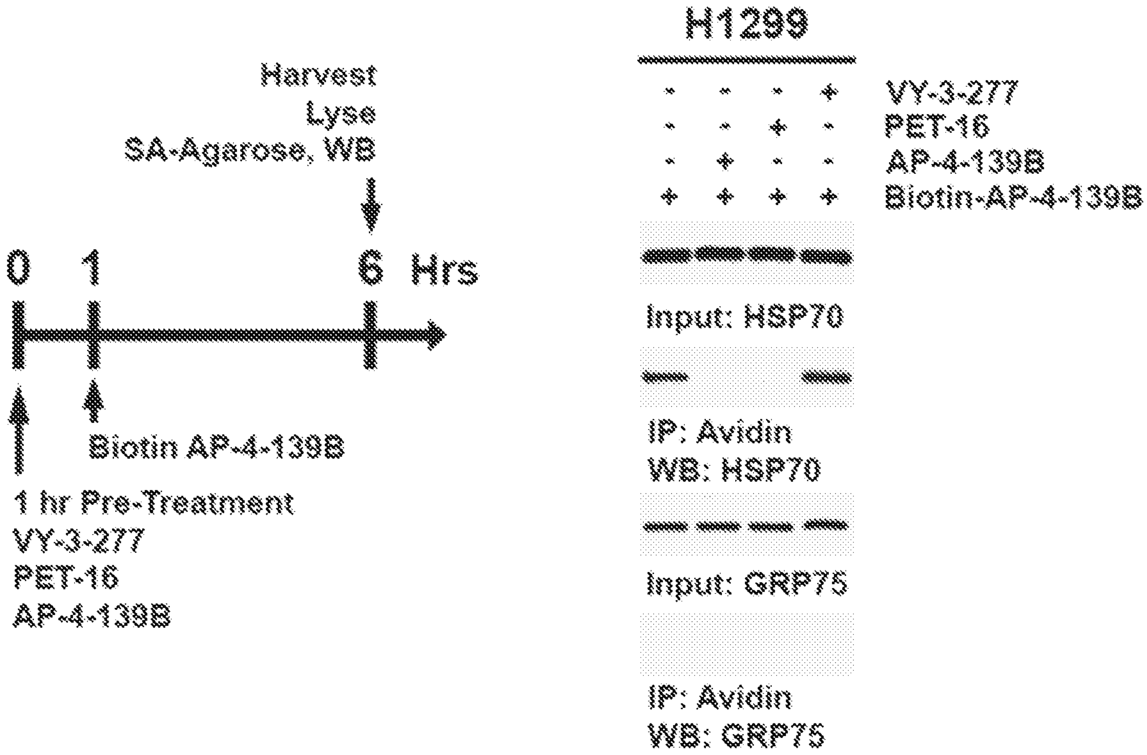
Figure 7C:
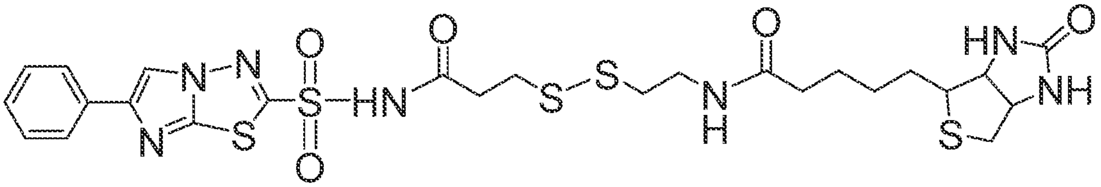

Next, versions of AP-3-97 and AP-4-139B were synthesized in which the TPP was replaced with a sulfonamide group, thus allowing biotinylation of the free amide group of these compounds according to published protocols (Leu et al., Mol Cell. 2009 Oct. 9; 36(1):15-27; Leu et al., Oncotarget. 2017 Jul. 11; 8(28):45656-45669). H1299 lung tumor cells were treated with biotinylated AP-4-139B (BAP-4-139B; structure shown in FIG. 7C) and BAP-3-97 and streptavidin agarose was used to pull-down interacting proteins. BAP-4-139B successfully precipitated a single protein from H1299 cells that was identified by LC/MS-MS to be HSP70 (HSPA1A, FIG. 1B). Tryptic peptides for other HSP70 family members (GRP75 and BiP) were not identified in this pulldown. Although it effectively inhibited HSP70 ATPase activity, BAP-3-97 failed to precipitate HSP70 in this assay, so this compound was not pursued further. BAP-4-139B was next used to test the hypothesis that this compound and PET-16 might compete for binding to the same binding pocket of HSP70; this is predicted based on similar structural moieties. A one-hour pre-incubation of cells with either PET-16 or AP-4-139B prevented the ability of BAP-4-139B to pull down HSP70, while VY-3-277 was unable to prevent binding (FIG. 1C). This finding supports the premise that both AP-4-139B and PET-16 likely bind to the same allosteric pocket in the substrate-binding domain of HSP70.

Figure 1D:
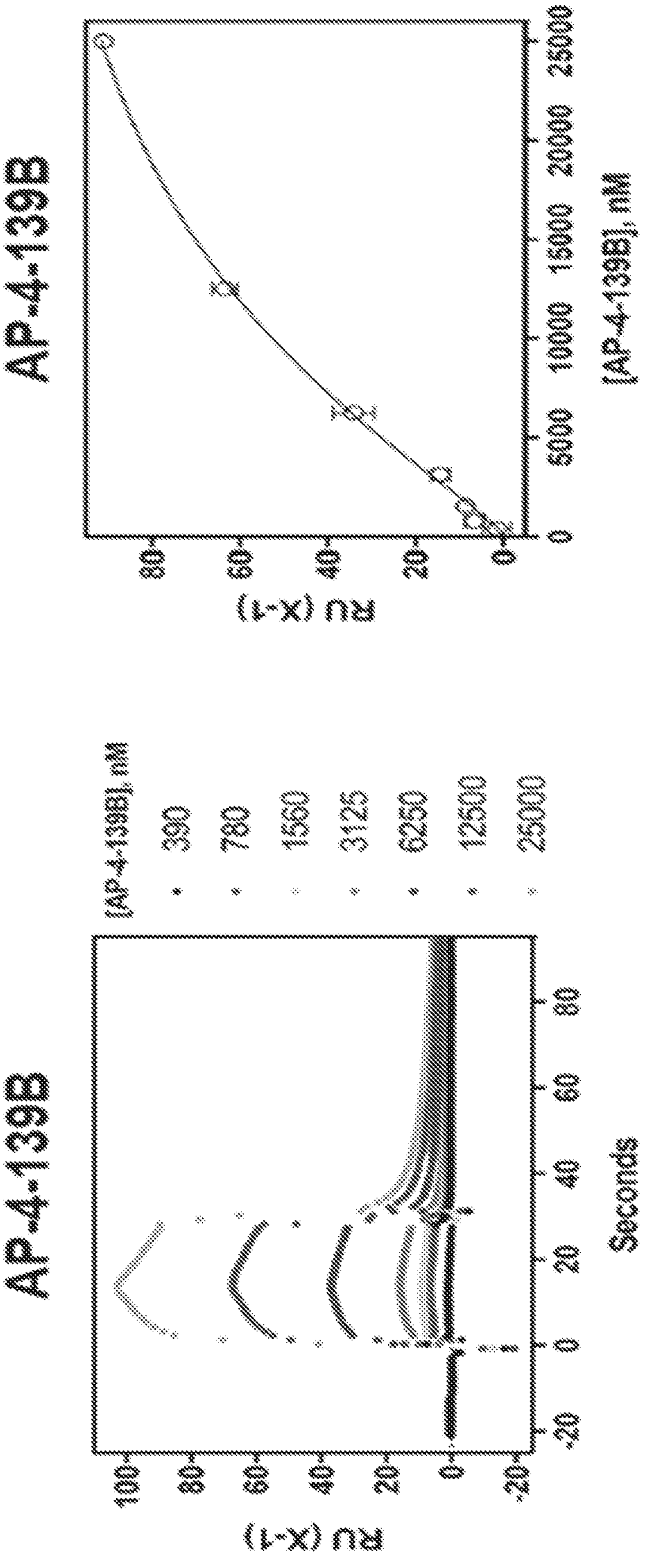
Figure 2A:
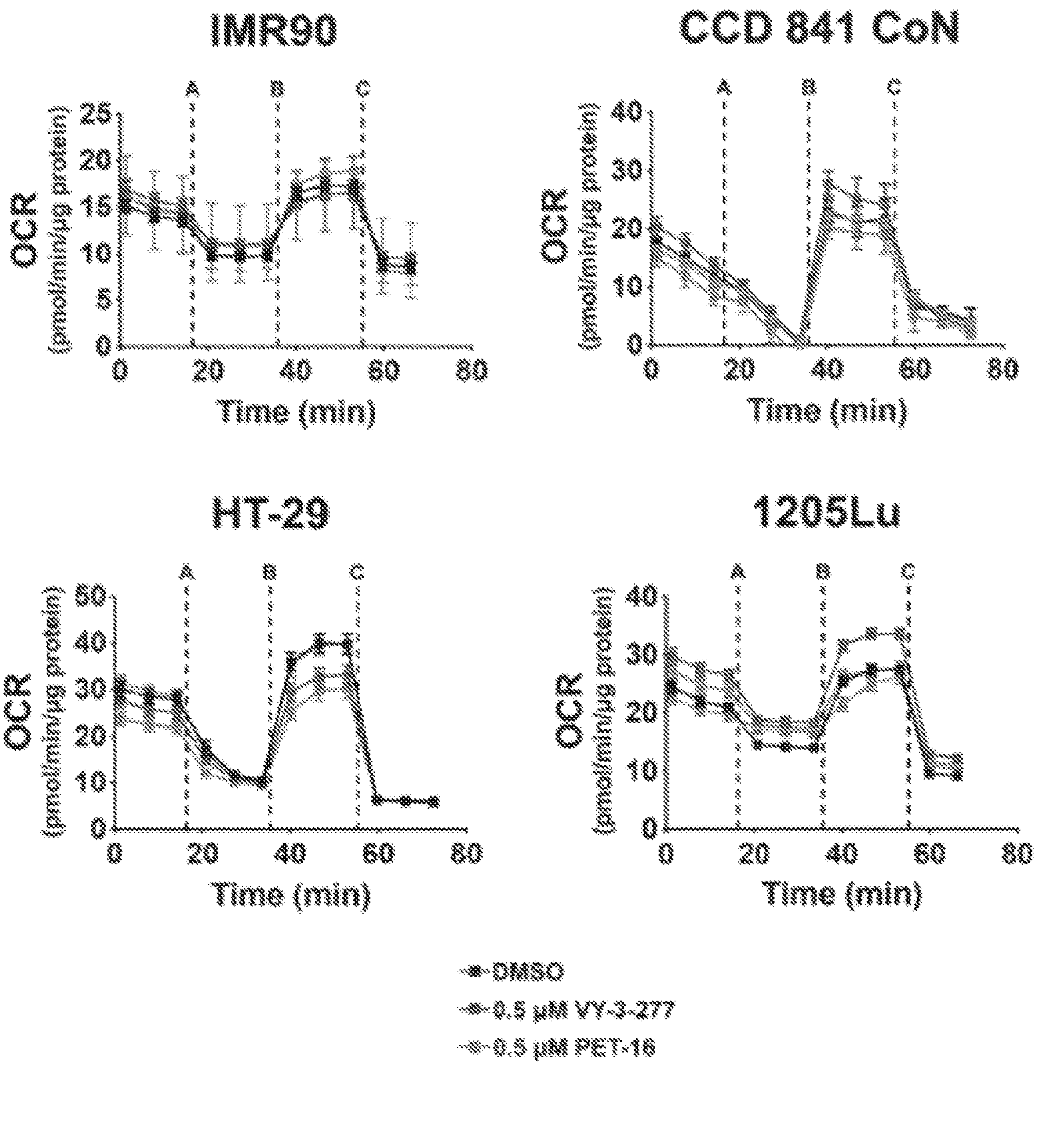
FIGS. 2A-2D show that the novel HSP70 inhibitor AP-4-139B affects mitochondrial function of tumor cells with minimal effects on non-transformed cells.
Figure 2B:
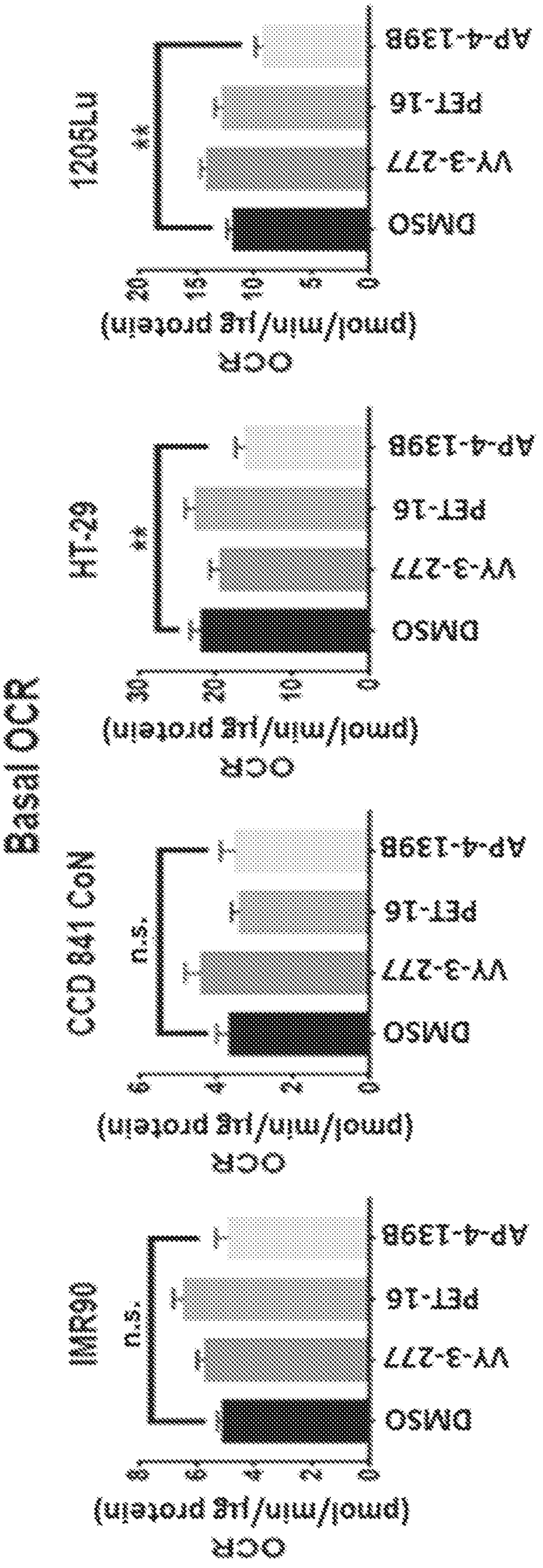
Figure 2C:
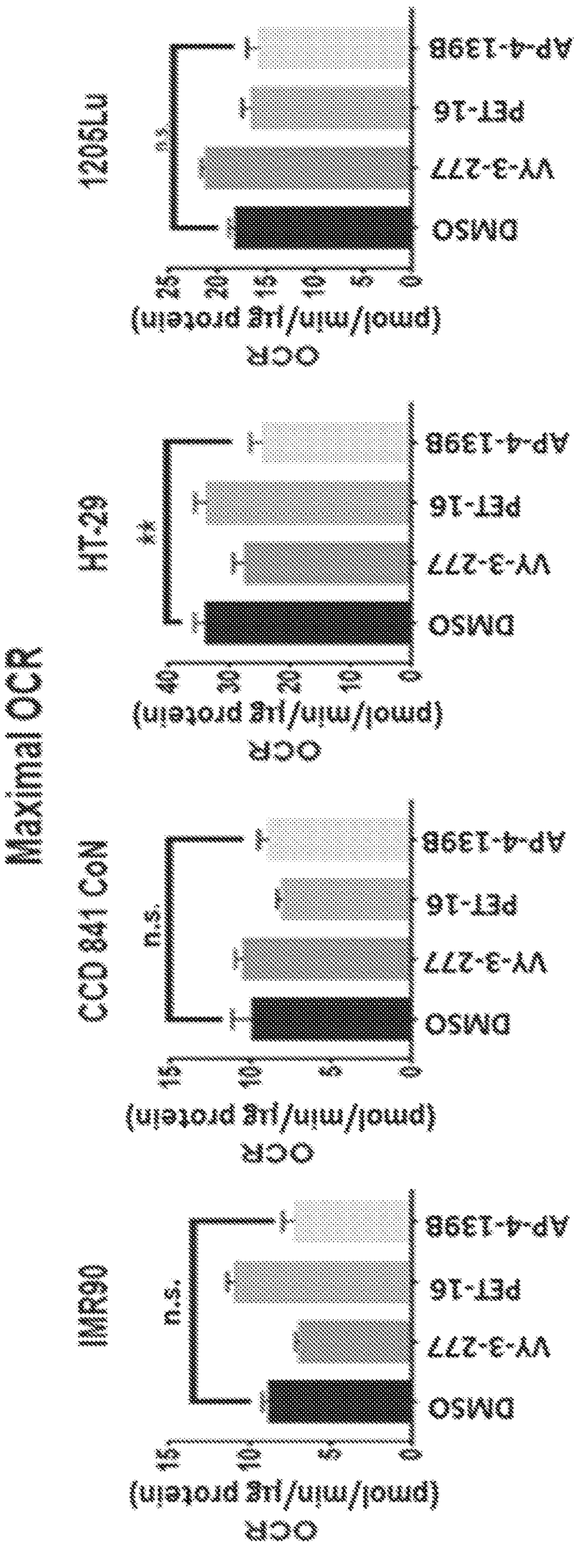
Figure 2D:
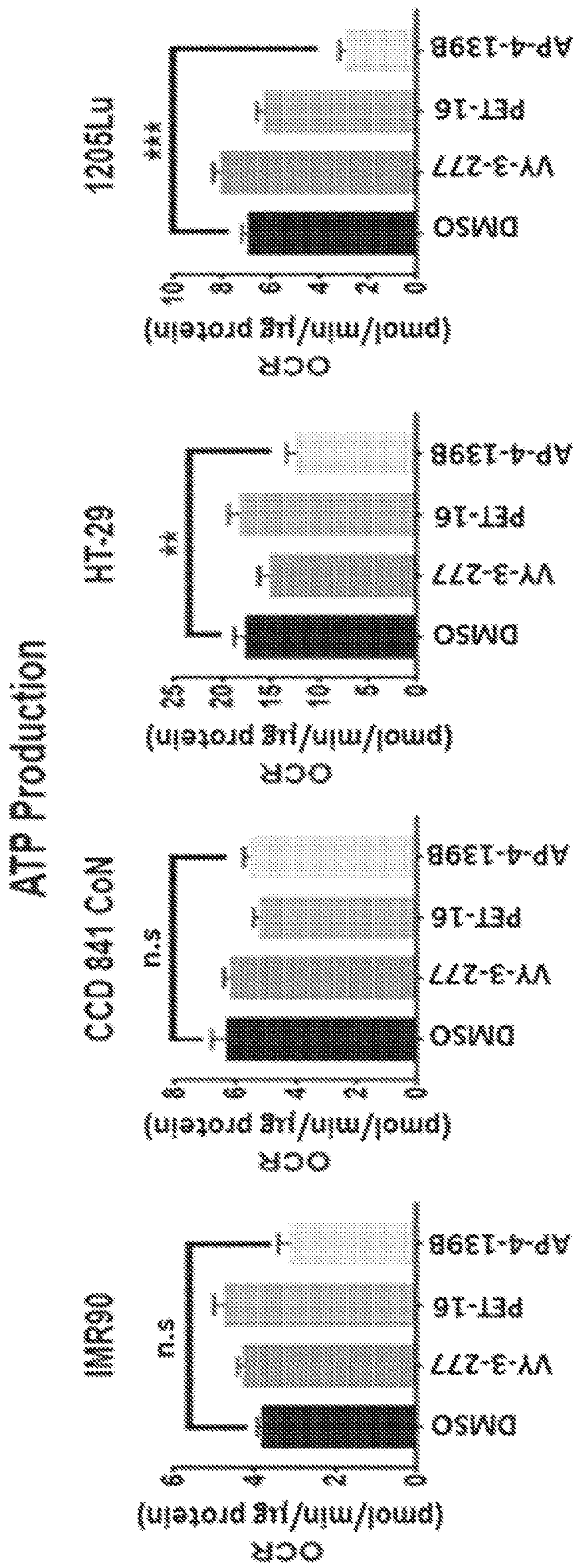
Figure 7D:
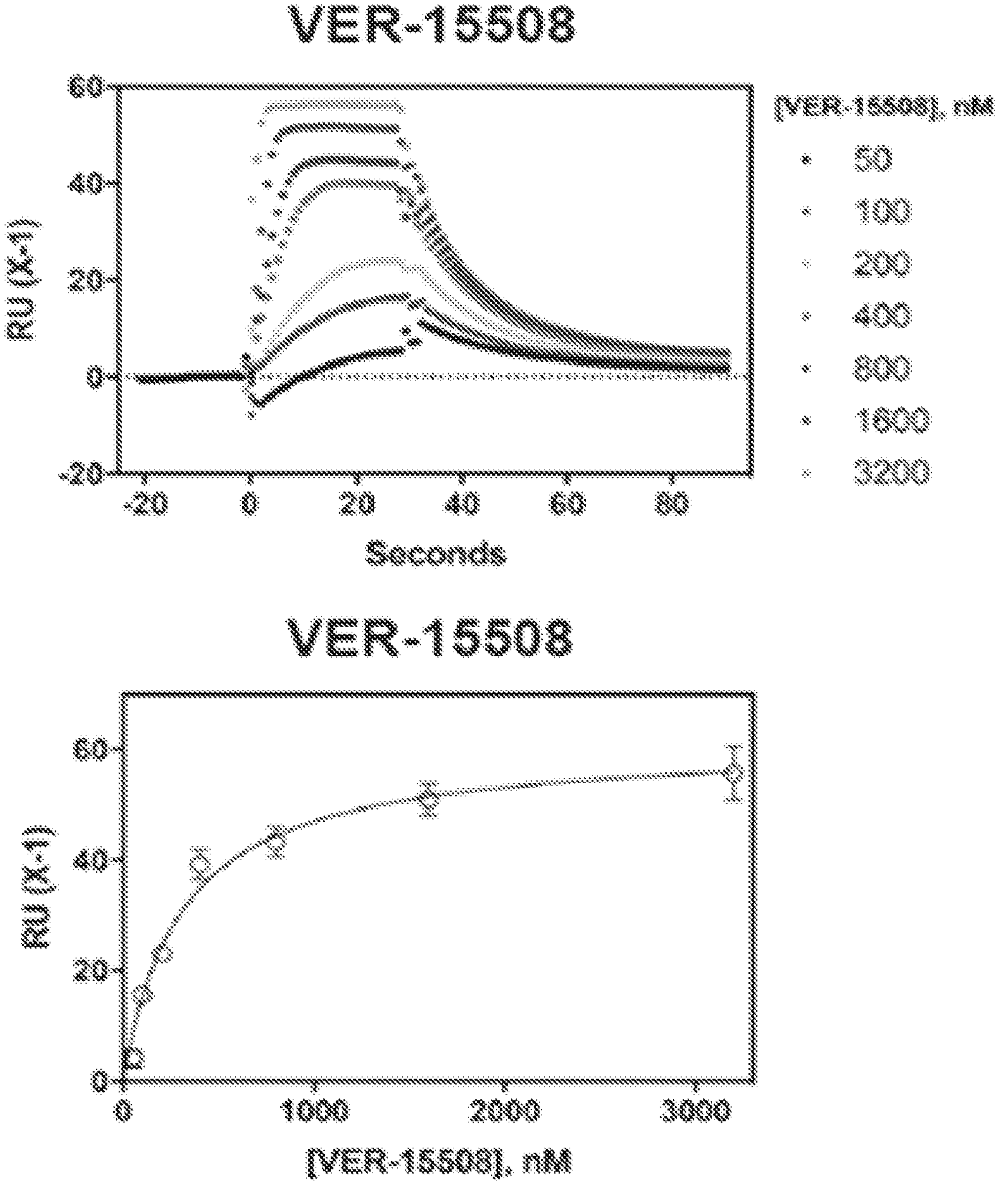

The next studies sought to determine whether AP-4-139B interacts directly with HSP70. To accomplish this, full-length His-tagged human HSP70 was used, and it was immobilized on a high affinity poly-Ni-NTA sensor chip for surface plasmon resonance experiments on a Biacore T200. This HSP70-loaded chip was incubated with AP-4-139B or the negative control VY-3-277. As a positive control the adenosine-derived HSP70 inhibitor Ver-155008 was used (Massey et al., Cancer Chemother Pharmacol. 2010 August; 66(3):535-45). Both AP-4-139B (FIG. 1D) and Ver-155008 (FIG. 7D) but not VY-3-277 reproducibly bound in concentration-dependent manner to sensor chips loaded with HSP70. These data support a direct association between HSP70 and AP-4-139B.

Figure 3A:
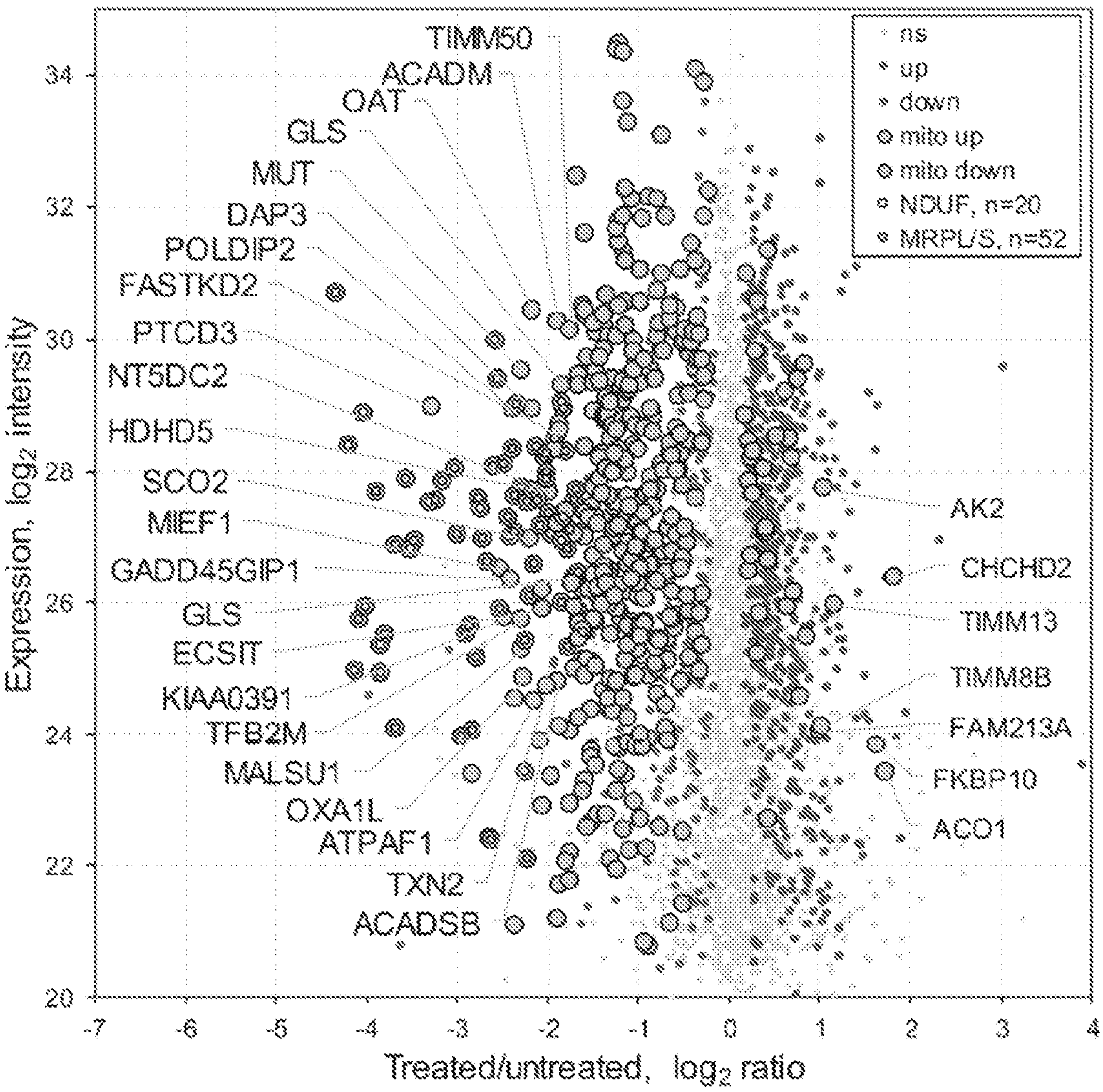
FIGS. 3A-3F show that AP-4-139B affects expression of HSP70 client proteins in multiple cellular compartments of the cell, including the mitochondria; mitochondrial targeting of this HSP70 inhibitor is facilitated by the triphenylphosphonium group.
Figure 3B:
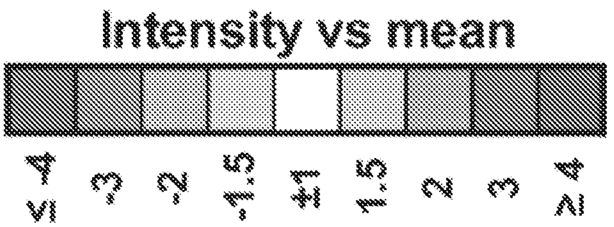
Figure 3C:
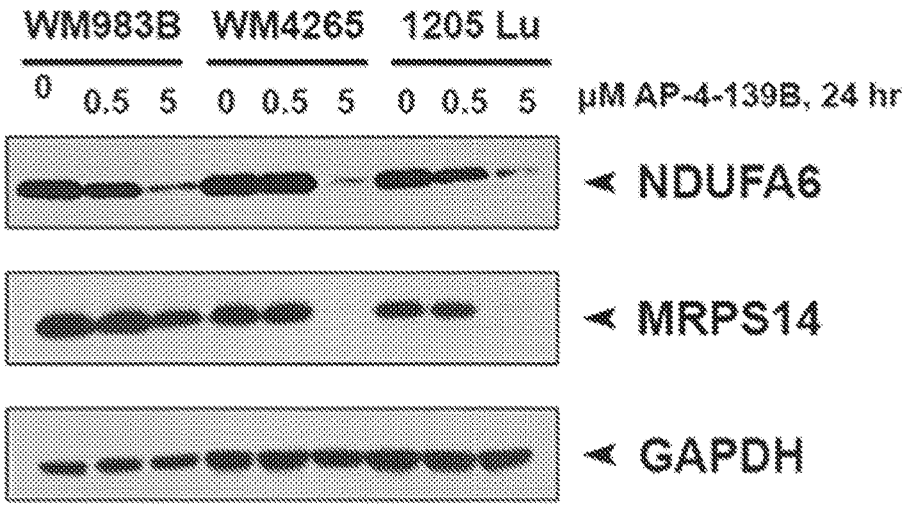
Figure 3D:
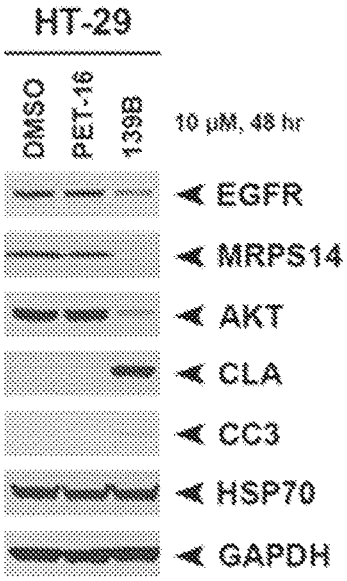
Figure 3E:
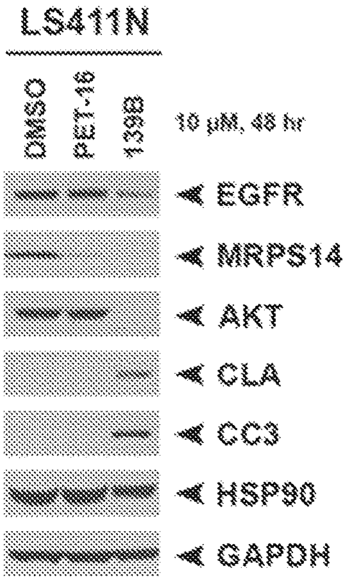
Figure 3F:
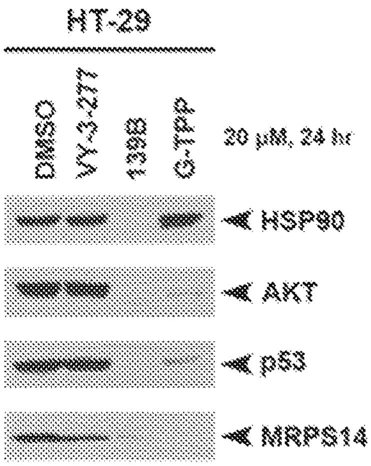
Figure 21:
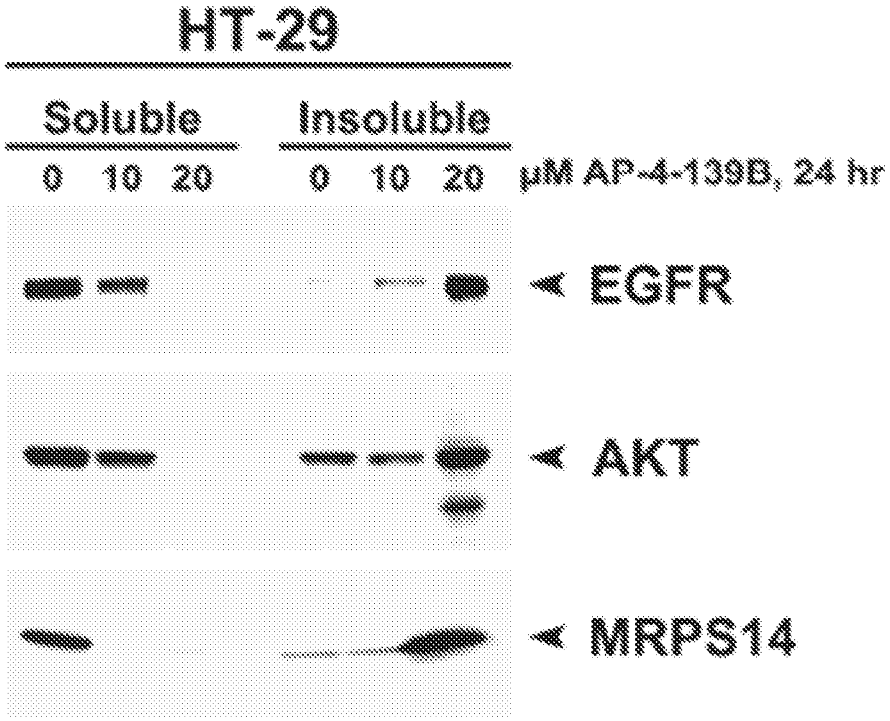
FIG. 21 shows HT-29 cells that were treated with indicated concentration of AP-4-139B for 24 hours. Cells were harvested in lysis buffer, fractionated into detergent-soluble (soluble) and detergent-insoluble (insoluble) preparations, and assayed by Western blot for the proteins indicated.
Figure 22A:
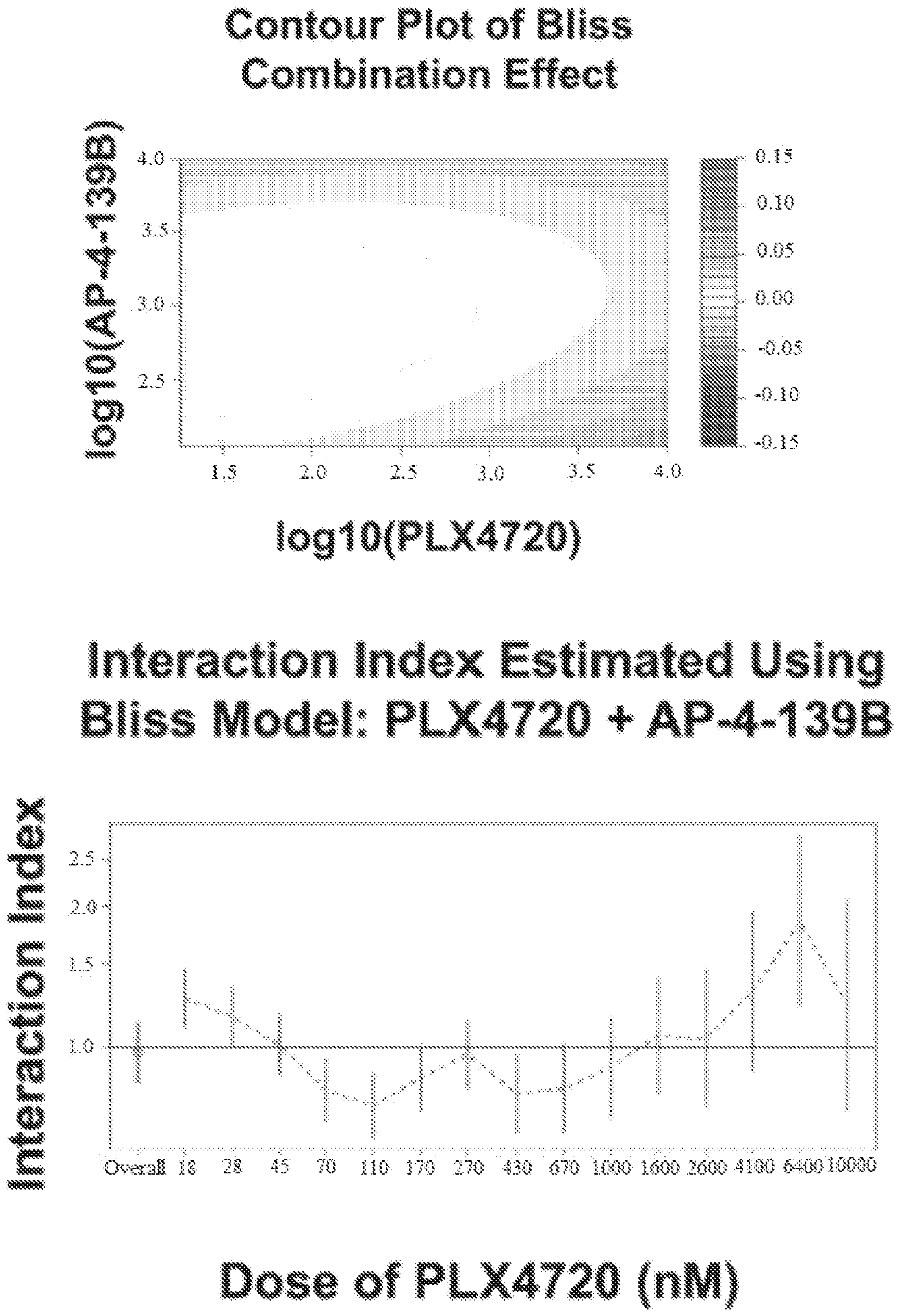
FIGS. 22A-22F shows that AP-4-139B synergizes with PLX4720 (BRAFi) in BRAF mutant colorectal cancer cells. Three different BRAF mutant colorectal cancer cell lines were subjected to HSP70 and BRAF inhibitor combination cell viability assays. Cells were plated in 384 well plates at a concentration of 500 cells per well. The next day, cells were treated for 72 hours followed by a Cell Titer Glo assay to assess viability. Luminescence was measured using an Envision plate reader. Shown are representative data of four independent replicates for each cell line. Data are represented as contour plots (color from white to read indicates the trend of synergistic effect) and interaction plots for each compound. The upper limit of the 95% confidence interval of an interaction index <1 indicates a synergistic effect. Note that the combination has a significant synergistic effect in a range of dose combinations for HT-29 and RKO cells and a significant synergistic effect at all dose combinations in LS411N cells.
Figure 22B:
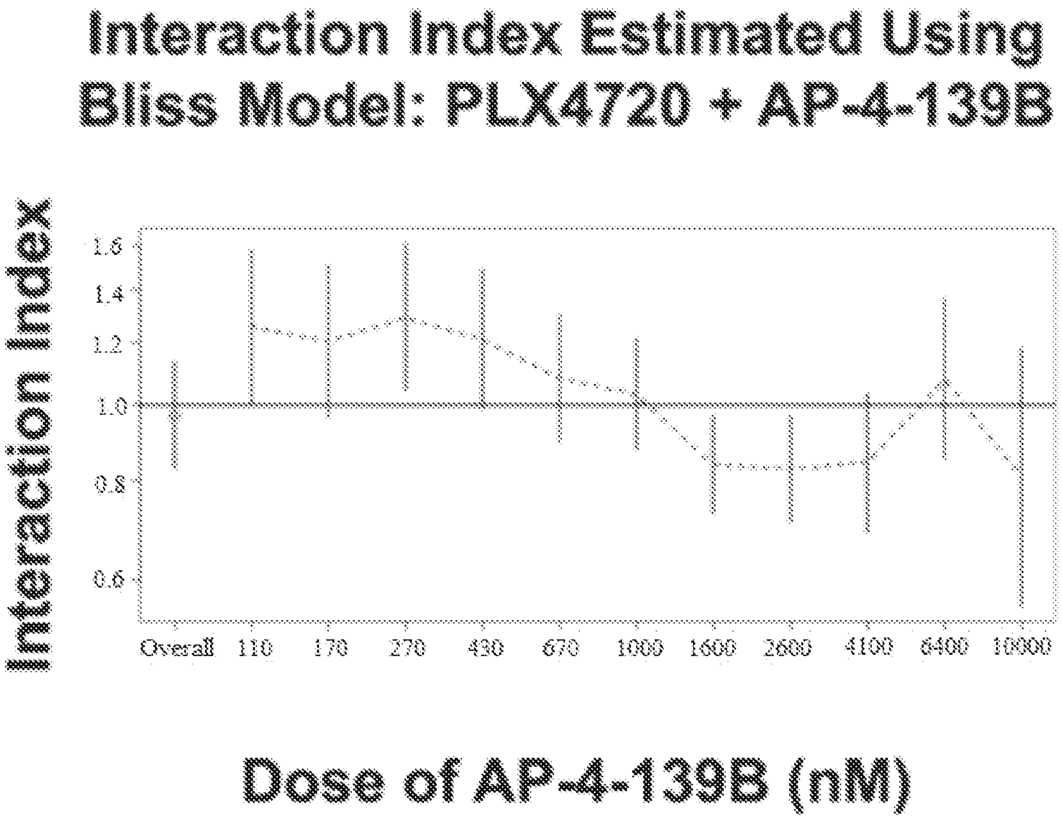
Figure 22C:
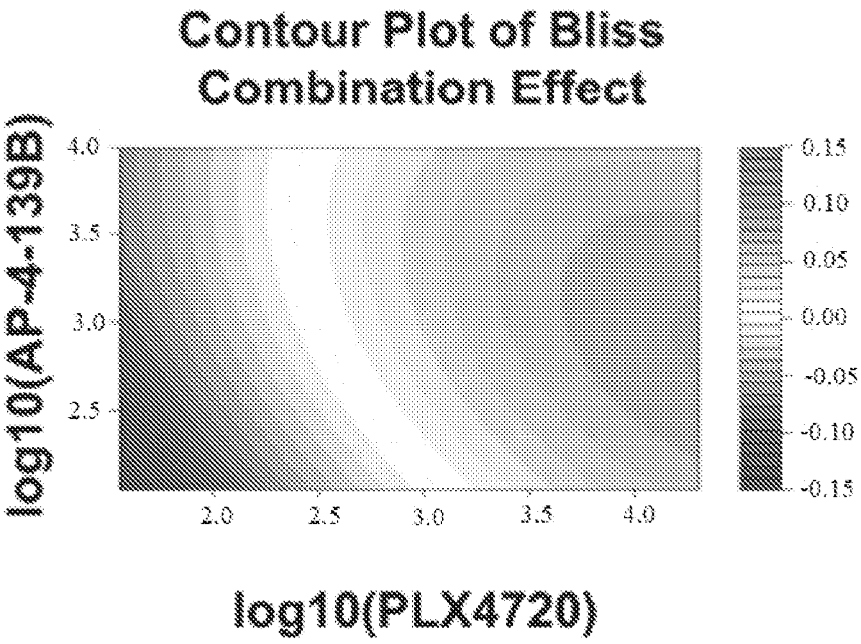
Figure 22D:
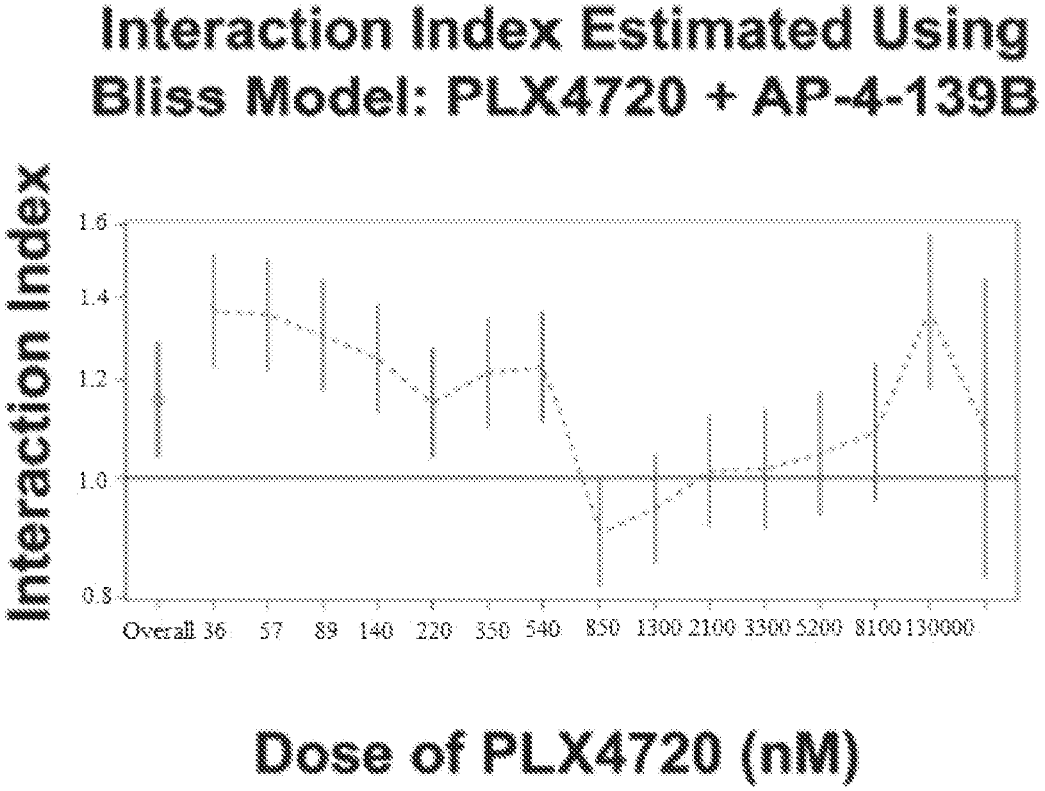
Figure 22D:
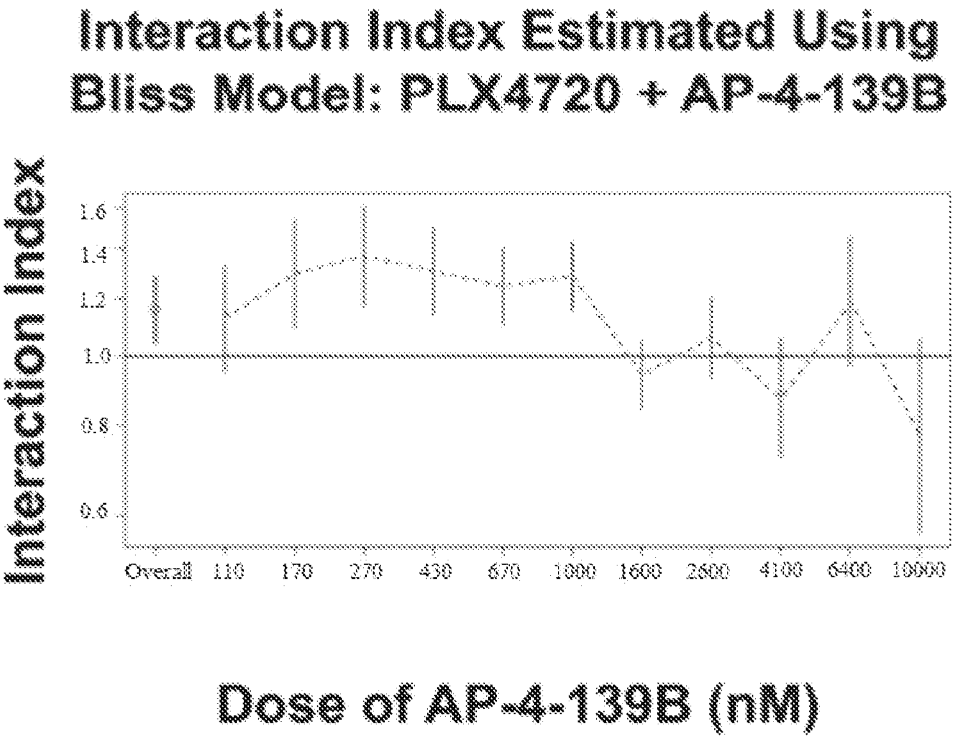
Figure 22E:
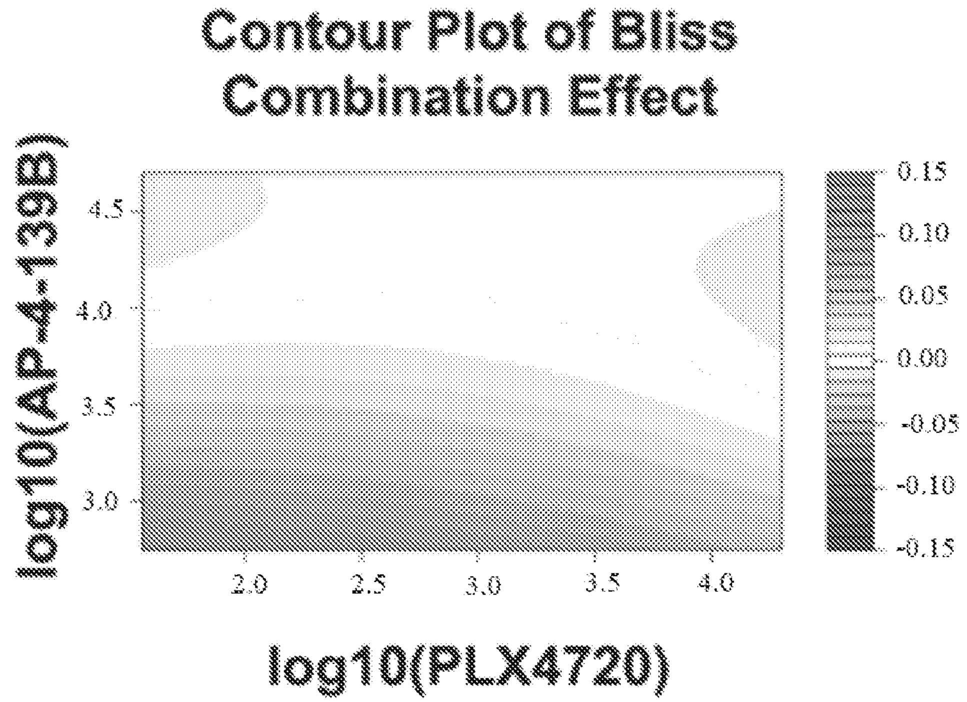
Figure 22E:
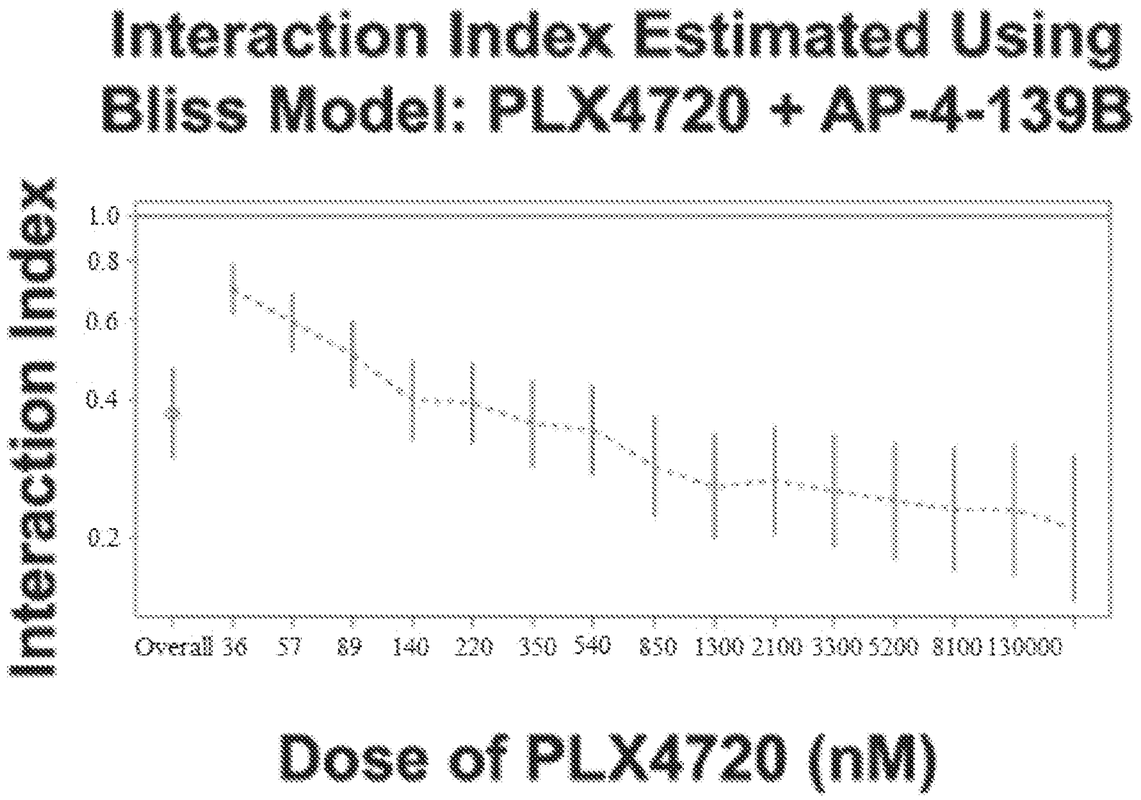
Figure 22F:
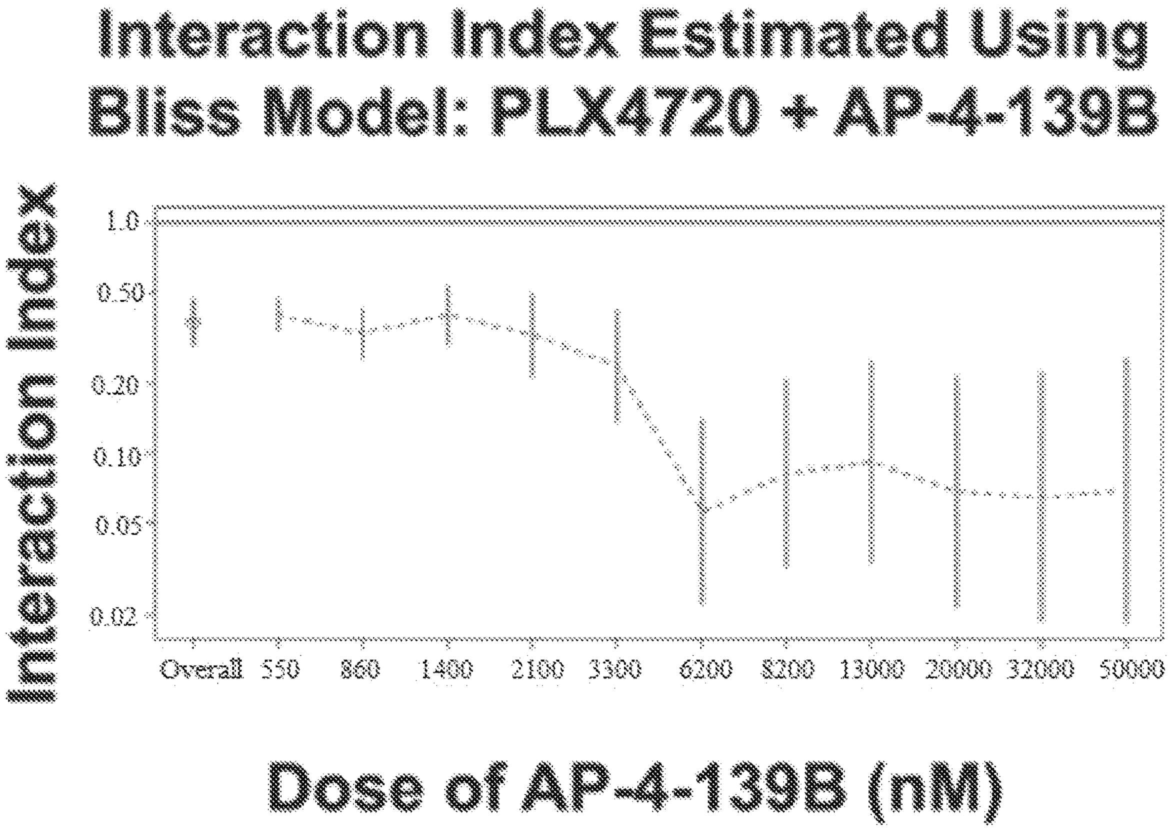

Example 2: AP-4-139B Inhibits Solubility of Client Proteins in Multiple Cellular Compartments, Including the Mitochondria In tumor but not non-transformed (i.e. normal) cells, a fraction of HSP70 resides at the mitochondria (Leu at al., Oncotarget. 2017 Jul. 11; 8(28):45656-45669). Triphenylphosphonium (TPP) is known to improve the biodistribution of compounds in the body, and to facilitate the transit of compounds through membranes, including the mitochondria. It was thus predicted that AP-4-139B might be mitochondrion-toxic. To test this premise, mitochondrial function was assessed on a Seahorse XFe96 Analyzer in normal human fibroblasts (IMR90) and normal colon epithelial cells (CCD 841 CoN) as controls, as well as in two tumor cell lines, the melanoma line 1205Lu and the colon carcinoma line HT-29. Each cell line was incubated for 24 hours with a sublethal concentration of PET-16, AP-4-139B, and the negative control VY-3-277. These analyses confirmed that normal IMR90 and CCD 841 CoN cells were largely unaffected by all three compounds, but that both 1205Lu and HT-29 tumor cell lines showed reduced basal oxygen consumption rate and ATP production when treated with AP-4-139B (FIGS. 2A-2D). At this concentration, PET-16 had minimal activity in these assays (FIGS. 2A-2D). Mitochondrial client proteins of HSP70 in cancer cells have not been identified. It was reasoned that the identity of such might facilitate understanding of the activity of AP-4-139B on mitochondrial function and tumor biology. Toward this goal, SILAC (Stable Isotope Labeling with Amino Acids in Cell Culture) was performed in tumor cells that were cultured for six passages in heavy and light isotope media prior to treatment with vehicle or 1 μM AP-4-139B for six hours (this timeframe was used in order to limit cell death and to minimize indirect effects of cell death). Treated and untreated cells were mixed at 1:1 ratio, pooled, and collected for mitochondria isolation, followed by trypsin digestion and liquid chromatography tandem mass spectrometry (LC-MS/MS), and two independent biological replicates were performed. 498 mitochondrial proteins were identified with significantly altered levels in the presence of AP-4-139B (FDR<10%), with the majority of proteins (n=462) down-regulated (FIG. 3A, in blue), and 125 of them downregulated at least 3-fold. A volcano plot of mitochondrial proteins showing altered level in the presence of AP-4-139B revealed fourteen proteins with >10-fold decreased abundance in the mitochondria from treated cells (FIG. 3B); these are potential HSP70 client proteins that become misfolded and insoluble following treatment with HSP70i. In this analysis very few proteins showed increased level in treated cells, and none of these were more than 2-fold increased (FIGS. 3A-3B, in red). Many of the proteins that showed the greatest decreases in inhibitor-treated cells were in the NDUF (NADH: ubiquinone oxidoreductase) and MRP (mitochondrial ribosomal) groups (FIG. 3B). Two of the top down-regulated proteins were selected for further analysis: MRPS14 and NDUFA6. Western blot analysis in several tumor cell lines following treatment with AP-4-139B showed significantly decreased level of MRPS14 and NDUFA6 in the treated tumor cell lines, while the level of GAPDH and other proteins remained unchanged (FIG. 3C). Western blot analysis in two different colorectal cancer cell lines treated with the $IC_{50}$ for AP-4-139B showed significantly decreased levels of MRPS14 and NDUFA6 after 24 hours of treatment, while the level of more than two dozen mitochondrial proteins, including BAK and CoxIV, was unaffected (FIG. 19 and FIGS. 20A-20D). Similar findings were made in three melanoma tumor lines (FIG. 3C). Two colorectal cancer cell lines (HT-29 and LS411N) were next analyzed for the level of conventional HSP70/HSP90 client proteins, such as AKT and EGFR. Interestingly, it was found that known HSP70/HSP90 client proteins were also decreased in AP-4-139B-treated cells, including EGFR (plasma membrane/endosome/lysosome), AKT (cytosol), and mutant p53 (nucleus) (FIGS. 3D-3F). An analysis of detergent soluble and insoluble fractions in AP-4-139B treated cells was consistent with these HSP70 clients misfolding and becoming insoluble after treatment (FIG. 21). These findings indicate that AP-4-139B broadly affects protein solubility in multiple compartments of the colorectal cancer cell, including the nucleus, the cytosol, and the mitochondria.

Figure 4A:
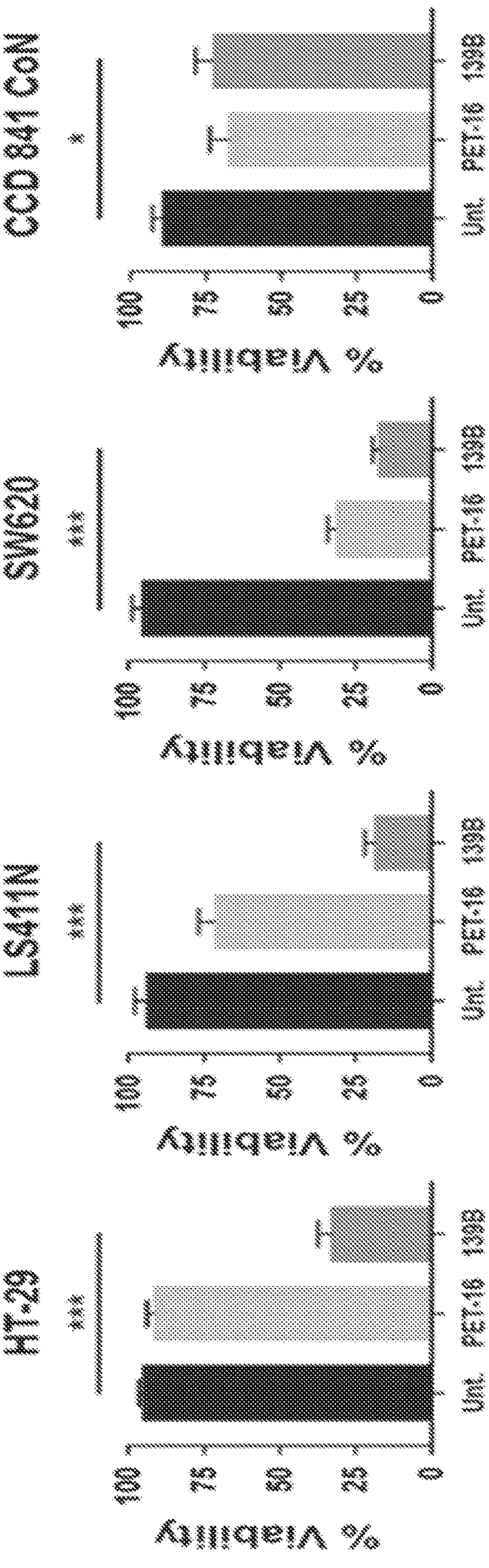
FIGS. 4A-4F show AP-4-139B is efficacious as a single agent against human CRC in vitro and in vivo.
Figure 8A:
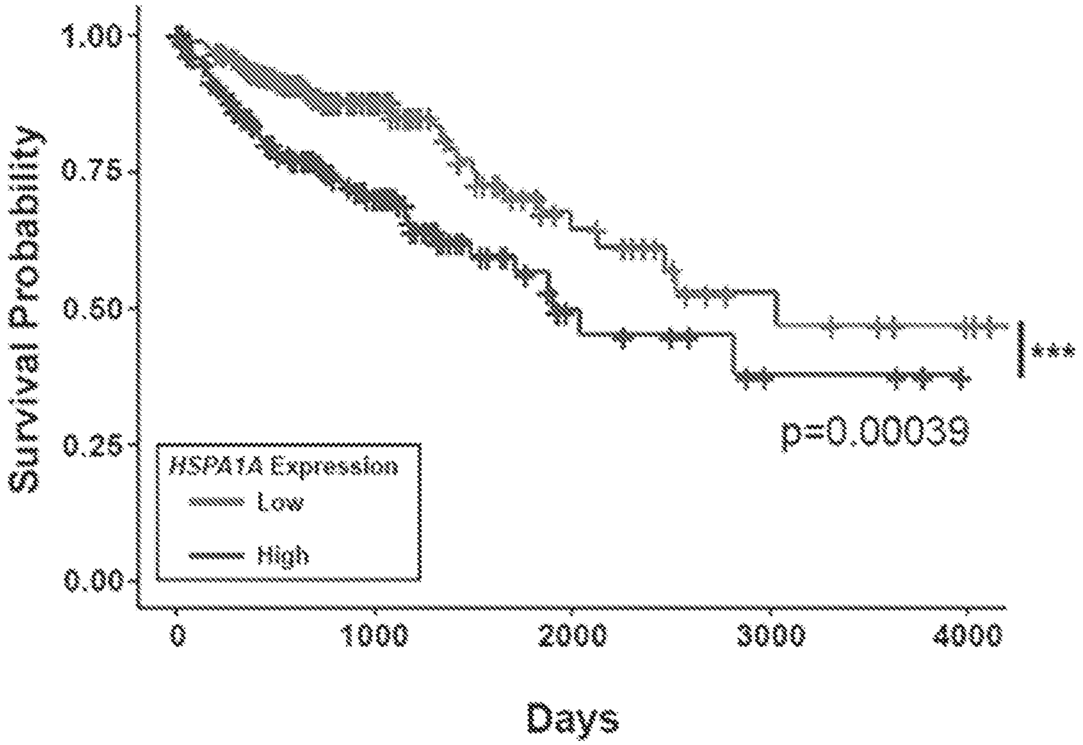
FIGS. 8A-8E show HSP70 inhibition is effective on mouse CRC cell lines.
Figure 8B:
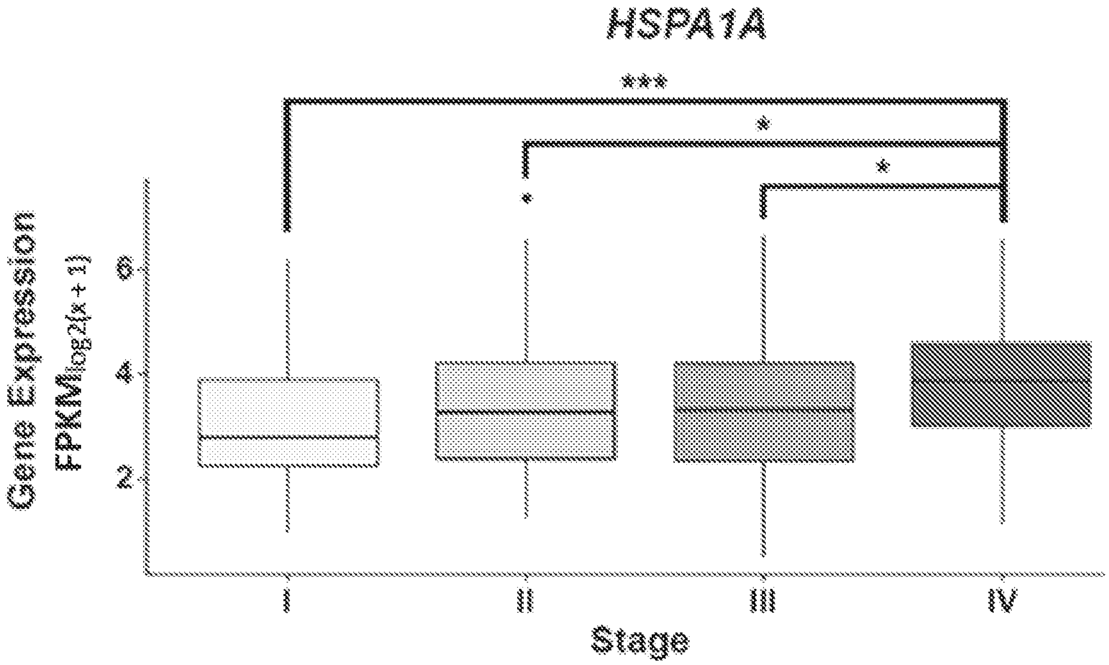

Example 3: Single Agent Efficacy of AP-4-13B in Colorectal Cancer (CRC) Cell Lines and Xenografts Cell viability analyses on human CRC lines treated with PET-16 or AP-4-139B were next performed, and this was compared to treatment of normal colon epithelial cells (CCD 841 CoN cells). PET-16 had modest ability to decrease CRC cell viability, whereas AP-4-139B was markedly more cytotoxic (FIG. 4A). In contrast these HSP70i showed modest toxicity to normal colon epithelial cells (CCD 841 CoN, FIG. 4A). This reduced cytotoxicity to normal colon cells was not due to decreased proliferative rate, as CCD 841 CoN cells showed a doubling time of approximately 24-30 hours (not shown). The relevance of HSP70 as a target for CRC was next confirmed. Specifically, TCGA data was analyzed for CRC, and the analysis showed that HSP70 (HSPA1A) is highest in stage IV CRC, and that high expression of HSP70 (HSPA1A) is associated with poor prognosis in CRC (FIGS. 8A-8B).

Figure 4B:
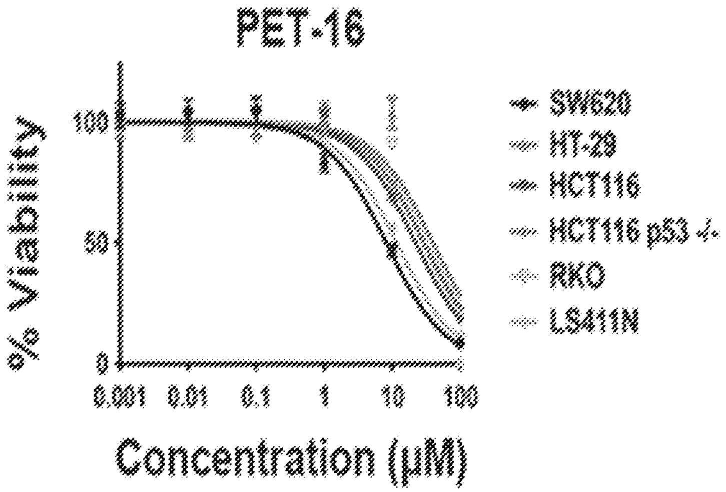
Figure 4B:
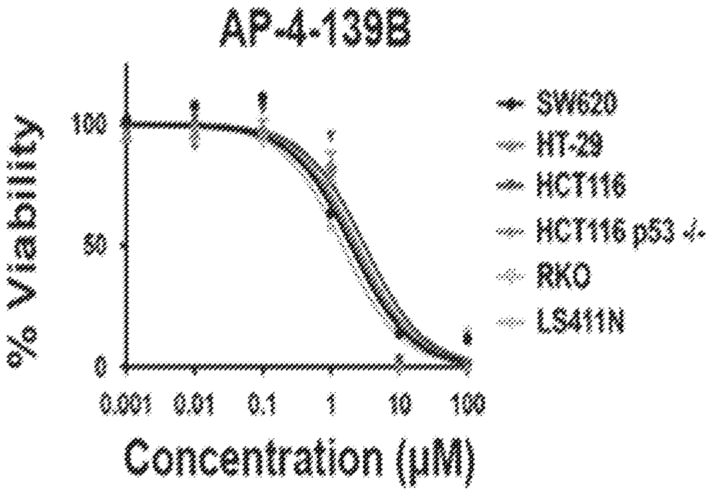
Figure 4C:
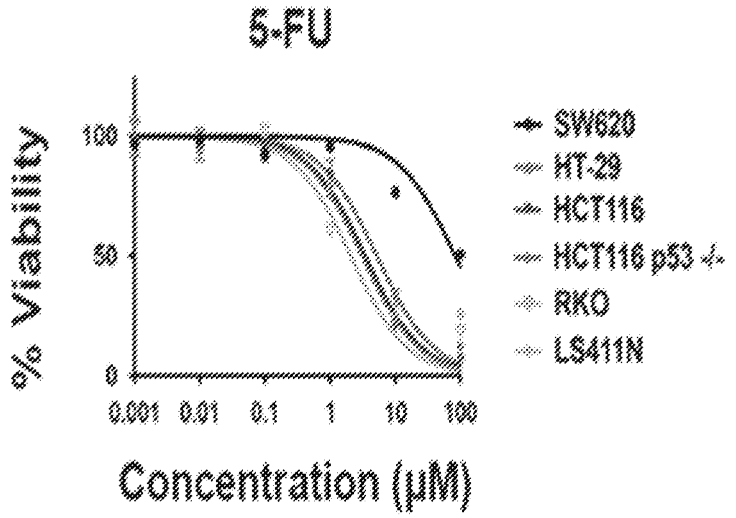
Figure 4C:
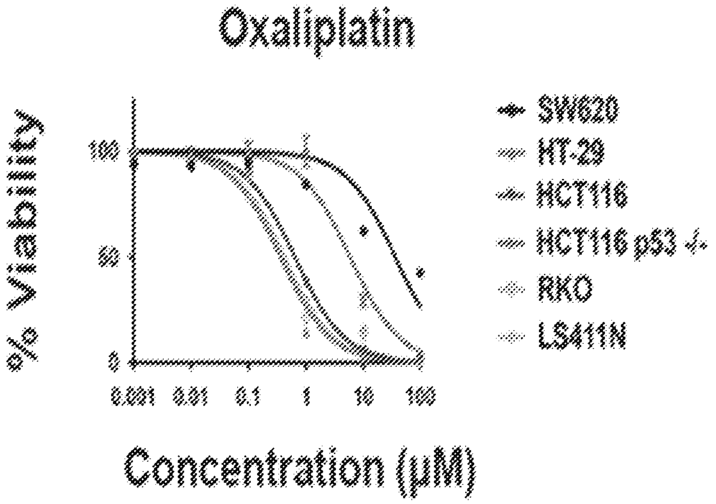

Next the $IC_{50}$ for AP-4-139B was assessed in six different CRC lines of different genotypes (KRas, BRAF, PTEN, p53) and different molecular phenotype (MSI/MSS; CpG island methylator phenotype+/−). The cytotoxicity of HSP70i described herein was also compared to agents used for the current standard of care for CRC, 5-fluoro-uracil (5-FU) and oxaliplatin. AP-4-139B showed comparable cytotoxicity ($IC_{50}$ 1.5-3 μM) in all CRC cell lines, regardless of genotype or molecular phenotype (FIG. 4B). In contrast 5-FU and oxaliplatin showed variable $IC_{50}$ in these cell lines, with SW620 cells highly resistant to both drugs (FIG. 4C). Significant synergy was also found with AP-4-139B combined with the BRAF inhibitor, PLX-4720, in BRAF-mutant colorectal cancer lines (FIGS. 22A-22F). Finally, the relevance of HSP70 as a target for colorectal cancer was further validated by analyzing The Cancer Genome Atlas data for colorectal cancer. The data showed that HSP70 (HSPA1A) is highest in stage IV colorectal cancer, and that high expression of HSP70 (HSPA1A) is associated with poor prognosis in colorectal cancer (FIGS. 8A-8B).

Figure 4D:
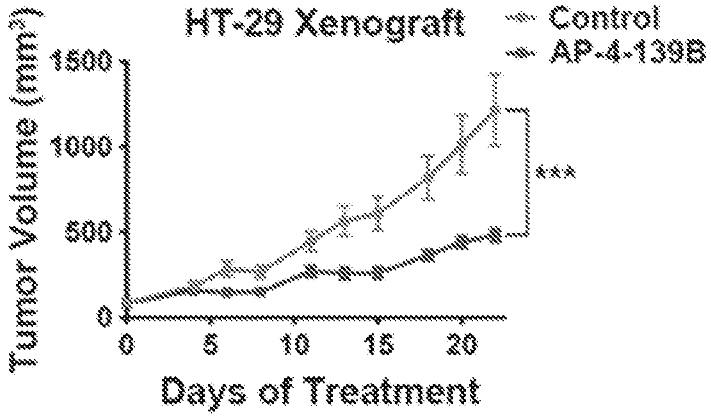
Figure 4E:
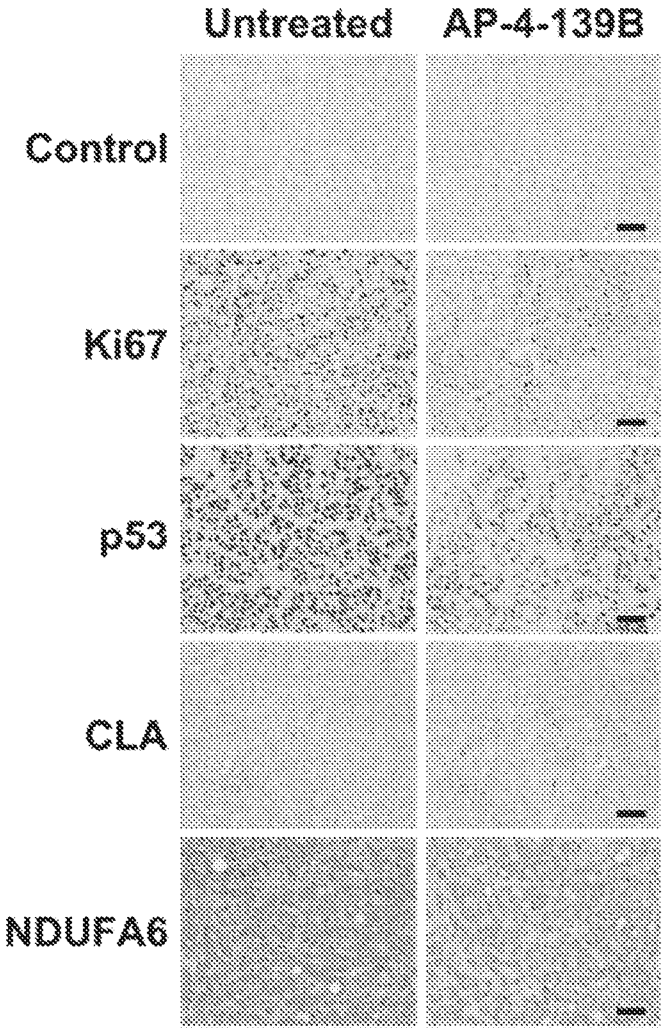
Figure 4F:
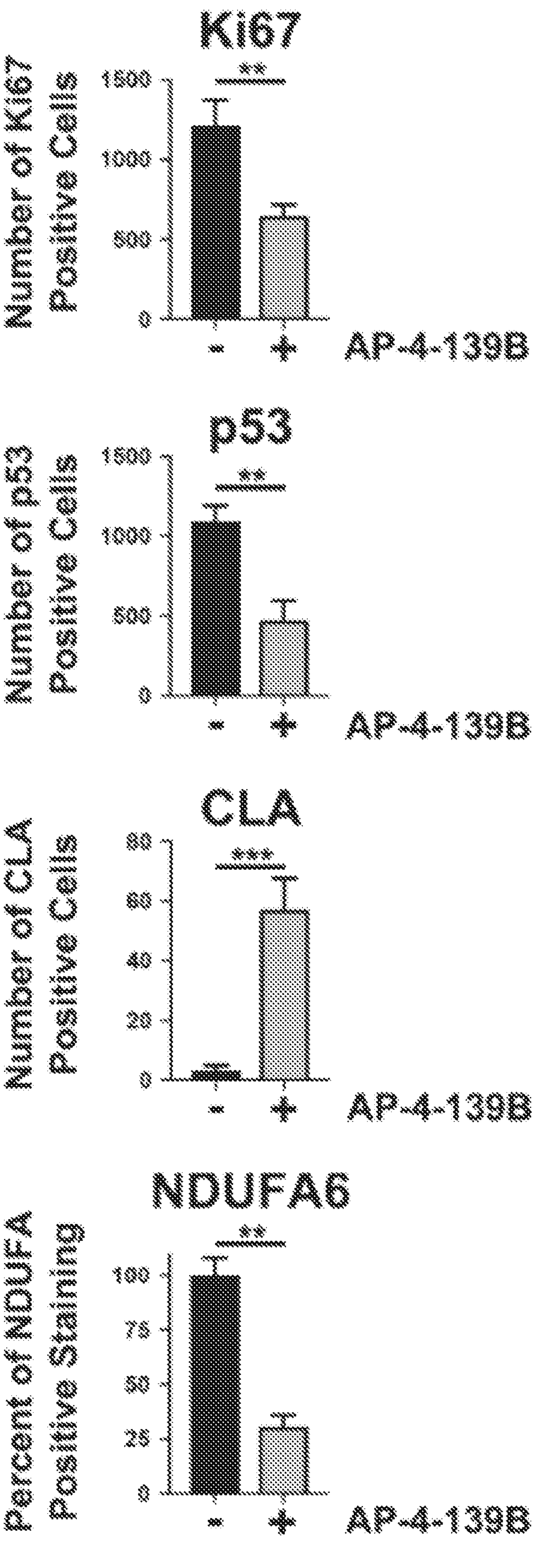
Figure 8C:
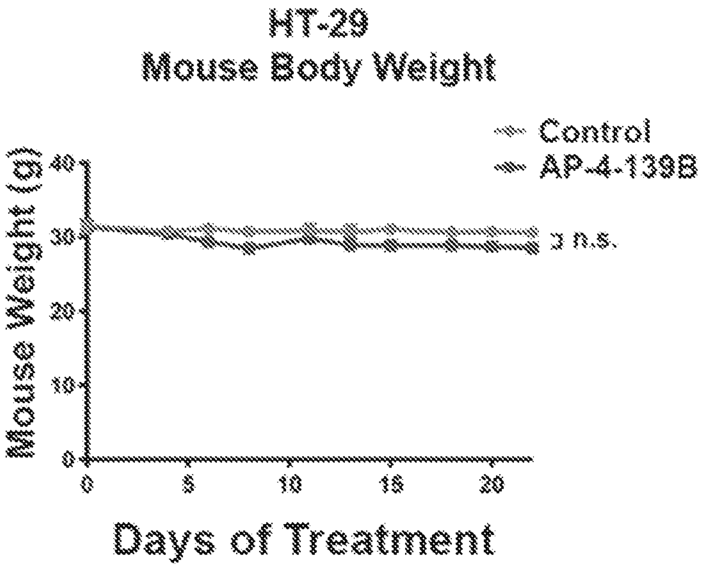
Figure 8D:
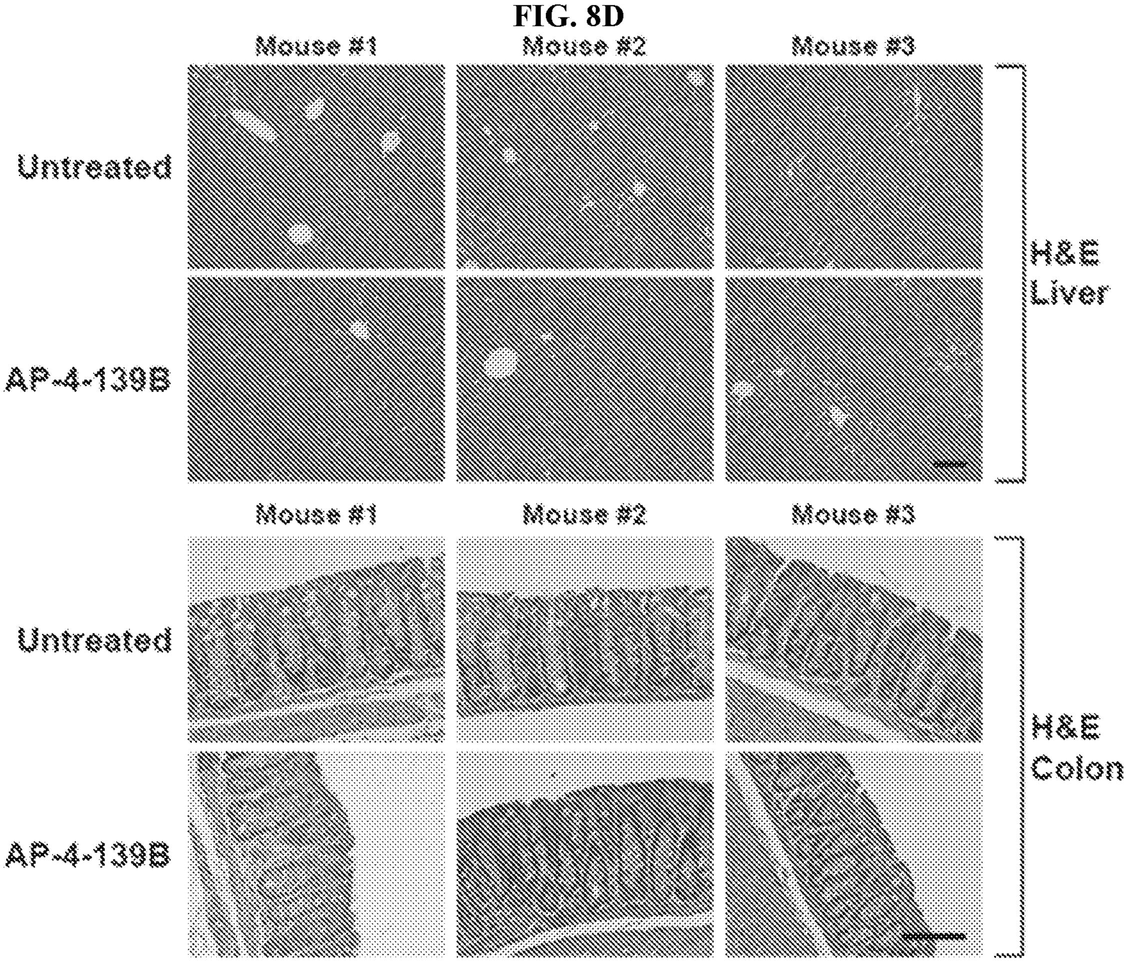
Figure 8E:
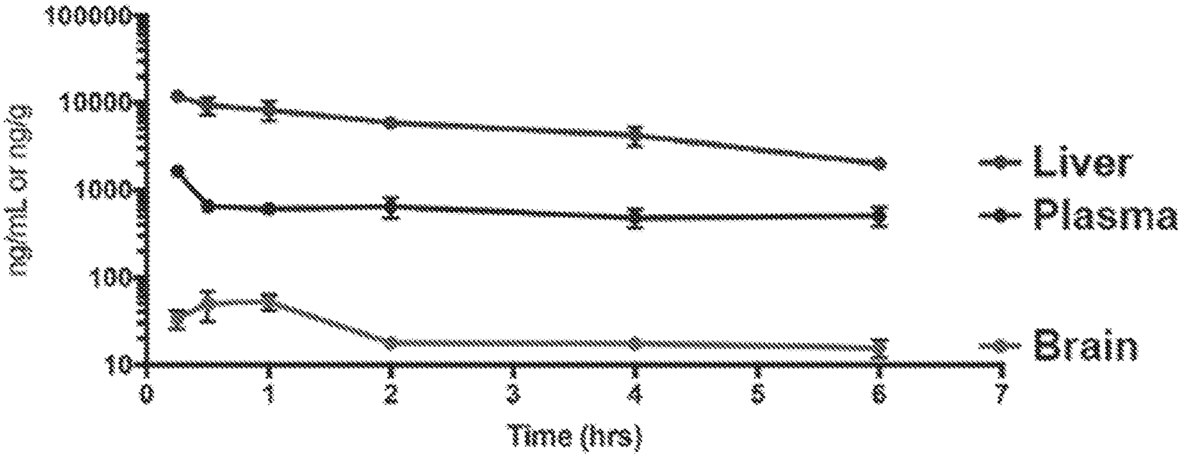
Figure 23:
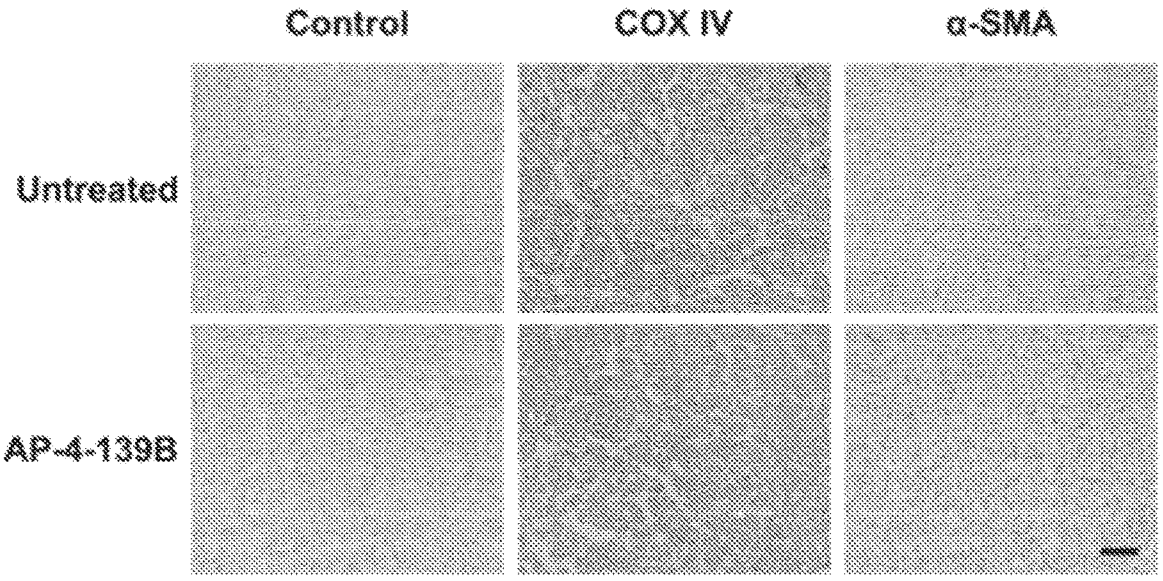
FIG. 23 shows the IHC analysis of HT-29 tumors in the presence or absence of the HSP70 inhibitor AP-4-139B. Shown are representative images of COXIV and a-SMA. n=5 mice per group. Scale bar=100 μm.

Analysis of the anti-tumor efficacy of AP-4-139B in vivo revealed that AP-4-139B significantly reduced the progression of HT-29 tumor xenografts, when mice were treated three times per week with 12.5 mg/kg of compound, or vehicle alone (FIG. 4D). In tumors, treatment with AP-4-139B led to reduced staining for Ki-67 as well as increased staining for cleaved lamin A (apoptosis, FIG. 4E, quantified in FIG. 4F). No evidence for toxicity was found at this dose, as there was no evidence of weight loss, or abnormal liver or colon architecture (FIGS. 8C-8D). At 10 mg/kg, AP-4-139B showed promising pharmacokinetics, with a >five-hour half-life in plasma and modest brain penetrance (FIG. 8E). No evidence was found that AP-4-139B caused obvious loss of mitochondria in treated tumors, as determined by COX IV staining, or was cytotoxic to the tumor microenvironment in these studies, as determined by equivalent staining for alpha smooth muscle actin in tumor-associated fibroblasts in treated and untreated tumors (FIG. 23).

Figure 24A:
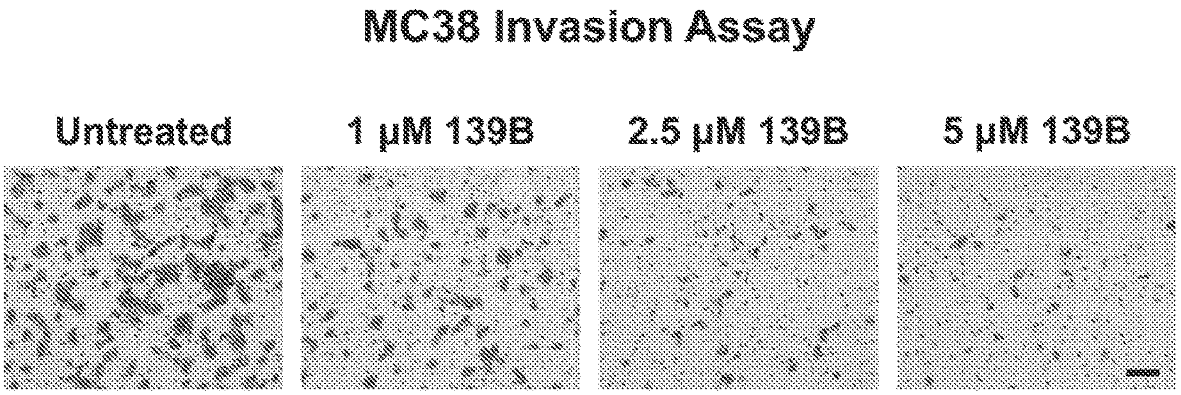
FIGS. 24A-24E show that AP-4-139B inhibits migration and invasion in vitro and metastasis in vivo.
Figure 24B:
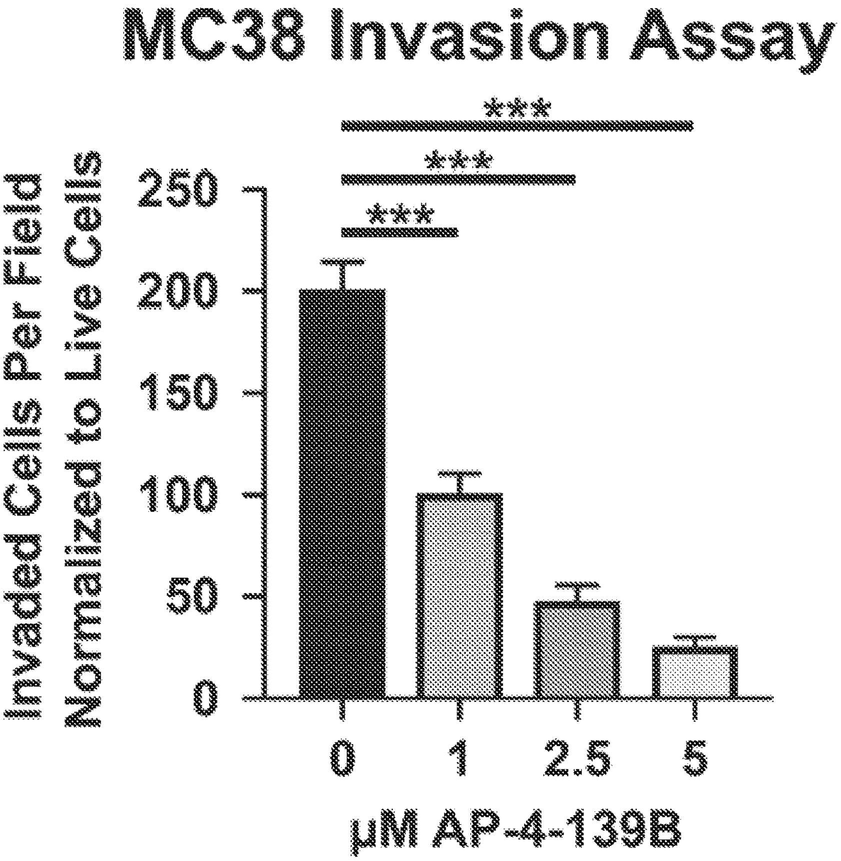
Figure 24C:
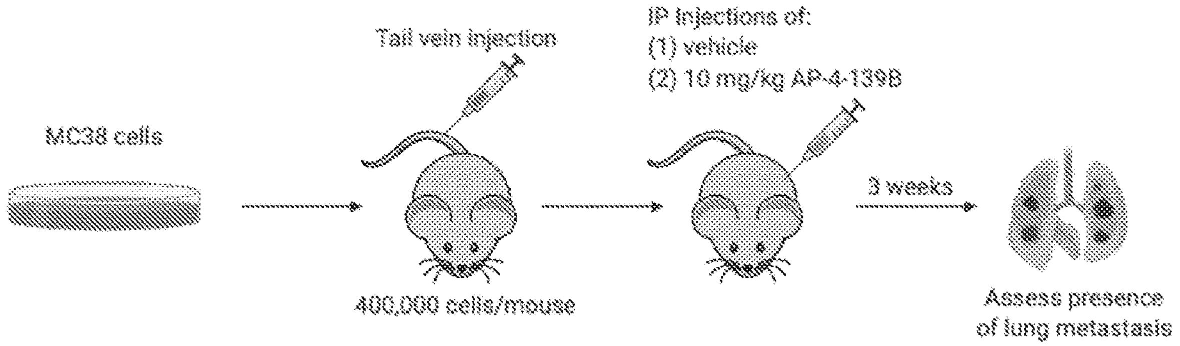
Figure 24D:
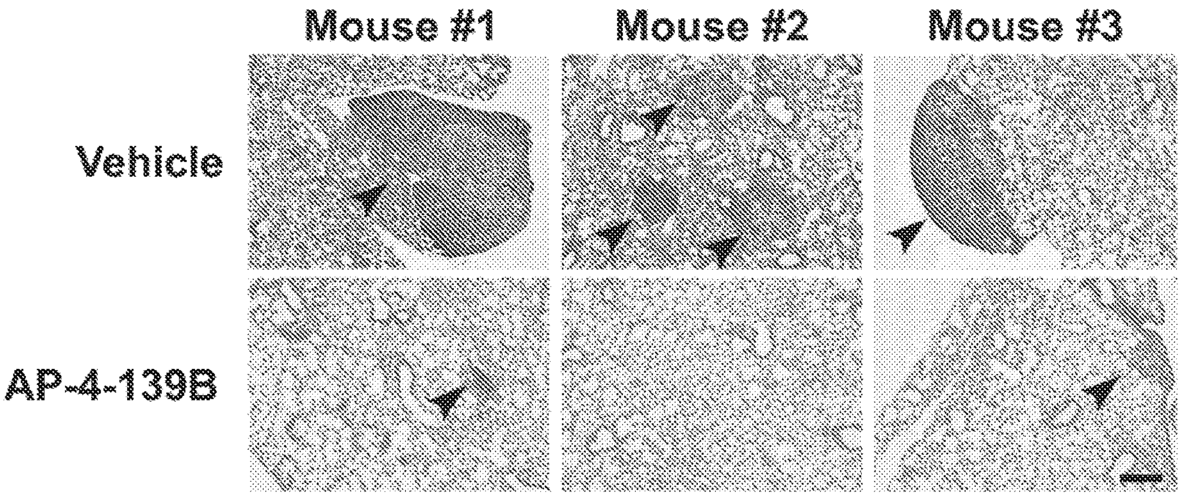
Figure 24E:
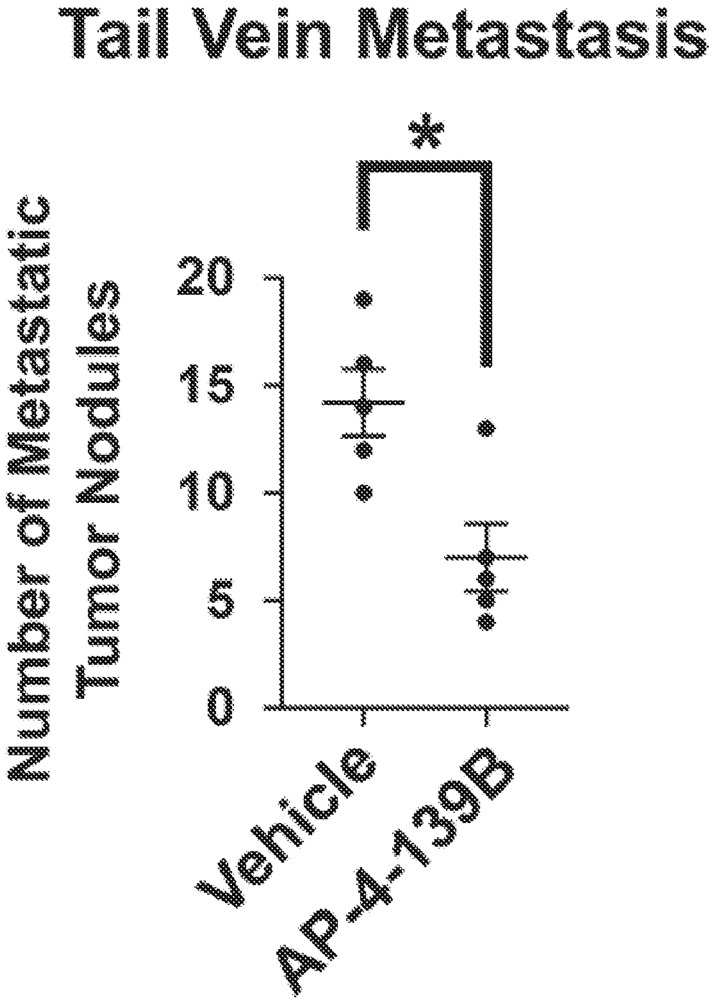

PET-16 inhibits melanoma invasion and metastasis. To address this in colorectal cancer, Boyden chamber invasion assays as well as in vivo metastasis assays were performed on the murine MC38 colorectal cancer line. It was found that low doses of AP-4-139B were sufficient to inhibit tumor cell migration and invasion (FIG. 24A). This inhibition was normalized to modest decreases in cell viability and was highly significant (FIG. 24B). Similarly, treatment of mice, in which MC38 cells were injected into the tail vein, with AP-4-139B led to markedly decreased number of tumor nodules in the lung (FIGS. 24C-24E). The combined data support the broad efficacy of AP-4-139B against colorectal cancer.

Figure 5A:
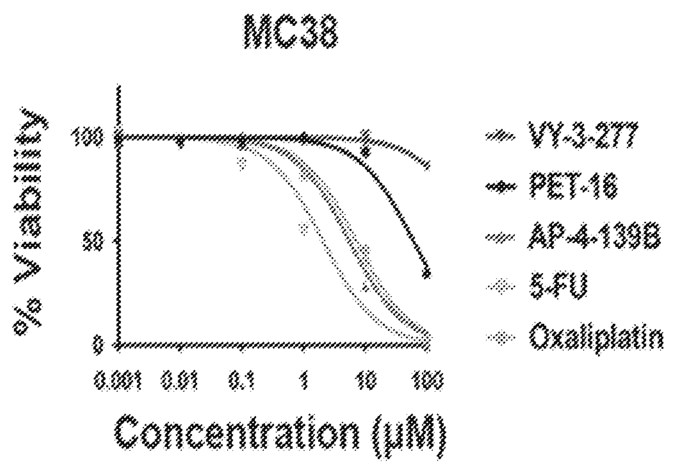
FIGS. 5A-5F show AP-4-139B is efficacious against CRC in an immunocompetent model, and causes immune cell recruitment.
Figure 5B:
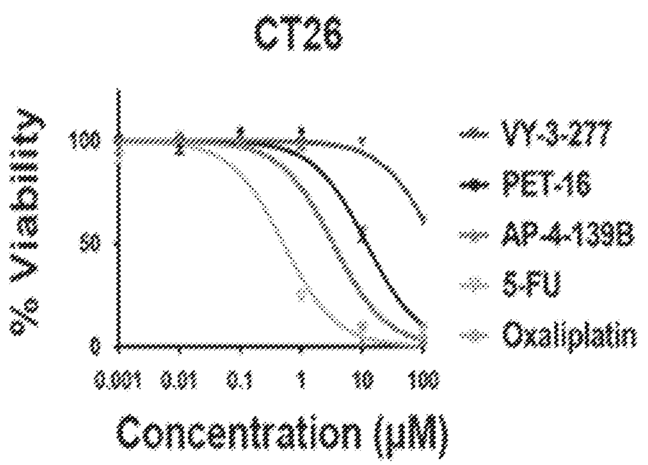
Figure 5C:
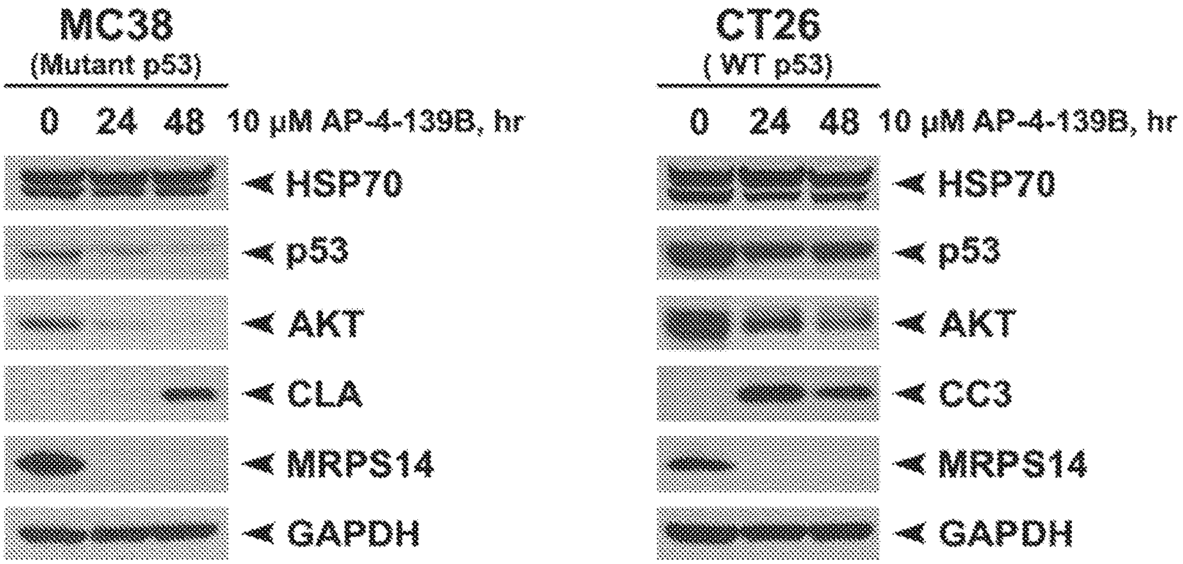
Figure 5D:
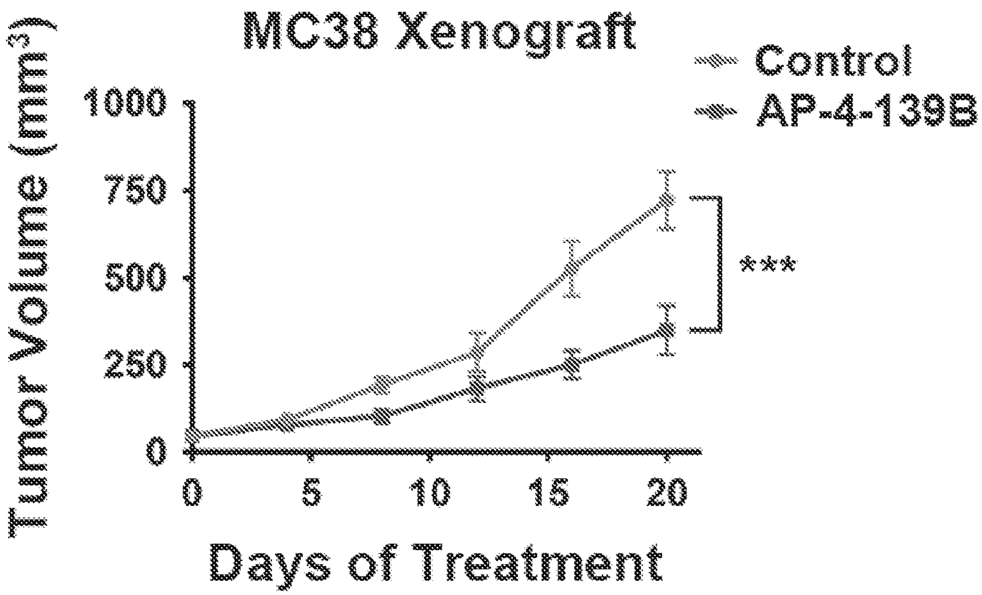
Figure 5E:
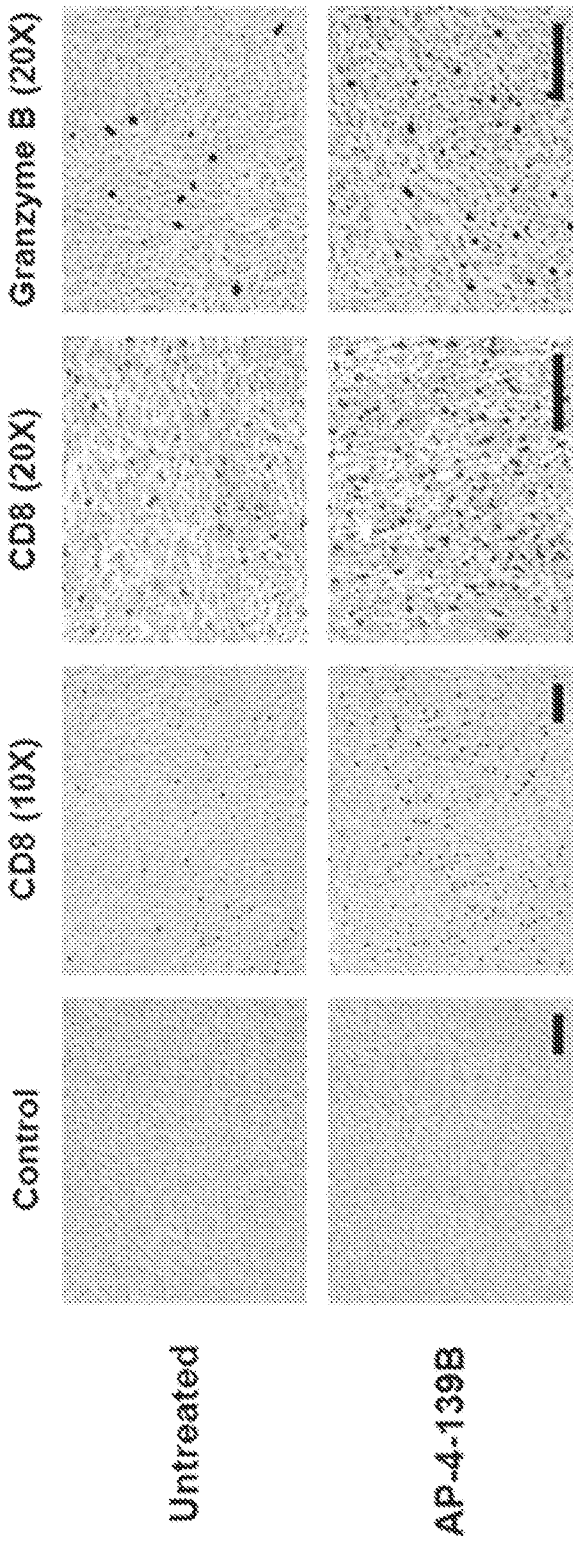
Figure 5F:
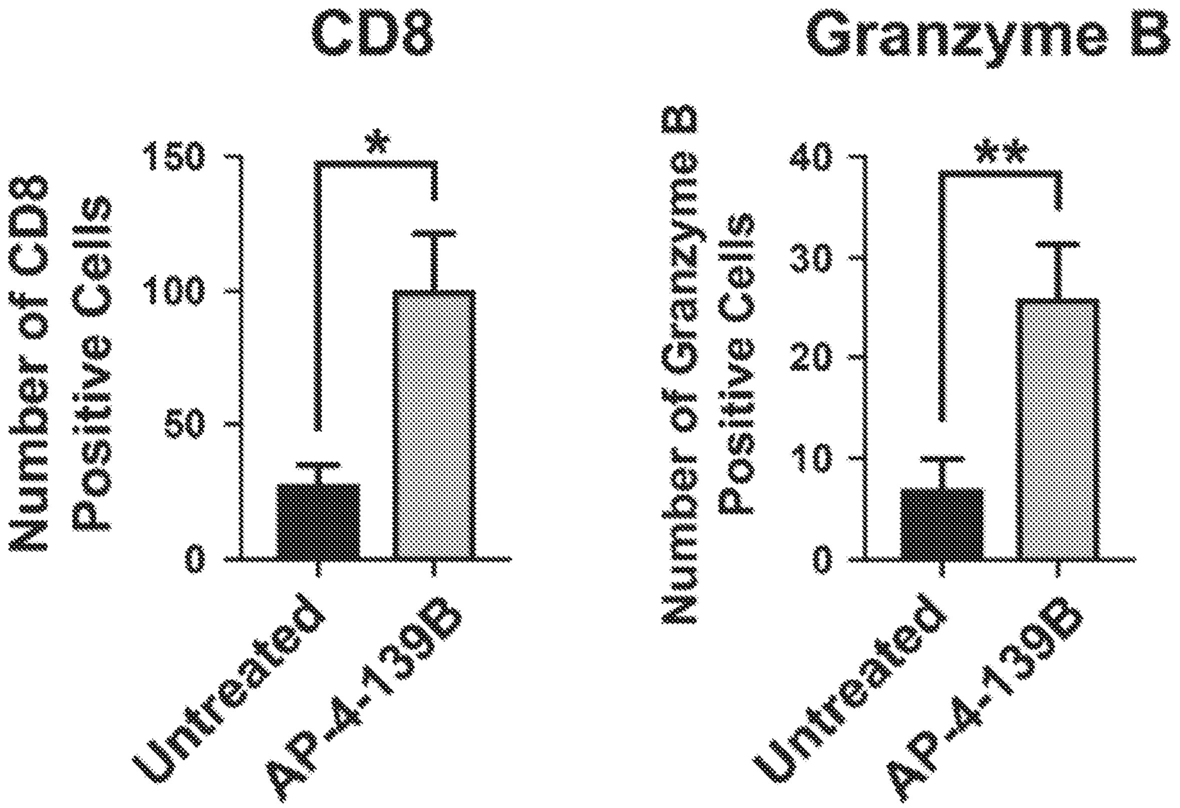
Figure 9A:
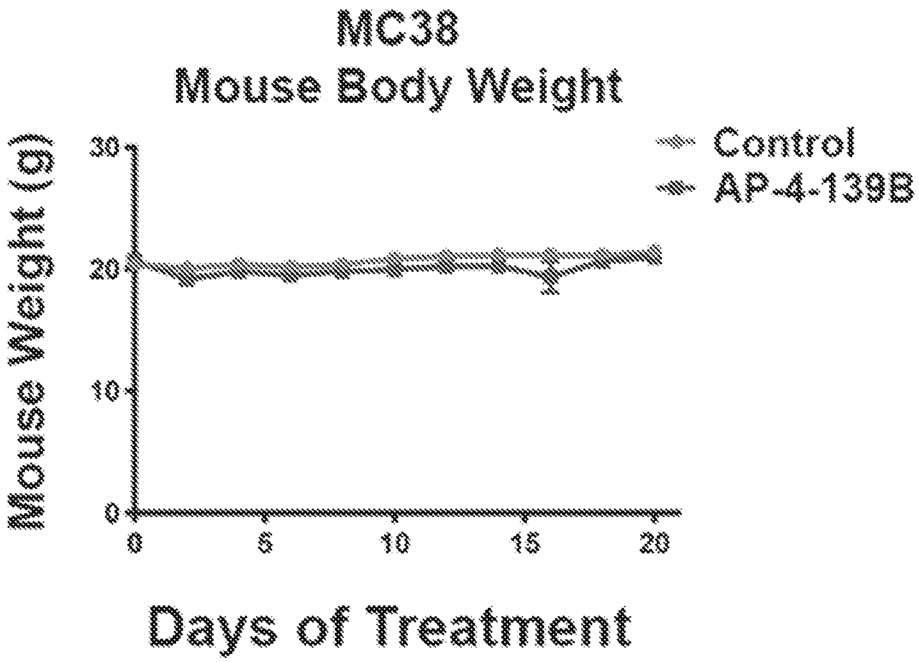
FIGS. 9A-9C show that HSP70 inhibition does not lead to toxicity in mice (as assessed by body weight) and leads to an increase in CD4 positive immune cell infiltrates in CRC tumors.
Figure 9B:
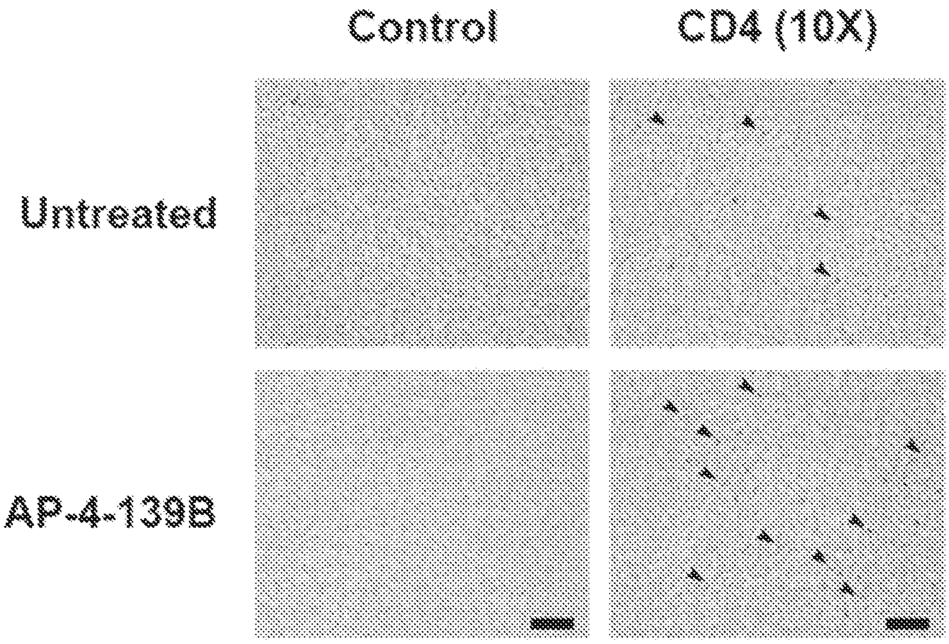
Figure 9C:
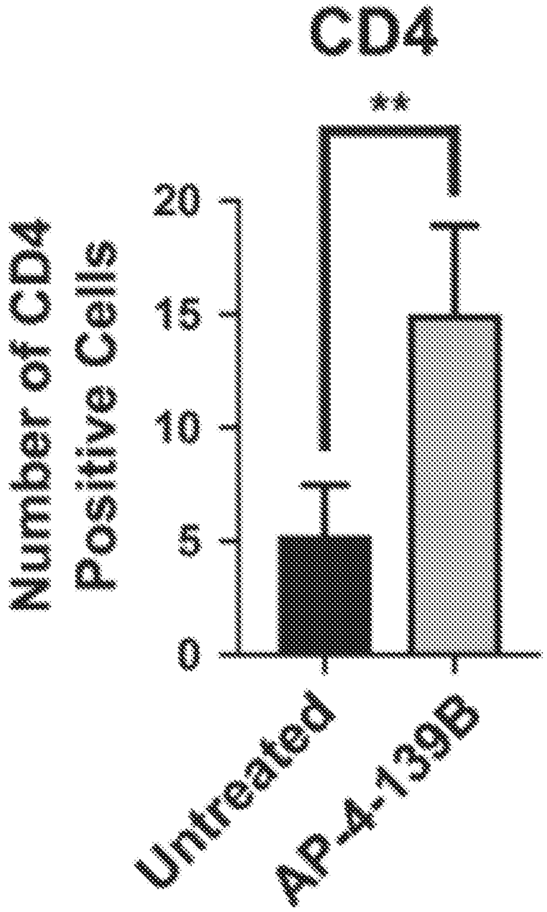

This work was extended to include immunocompetent models of murine CRC. First, it was found that AP-4-139B demonstrated comparable cytotoxicity in two murine CRC lines, MC38 and CT26, with $IC_{50}$s that were comparable to that of oxaliplatin (FIGS. 5A-5B). Studies described herein also showed that two clients, mutant p53 and MRPS14, exhibited decreased levels in treated MC38 cells (FIG. 5C). There was concomitant loss of HSP70 client proteins in these murine colorectal cancer lines (FIG. 5C). In a syngeneic model of MC38 tumors, AP-4-139B showed significant efficacy as a single agent ($p<0.001$, FIG. 5D), again with no evidence of weight loss in the mice throughout the course of treatment (FIG. 9A). Analysis of the histology of tumors from treated and untreated animals revealed what appeared to be increased infiltration of leukocytes in treated tumors. Immunohistochemical staining confirmed a large percentage of infiltrating $CD8^+$ T cells in treated tumors; this included many cells that were positive for Granzyme B, suggestive of activated T cells (FIGS. 5E-5F). An increase in CD4+ T cells in treated tumors was also noted (FIGS. 9B-9C). The combined data suggested that AP-4-139B treatment may enhance immune cell infiltration into tumors.

Example 4: Increased Immune Cell Infiltration Caused by AP-4-139B

Figure 10A:
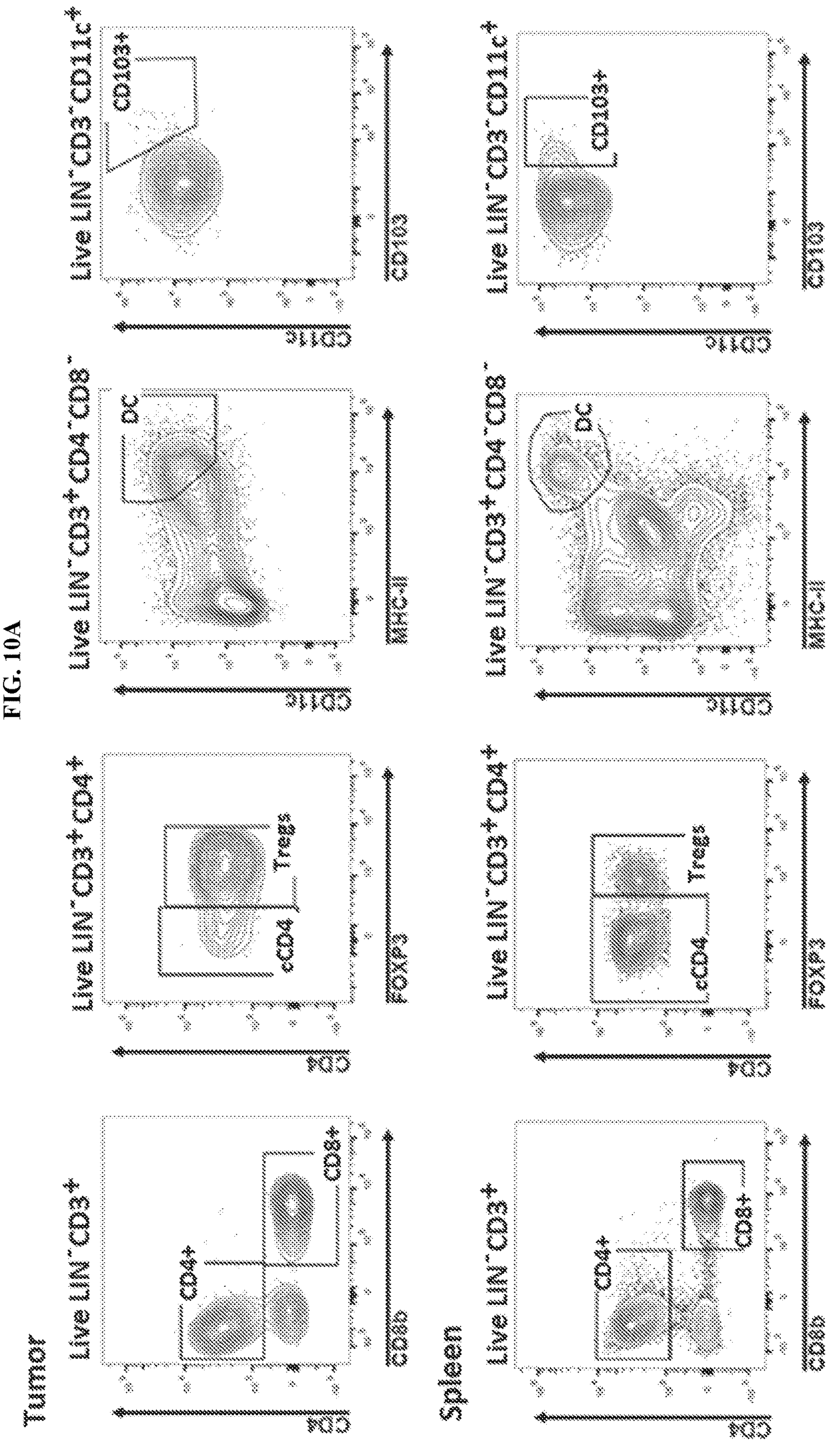
FIGS. 10A-10B show that HSP70 inhibition leads to an increase in immune cell infiltrates in CRC tumors and increased markers of immunogenic cell death.
Figure 10B:
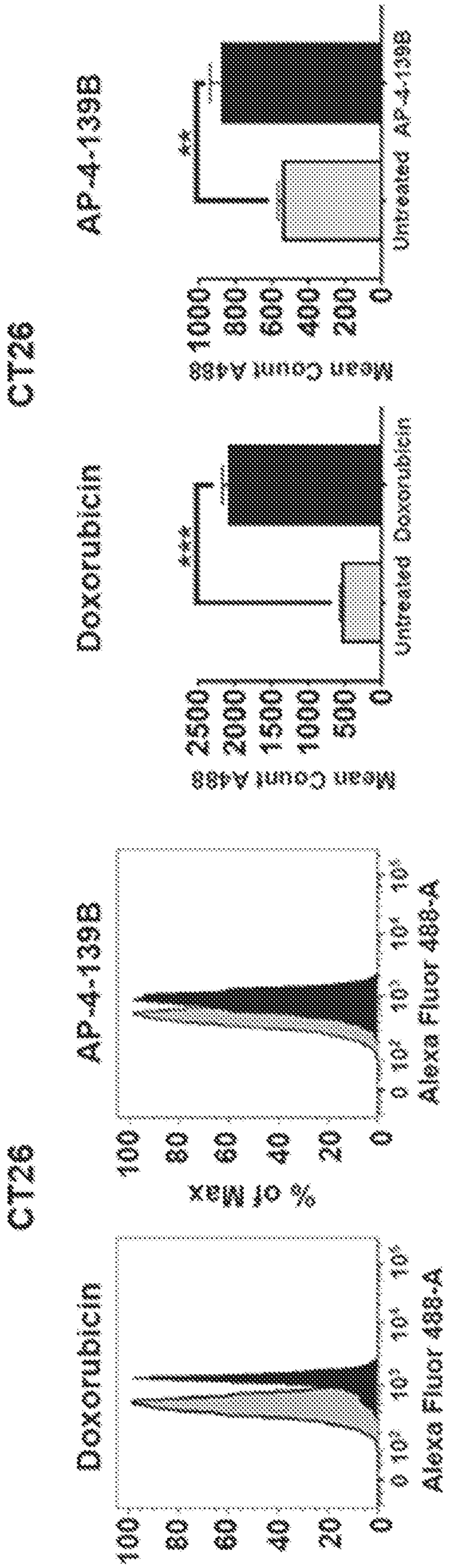

To follow up on findings described herein, flow cytometric immunophenotyping of MC38 tumors treated with vehicle or AP-4-139B was performed. The immunophenotyping gating strategy outlined (FIG. 10A) was used on treated and untreated tumors, and immune cell infiltrates were normalized to tumor weight. The immune cell populations from the tumors of treated and untreated mice was also compared to that of their spleens. These analyses revealed significantly increased immune cell infiltrates ($CD4^+$ T cell, $CD8^+$ T cell, dendritic cells, regulatory T cells (Tregs)) in tumors treated with AP-4-139B compared to vehicle control (FIG. 6A, FIGS. 27A-27D). There were no changes in abundance of these cell types in the spleens of treated mice (FIG. 6A bottom panels), suggesting that AP-4-139B does not alter immune cell populations, but rather induces immune cell infiltration into tumors.

The next studies sought to identify the potential mechanism underlying immune cell recruitment by AP-4-139B. It was reasoned was that one possibility might be that HSP70 inhibition causes release of Danger-Associated Molecular Patterns, or DAMPs, which would be predicted to lead to subsequent immune cell recruitment. To test this premise, three different assays for DAMP release/exposure were performed (Galluzzi et al., Nat Rev Immunol. 2017 February; 17(2):97-111; Zhou et al., J Cell Mol Med. 2019 August; 23(8):4854-4865). First, release of HMGB1 was assessed. Second, ATP release from treated cells was monitored. Third, flow cytometry with a fluorochrome-linked antibody to calreticulin was performed, to assay for the plasma membrane localization of this ER-stress protein. For each of these assays different concentrations of AP-4-139B were used, including one that was near the $IC_{50}$, as well as early timepoints including 3 and 8 hours, which are long before evidence of caspase cleavage and cell death. It was found that AP-4-139B reproducibly induced HMGB1 secretion (FIG. 6B), ATP release (FIG. 6C) and calreticulin mobilization to the plasma membrane (FIG. 6D; doxorubicin is positive control). The combined data support the premise that secretion of DAMPs by HSP70i-treated cells may be responsible for the observed immune cell recruitment in treated tumors.

The next studies sought to dissect the potential mechanism underlying DAMP secretion by AP-4-139B. Specifically, the next studies sought to determine whether chaperone inhibition or mitochondrio-toxicity was responsible for DAMP release. To address this issue, ATP release assays in cells treated with AP-4-139B were performed, and this HSP70i was compared to three other compounds: the HSP90 inhibitor 17-AAG, which functions as a chaperone inhibitor, and the compound metformin, which is a complex I inhibitor that compromises mitochondrial function. The compound Gamitrinib (G-TPP) was also analyzed, which is an HSP90 inhibitor that exclusively localizes to the mitochondria and is mitochondrio-toxic (Kang et al., J Clin Invest. 2009 March; 119 (3): 454-64). In order to eliminate interference from cell death, multiple concentrations of these compounds were used, and cells were analyzed after 3 hours. In this assay, AP-4-139B caused the most significant release of ATP in treated cells, particularly at the highest doses (FIG. 6E). Both the HSP90 inhibitor 17-AAG, and the complex I inhibitor metformin, also induced ATP release, albeit to a lesser extent. The mitochondrio-toxic compound G-TPP also showed activity in this assay (FIG. 6E). These data suggest the both the chaperone inhibition and the mitochondrial toxicity induced by AP-4-139B are likely contributing to DAMP release.

Figure 25A:
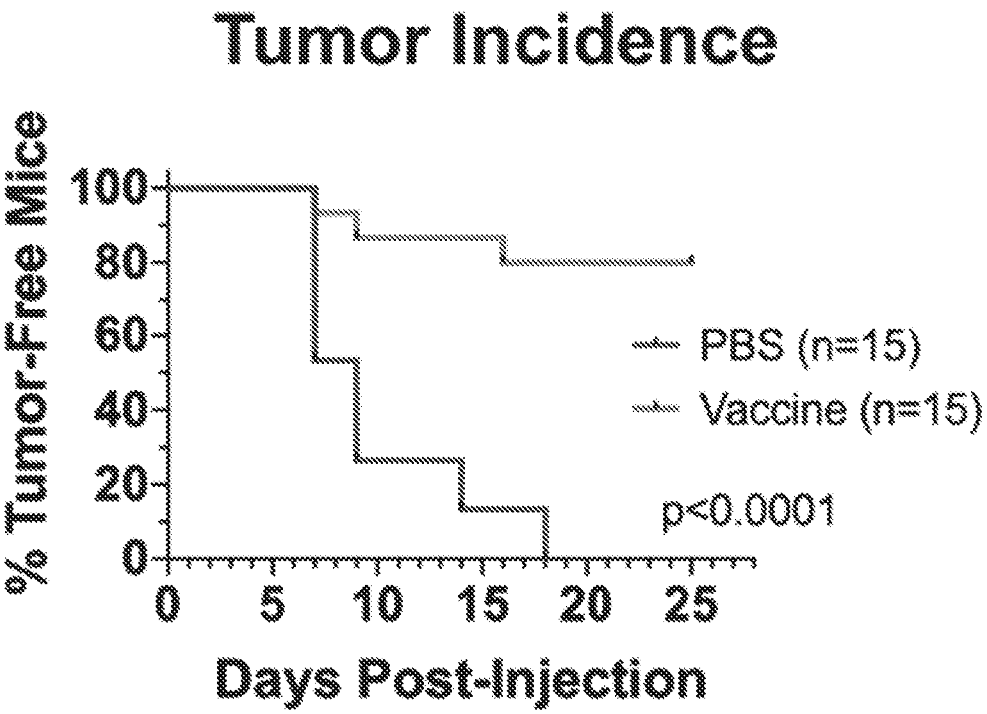
FIGS. 25A-25B show that AP-4-139B-treated cells function as a tumor vaccine.
Figure 25B:
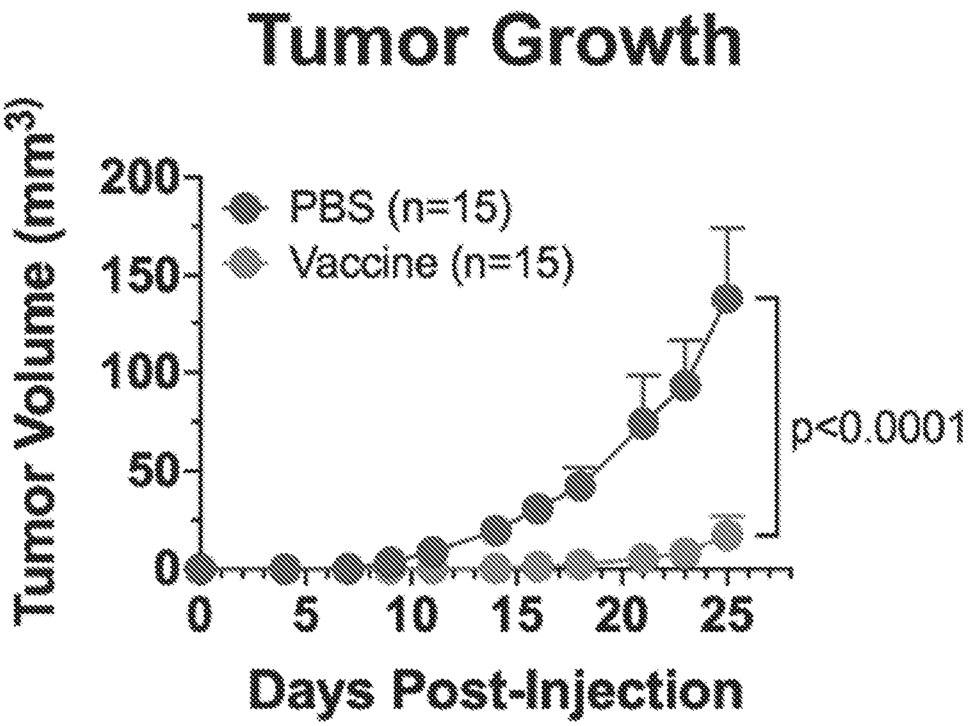

The gold-standard assay for immunogenic cell death is the ability of treated cells to serve as an effective tumor vaccine; such has been seen for another HSP70i (Schmitt, E. et al., Cancer Res., 2006, 66:4191-4197). To test this premise, either vehicle or 139B-treated MC38 cells were injected into the left flank of mice, and then 10 days later, untreated MC38 cells were injected into the right flank. Tumor incidence and the size of tumors on the right flank were then compared. Only 3 of 15 mice developed tumors in the vaccine-treated mice, compared with 15 of 15 in the control (FIG. 25A; $P<0.0001$). Consistent with this, tumor size in vaccine-treated mice was markedly reduced compared with control (FIG. 25B). The combined data support the premise that AP-4-139B is capable of inducing immunogenic cell death in vivo.

Example 5: Combination Studies with BRAF Inhibitor and MEK Inhibitor

Combination studies were performed with AP-4-139B and a BRAF inhibitor (TRAM, TRAM-34, or Vemurafenib) or a MEK inhibitor (PD0325901 or Mirdametinib).

In drug combination effect analysis for each two drug combination, a contour plot was generated (color from white to red indicates the trend of synergistic effect) [Zhao et al., 2014, Journal of Biomolecular Screening 19(5):817-821]. To evaluate if there is an overall significant synergistic effect and at which dose levels the combination would reach significant synergistic effect, Interaction indexesa with 95% confidence intervals were calculated at various doses of each studied drug when combined with the other drug (Interaction index<1 indicates synergistic effect, the vertical bar below the line of 1.0 indicates significant synergistic effect) [Liu et al., 2018, Statistics in Biopharmaceutical Research, DOI: 10.1080/19466315.2018.1437071.]

Figure 11:
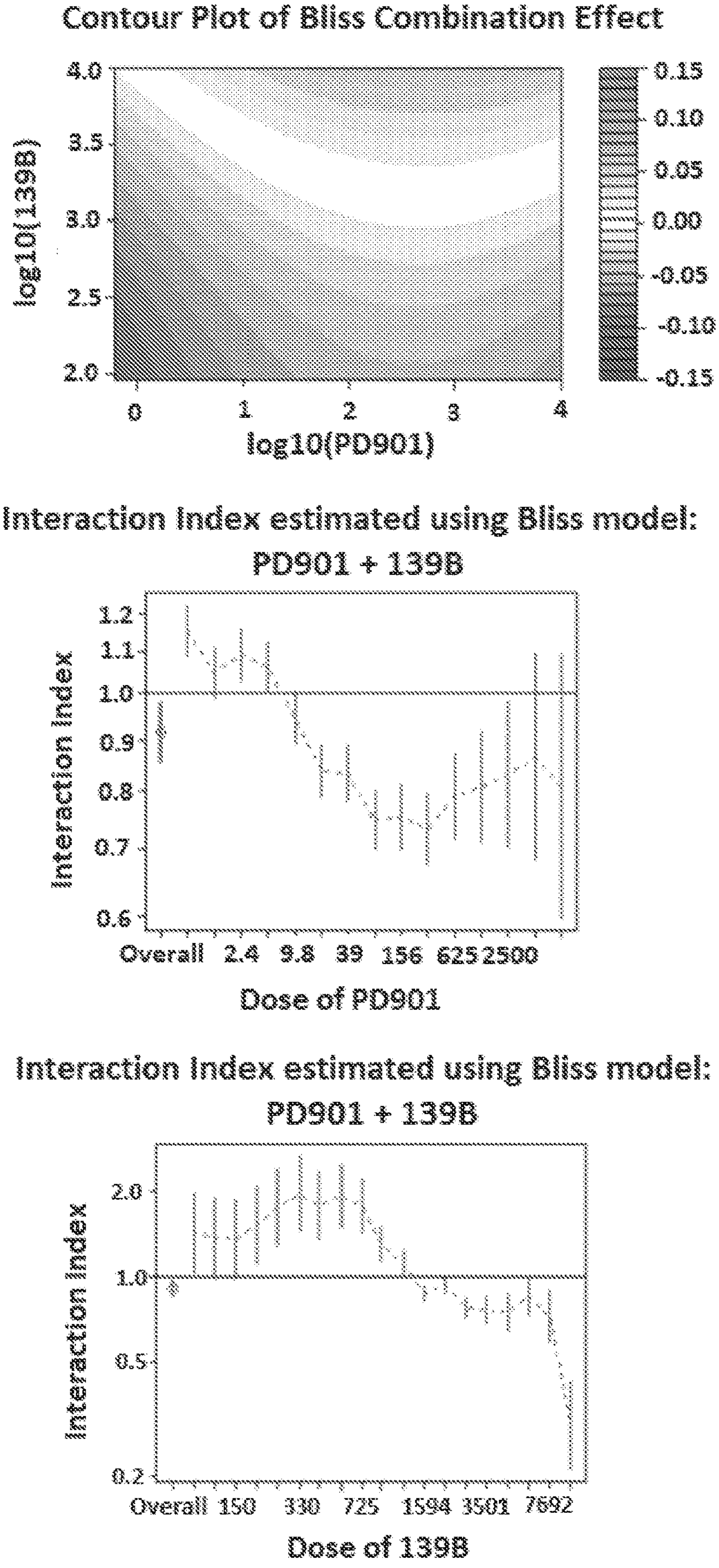
FIG. 11 illustrates combination studies of Mirdametinib (MEK inhibitor) and AP-4-139B.

The combination of Mirdametinib and AP-4-139B has significant synergistic effect (overall interaction index=0.91, 95% confidence interval 0.86-0.98). A strong synergistic effect was seen mainly in the dose range of Mirdametinib at 9.8-2,500 nM combined with AP-4-139B ≥1,594 nM. See FIG. 11.

Figure 12:
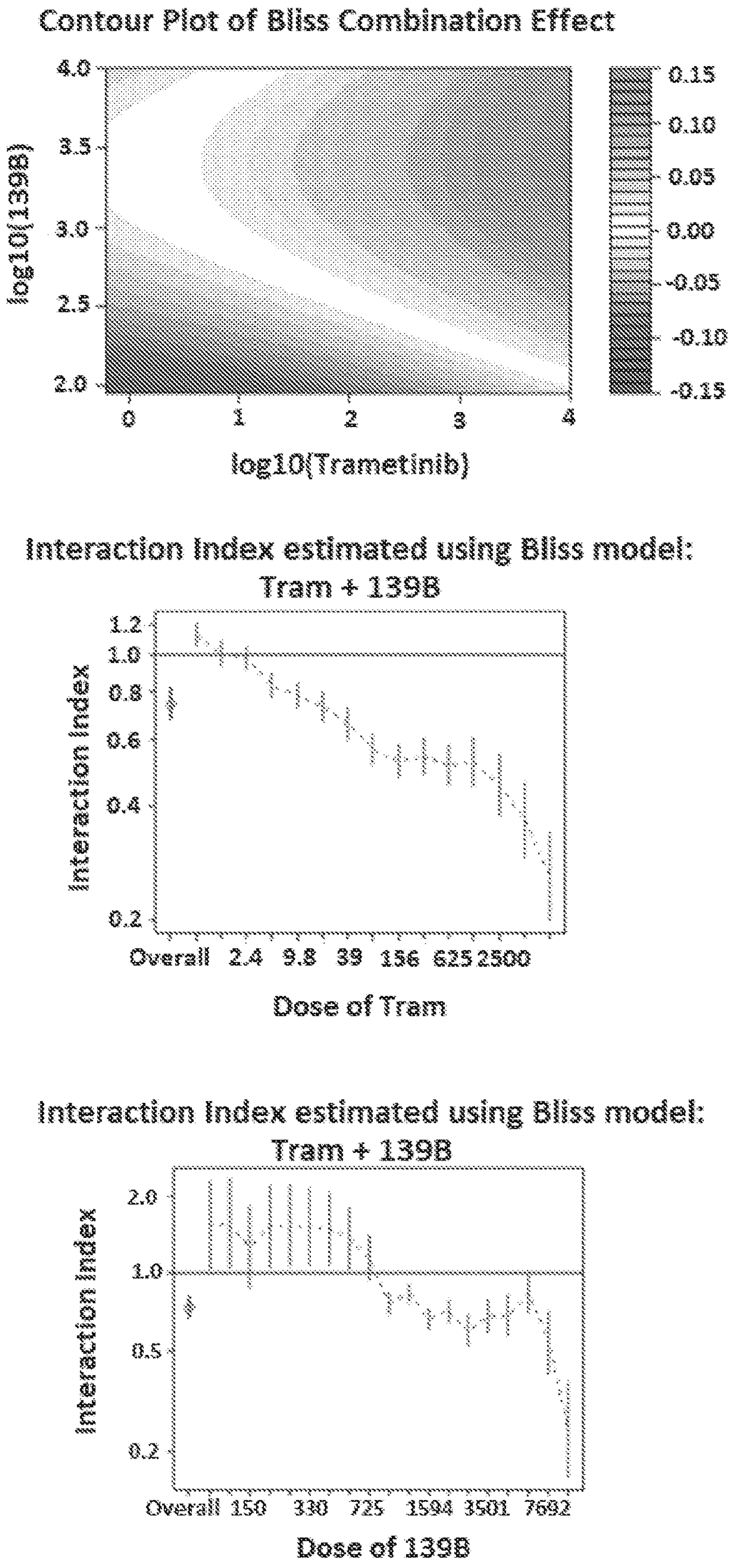
FIG. 12 illustrates combination studies of Vemurafenib (BRAF inhibitor) and AP-4-139B.

The combination of Vemurafenib and AP-4-139B has significant synergistic effect (overall interaction index=0.74, 95% confidence interval 0.68-0.81). A strong synergistic effect was seen mainly in the dose range of Vemurafenib ≥4.9 nM combined with AP-4-139B≥943 nM. See FIG. 12.

Figure 13:
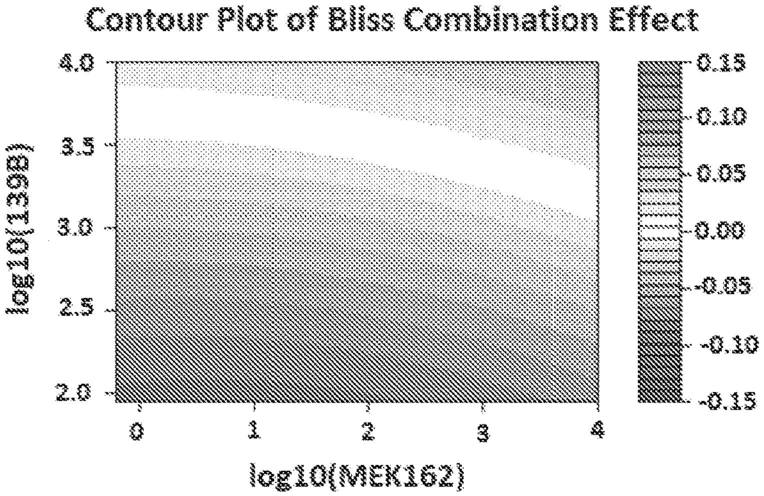
FIG. 13 illustrates combination studies of Binimetinib (MEK inhibitor) and AP-4-139B.
Figure 13:
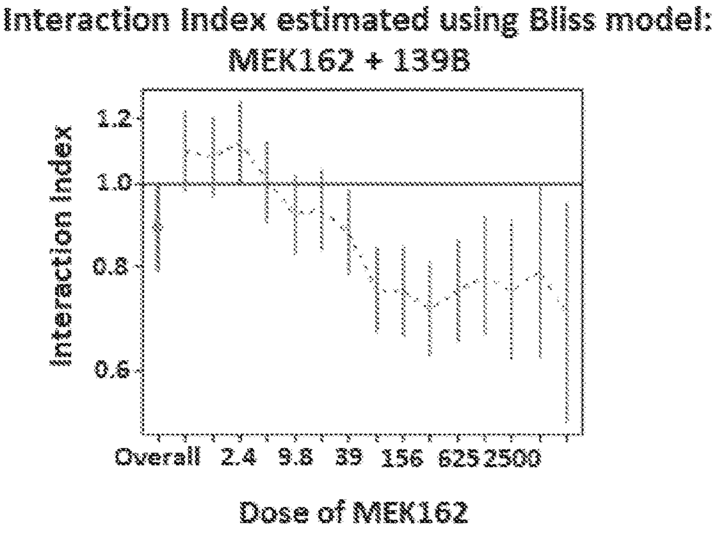
Figure 13:
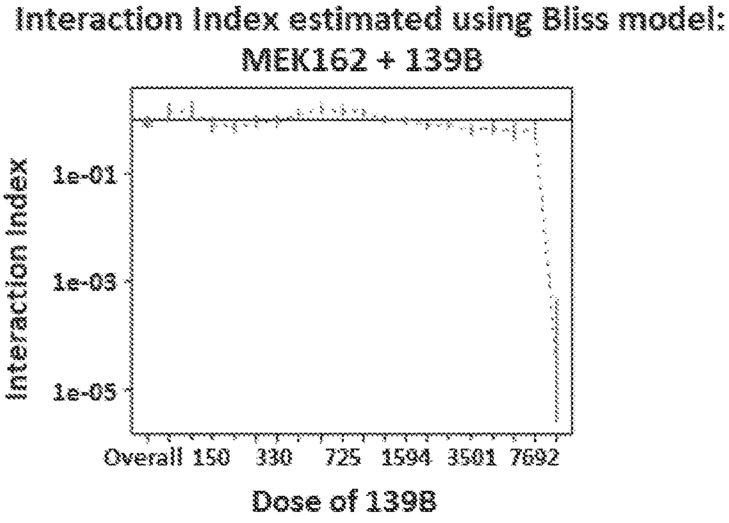

The combination of binimetinib and AP-4-139B has synergistic effect (overall interaction index=0.89, 95% confidence interval 0.79-1.00). A strong synergistic effect was seen mainly in the dose range of binimetinib ≥39 nM combined with AP-4-139B>2,693 nM. See FIG. 13.

Overall, all the tested combinations show significant synergistic effect.

Figure 14:
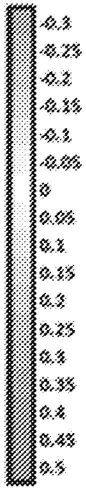
FIG. 14 shows synergy of AP-4-139B with BRAF inhibitor Vemurafenib. Red: evidence of synergy.

FIG. 14 shows that the BRAF inhibitor Vemurafenib synergizes with AP-4-139B in cultured CRC cell lines (RKO and LS411N).

Example 5: Xenograph Results

Figure 15:
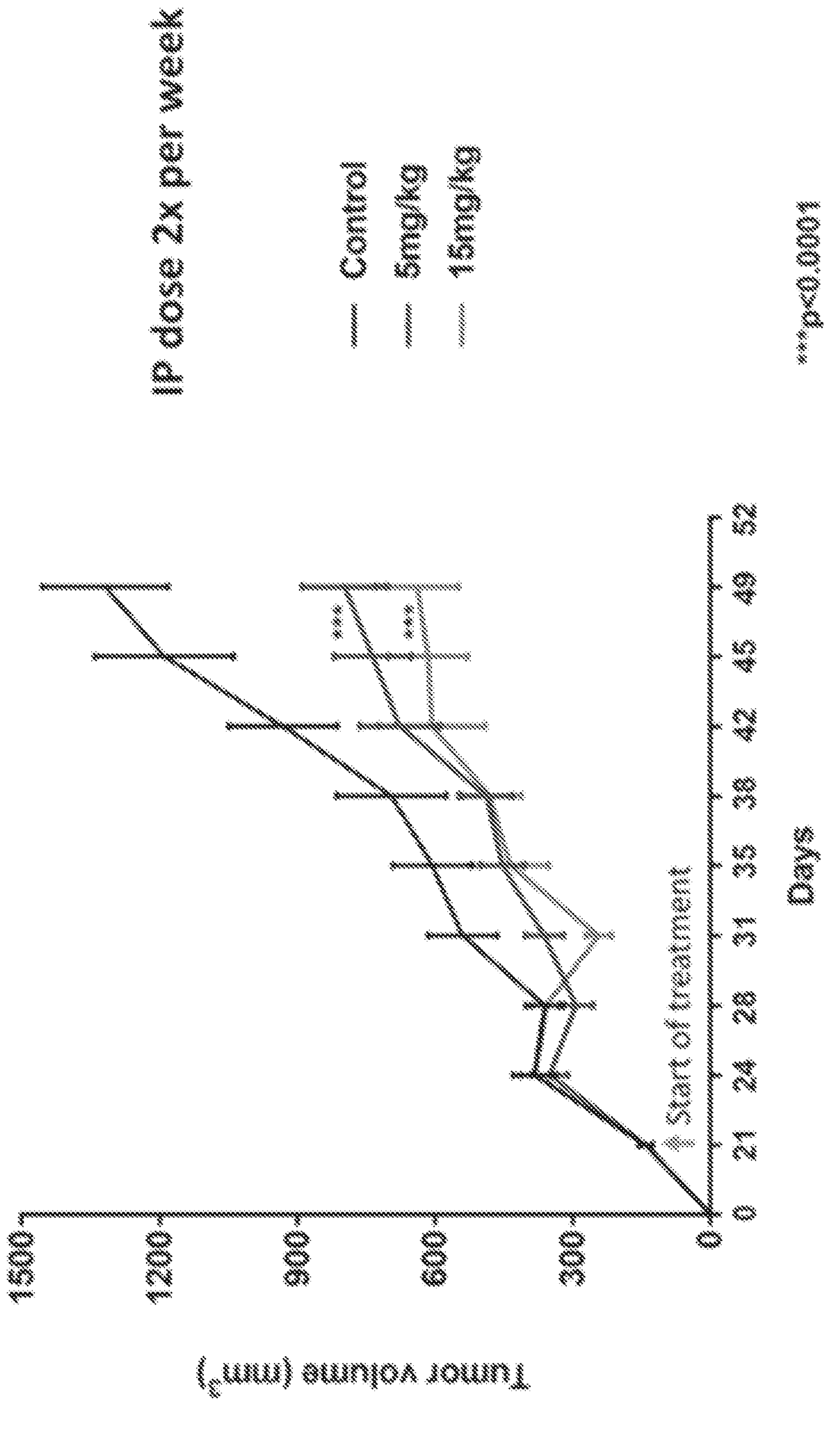
FIG. 15 shows that AP-4-139B is efficacious as a single agent in inhibiting tumor growth in a 1205LU melanoma xenograph in mice. 1205LU melanoma xenografts in NSG mice were established. When tumors reached 100 $mm^3$ in volume, mice were treated twice per week with the i.p. doses of AP-4-139B indicated.
Figure 16:
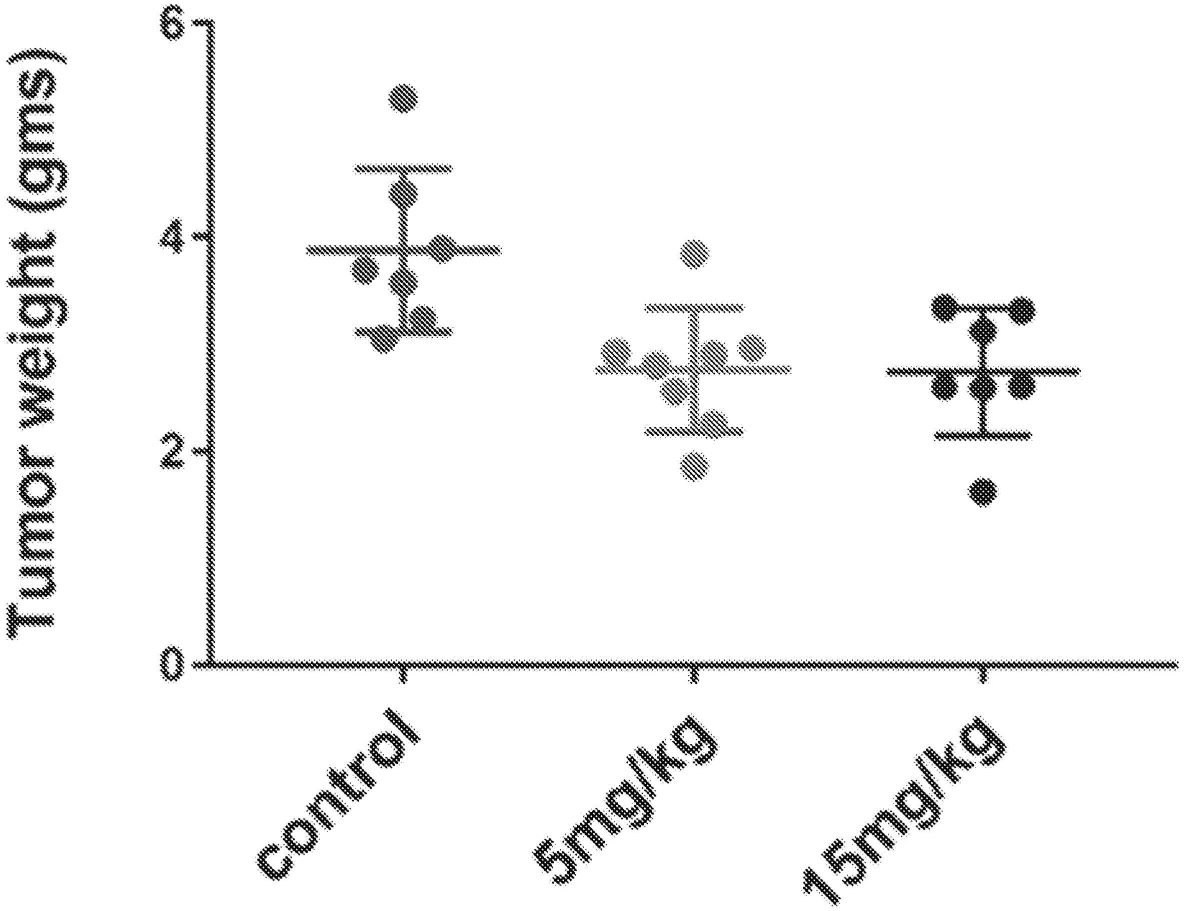
FIG. 16 shows that AP-4-139B is efficacious as a single agent in reducing tumor weight in a 1205Lu melanoma xenograph in mice.

AP-4-139B was tested as a single agent in a 1205Lu melanoma xenograph in mice. 1205LU melanoma xenografts in NSG mice were established. When tumors reached 100 $mm^3$ in volume, mice were treated twice per week with the i.p. doses of AP-4-139B indicated. AP-4-139B was found to inhibit tumor growth (FIG. 15) and reduce tumor weight (FIG. 16) in that model.

Figure 17:
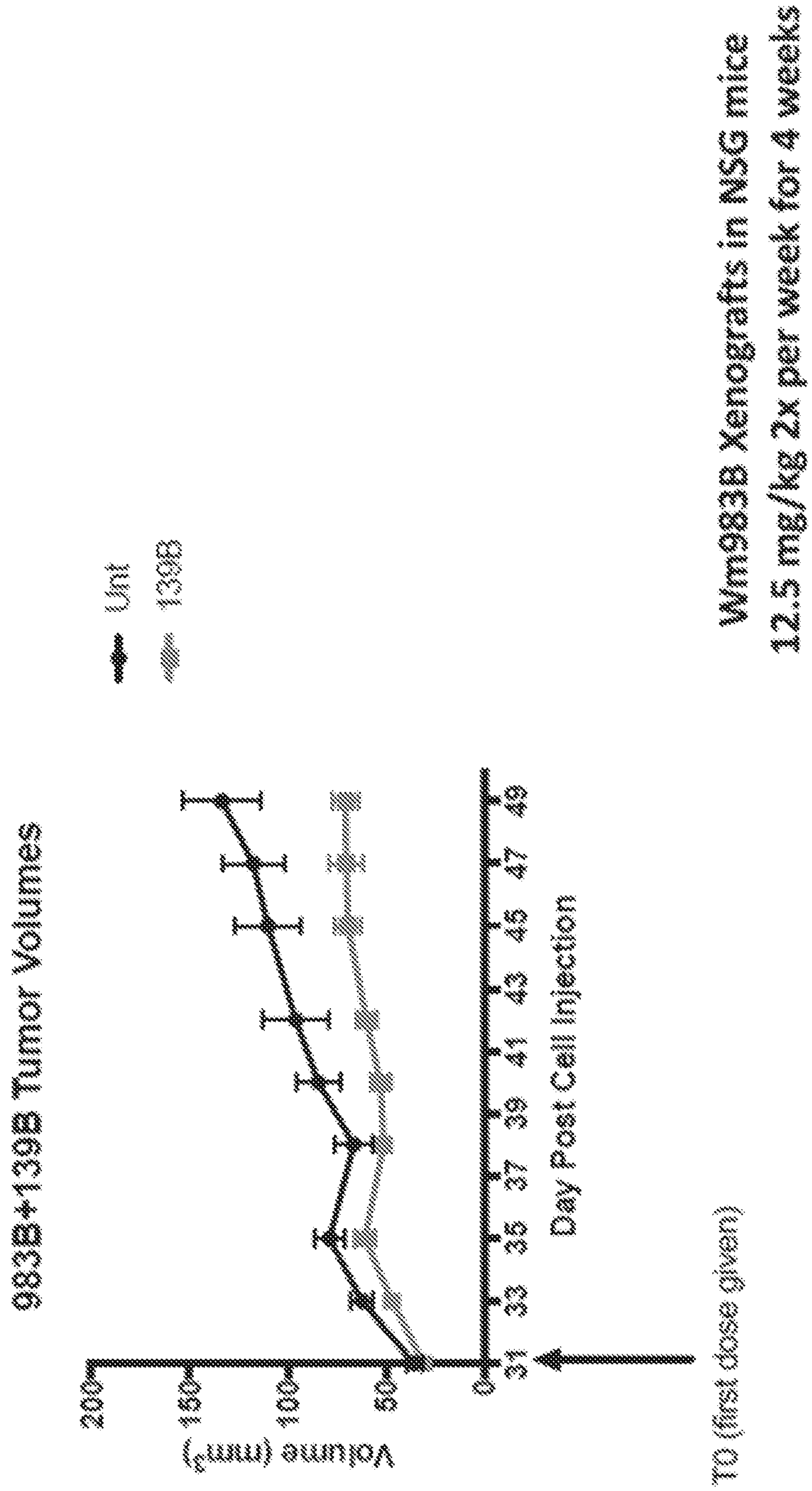
FIG. 17 shows that AP-4-139B is efficacious as a single agent in inhibiting tumor growth in a WM983B melanoma xenograph in mice. WM983B tumor xenografts were established in NSG mice. When tumors reached 50 $mm^3$, mice were treated with i.p. doses of AP-4-139B at 12.5 mg/kg twice per week. Tumors were collected at the end of the experiment and assessed for the level of the client protein MRPS14.
Figure 18:
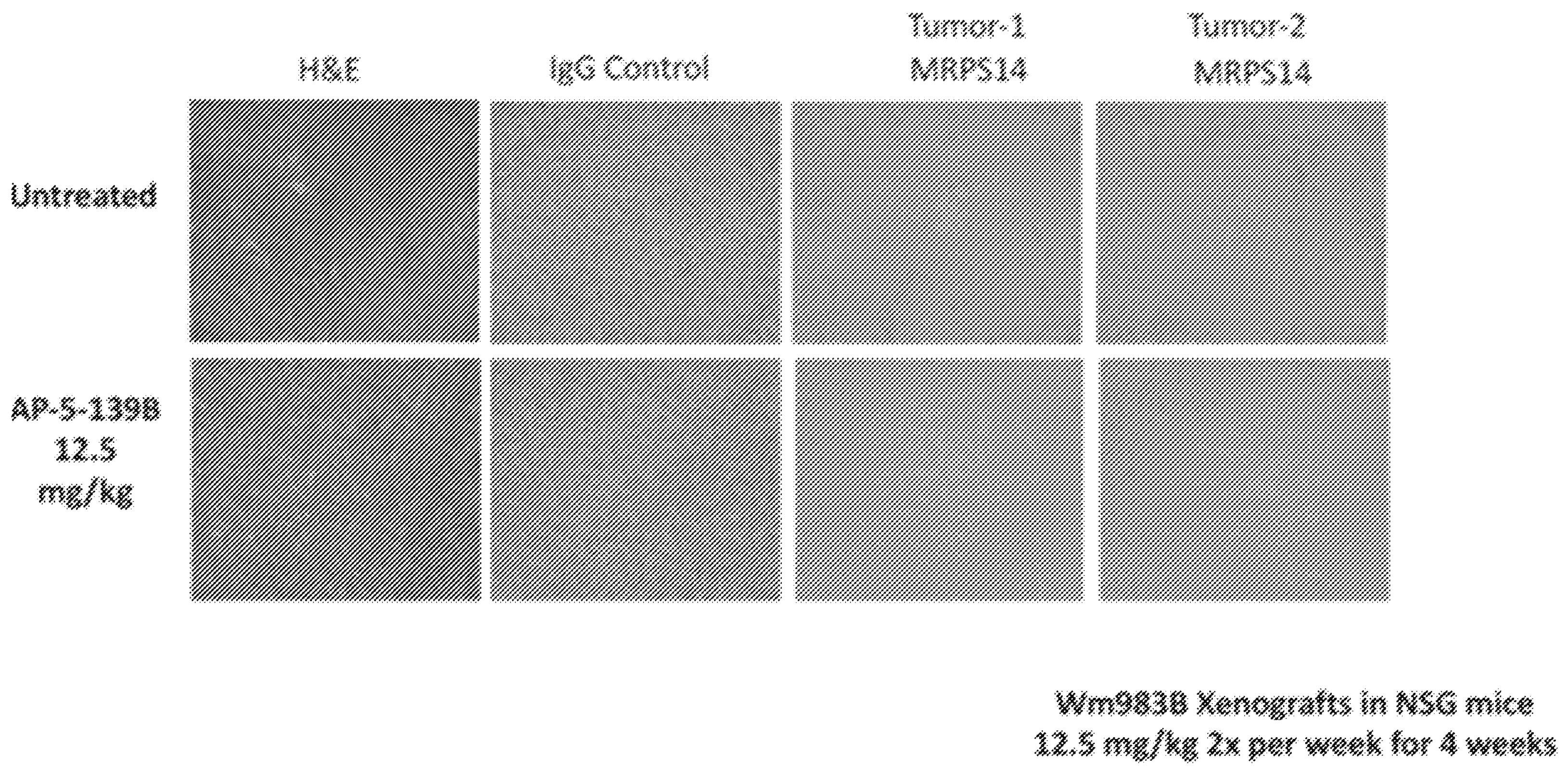
FIG. 18 comprises a series of images illustrating IHC of WM983B treated tumors using IgG negative control or antisera to MRPS14t. Tumors treated with AP-5-139B lose mitochondrial protein MPS14.
Figure 19:
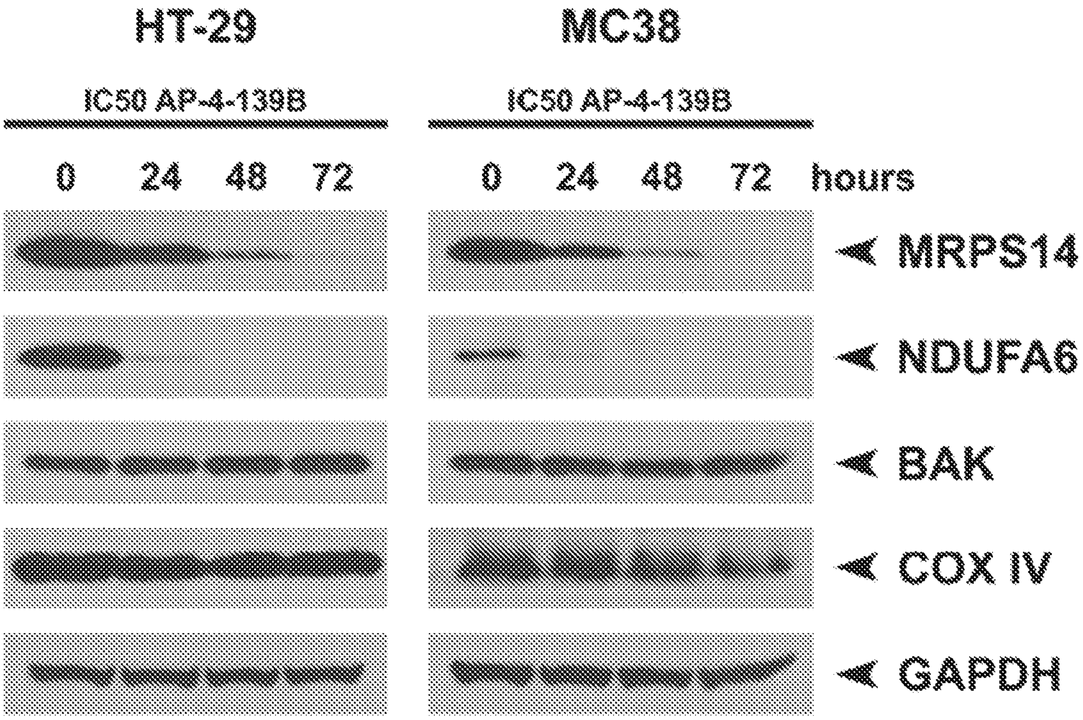
FIG. 19 shows HT-29 and MC38 cells that were treated with the respective $IC_{50}$ of AP-4-139B for the indicated time points. Cell lysates were subjected to Western blot analysis, and immunoblotted for MRPS14, NDUFA6, BAK, COXIV, and GAPDH (loading control).
Figure 20B:
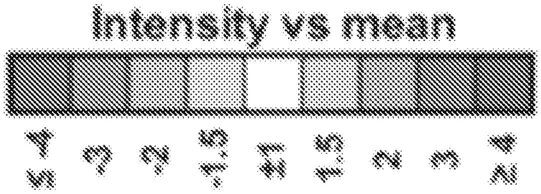

AP-4-139B was tested as a single agent in a WM983B melanoma xenograph in mice. WM983B tumor xenografts were established in NSG mice. When tumors reached 50 $mm^3$, mice were treated with i.p. doses of AP-4-139B at 12.5 mg/kg twice per week. Tumors were collected at the end of the experiment and assessed for the level of the client protein MRPS14. AP-4-139B was found to inhibit tumor growth (FIG. 17) in that model. Further, those tumors treated with AP-5-139B were found to lose mitochondrial protein MPS14 (FIG. 18).

Example 6: Synthesis

All reactions were conducted under an inert gas atmosphere (nitrogen or argon) using a Teflon-coated magnetic stir bar at the temperature indicated. Commercial reagents and anhydrous solvents were used without further purification. Removal of solvents was conducted by using a rotary evaporator, and residual solvent was removed from nonvolatile compounds using a vacuum manifold maintained at approximately 1 Torr. All yields reported are isolated yields.

Preparative reversed-phase high pressure liquid chromatography (RP-HPLC) was performed using a Gilson GX-271 semi-prep HPLC, eluting with a binary solvent system A and B using a gradient elusion (A, $H_2O$ with 0.1% trifluoroacetic acid (TFA); B, $CH_3CN$ with 0.1% TFA) with UV detection at 220 nm.

Low-resolution mass spectral (MS) data were determined on an Water Acquity QDa LCMS mass spectrometer with UV detection at 254 nm. $^1H$ NMR spectra were obtained on a Bruker Avance II 400 (400 MHz) spectrometer. Chemical shifts (δ) are reported in parts per million (ppm) relative to residual undeuterated solvent as an internal reference. The following abbreviations were used to explain the multiplicities: s=single; d=doublet, t=triplet, q=quartet, dd=doublet of doublets, dt=doublet of triplets, m=multiplet, br=broad.

Triphenyl(phenylethynyl)phosphonium bromide (PET-16; AP-1-54)

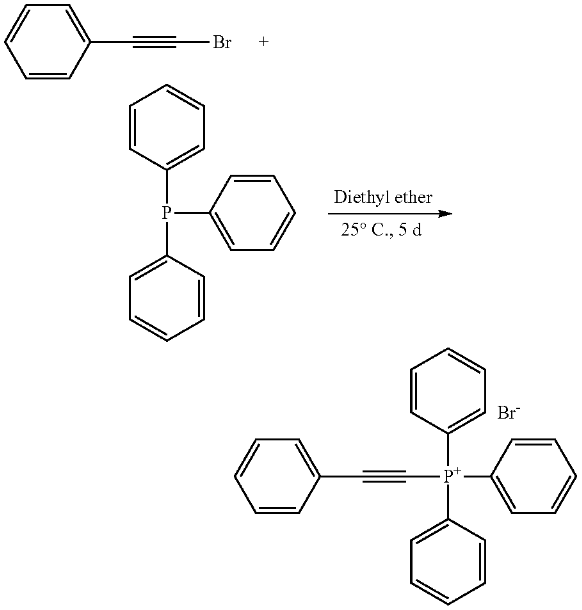

To a stirred solution of triphenylphosphine (2.913 g, 11.11 mmol) in diethyl ether (50 mL) was added (bromoethynyl) benzene (2.0 g, 11.11 mmol) slowly at room temperature and the reaction mixture was stirred for 5d at room temperature (RT) under a nitrogen atmosphere. The resulting precipitate was filtered off and washed with diethyl ether, then dried under high vacuum to afford the title compound (3.929 g, 8.89 mmol) as a white solid. The product was confirmed by $^1H$ NMR and mass spectrometry. $^1H$ NMR (400 MHz, $CDCl_3$) δ 7.99-7.90 (m, 3H), 7.90-7.79 (m, 14H), 7.66 (t, J=7.6 Hz, 1H), 7.55 (t, J=7.7 Hz, 2H). Mass m/z: calcd for $[C_{26}H_{20}P]^+$ $[M]^+$, 363.13; found, 363.22.

((6-Methoxynaphthalen-2-yl)ethynyl)triphenylphosphonium bromide (AP-3-49)

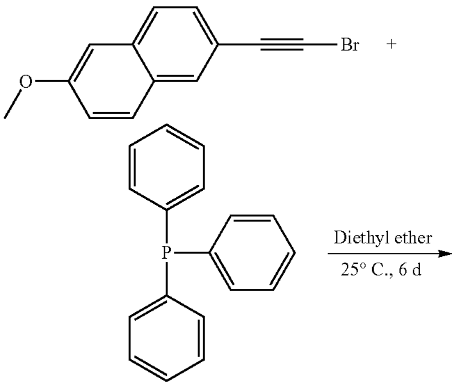

-continued

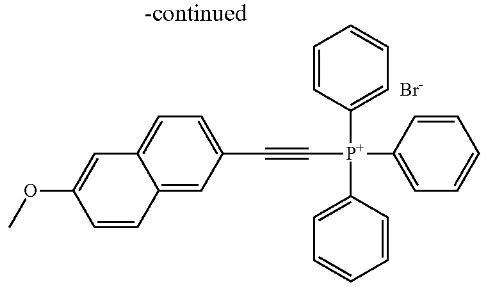

To a stirred solution of triphenylphosphine (0.1 g, 0.38 mmol) in diethyl ether (5 mL) was added 2-(bromoethynyl)-6-methoxynaphthalene (0.101 g, 0.38 mmol) slowly at room temperature and the reaction mixture was stirred for 5d at RT under a nitrogen atmosphere. The resulting precipitate was filtered off and washed with diethyl ether, then dried under high vacuum to afford the title compound (0.13 g, 0.25 mmol) as a white solid. The product was confirmed by $^1$H NMR and mass spectrometry. $^1$H NMR (400 MHz, $CDCl_3$) δ 8.48 (s, 2H), 8.01-7.77 (m, 28H), 7.75-7.59 (m, 3H), 7.37-7.05 (m, 6H), 3.95 (d, J=15.9 Hz, 5H). Mass m/z: calcd for $[C_{31}H_{24}OP]^+$ $[M]^+$, 443.16; found, 443.39.

((3-Fluorophenyl)ethynyl)triphenylphosphonium bromide (AP-3-48)

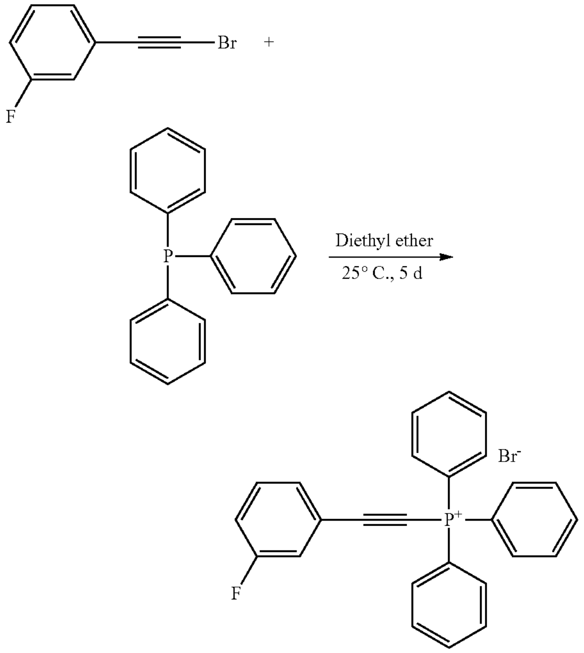

To a stirred solution of triphenylphosphine (0.1 g, 0.51 mmol) in diethyl ether (5 mL) was added 2-(bromoethynyl)-6-methoxynaphthalene (0.133 g, 0.51 mmol) slowly at room temperature and the reaction mixture was stirred for 5d at RT under a nitrogen atmosphere. The resulting precipitate was filtered off and washed with diethyl ether and dried under high vacuum to afford the title compound (0.191 g, 0.41 mmol) as a white colored solid. The product was confirmed by $^1$H NMR and LC-MS. $^1$H NMR (400 MHz, $CDCl_3$) δ 8.00-7.77 (m, 16H), 7.58 (ddd, J=17.3, 15.0, 9.4 Hz, 2H), 7.35 (td, J=8.4, 2.4 Hz, 1H). Mass m/z: calcd for $[C_{26}H_{19}FP]^+$ $[M]^+$, 381.12; found, 381.37.

1-Phenyl-2-(piperidin-1-ylsulfonyl)ethenone

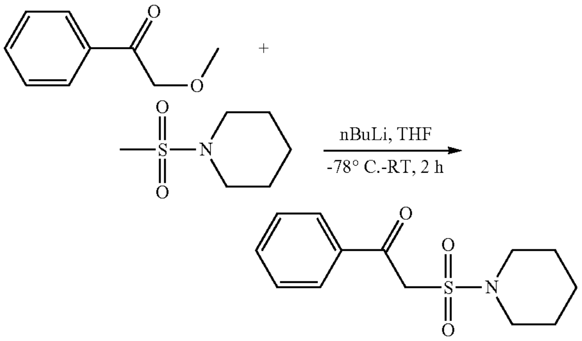

To a stirred solution of 1-(methylsulfonyl)piperidine (1.0 g, 6.16 mmol) in anhydrous THF (30 mL) at −78° C. under a nitrogen atmosphere was added n-butyllithium (1.6 M in THF) (5.0 mL, 8.01 mmol) dropwise. The reaction mixture was then warmed to 0° C. and stirred for 30 mins and then cooled to −78° C. before adding ethyl benzoate (0.838 g, 6.16 mmol) in THF (5 mL)). The reaction mixture was stirred for 1 h and slowly brought to 0° C. The reaction was quenched with aq sat $NH_4Cl$ and the product was extracted with ethyl acetate. The organic layers were combined and washed with aq 1N HCl, aq sat $NaHCO_3$, brine solution, and then dried over anhydrous $Na_2SO_4$. The solvent was removed under reduced pressure to obtain the crude product, which was purified by flash column chromatography using EtOAc/Hexane to afford the title compound (1.15 g, 4.31 mmol) as a white solid. The product was confirmed by $^1$H NMR and LC-MS. $^1$H NMR (400 MHz, $CDCl_3$) δ 8.11-7.99 (m, 2H), 7.64 (t, J=7.4 Hz, 1H), 7.51 (dd, J=15.3, 7.8 Hz, 2H), 4.54 (s, 2H), 3.32 (dd, J=12.4, 7.6 Hz, 4H), 1.79-1.47 (m, 6H). Mass m/z: calcd for $[C_{13}H_{18}NO_3S]^+$ $[M+H]^+$, 268.10 found, 268.23.

1-(Phenylethynylsulfonyl)piperidine (AP-3-148)

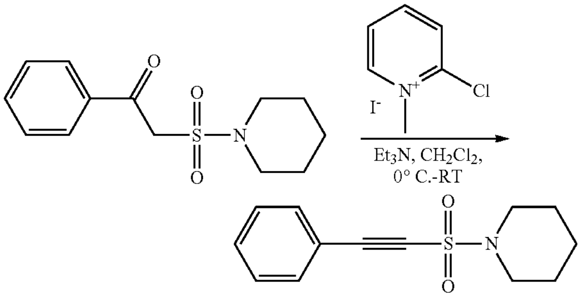

To a stirred solution of 1-phenyl-2-(piperidin-1-ylsulfonyl)ethenone (0.721 g, 2.70 mmol) in anhydrous $CH_2Cl_2$ (20 mL) at 0° C. was added triethylamine (1.3 mL, 9.26 mmol) and 2-chloro-1-methylpyridinium iodide (1.18 g, 4.63 mmol) simultaneously, and then the reaction mixture was slowly brought to RT and stirred for 16 h. Completion of the reaction was confirmed by TLC and quenched with cold water. The product was extracted with ethyl acetate (15 ml×2) and the organic layers were combined and washed with aq 1N HCl, aq sat $NaHCO_3$, brine solution, and then dried over anhydrous $Na_2SO_4$. The solvent was removed under reduced pressure to obtain the crude product, which was purified by flash column chromatography using Ethyl acetate/Hexane to afford the title compound (0.538 g, 2.16 mmol) as a white colored solid. The product was confirmed by $^1H$ NMR and LC-MS. $^1H$ NMR (400 MHz, $CDCl_3$) δ 7.62-7.55 (m, 2H), 7.52-7.46 (m, 2H), 7.40 (ddd, J=7.0, 6.0, 2.9 Hz, 1H), 3.30-3.10 (m, 4H), 1.76 (dt, J=11.4, 5.8 Hz, 4H), 1.62-1.38 (m, 2H). Mass m/z: calcd for $[C_{13}H_{16}NO_2S]^+$ $[M+H]^+$, 250.09; found, 250.22.

Naphthalen-2-ylethynyl)triphenylphosphonium bromide (AP-3-24)

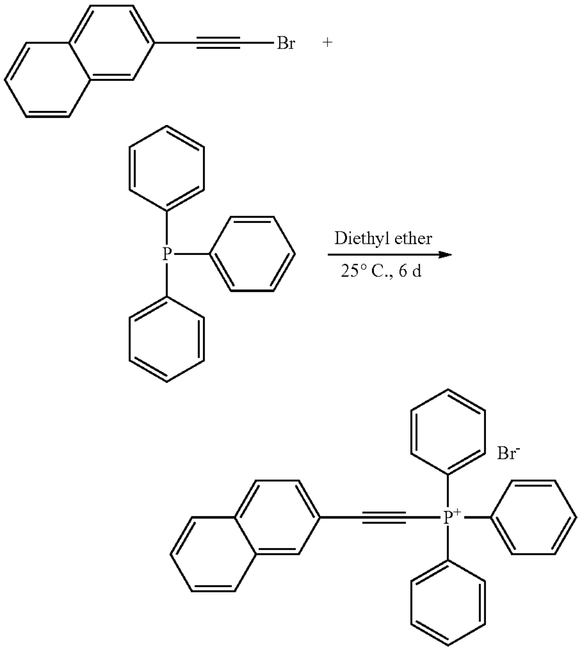

To a stirred solution of triphenylphosphine (0.453 g, 1.74 mmol) in diethyl ether (10 mL) was added 2-(bromoethynyl) naphthalene (0.4 g, 1.74 mmol) slowly at room temperature and the reaction mixture was stirred for 5d at RT under nitrogen atmosphere. The resulting precipitate was filtered off and washed with diethyl ether, and dried under high vacuum to afford the title compound (0.42 g, 0.85 mmol) as a white colored solid, which was confirmed by $^1H$ NMR and LC-MS. $^1H$ NMR (400 MHz, $CDCl_3$) δ 8.60 (s, 1H), 8.04 (t, J=8.9 Hz, 1H), 8.00-7.80 (m, 17H), 7.77 (dd, J=8.5, 1.5 Hz, 1H), 7.70-7.56 (m, 2H). Mass m/z: calcd for $[C_{30}H_{22}P]^+$ $[M]^+$, 413.15; found, 413.28.

Triphenyl(thiophen-3-ylethynyl)phosphonium bromide (AP-3-22)

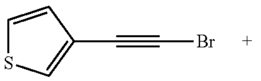

-continued

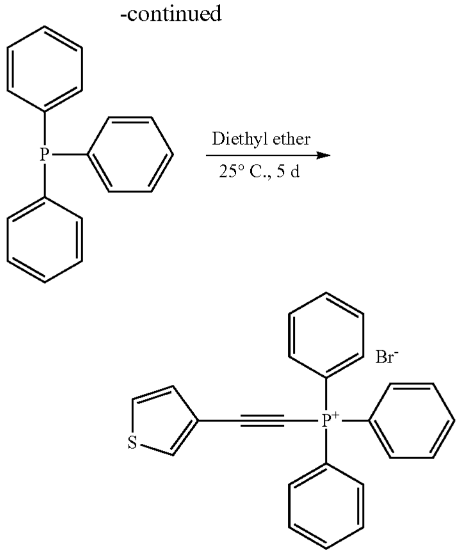

To a stirred solution of triphenylphosphine (0.560 g, 2.14 mmol) in diethyl ether (10 mL) was added 3-(bromoethynyl) thiophene (0.4 g, 2.14 mmol) slowly at room temperature, and the reaction mixture was stirred for 5d at RT under nitrogen atmosphere. The resulting precipitate was filtered off and washed with diethyl ether, then dried under high vacuum to afford the title compound (0.450 g, 1.0 mmol) as a white colored solid, which was confirmed by $^1H$ NMR and LC-MS. $^1H$ NMR (400 MHz, $CDCl_3$) δ 8.57 (t, J=1.8 Hz, 1H), 7.98-7.87 (m, 4H), 7.87-7.76 (m, 12H), 7.52-7.44 (m, 2H). Mass m/z: calcd for $[C_{24}H_{18}PS]^+]$ $[M]^+$, 369.09; found, 369.16.

((3-Methoxyphenyl)ethynyl)triphenylphosphonium bromide (AP-3-23)

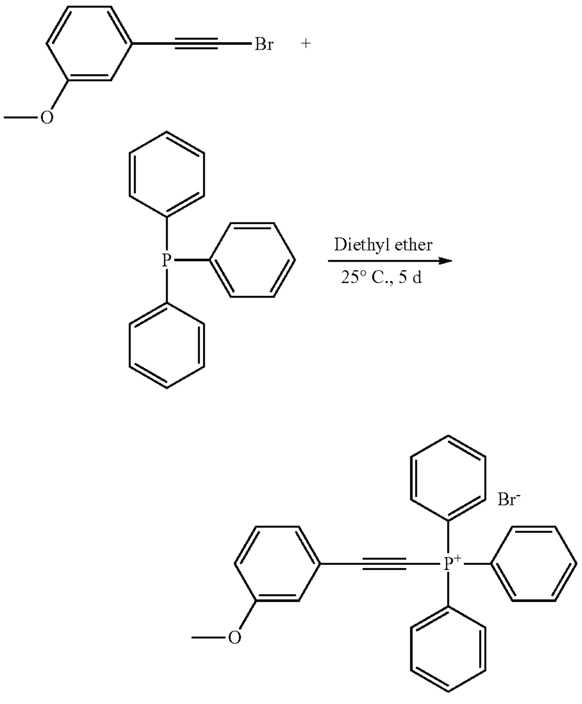

To a stirred solution of triphenylphosphine (0.507 g, 1.74 mmol) in diethyl ether (10 mL) was added 3-(bromoethynyl) thiophene (0.408 g, 1.74 mmol) slowly at room temperature and the reaction mixture was stirred for 5d at RT under nitrogen atmosphere. The resulting precipitate was filtered off and washed with diethyl ether, then dried under high vacuum to afford the title compound (0.504 g, 1.0 mmol) as a white colored solid, which was confirmed by $^1H$ NMR and LC-MS. $^1H$ NMR (400 MHz, $CDCl_3$) δ 7.99-7.73 (m, 15H), 7.49-7.36 (m, 3H), 7.21-7.13 (m, 1H), 3.92 (s, 3H). Mass m/z: calcd for $[C_{27}H_{22}OP]^+$ $[M]^+$, 393.14; found, 393.27.

Tert-butyl 4-(2-(3-chlorophenyl)-2-oxoethylsulfonyl)piperazine-1-carboxylate

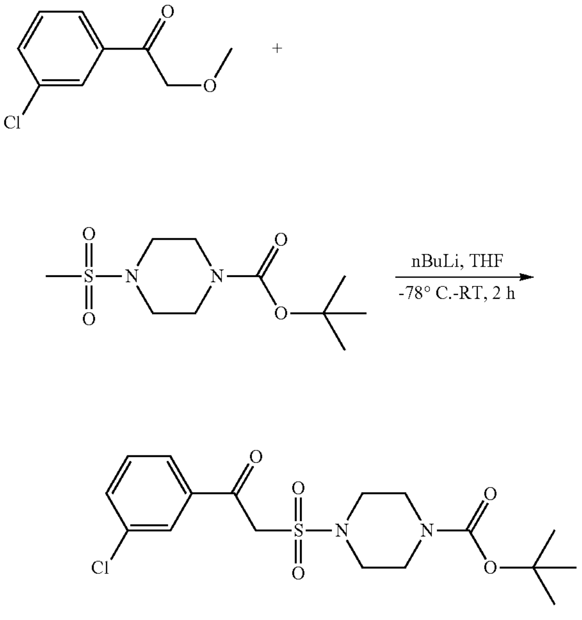

To a stirred solution of tert-butyl 4-(methylsulfonyl)piperazine-1-carboxylate (1.0 g, 3.79 mmol) in anhydrous THF solution (30 mL) at −78° C. under nitrogen atmosphere was added n-butyllithium (1.6 M in THF) (4.7 mL, 6.78 mmol) dropwise. The reaction mixture was then warmed to 0° C. and stirred for 30 mins, and then cooled to −78° C. before adding tert-butyl 4-(methylsulfonyl)piperazine-1-carboxylate (0.643 g, 3.39 mmol) in THF (5 mL)). The reaction mixture was stirred for 1 h slowly and brought to 0° C. The reaction was quenched with aq sat $NH_4Cl$, and the product was extracted with ethyl acetate. The organic layers were combined and washed with aq 1N HCl, aq sat $NaHCO_3$, brine solution, and then dried over anhydrous $Na_2SO_4$. The solvent was removed under reduced pressure to obtain the crude product which was purified by flash column chromatography using Ethyl acetate/Hexane to afford the title compound (0.873 g, 2.27 mmol) as a white solid. The product was confirmed by $^1H$ NMR and LC-MS. $^1H$ NMR (400 MHz, $CDCl_3$) δ 7.99 (t, J=1.8 Hz, 1H), 7.91 (d, J=7.9 Hz, 1H), 7.69-7.56 (m, 1H), 7.48 (t, J=7.9 Hz, 1H), 4.54 (s, 2H), 3.57-3.42 (m, 4H), 3.38-3.23 (m, 4H), 1.48 (s, 9H). Mass m/z: calcd for $[C_{17}H_{22}ClN_2O_5S]^+$ [M–H]+, 401.88; found, 401.23.

Tert-butyl 4-((3-chlorophenyl)ethynylsulfonyl)piperazine-1-carboxylate (AP-3-147)

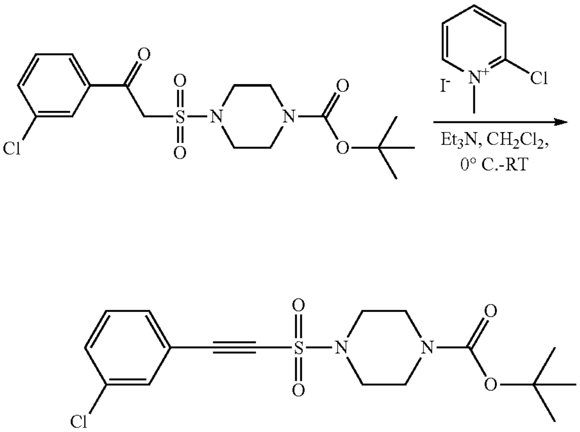

To a stirred solution of tert-butyl 4-(2-(3-chlorophenyl)-2-oxoethylsulfonyl)piperazine-1-carboxylate (0.466 g, 1.16 mmol) in anhydrous $CH_2Cl_2$ (20 mL) at 0° C. was added triethylamine (0.5 mL, 3.47 mmol) and 2-chloro-1-methylpyridinium iodide (0.443 g, 1.73 mmol) simultaneously, then the reaction mixture was slowly brought to RT and stirred for 16 h. Completion of the reaction was confirmed by TLC, then the reaction was quenched with cold water and the product was extracted with ethyl acetate (10 mL×2). The organic layers were washed with aq 1N HCl, aq sat $NaHCO_3$, brine solution, and dried over anhydrous $Na_2SO_4$. The solvent was removed under reduced pressure to obtain crude product which was purified by flash column chromatography using Ethyl acetate/Hexane to afford the title compound (0.353 g, 0.2 mmol) as a white colored solid. The product was confirmed by $^1H$ NMR and LC-MS. $^1H$ NMR (400 MHz, $CDCl_3$) δ 7.69-7.42 (m, 3H), 7.34 (dd, J=27.2, 19.6 Hz, 1H), 3.61 (m, 4H), 3.23 (m, 4H), 1.47 (s, 9H). Mass m/z: calcd for $[Cl_2H_{14}ClN_2O_2S]^+$ $[(M\text{–}Boc)+H]^+$, 285.05; found, 285.13.

Triphenyl(m-tolylethynyl)phosphonium bromide (AP-3-19)

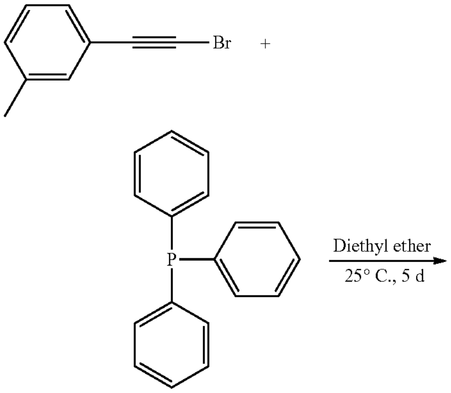

-continued

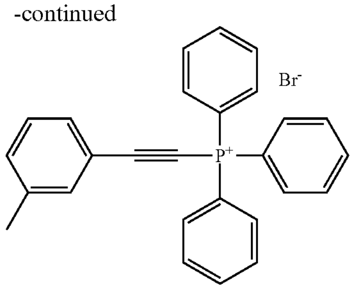

To a stirred solution of triphenylphosphine (0.545 g, 2.06 mmol) in diethyl ether (10 mL) was added 3-(bromoethynyl) thiophene (0.4 g, 2.06 mmol) slowly at room temperature and the reaction mixture was stirred for 5d at RT under a nitrogen atmosphere. The resulting precipitate was filtered off, washed with diethyl ether, and dried under high vacuum to afford the title compound (0.423 g, 0.93 mmol) as a white solid. The product was confirmed by $^1$H NMR and LC-MS. $^1$H NMR (400 MHz, $CDCl_3$) δ 7.92 (td, J=8.9, 5.5 Hz, 3H), 7.85 (dd, J=14.7, 6.2 Hz, 12H), 7.66 (d, J=9.6 Hz, 2H), 7.44 (dt, J=14.9, 7.6 Hz, 2H), 2.43 (s, 3H). Mass m/z: calcd for $[C_{27}H_{22}P]^+$ $[M]^+$, 377.15; found, 377.26.

((3-Chlorophenyl)ethynyl)triphenylphosphonium bromide (AP-3-140)

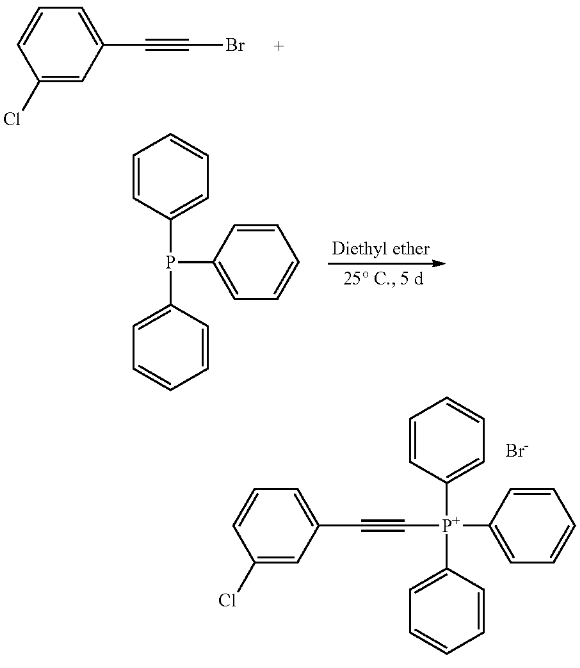

To a stirred solution of triphenylphosphine (0.545 g, 2.06 mmol) in diethyl ether (10 mL) was added 3-(bromoethynyl) thiophene (0.4 g, 2.06 mmol) slowly at room temperature and the reaction mixture was stirred for 5d at RT under nitrogen atmosphere. The resulting precipitate was filtered off, washed with diethyl ether, and dried under high vacuum to afford the title compound (0.342 g, 0.72 mmol) as a white solid. The product was confirmed by $^1$H NMR and LC-MS. $^1$H NMR (400 MHz, $CDCl_3$) δ 8.00-7.90 (m, 4H), 7.90-7.80 (m, 12H), 7.78 (s, 1H), 7.64-7.51 (m, 2H). Mass m/z: calcd for $[C_{26}H_{19}ClP]^+$ $[M]^+$, 397.09; found, 397.26.

2-phenylethynesulfonamide (AP-3-69)

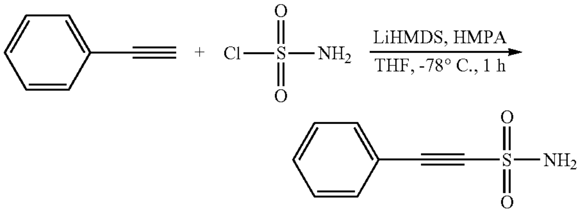

To a stirred solution of ethynylbenzene (3.6 g, 35.29 mmol) in 100 mL of anhydrous THF at −78° C. under a nitrogen atmosphere was added lithium bis(trimethylsilyl) amide (1 M in THF) (30.1 mL, 35.29 mmol) dropwise, then the reaction was stirred for 30 min. After which hexamethylphosphoric acid triamide (5.94 g, 35.29 mmol) was added, with an additional 10 min of stirring. Freshly prepared sulfamoyl chloride (620 mg, 5.4 mmol) dissolved in anhydrous THF (5 mL) was subsequently added and the reaction mixture was left to stir for 1 h, maintaining the temperature at −78° C. Then the reaction mixture was allowed to warm to RT before adding EtOAc (100 mL). The mixture was then washed with aqueous $NH_4Cl$ (50 mL). The aqueous layer was extracted with EtOAc (3×50 mL), the organic layers combined, dried over anhydrous $Na_2SO_4$, and concentrated under reduced pressure. The resulting crude oil was purified by column chromatography eluting with 30% EtOAc/hexane to afford the title compound (3.51 g, 19.39 mmol) as a white solid. The product was confirmed by $^1$H NMR and LC-MS. $^1$H NMR (400 MHz, DMSO) δ 8.25 (s, 2H), 7.68-7.54 (m, 3H), 7.50 (t, J=7.4 Hz, 2H). Mass m/z: calcd for $[C_8H_6NO_2S]^+$ $[M-H]^+$, 180.01; found, 180.14.

Protocol 1 for Preparing (6-(biphenyl-4-ylsulfonamido)hexyl)triphenylphosphonium Salt

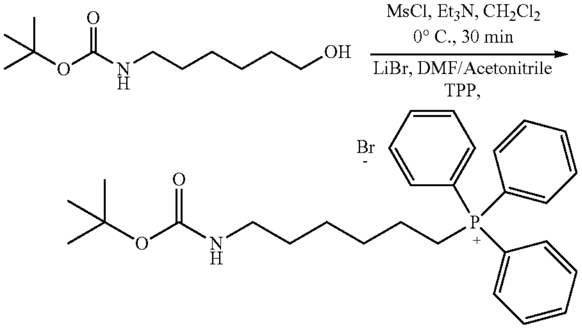

6-((Tert-Butoxycarbonyl)amino)hexyl)triphenylphosphonium bromide

A stirred solution of tert-butyl 6-hydroxyhexylcarbamate (1 g, 4.6 mmol), and triethylamine (930 mg, 9.21 mmol) in 20 ml of $CH_2Cl_2$ was cooled to 0° C. Methanesulfonyl chloride (840 mg, 7.37 mmol) was then added slowly, and stirring was continued for 30 min at 0° C. The reaction mixture was then diluted with dichloromethane (10 mL), washed with water (3×15 mL), dried over anhydrous $Na_2SO_4$, and filtered. The solvent was removed in vacuo. The mesylates were then reacted immediately to next step.

A mixture of 6-((tert-butoxycarbonyl)amino)hexyl methanesulfonate, triphenyl phosphine (2.414 g, 9.22 mmol) and LiBr (800 mg, 9.22 mmol) in acetonitrile/dimethylformamide (3:1.20 ml) was heated to reflux for 2 days. After removal of the solvent, the compound was purified using $CH_2Cl_2$/MeOH as an eluent to yield product (1.38 g, yield 65%). The product was confirmed by LC-MS, [M+H]+462.

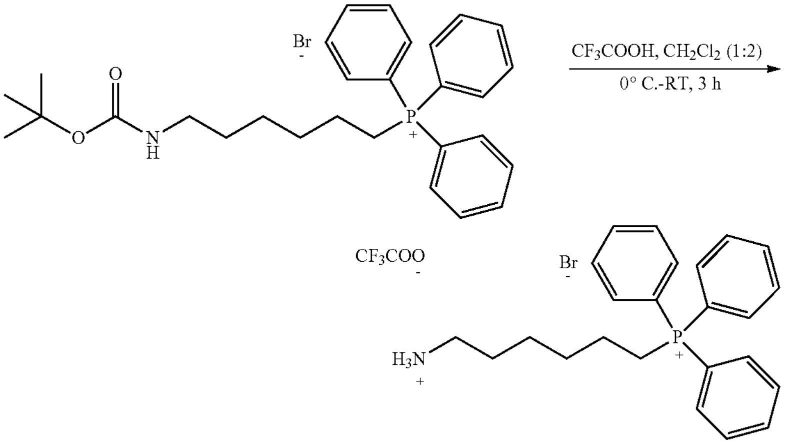

((6-Ammoniohexyl)triphenylphosphonium) bromide 6-((Tert-Butoxycarbonyl)amino)hexyl)triphenylphosphonium bromide (1 g) was dissolved in $CH_2Cl_2$/TFA solution (v/v=1/2, 20 mL) and stirred at room temperature for 3 h. The solution was first concentrated under reduced pressure. The crude product was co-distilled with toluene (3×15 ml), and the obtained product was used for next step without further purification. The product was confirmed by LC-MS, [M+H]+362.

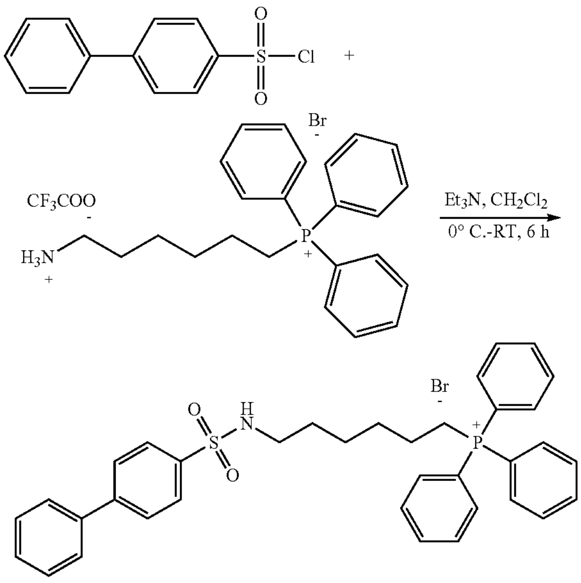

(6-(biphenyl-4-ylsulfonamido)hexyl)triphenylphosphonium bromide

To a stirred solution of ((6-Ammoniohexyl)triphenylphosphonium) bromide (175 mg 0.39 mmol) and $Et_3N$ (120 mg, 1.20 mmol) in 10 ml $CH_2Cl_2$, biphenyl-4-sulfonyl chloride (100 mg 0.39 mmol) was added slowly at 0° C., and stirring was continued for 6 h at room temperature. Completion of the reaction was confirmed by TLC. The reaction mixture was quenched with cold water, and the product was extracted with $CH_2Cl_2$. The organic layer was dried over anhydrous sodium sulfate. The solvent was evaporated at reduced pressure. The crude product was purified by flash column chromatography to yield white color solid (169 mg yield 65%). The product was confirmed by LC-MS, [M+H]+578.

Protocol 2 for Preparing (6-(biphenyl-4-ylsulfonamido)hexyl)triphenylphosphonium Salt (6-(Tert-butoxycarbonylamino)hexyl)triphenylphosphonium bromide

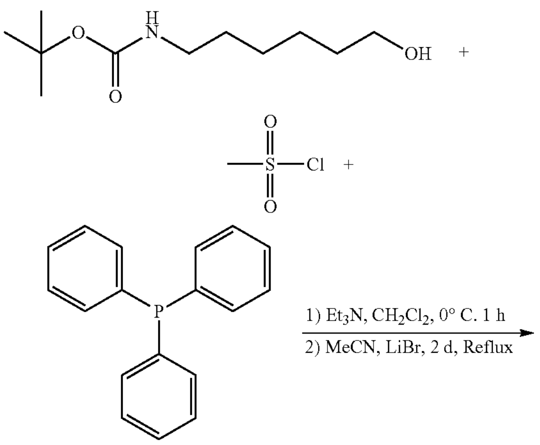

-continued

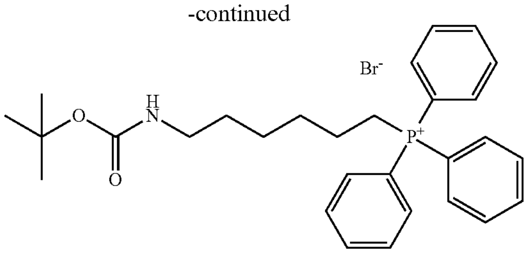

To a solution of tert-butyl 6-hydroxyhexylcarbamate (10 g, 46.04 mmol) and TEA (13.95 g, 138.14 mmol) in anhydrous $CH_2Cl_2$ (150 mL) was added methanesulfonyl chloride (6.3 g, 55.25 mmol) slowly at 0° C. Then the reaction mixture was brought to RT and stirred for 3 hours. Completion of the reaction was confirmed by TLC, after which the reaction was quenched with cold water, and the product was extracted with $CH_2Cl_2$ (100 mL×2). The organic layers were combined and washed with aq 1N HCl, aq sat $NaHCO_3$, brine solution, and dried over anhydrous $Na_2SO_4$. The mixture was concentrated under reduced pressure to obtain crude mesylate which was dissolved in DMF/MeCN (1:3) (100 mL) and used immediately in the next step. Then LiBr (4.0 g, 92.08 mmol) and triphenyl phosphine (14.5 g, 55.24 mmol) were added simultaneously at room temperature and the reaction mixture was stirred for 48 h under reflux conditions. Then the volatiles were removed under reduced pressure, and cold water was added to the residue. The product was extracted with $CH_2Cl_2$ (100 mL×2), the organic layers were combined and washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (12.71 g, 23.48 mmol) as a white colored solid. The product was confirmed by $^1H$ NMR and LC-MS. $^1H$ NMR (400 MHz, $CDCl_3$) δ 8.02 (s, 1H), 7.85 (dt, J=13.5, 6.7 Hz, 6H), 7.79 (d, J=7.1 Hz, 2H), 7.75-7.66 (m, 6H), 4.82 (s, 1H), 3.84 (d, J=13.2 Hz, 2H), 3.08 (t, J=15.3 Hz, 2H), 1.73-1.48 (m, 4H), 1.49-1.31 (m, 13H). Mass m/z: calcd for $[C_{29}H_{37}NO_2P]^+]$ $[M]^+$, 462.26; found, 462.28.

(6-Ammoniohexyl)triphenylphosphonium 2,2,2-trifluoroacetate bromide

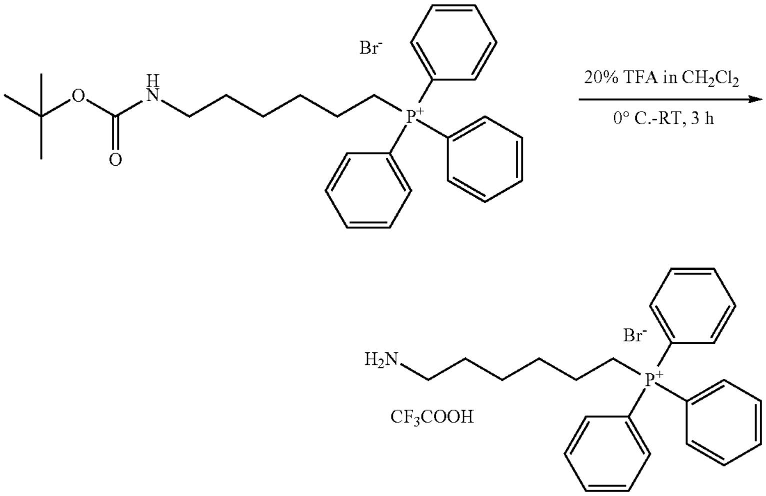

(6-(Tert-butoxycarbonylamino)hexyl)triphenylphosphonium bromide (5 g, 10.82 mmol) was added to anhydrous dichloromethane and cooled to 0° C. in a 50 mL round bottom flask, then trifluoroacetic acid (10.00 mL) was added. The reaction mixture was warmed to room temperature and monitored by TLC until complete. The reaction mixture was then concentrated under reduced pressure and co-distilled with dry toluene to afford the trifluoroacetate salt (6.0 g, 10.81 mmol) as thick light-yellow colored liquid. The product was confirmed by $^1H$ NMR and LC-MS. $^1H$ NMR (400 MHz, $CDCl_3$) δ 8.10 (s, 1H), 7.83 (t, J=7.3 Hz, 3H), 7.74-7.45 (m, 14H), 3.16 (dd, J=34.2, 21.0 Hz, 2H), 3.06 (s, 4H), 1.86-1.61 (m, 4H), 1.55 (dd, J=20.3, 13.5 Hz, 2H), 1.48 (d, J=6.4 Hz, 2H). Mass m/z: calcd for $[C_{24}H_{29}NP]^+$ $[M]^+$, 362.20.15; found, 362.22.

(6-(Biphenyl-4-ylsulfonamido)hexyl)triphenylphosphonium bromide (AP-3-90)

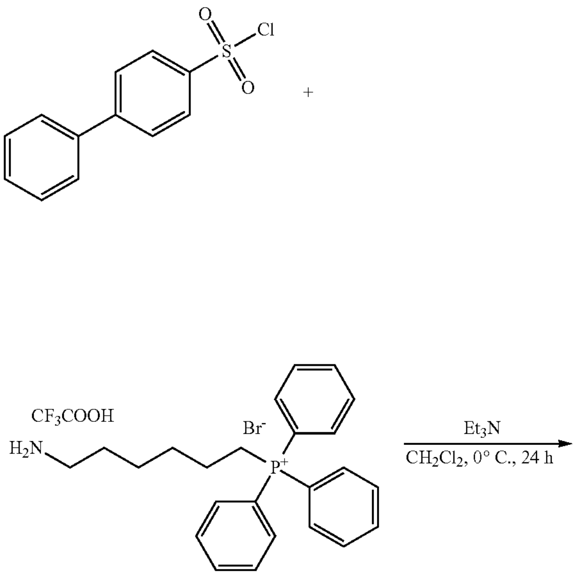

-continued

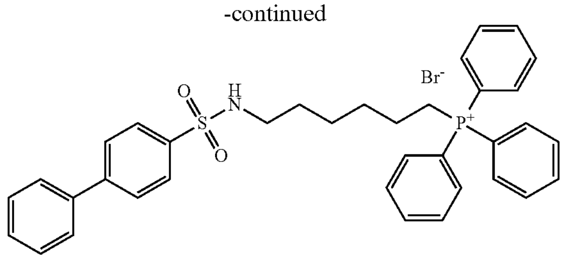

To a stirred solution of (6-aminohexyl)triphenylphosphonium bromide trifluroacetate (0.219 g, 0.39 mmol) in anhydrous $CH_2Cl_2$ (6 mL) at 0° C. under nitrogen atmosphere was added triethylamine (0.2 g, 1.98 mmol) and biphenyl-4-sulfonyl chloride (0.03 g, 0.39 mmol) simultaneously, then the reaction mixture was brought RT and stirred for 24 hours. Completion of the reaction was confirmed by TLC, after which the reaction was quenched with cold water. The product was extracted with $CH_2Cl_2$ (15 mL×2) and the combined organic layers were washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.195 g, 0.23 mmol) as a white colored solid. The product was confirmed by $^1$H NMR and LC-MS. $^1$H NMR (400 MHz, $CDCl_3$) δ 7.99 (dd, J=40.8, 8.3 Hz, 2H), 7.89-7.74 (m, 7H), 7.68 (ddd, J=20.3, 10.2, 5.7 Hz, 6H), 7.60-7.51 (m, 2H), 7.50-7.32 (m, 3H), 3.71 (s, 2H), 2.98 (s, 2H), 1.72 (d, J=37.6 Hz, 2H), 1.51 (dd, J=70.2, 18.4 Hz, 6H). Mass m/z: calcd for $[C_{36}H_{37}NO_2PS]^+$ $[M]^+$, 578.23; found, 578.32.

(6-(Dibenzo[b,d]furan-3-sulfonamido)hexyl)triphenylphosphonium bromide (Ap-3-97)

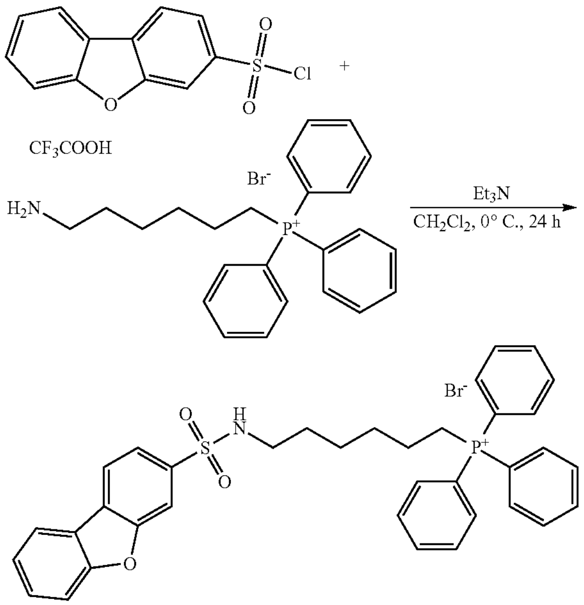

To a stirred solution of (6-aminohexyl)triphenylphosphonium bromide trifluroacetate (0.063 g, 0.12 mmol) in anhydrous $CH_2Cl_2$ (6 mL) at 0° C. under nitrogen atmosphere was added triethylamine (0.61 g, 0.56 mmol) and dibenzo[b,d]furan-3-sulfonyl chloride (0.03 g, 0.12 mmol) simultaneously. Then the reaction mixture was brought to RT and stirred for 24 hours. Completion of the reaction was confirmed by TLC, after which the reaction was quenched with cold water. The product was then extracted with $CH_2Cl_2$ (15 mL×2) and the combined organic layers were washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.043 g, 0.07 mmol) as a white colored solid. The product was confirmed by $^1$H NMR and LC-MS. $^1$H NMR (400 MHz, $CDCl_3$) δ 8.21 (d, J=1.0 Hz, 1H), 8.09-8.01 (m, 1H), 8.02-7.89 (m, 2H), 7.85-7.74 (m, 8H), 7.73-7.62 (m, 6H), 7.56-7.44 (m, 2H), 7.35 (dt, J=21.4, 7.3 Hz, 1H), 3.87-3.45 (m, 2H), 2.98 (d, J=5.6 Hz, 2H), 1.74-1.41 (m, 8H). Mass m/z: calcd for $[C_{36}H_{35}NO_3PS]^+$ $[M]^+$, 592.21; found, 592.54.

1-(3-aminopropyl)pyridin-1-ium bromide hydrobromide

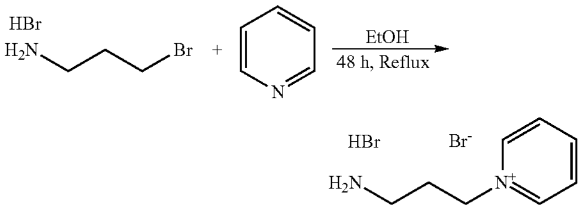

Pyridine (2.15 g, 10.43 mmol) and 3-bromopropan-1-amine hydrobromide (5.0 g, 22.84 mmol) were combined in absolute EtOH (50 mL) and heated at 80° C. (oil bath) for 48 h. After the solution was cooled to room temperature, the precipitate was filtered off, washed with absolute EtOH (4×10 mL), diethyl ether, and dried under high vacuum to afford the title compound (4.73 g, 70% yield) as a white colored solid. The product was confirmed by $^1$H NMR and LC-MS. $^1$H NMR (400 MHz, DMSO) δ 9.17 (d, J=5.9 Hz, 2H), 8.65 (t, J=7.7 Hz, 1H), 8.19 (dd, J=32.6, 25.8 Hz, 2H), 7.83 (d, J=88.1 Hz, 3H), 4.76 (t, J=7.1 Hz, 2H), 2.88 (dd, J=12.6, 6.3 Hz, 2H), 2.39-2.00 (m, 2H). Mass m/z: calcd for [C8H13N2+] [M]+, 137; found, 137.17.

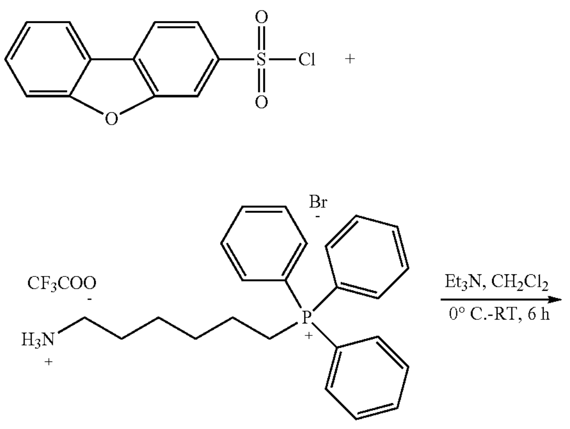

-continued

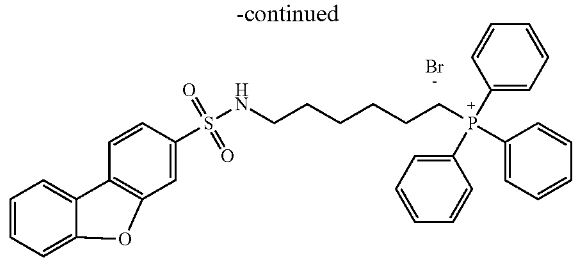

(6-(dibenzo[b,d]furan-3-sulfonamido)hexyl)triphenylphosphonium bromide

To a stirred solution of ((6-Ammoniohexyl)triphenylphosphonium) bromide (166 mg, 0.37 mmol) and $Et_3N$ (120 mg, 1.20 mmol) in 10 ml $CH_2Cl_2$, dibenzo[b,d]furan-3-sulfonyl chloride (100 mg 0.37 mmol) was added slowly at 0° C., and stirring was continued for 6 h at room temperature. Completion of the reaction was confirmed by TLC. The reaction mixture was quenched with cold water, the product was extracted with $CH_2Cl_2$, and the organic layer was dried over anhydrous sodium sulphate. The solvent was evaporated at reduced pressure. Crude product was purified by flash column chromatography to yield white color solid (133 mg, yield 60%). The product was confirmed by LC-MS, [M+H]+ 592.

1-(3-(3'-Methylbiphenyl-4-ylsulfonamido)propyl) pyridinium bromide (AP-3-231)

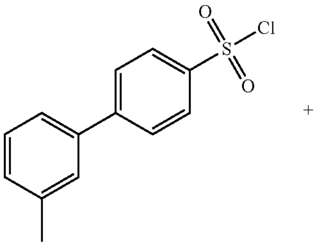

-continued

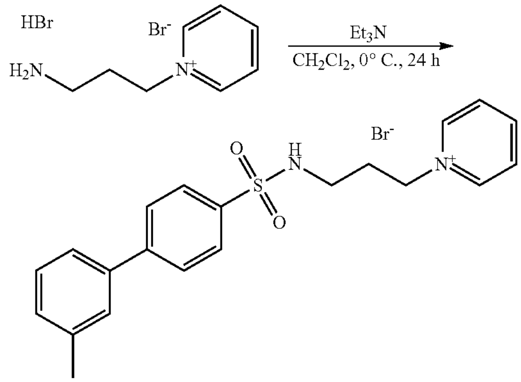

To a stirred solution of 1-(3-aminopropyl)pyridinium bromide hydrobromide (0.1 g, 0.33 mmol) in anhydrous $CH_2Cl_2$ (10 mL) at 0° C. under nitrogen atmosphere was added triethylamine (0.169 g, 1.67 mmol) and 3'-methylbiphenyl-4-sulfonyl chloride (0.098 g, 0.37 mmol) simultaneously, then the reaction mixture was brought to RT and stirred for 24 hours. Completion of the reaction was confirmed by TLC, after which it was quenched with cold water. The product was extracted with $CH_2Cl_2$ (15 mL×2) and the combined organic layers were washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.105 g, 0.23 mmol) as a light-yellow colored solid. The product was confirmed by $^1H$ NMR and LC-MS. $^1H$ NMR (400 MHz, $CD_3OD$) δ 9.02 (d, J=6.0 Hz, 2H), 8.61 (t, J=7.9 Hz, 1H), 8.13 (t, J=6.8 Hz, 2H), 7.88 (d, J=8.1 Hz, 2H), 7.80 (d, J=8.1 Hz, 2H), 7.54-7.41 (m, 2H), 7.36 (t, J=7.6 Hz, 1H), 7.24 (d, J=7.3 Hz, 1H), 4.79 (t, J=7.0 Hz, 2H), 2.95 (t, J=6.0 Hz, 2H), 2.42 (s, 3H), 2.31-2.14 (m, 2H). Mass m/z: calcd for $[C_{21}H_{23}N_2O_2S]^+$ [M]+, 367.15; found, 367.35.

Tert-butyl 6-(4-(7-(diethylamino)-2-oxo-2H-chromene-3-carbonyl)piperazin-1-yl) hexylcarbamate

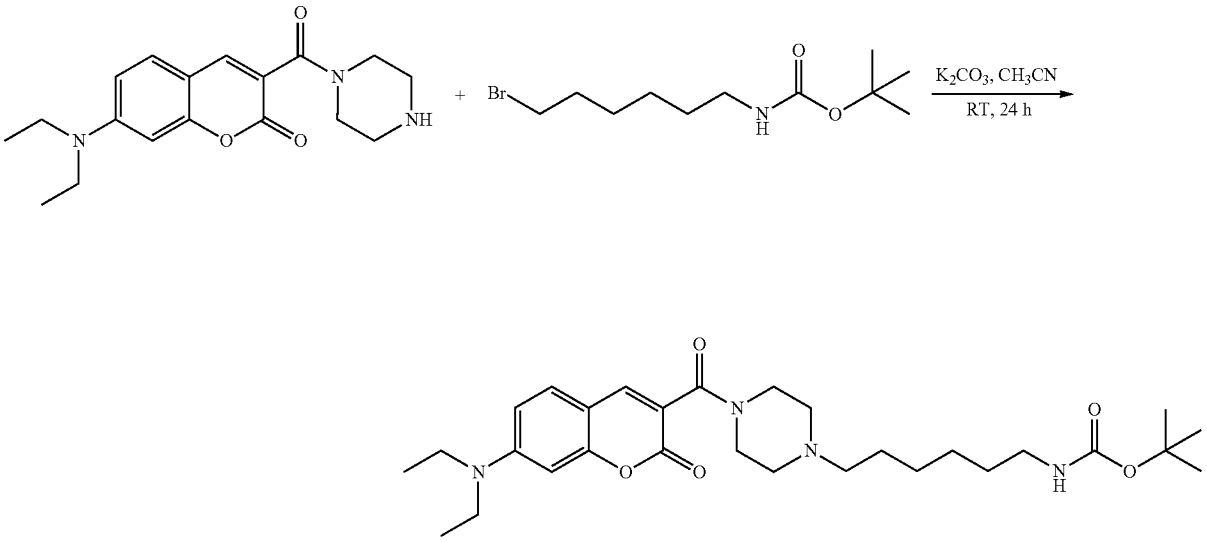

To a stirred solution of 7-(diethylamino)-3-(piperazine-1-carbonyl)-2H-chromen-2-one (300 mg, 0.94 mmol) and tert-butyl 6-bromohexylcarbamate (306 mg, 1.09 mmol) in anhydrous acetonitrile (30 mL) at RT was added anhydrous potassium carbonate (377 mg, 2.73 mmol) and stirred for 24 h at RT. Completion of the reaction was confirmed by TLC, and the volatiles were removed under reduced pressure. The crude product was diluted with ethyl acetate and washed with water, brine solution, and dried over anhydrous $Na_2SO_4$. The resulting crude product was purified by flash column chromatography using Ethyl acetate/Hexane to afford the title compound (346 mg, 0.65 mmol) as a pale-yellow liquid. The product was confirmed by 1H NMR and LC-MS. $^1H$ NMR (400 MHz, $CDCl_3$) δ 7.82 (s, 1H), 7.34-7.21 (m, 1H), 6.60 (dd, J=8.9, 2.4 Hz, 1H), 6.47 (d, J=2.3 Hz, 1H), 4.63 (s, 1H), 3.77 (s, 2H), 3.43 (q, J=7.1 Hz, 6H), 3.10 (dd, J=12.8, 6.3 Hz, 2H), 2.48 (d, J=17.8 Hz, 4H), 2.33 (dd, J=26.5, 18.8 Hz, 2H), 1.57-1.37 (m, 13H), 1.32 (dt, J=18.2, 9.2 Hz, 4H), 1.27-1.13 (m, 6H). Mass m/z: calcd for $[C_{29}H_{45}N_4O_5]^+$ $[M+H]^+$, 529.34; found, 529.47.

3-(4-(6-aminohexyl)piperazine-1-carbonyl)-7-(diethylamino)-2H-chromen-2-one tris(2,2,2-trifluoroacetate)

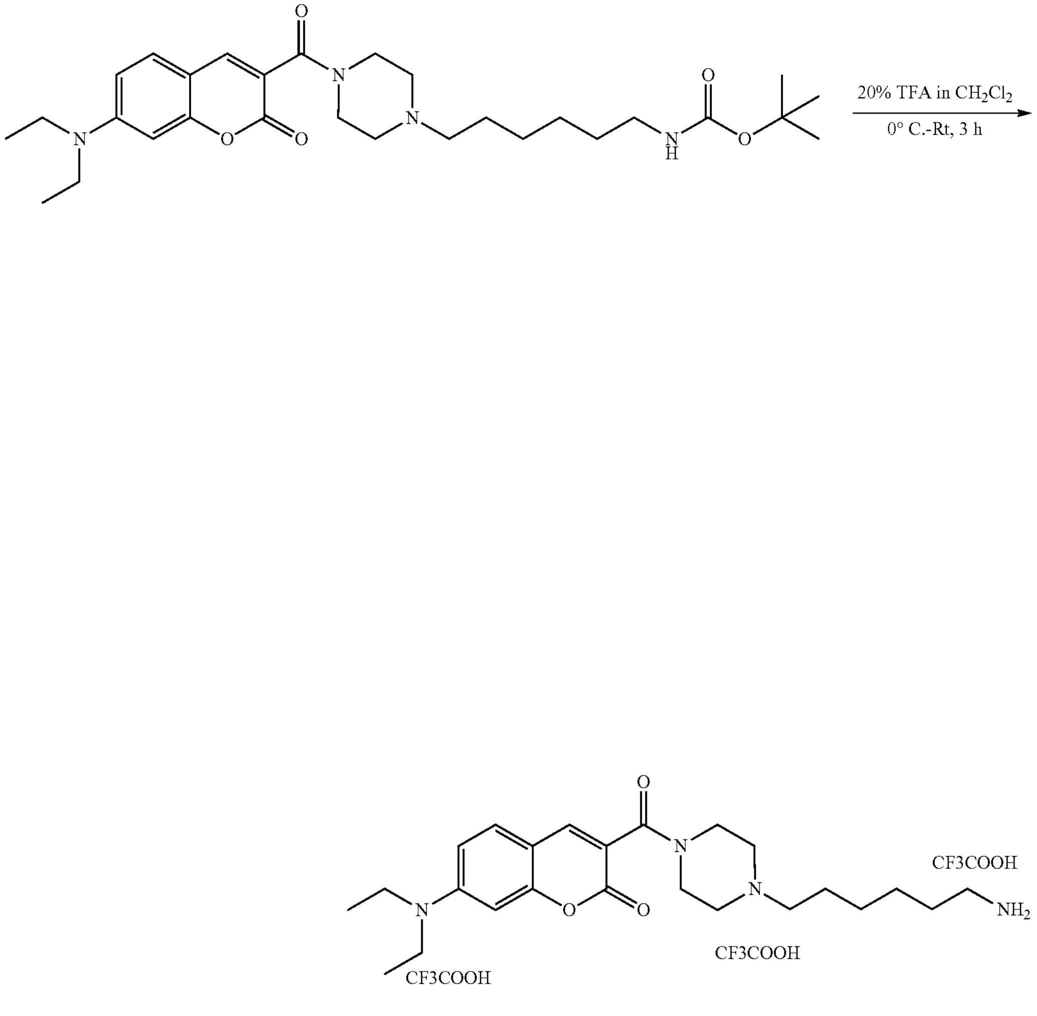

To a stirred solution of tert-butyl 6-(4-(7-(diethylamino)-2-oxo-2H-chromene-3-carbonyl)piperazin-1-yl)hexylcarbamate (340 mg, 0.64 mmol) in anhydrous dichloromethane (8 mL) at 0° C. was added trifluoroacetic acid (2.0 mL). The reaction was warmed to room RT and stirred for 2 h after which the completion of the reaction was confirmed TLC. The reaction mixture was then concentrated under reduced pressure and co-distilled with dry toluene (2×5 mL) to afford the trifluoroacetate salt (495 mg, 0.64 mmol) as a thick light-yellow liquid. The product was confirmed by $^1$H NMR and LC-MS. $^1$H NMR (400 MHz, DMSO) δ 8.04 (s, 1H), 7.73 (s, 3H), 7.53 (d, J=9.0 Hz, 1H), 6.77 (dd, J=9.0, 2.3 Hz, 1H), 6.57 (d, J=2.2 Hz, 1H), 4.52 (s, 1H), 3.86 (s, 1H), 3.65-3.28 (m, 6H), 3.10 (t, J=25.3 Hz, 5H), 2.86-2.67 (m, 2H), 1.71-1.57 (m, 2H), 1.52 (q, J=7.0 Hz, 2H), 1.29 (dd, J=18.5, 15.5 Hz, 4H), 1.13 (t, J=7.0 Hz, 6H). Mass m/z: calcd for $[C_{24}H_{37}N_4O_3]^+$ $[M+H]^+$, 429.29; found, 429.44.

N-(6-(4-(7-(diethylamino)-2-oxo-2H-chromene-3-carbonyl)piperazin-1-yl)hexyl)biphenyl-4-sulfonamide (AP-3-95)

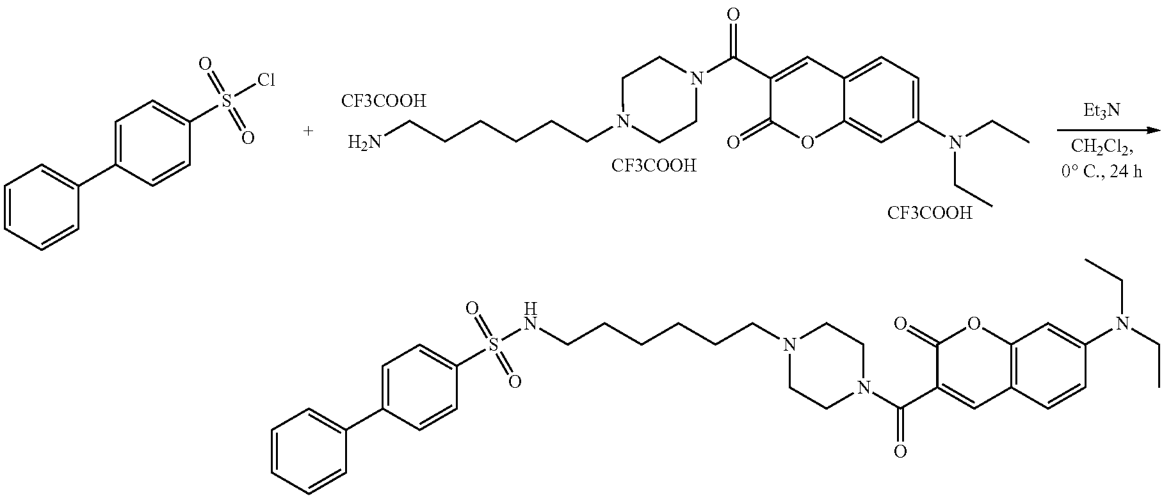

AP-3-95

To a stirred solution of 3-(4-(6-aminohexyl)piperazine-1-carbonyl)-7-(diethylamino)-2H-chromen-2-one tris(2,2,2-trifluoroacetate) (0.092 g, 0.12 mmol) in anhydrous $CH_2Cl_2$ (5 mL) at 0° C. under a nitrogen atmosphere was added triethylamine (0.057 g, 0.56 mmol) and biphenyl-4-sulfonyl chloride (0.03 g, 0.12 mmol) simultaneously. Then the reaction mixture was brought to RT and stirred for 24 hours. Completion of the reaction was confirmed by TLC, after which it was quenched with cold water, and the product was extracted with $CH_2Cl_2$ (10 mL×2). The combined organic layers were washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.57 g, 0.09 mmol) as a light-yellow colored thick solid. The product was confirmed by $^1$H NMR and LC-MS. $^1$H NMR (400 MHz, $CDCl_3$) δ 7.92 (d, J=8.4 Hz, 2H), 7.82 (s, 1H), 7.73 (d, J=8.4 Hz, 2H), 7.65-7.55 (m, 2H), 7.54-7.37 (m, 3H), 7.35-7.23 (m, 3H), 6.59 (dd, J=8.9, 2.4 Hz, 1H), 6.45 (t, J=12.7 Hz, 1H), 4.43 (s, 1H), 3.75 (s, 2H), 3.43 (dd, J=14.2, 7.1 Hz, 5H), 3.00 (dd, J=13.4, 6.8 Hz, 2H), 2.42 (t, J=22.3 Hz, 4H), 2.38-2.20 (m, 2H), 1.55-1.31 (m, 4H), 1.37-1.02 (m, 10H). Mass m/z: calcd for $[C_{36}H_{45}N_4O_5S]^+$ $[M+H]^+$, 645.31; found, 645.55.

1-(3-(Biphenyl-4-ylsulfonamido)propyl)pyridinium (AP-3-229)

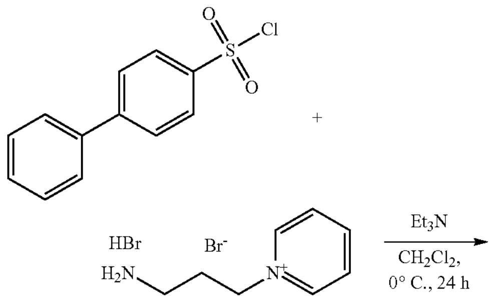

-continued

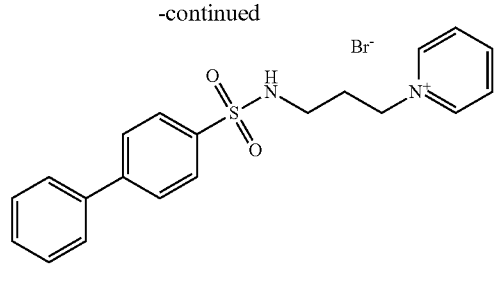

To a stirred solution of 1-(3-aminopropyl)pyridinium bromide hydrobromide (0.1 g, 0.33 mmol) in anhydrous $CH_2Cl_2$ (10 mL) at 0° C. under a nitrogen atmosphere was added triethylamine (0.169 g, 1.67 mmol) and dibenzo[b,d]furan-3-sulfonyl chloride (0.093 g, 0.33 mmol) simultaneously. Then the reaction mixture was brought to RT and stirred for 24 hours. Completion of the reaction was confirmed by TLC, and the reaction was quenched with cold water. The product was extracted with $CH_2Cl_2$ (15 mL×2) and the combined organic layers were washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.108 g, 0.25 mmol) as a light-yellow colored solid. The product was confirmed by $^1H$ NMR and LC-MS. $^1H$ NMR (400 MHz, $CD_3OD$) δ 9.02 (d, J=5.8 Hz, 2H), 8.61 (t, J=7.8 Hz, 1H), 8.13 (t, J=6.6 Hz, 2H), 7.89 (d, J=7.7 Hz, 2H), 7.82 (d, J=8.0 Hz, 2H), 7.65 (dd, J=15.7, 7.5 Hz, 2H), 7.53-7.31 (m, 3H), 4.78 (t, J=7.0 Hz, 2H), 2.96 (t, J=6.0 Hz, 2H), 2.39-2.09 (m, 2H). Mass m/z: calcd for $[C_{20}H_{21}N_2O_2S]^+$ $[M]^+$, 353.13; found, 353.34.

1-(3-(3'-Methoxybiphenyl-4-ylsulfonamido)propyl) pyridinium bromide (AP-3-230)

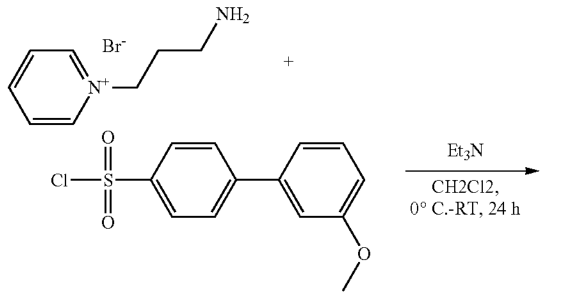

-continued

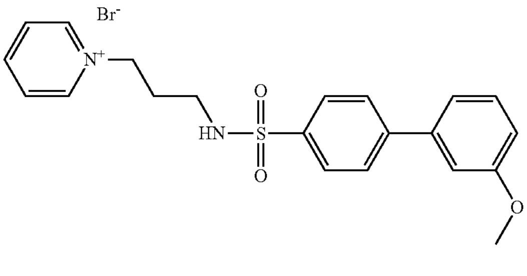

To a stirred solution of 1-(3-aminopropyl)pyridinium bromide hydrobromide (0.1 g, 0.33 mmol) in anhydrous $CH_2Cl_2$ (10 mL) at 0° C. under nitrogen atmosphere was added triethylamine (0.169 g, 1.67 mmol) and 3'-methoxybiphenyl-4-sulfonyl chloride (0.094 g, 0.33 mmol) simultaneously. Then the reaction mixture was to brought RT and stirred for 24 hours. Completion of the reaction was confirmed by TLC, after which it was quenched with cold water and the product extracted with $CH_2Cl_2$ (15 mL×2). The organic layers were combined and washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.101 g, 0.21 mmol) as a light-yellow colored solid. The product was confirmed by $^1H$ NMR and LC-MS. $^1H$ NMR (400 MHz, $CD_3OD$) δ 9.02 (d, J=5.9 Hz, 2H), 8.61 (t, J=7.8 Hz, 1H), 8.13 (t, J=6.8 Hz, 2H), 7.87 (t, J=12.7 Hz, 2H), 7.81 (d, J=8.3 Hz, 2H), 7.39 (t, J=8.0 Hz, 1H), 7.31-7.14 (m, 2H), 6.99 (d, J=8.2 Hz, 1H), 4.79 (t, J=7.0 Hz, 2H), 3.86 (s, 3H), 2.95 (t, J=6.1 Hz, 2H), 2.42-2.16 (m, 2H). Mass m/z: calcd for $[C_{21}H_{23}N_2O_3S]^+$ $[M]^+$, 383.14; found, 383.45.

N-(6-(4-(7-(Diethylamino)-2-oxo-2H-chromene-3-carbonyl)piperazin-1-yl)hexyl)dibenzo[b,d]furan-3-sulfonamide (AP-3-96)

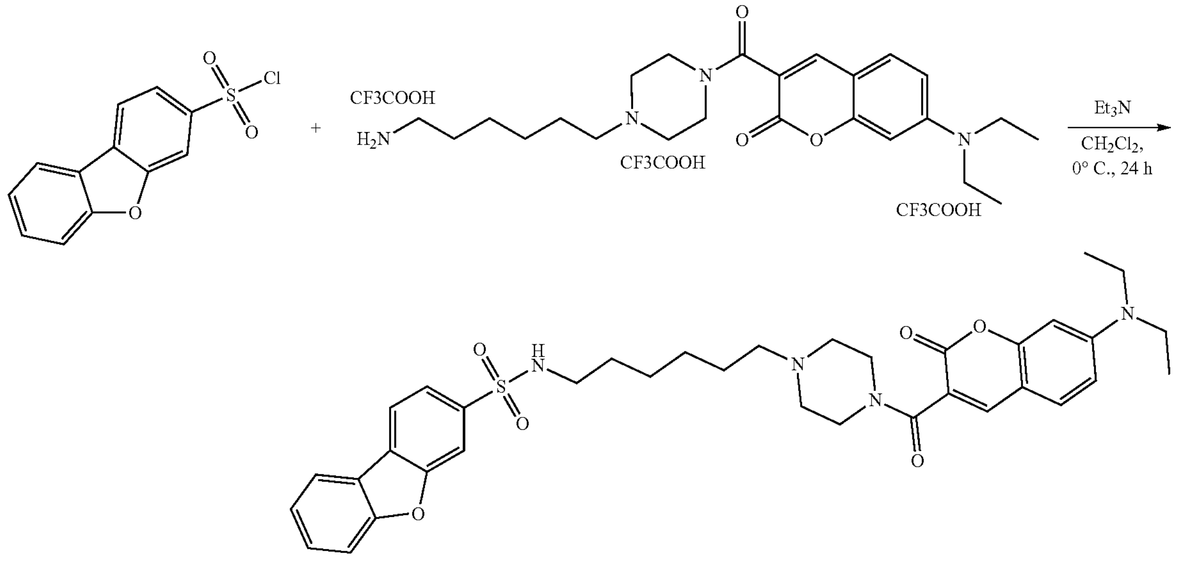

To a stirred solution of 3-(4-(6-aminohexyl)piperazine-1-carbonyl)-7-(diethylamino)-2H-chromen-2-one tris(2,2,2-trifluoroacetate) (0.087 g, 0.12 mmol) in anhydrous $CH_2Cl_2$ (5 mL) at 0° C. under a nitrogen atmosphere was added triethylamine (0.057 g, 0.56 mmol) and dibenzo[b,d]furan-3-sulfonyl chloride (0.03 g, 0.12 mmol) simultaneously. Then the reaction mixture was brought to RT and stirred for 24 hours. Completion of the reaction was confirmed by TLC, after which the reaction was quenched with cold water, and the product was extracted with $CH_2Cl_2$ (10 mL×2). The combined organic layers were washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.52 g, 0.08 mmol) as a light-yellow colored thick solid. The product was confirmed by 1H NMR and LC-MS. $^1H$ NMR (400 MHz, $CDCl_3$) δ 8.51 (s, 1H), 8.13-7.89 (m, 2H), 7.82 (s, 1H), 7.58 (ddd, J=38.5, 26.6, 16.0 Hz, 3H), 7.47-7.32 (m, 1H), 7.31-7.18 (m, 1H), 6.58 (d, J=8.3 Hz, 1H), 6.47 (s, 1H), 4.67 (s, 1H), 3.66 (d, J=59.4 Hz, 2H), 3.54-3.25 (m, 6H), 2.99 (d, J=6.4 Hz, 2H), 2.38 (t, J=24.1 Hz, 4H), 2.15 (dd, J=83.8, 15.2 Hz, 2H), 1.40 (dd, J=52.1, 24.6 Hz, 4H), 1.22 (t, J=6.7 Hz, 10H). Mass m/z: calcd for $[C_{36}H_{43}N_4O_6S]^+$ $[M+H]^+$, 659.29; found, 659.56.

5-(6-Bromohexyl)-1,3,4-thiadiazol-2-amine

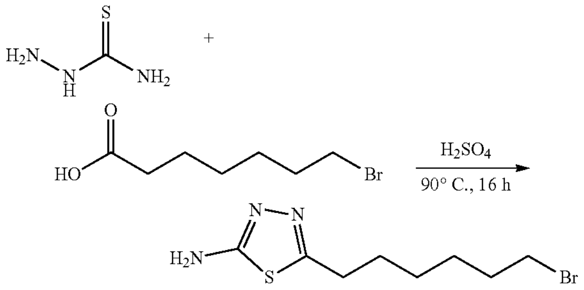

7-bromoheptanoic acid (7.1 g, 33.96 mmol), concentrated sulfuric acid (25 mL), and thiosemicarbazide (3.71 g, 40.75 mmol) were slowly heated to 80-90° C. for 16 h. After cooling, the reaction mixture was poured onto crushed ice. The mixture was neutralized with 10% aqueous ammonia and extracted with ethyl acetate (3×100 mL). The combined organic extracts were washed with 10% $Na_2CO_3$ (2×50 mL), water (100 mL), and brine (100 mL), dried over $Na_2SO_4$, filtered, and concentrated under reduced pressure. The residue was purified by silica gel flash column chromatography to afford the title compound (4.81 g, 18.28 mmol) as a light-yellow colored solid. The product was confirmed by $^1H$ NMR and LC-MS. $^1H$ NMR (400 MHz, $CDCl_3$) δ 5.10 (s, 2H), 3.41 (t, J=6.7 Hz, 2H), 2.92 (t, J=7.5 Hz, 2H), 1.96-1.80 (m, 2H), 1.75 (dt, J=14.5, 7.4 Hz, 2H), 1.46 (dt, J=12.8, 11.1 Hz, 4H). Mass m/z: calcd for $[C_8H_{15}BrN_3S]^+$ $[M+H]^+$, 264.02; found, 264.03, 266.03.

2-(6-Bromohexyl)-6-phenylimidazo[2,1-b][1,3,4] thiadiazole

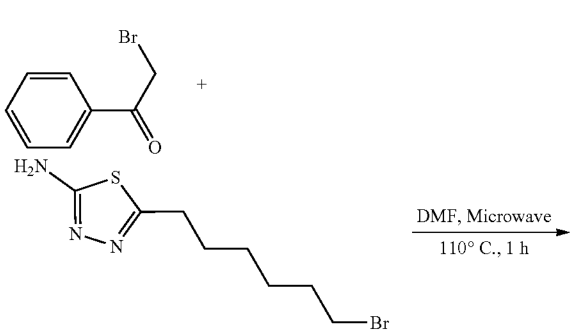

-continued

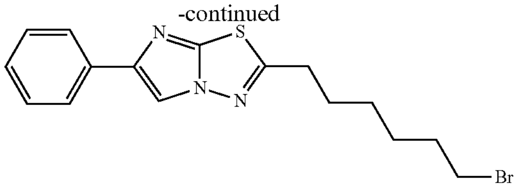

5-(6-bromohexyl)-1,3,4-thiadiazol-2-amine (3.484 g, 13.247 mmol) and 2-bromo-1-phenyl ethanone were combined in dry DMF (15 mL) and the reaction mixture was heated in a sealed tube in a microwave at 110° C. for 30 min. After which the solvent was removed under reduced pressure and the crude product was diluted with water. The mixture was extracted with $CH_2Cl_2$ and the combined organic layers were washed with brine solution, and dried over anhydrous $Na_2SO_4$. The crude product was purified by flash column chromatography using $CH_2Cl_2$/MeOH to afford the title compound (2.88 g, 7.95 mmol) as a light-brown colored solid. The product was confirmed by $^1H$ NMR and LC-MS. $^1H$ NMR (400 MHz, $CDCl_3$) δ 7.96 (s, 1H), 7.81 (d, J=7.7 Hz, 2H), 7.41 (t, J=7.5 Hz, 2H), 7.32-7.16 (m, 1H), 3.47-3.33 (m, 2H), 2.99 (t, J=7.5 Hz, 2H), 1.95-1.75 (m, 4H), 1.56-1.36 (m, 4H). Mass m/z: calcd for $[C_{16}H_{19}BrN_3S]^+$ $[M+H]^+$, 364.05; found, 364.16, 366.16.

Triphenyl(6-(6-phenylimidazo[2,1-b][1,3,4]thiadiazol-2-yl)hexyl)phosphonium bromide (AP-4-139b)

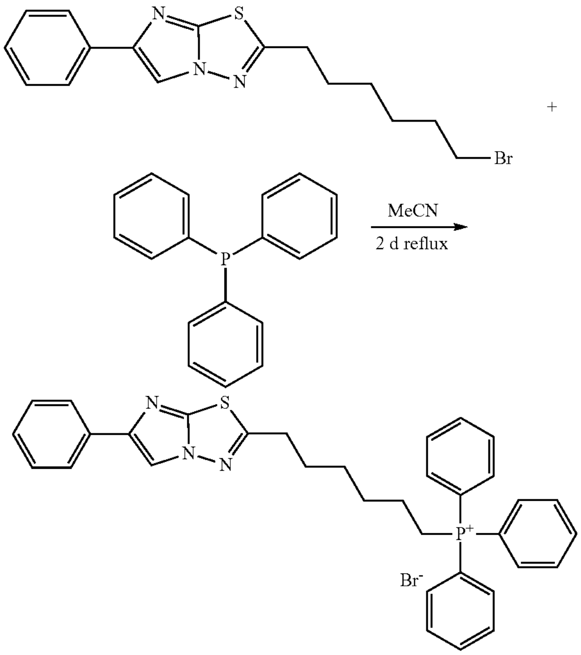

2-(6-bromohexyl)-6-phenylimidazo[2,1-b][1,3,4]thiadiazole (1.0 g, 0.75 mmol) and triphenyl phosphine (1.44 g, 5.5 mmol) in ACN/DMF (3:1.120 mL) was heated to reflux for 2 days. After removal of the solvent under reduced pressure, the compound was purified by flash column chromatography using $CH_2Cl_2$/MeOH to afford the title compound (1.12 g, 1.78 mmol) as a light-yellow colored solid. The product was confirmed by $^1H$ NMR and LC-MS. $^1H$ NMR (400 MHz, $CDCl_3$) δ 7.91 (d, J=4.5 Hz, 1H), 7.87 (dd, J=12.6, 7.4 Hz, 5H), 7.78 (dd, J=9.4, 7.3 Hz, 4H), 7.69 (ddd, J=15.4, 9.6, 5.6 Hz, 6H), 7.39 (q, J=7.8 Hz, 2H), 7.31-7.27 (m, 1H), 3.93 (t, J=14.2 Hz, 2H), 3.12-2.83 (m, 2H), 1.78 (dt, J=15.1, 7.5 Hz, 2H), 1.65 (dd, J=16.9, 9.2 Hz, 4H), 1.46 (dt, J=15.2, 7.8 Hz, 2H). Mass m/z: calcd for $[C_{34}H_{33}N_3PS]^+$ $[M]^+$, 546.21; found, 546.21.

12,12-Dimethyl-6,10-dioxo-1,1,1-triphenyl-5,11-dioxa-9-aza-1-phosphoniatridecane bromide

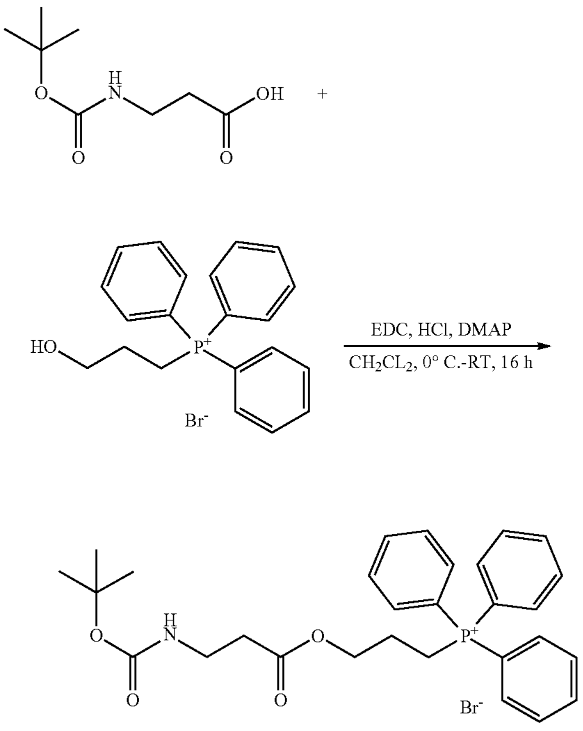

To a stirred solution of 3-(tert-butoxycarbonylamino) propanoic acid (1.5 g, 3.74 mmol) and (3-hydroxypropyl) triphenylphosphonium bromide (0.707 g, 3.74 mmol) in anhydrous $CH_2Cl_2$ (30 mL) at 0° C. was added N,N-dimethylpyridin-4-amine (1.14 g, 9.34 mmol) and N-(3-dimethylaminopropyl)-N'-ethylcarbodiimide hydrochloride (0.932 g, 4.86 mmol) simultaneously, then the reaction mixture was slowly brought to RT and stirred for 16 h. Completion of the reaction was confirmed by TLC, then the reaction was quenched with cold water and the product was extracted with $CH_2Cl_2$ (30 mL×2). The combined organic layers were washed with aq 1N HCl, aq sat $NaHCO_3$, brine solution, and then dried over anhydrous $Na_2SO_4$. The resulting crude product was purified by flash column chromatography using $CH_2Cl_2$/MeOH to afford the title compound (1.92 g, 0.3.36 mmol) as a white colored solid. The product was confirmed by $^1H$ NMR and LC-MS. $^1H$ NMR (400 MHz, $CDCl_3$) δ 7.89 (dd, J=12.5, 7.8 Hz, 5H), 7.80 (t, J=7.3 Hz, 3H), 7.72 (dd, J=7.4, 2.7 Hz, 5H), 5.22 (s, 1H), 4.41 (t, J=6.0 Hz, 2H), 4.08 (dt, J=35.2, 14.9 Hz, 2H), 3.32 (t, J=24.4 Hz, 2H), 2.63-2.39 (m, 2H), 1.97 (t, J=27.5 Hz, 2H), 1.41 (d, J=8.5 Hz, 9H). Mass m/z: calcd for $[C_{29}H_{35}NO_4P]^+$ $[M]^+$, 392.45; found, 392.36.

(3-(3-aminopropanoyloxy)propyl)triphenylphosphonium bromide hydrochloride

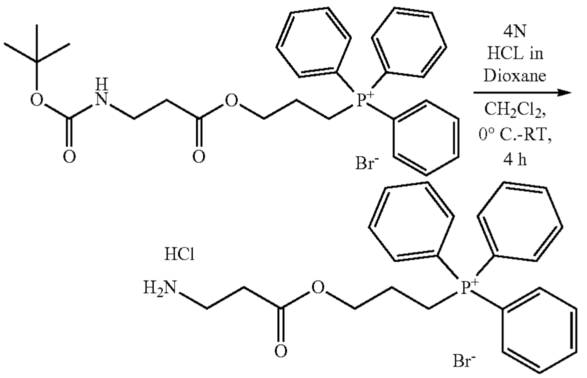

To a stirred solution of 12,12-dimethyl-6,10-dioxo-1,1,1-triphenyl-5,11-dioxa-9-aza-1-phosphoniatridecane bromide (1.8 g, 3.5 mmol) in anhydrous $CH_2Cl_2$ (30 mL) at 0° C. was added 4N HCL in dioxane dropwise, then the reaction mixture was brought to room RT and stirred for 4 h. After which the reaction mixture was concentrated under reduced pressure and co-distilled with dry toluene to afford the title compound (1.59 g, 3.1 mmol) as a white solid. The product confirmed by $^1H$ NMR and LC-MS. $^1H$ NMR (400 MHz, DMSO) δ 8.20 (s, 2H), 7.92 (t, J=6.8 Hz, 4H), 7.82 (dd, J=19.3, 7.1 Hz, 11H), 4.17 (t, J=6.0 Hz, 2H), 3.70 (t, J=14.7 Hz, 2H), 3.09-2.91 (m, 2H), 2.75 (t, J=7.0 Hz, 2H), 1.89 (d, J=6.9 Hz, 2H). Mass m/z: calcd for $[C_{24}H_{27}NO_2P]^+$ $[M]^+$, 392.45; found, 392.36.

(3-(3-(Biphenyl-4-ylsulfonamido)propanoyloxy) propyl)triphenylphosphonium bromide (AP-4-195)

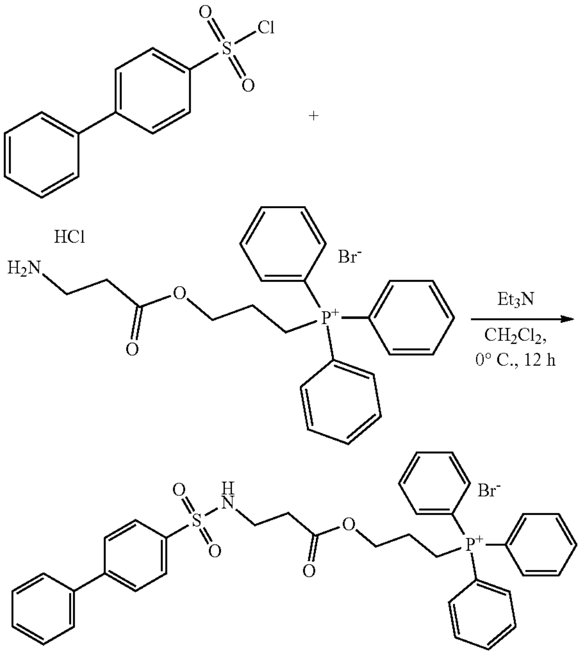

To a stirred solution of (3-(3-aminopropanoyloxy)propyl) triphenylphosphonium bromide hydrochloride (0.201 g, 0.4 mmol) in anhydrous $CH_2Cl_2$ (6 mL) at 0° C. under nitrogen atmosphere was added triethylamine (0.119 g, 1.18 mmol) and dibenzo[b,d]furan-3-sulfonyl chloride (0.1 g, 0.4 mmol) simultaneously, then the reaction mixture was brought to RT and stirred for 24 hours. Completion of the reaction was confirmed by TLC. The reaction was then quenched with cold water and the product was extracted with $CH_2Cl_2$ (15 mL×2). The organic layers were combined and washed with aq 1N HCl, aq sat $NaHCO_3$, brine solution, and dried over anhydrous $Na_2SO_4$. The obtained crude product was purified by flash column chromatography using $CH_2Cl_2$/MeOH to afford the title compound (0.19 g, 0.28 mmol) as a white colored solid. The product confirmed by $^1$H NMR and LC-MS. $^1$H NMR (400 MHz, $CDCl_3$) δ 7.95 (d, J=8.1 Hz, 2H), 7.79 (dd, J=12.7, 7.6 Hz, 7H), 7.70 (t, J=8.7 Hz, 6H), 7.60 (d, J=7.5 Hz, 2H), 7.47 (t, J=7.3 Hz, 2H), 7.43-7.35 (m, 1H), 4.30 (s, 2H), 3.73 (s, 2H), 3.23 (s, 2H), 2.82-2.47 (m, 2H), 2.00 (s, 2H). Mass m/z: calcd for $[C_{36}H_{35}NO_4PS]^+$ $[M]^+$, 608.20; found, 608.23.

(5-Oxo-5-(5-phenylpyrazin-2-ylamino)pentyl)triphenylphosphonium bromide (AP-4-226)

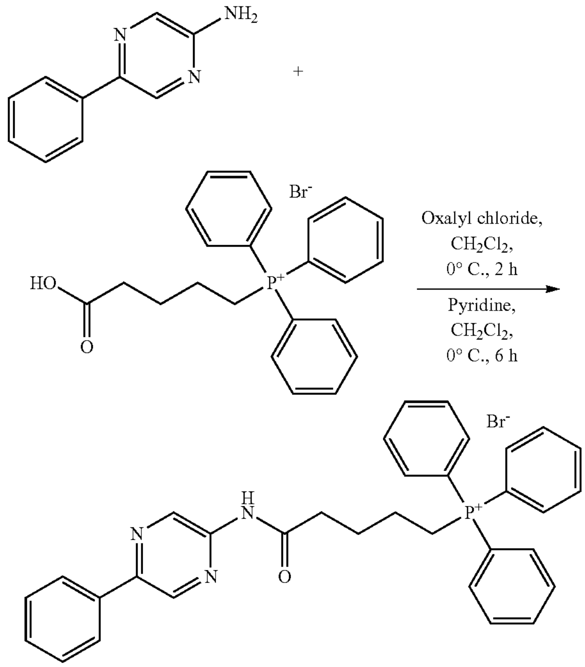

To a stirred solution of (4-carboxybutyl)triphenylphosphonium bromide (0.258 g, 0.58 mmol) in (10 mL) of anhydrous $CH_2Cl_2$ and a catalytic amount of DMF (5 mg) at 0° C. under nitrogen atmosphere was added oxalyl chloride (0.096 g, 0.76 mmol) drop wise, then the reaction mixture was brought to RT and stirred for 2 hours. The volatiles were evaporated under reduced pressure, co-distilled with dry toluene (10 mL), and dried under high vacuum. The obtained acid chloride was dissolved in anhydrous $CH_2Cl_2$ (5 mL) and added dropwise to a premixed solution of 5-phenylpyrazin-2-amine (0.1 g, 0.58 mmol) and pyridine (0.0.139 g, 1.75 mmol) in anhydrous $CH_2Cl_2$ (10 mL) at 0° C. under nitrogen atmosphere. The reaction mixture was slowly brought to RT and stirred for 6 h. After completion of the reaction, it was quenched with cold water and the product was extracted with $CH_2Cl_2$ (10 mL×2). The combined organic layers were washed with water, aq 1N HCl, aq sat $NaHCO_3$, brine solution, and dried over anhydrous $Na_2SO_4$. The solvent was removed under reduced pressure and the crude product was purified by flash silica gel chromatography using $CH_2Cl_2$/MeOH to afford the title compound (0.25 g, 0.42 mmol) as a light-yellow colored solid. The product was confirmed by $^1$H NMR and LC-MS. $^1$H NMR (400 MHz, $CDCl_3$) δ 10.74 (s, 1H), 9.38 (s, 1H), 8.78 (s, 1H), 7.97 (d, J=7.8 Hz, 2H), 7.84 (dt, J=22.8, 11.4 Hz, 6H), 7.75-7.67 (m, 3H), 7.64 (dd, J=7.4, 2.8 Hz, 6H), 7.49 (t, J=7.5 Hz, 2H), 7.42 (t, J=7.2 Hz, 1H), 3.88 (dd, J=16.5, 13.2 Hz, 2H), 3.13 (t, J=6.9 Hz, 2H), 2.17-1.94 (m, 2H), 1.76 (d, J=14.6 Hz, 2H). Mass m/z: calcd for $[C_{33}H_{31}N_3OP]^+$ $[M]^+$, 516.22; found, 516.26.

(3-Oxo-3-(2-(6-phenylimidazo[2,1-b][1,3,4]thiadiazol-2-yl)ethoxy)propyl) triphenylphosphonium bromide (AP-4-198)

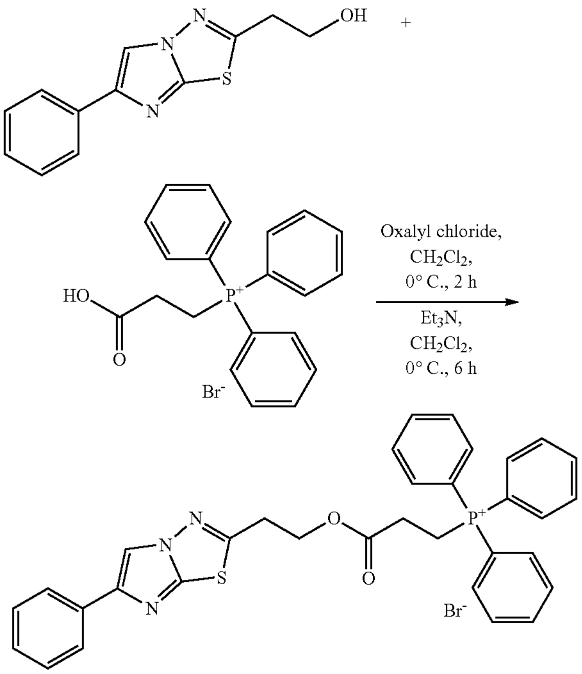

To a stirred solution of 2-carboxyethyl)triphenylphosphonium bromide (0.2 g, 0.48 mmol) in anhydrous $CH_2Cl_2$ (10 mL) and a catalytic amount of DMF (5 mg) at 0° C. under nitrogen atmosphere was added oxalyl chloride (0.122 g, 0.96 mmol) drop wise, then the reaction mixture was brought RT and stirred for 2 hours. The volatiles were evaporated under reduced pressure and co-distilled with dry toluene (10 mL), and then the residue was dried under high vacuum. The obtained acid chloride was dissolved in anhydrous $CH_2Cl_2$ (5 mL) and added dropwise to a premixed solution of 2-(6-phenylimidazo[2,1-b][1,3,4]thiadiazol-2-yl)ethanol (0.117 g, 0.48 mmol) and triethyl amine (0.122 g, 1.2 mmol) in (10 mL) of anhydrous $CH_2Cl_2$ at 0° C. under nitrogen atmosphere. Slowly the reaction mixture was brought to RT and stirred for 6 h. After completion of the reaction, it was quenched by addition of cold water, and the product was extracted with $CH_2Cl_2$ (10 mL×2). The combined organic layers were washed with water, aq 1N HCl, aq sat $NaHCO_3$, brine solution, and dried over anhydrous $Na_2SO_4$. The solvent was removed under reduced pressure to afford crude product which was purified by flash silica gel chromatography by using $CH_2Cl_2$/MeOH to afford the title compound (0.262 g, 0.41 mmol) as light colored solid. The product was confirmed by $^1$H NMR and LC-MS. $^1$H NMR (400 MHz, $CDCl_3$) δ 7.96 (s, 1H), 7.90-7.74 (m, 9H), 7.69 (d, J=4.5 Hz, 5H), 7.41 (t, J=7.5 Hz, 2H), 7.35-7.27 (m, 2H), 7.34-7.18 (m, 2H), 4.32 (dd, J=12.5, 6.6 Hz, 4H), 3.29 (t, J=5.9 Hz, 2H), 3.18-3.05 (m, 2H). Mass m/z: calcd for $[C_{33}H_{29}N_3O_2PS]^+$ $[M]^+$, 562.17; found, 562.22.

(3-(3-(Dibenzo[b,d]furan-3-sulfonamido)propanoyloxy)propyl)triphenylphosphonium bromide (AP-4-196)

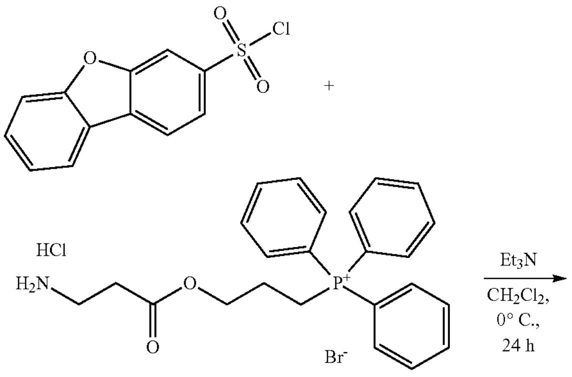

-continued

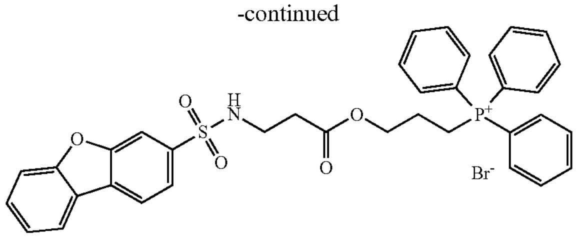

To a stirred solution of (3-(3-aminopropanoyloxy)propyl) triphenylphosphonium bromide hydrochloride (0.19 g, 0.373 mmol) in anhydrous $CH_2Cl_2$ (6 mL) at 0° C. under nitrogen atmosphere was added triethylamine (0.115 g, 1.12 mmol) and dibenzo[b,d]furan-3-sulfonyl chloride (0.1 g, 0.373 mmol) simultaneously, then the reaction mixture was brought to RT and stirred for 24 hours. Completion of the reaction was confirmed by TLC. The reaction was quenched with cold water and the product was extracted with $CH_2Cl_2$ (15 mL×2). The organic layers were combined and washed with aq 1N HCl, aq sat $NaHCO_3$, brine solution, and dried over anhydrous $Na_2SO_4$. The resulting crude product was purified by flash column chromatography using $CH_2Cl_2$/MeOH to afford the title compound (0.21 g, 0.3 mmol) as a white colored solid. The product confirmed by $^1$H NMR and LC-MS. $^1$H NMR (400 MHz, $CDCl_3$) δ 8.94 (t, J=5.7 Hz, 1H), 8.22 (s, 1H), 8.12 (d, J=8.2 Hz, 1H), 8.04 (d, J=8.2 Hz, 1H), 7.94 (tt, J=28.8, 14.5 Hz, 6H), 7.83-7.66 (m, 9H), 7.59 (d, J=8.2 Hz, 1H), 7.52 (t, J=7.7 Hz, 1H), 7.38 (t, J=7.5 Hz, 1H), 4.33 (s, 2H), 4.11 (t, J=14.5 Hz, 2H), 3.35-3.19 (m, 2H), 2.82-2.68 (m, 2H), 1.95 (d, J=41.6 Hz, 2H). Mass m/z: calcd for $[C_{36}H_{33}NO_5PS]^+$ [M]+, 622.18; found, 622.34.

Synthesis of certain exemplary compounds of the disclosure is exemplified herein:

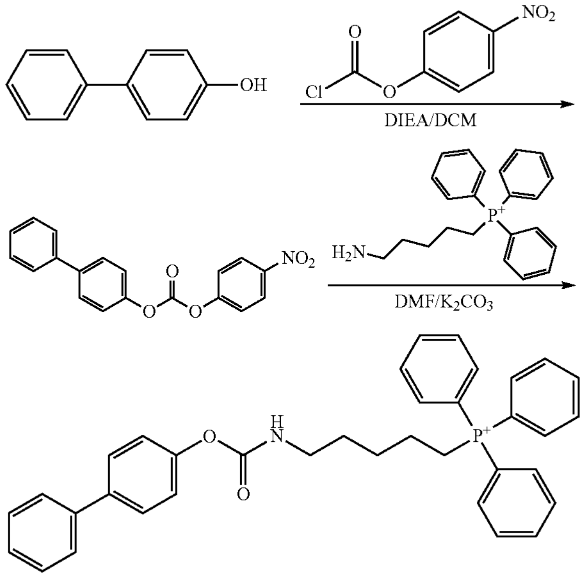

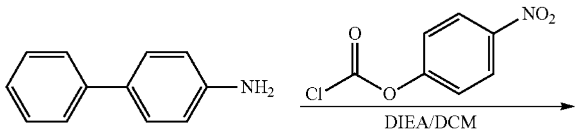

-continued
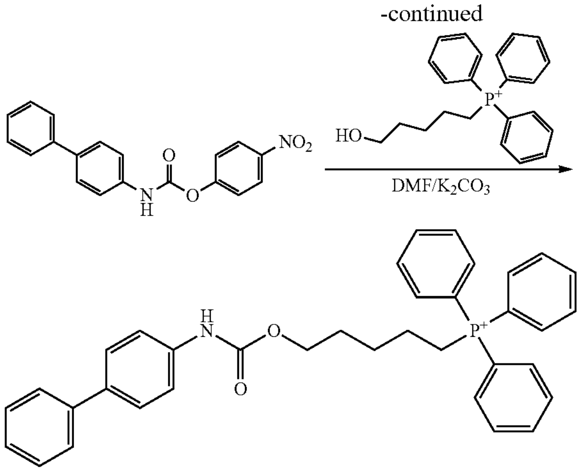
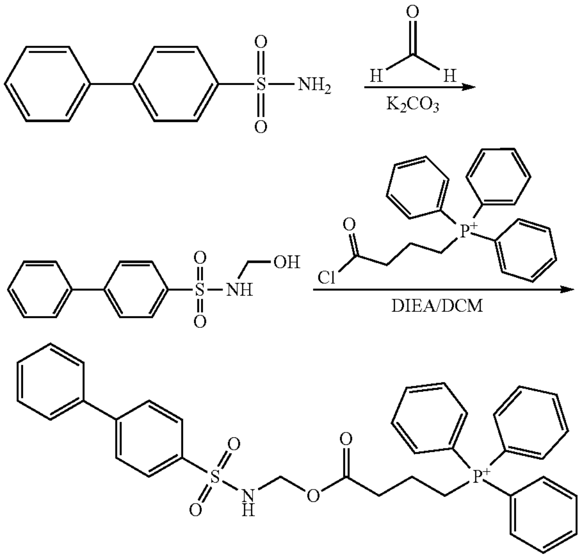
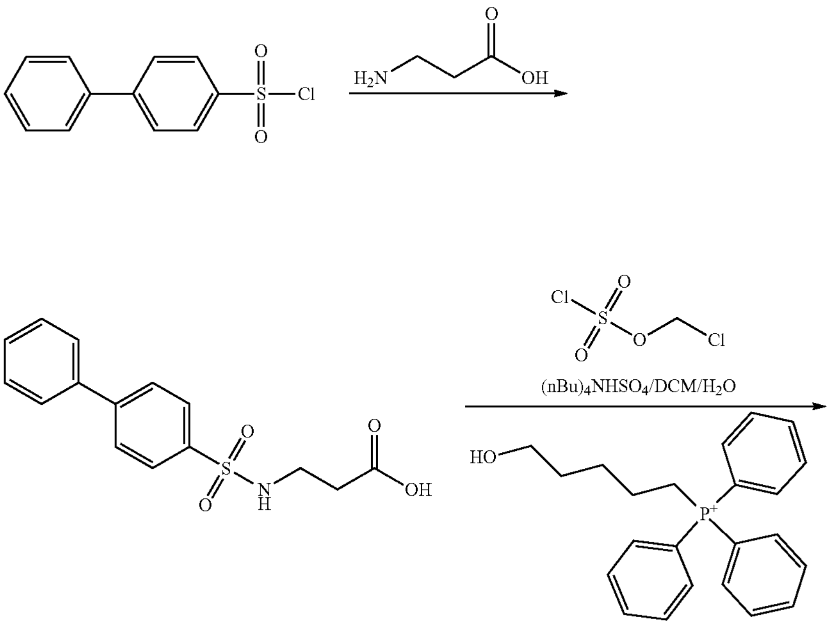

-continued
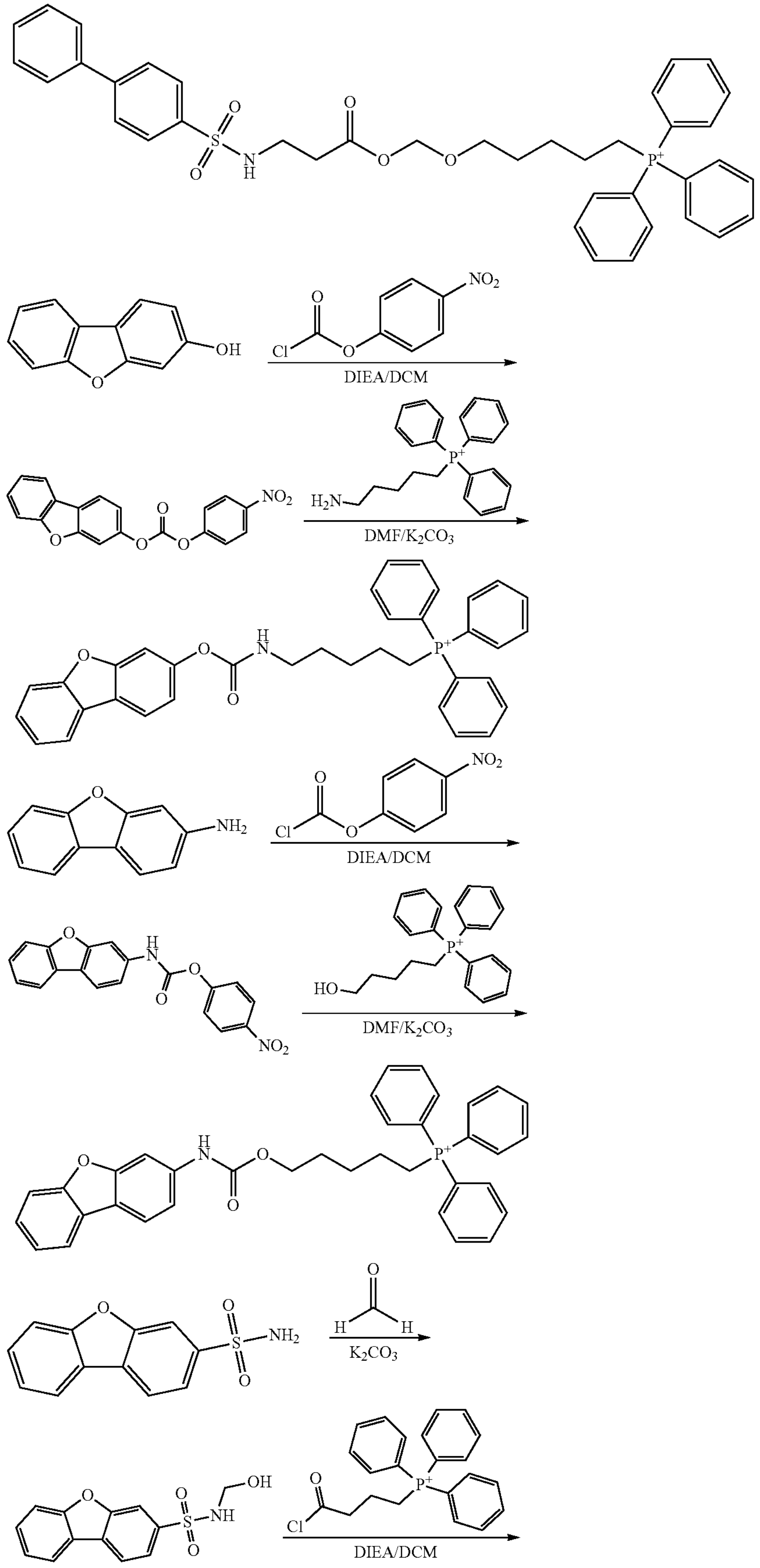

-continued

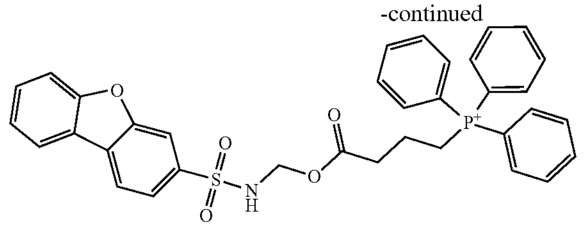

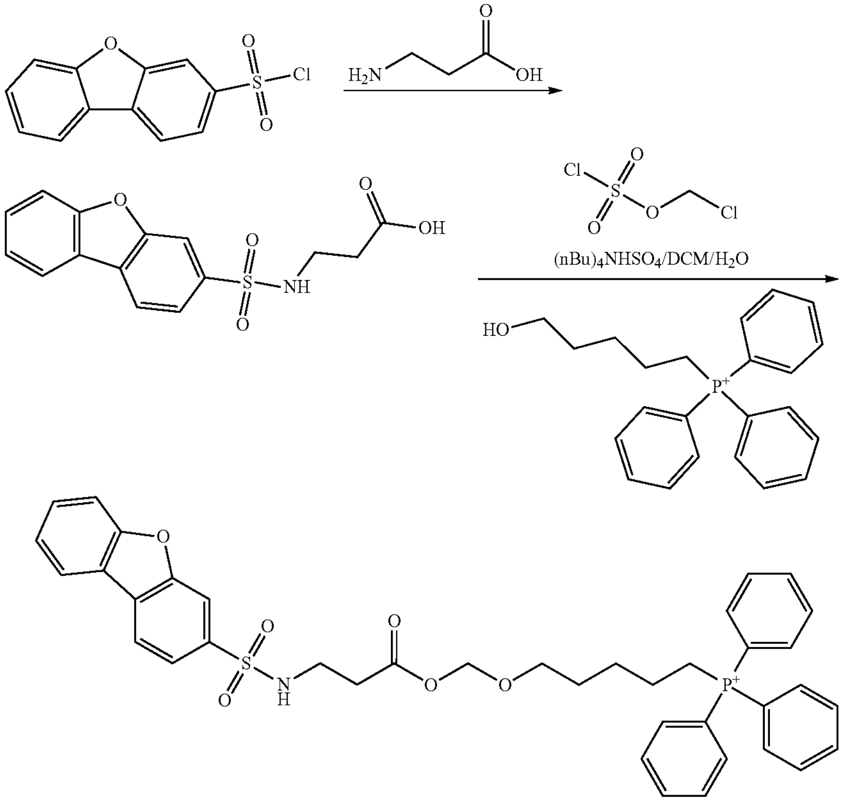

Selected Discussion

Cancer cells tend to be far more sensitive than normal cells to inhibitors of chaperones like HSP70 and HSP90. Without wishing to be limited by any theory, this is believed to be due to the genetic instability, nutrient and oxygen deprivation, and abundance of mutated and misfolded proteins in cancer cells. Recognition of this fact has fueled research on HSP90 inhibitors for many years and these inhibitors have performed well in clinical trials for certain cancer types, including acute myeloid leukemia, HER2-positive breast cancers, and anaplastic lymphoma kinase rearrangement-positive lung cancers. Research on inhibitors of HSP70 and other HSPs is gathering momentum. Herein some of the necessary criteria for a successful chaperone inhibitor program have been established: active (AP-4-139B) and inactive (VY-3-277) analogs have been identified, affinity reagents (BAP-4-139B) have been established, a direct interaction has been shown, a reliable high-throughput ATPase assay has been developed in which to test derivatives, and measurable effects on client proteins in cancer cells have been identified and shown, as well as single-agent efficacy in tumors without signs of toxicity.

Several other groups have explored HSP70 is as anticancer agents in preclinical models of cancer. In general, these compounds have shown significant anticancer activity with limited toxicity to normal cells. The novel compounds and data presented herein differ from these other studies because the novel inhibitors are mitochondria directed by virtue of the TPP moiety. Consequently, the novel HSP70 is affects client proteins broadly distributed in the cancer cell, in the cytosol, the nucleus, and the mitochondria. Data is provided herein demonstrating that these HSP70 is induce DAMP release and immunogenic cell death. These data may explain previous reports that suggest that HSP70 is influence the immune system and/or induce immune-mediated cell death. Release of DAMPs and localization of calreticulin to the plasma membrane are hallmarks of immunogenic cell death. Whereas there is some uncertainty about whether these three markers together are always harbingers of immunogenic cell death, the findings herein that AP-4-139B treated cells function as a tumor vaccine, and that AP-4-139B induces $CD8^+$ T cell and other immune cell recruitment, lend support to the premise that this (and potentially other) HSP70 is function by enhancing this form of cell death.

Figure 26:
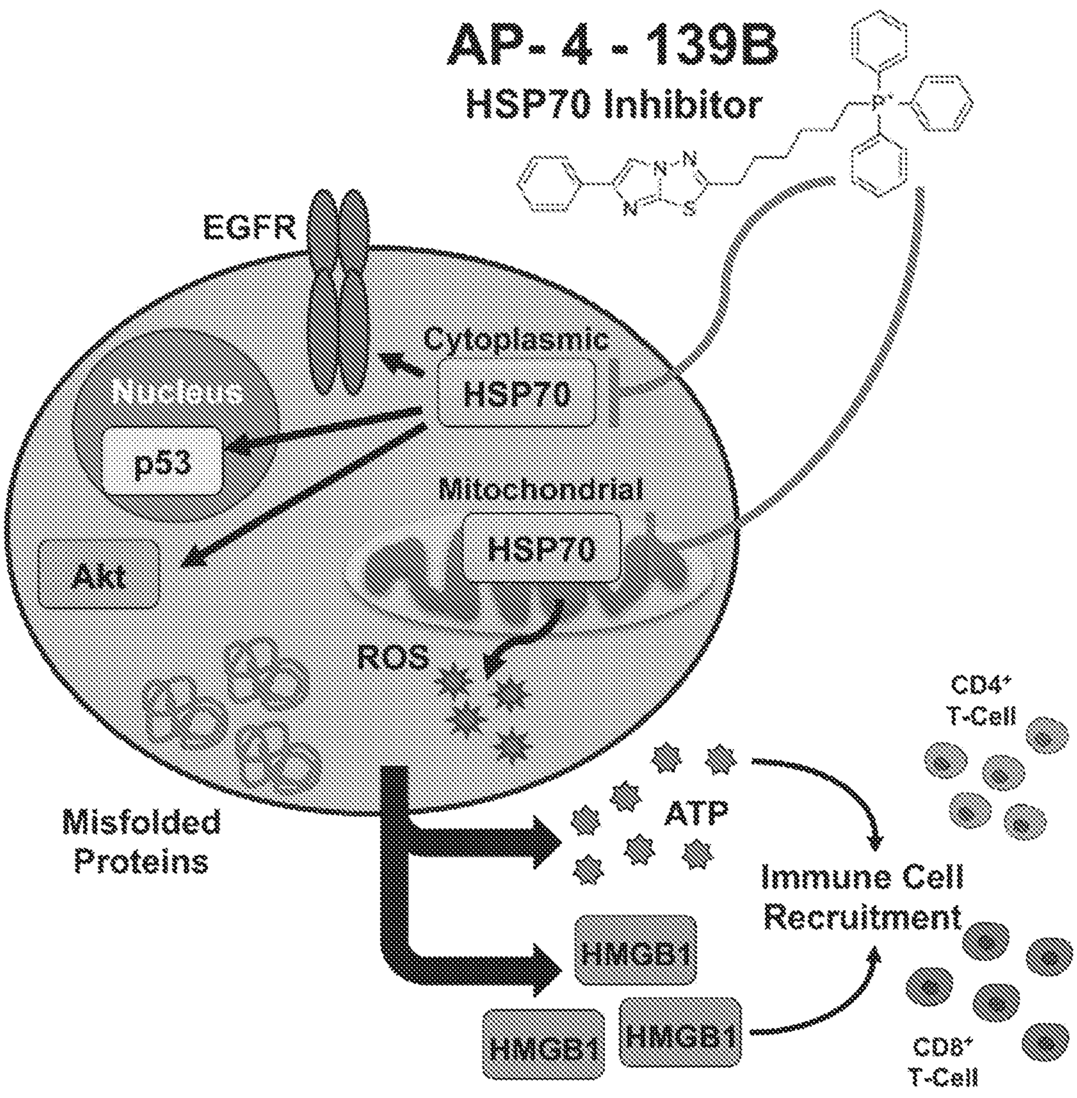
FIG. 26 is a model depicting the role of the HSP70 inhibitor AP-4-139B as an anti-cancer agent. Shown is a molecular cartoon highlighting the role of AP-4-139B: (1) it affects non-mitochondrial client proteins, such as EGFR, mutant p53, and AKT; (2) it affects novel mitochondrial client proteins, including MRPS14 and NDUFA6; and (3) it leads to the release of DAMPs (ATP, HMGB1, calreticulin translocation to the cell membrane), in turn promoting immunogenic cell death.
Figure 27A:
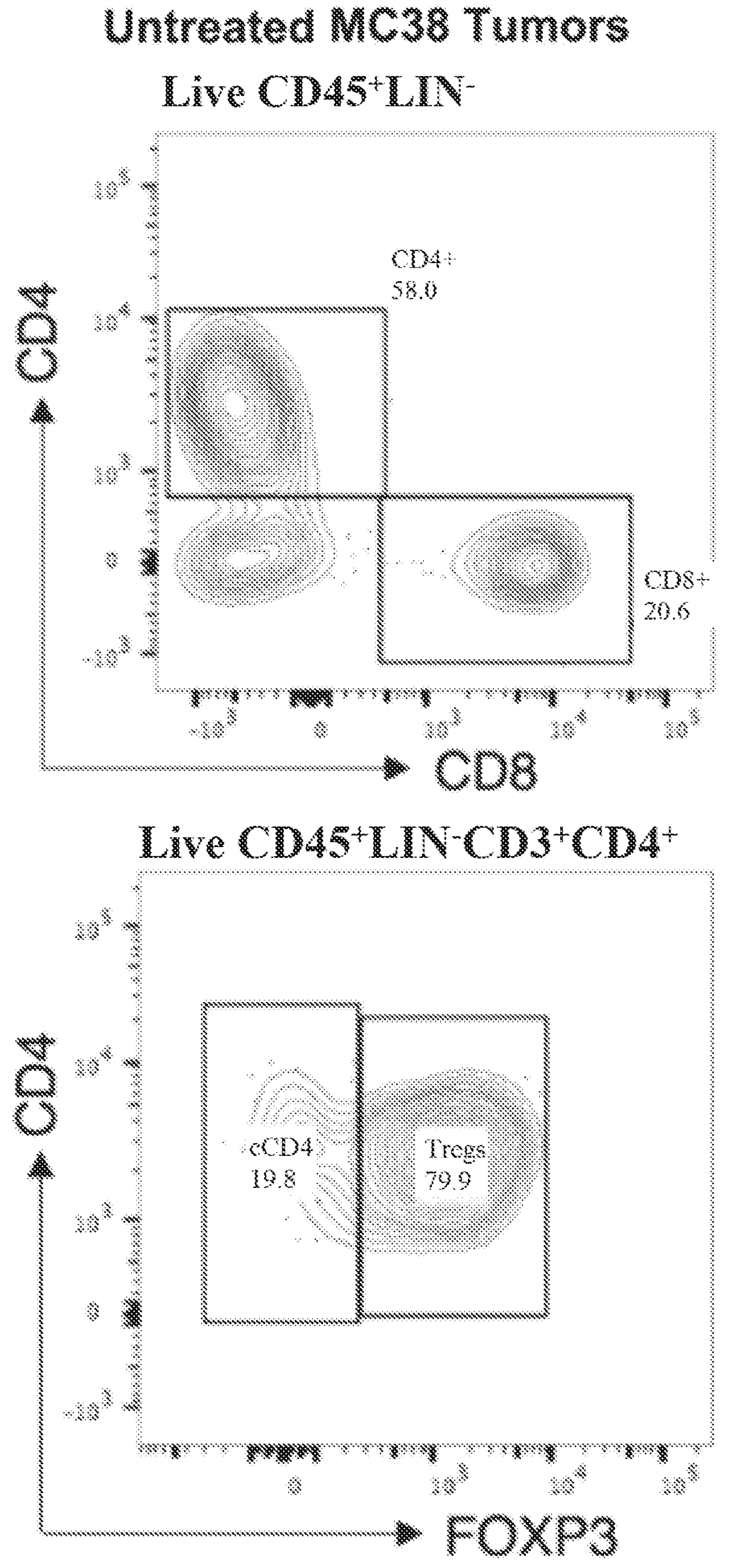
FIGS. 27A-27D show a gating strategy for immune cell populations of MC38 tumors either untreated or treated with AP-4-139B.
Figure 27B:
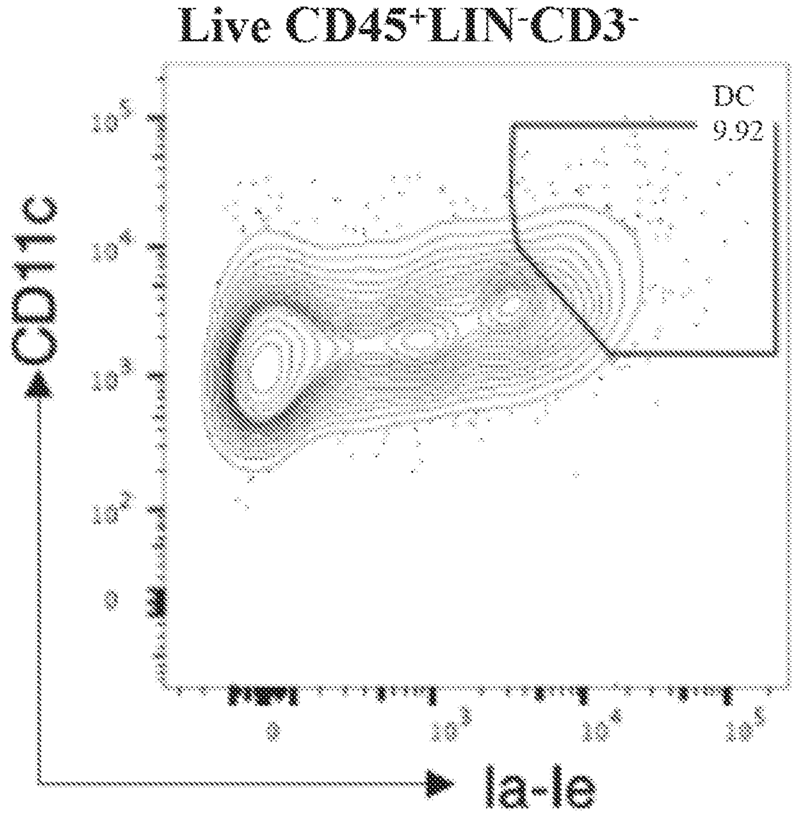
Figure 27C:
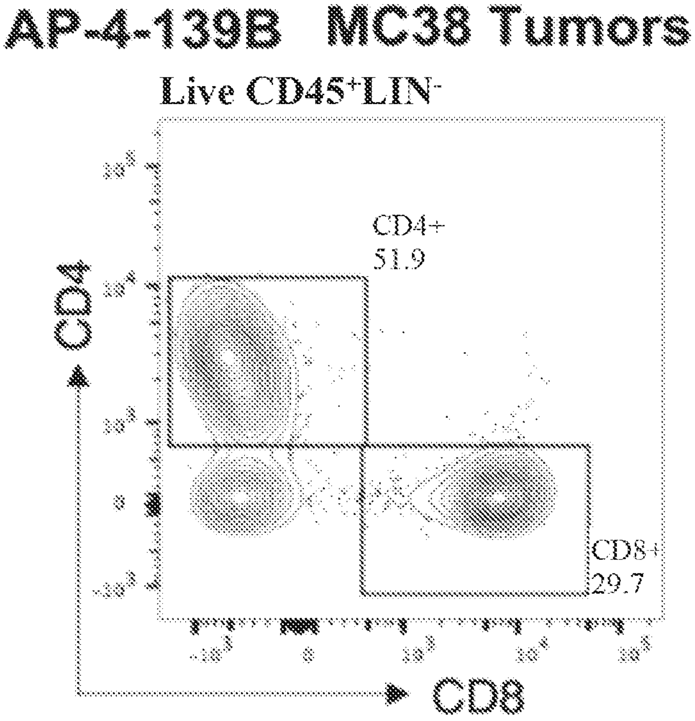
Figure 27D:
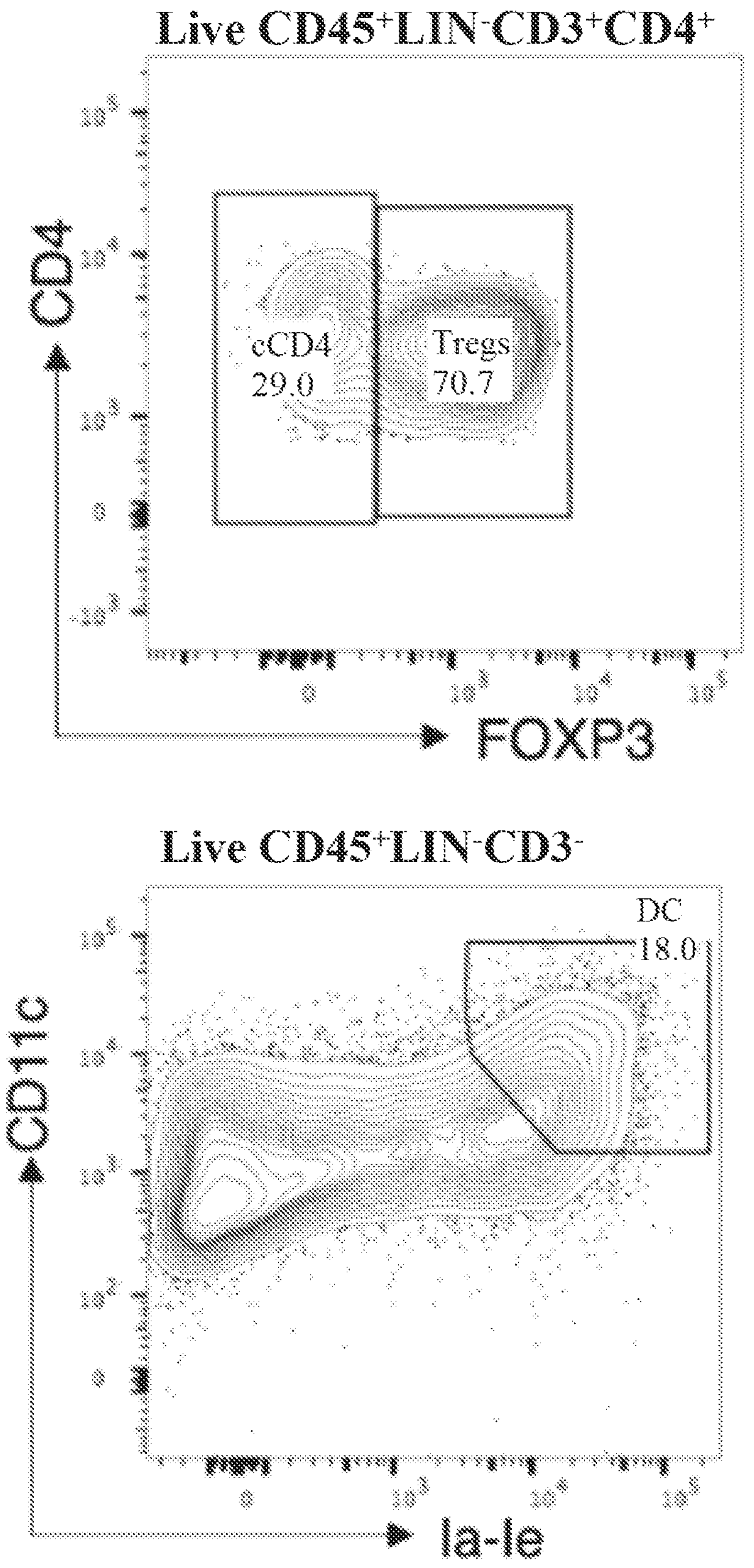

Currently, there is much that is unknown regarding the nature of the stimuli that induce immunogenic cell death. However, there have been two consistent components of this cell death pathway: the induction of ER stress and the accumulation of reactive oxygen species (ROS). It is notable that HSP70 is lead to the accumulation of misfolded proteins and concomitant ER stress. Furthermore, by designing the disclosed compounds to traffic to the mitochondria, the compounds disrupt mitochondrial function, which would be predicted to lead to significant mitochondrial ROS. These two facets may explain the superior ability of AP-4-139B to induce markers of immunogenic cell death (FIG. 6E). It is important to note that inducing enhanced immune cell infiltration is only part of the mechanism of anticancer activity of AP-4-139B, because this inhibitor also functions in the nucleus and cytosol, where it causes loss of client proteins like AKT and EGFR (FIG. 26). In sum, the novel and diverse mechanisms of action of AP-4-139B, combined with the importance of HSP70 in late-stage colorectal cancer, support the use of this compound for colorectal cancer therapy. Because HSP70 is overexpressed in many other cancers, the findings herein have relevance to other cancer types as well.

The disclosures of each and every patent, patent application, and publication cited herein are hereby incorporated herein by reference in their entirety.

While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A compound of formula (I), or a salt, solvate, enantiomer, or tautomer thereof:

BINDER-X—$(Z_1)_{m1}$—Y—$(Z_2)_{m2}$-L (I), wherein:

BINDER is selected from the group consisting of:

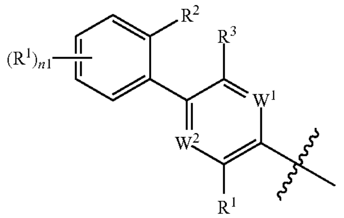

and

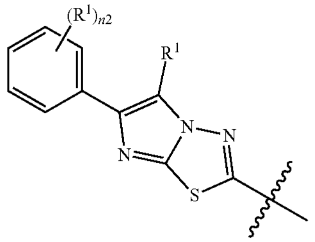

;

wherein:

$R^2$ and $R^3$ are each independently $R^1$, or $R^2$ and $R^3$ combine to form —O—, —S—, —NH—, or —N($C_1$-$C_6$ alkyl)-;

$W^1$ is C($R^1$) or N;

$W^2$ is C($R^1$) or N;

each occurrence of $R^1$ is independently selected from the group consisting of H, $C_1$-$C_6$ alkyl, $C_1$-$C_6$ haloalkyl, $C_1$-$C_6$ alkoxy, $C_1$-$C_6$ haloalkoxy, fluoro, chloro, bromo, iodo, cyano, nitro, —N(R')(R'), —C(=O)OR', and —C(=O)NR'R', wherein each occurrence of R' is independently H or $C_1$-$C_6$ alkyl;

n1 is selected from the group consisting of 0, 1, 2, 3, and 4;

n2 is selected from the group consisting of 0, 1, 2, 3, 4, and 5;

X is selected from the group consisting of —$(CH_2)_{1-5}$, —$(CH_2CH_2O)_{1-5}$, —$(OCH_2CH_2)_{1-5}$, —NHS(=O)$_2$—*, —S(=O)$_2$NH—*, —OC(=O)NH—*, and —NHC(=O)O—*, wherein the bond marked with * is formed with $Z_1$;

Y is selected from the group consisting of a chemical bond, *—OC(=O)—, and *—C(=O)O—, wherein the bond marked with * is formed with $Z_1$;

each occurrence of $Z_1$ is independently selected from the group consisting of bond, —$CH_2$—, —$OCH_2CH_2$—, and —$CH_2CH_2O$—;

each occurrence of $Z_2$ is independently selected from the group consisting of bond, —$CH_2$—, —$OCH_2CH_2$—, and —$CH_2CH_2O$—;

m1 is selected from the group consisting of 1, 2, 3, 4, 5, 6, 7, 8, 9, and 10;

m2 is selected from the group consisting of 1, 2, 3, 4, 5, 6, 7, 8, 9, and 10;

with the proviso that X—$(Z_1)_{m1}$—Y—$(Z_2)_{m2}$-L does not comprise a O—O bond;

L is a group selected from the group consisting of:

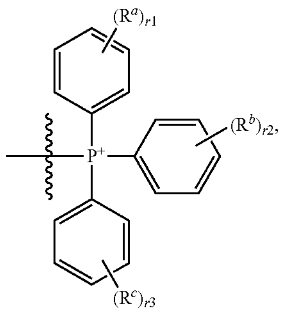

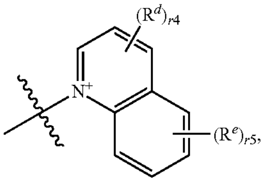

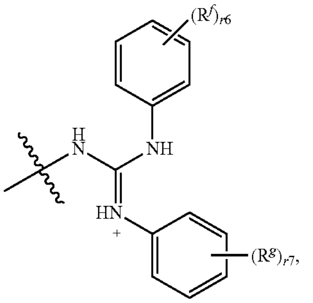

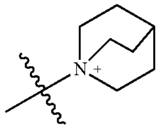

,

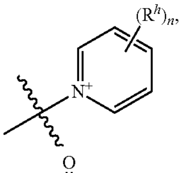

and

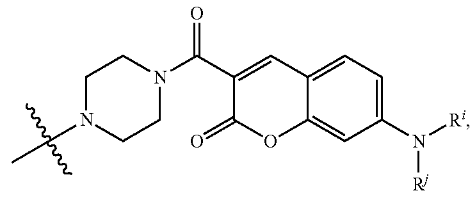

wherein:

each occurrence of $R^a$, $R^b$, $R^c$, $R^d$, $R^e$, $R^f$, $R^g$, and $R^h$ is independently selected from the group consisting of H, $C_1$-$C_6$ alkyl, $C_1$-$C_6$ haloalkyl, $C_1$-$C_6$ alkoxy, $C_1$-$C_6$ haloalkoxy, fluoro, chloro, bromo, iodo, cyano, nitro, —N(R")(R"), —C(=O)OR", and —C(=O)NR"R", wherein each occurrence of R" is independently H or $C_1$-$C_6$ alkyl;

$R^i$ and $R^j$ are independently H or optionally substituted $C_1$-$C_6$ alkyl;

each occurrence of n, r1, r2, r3, r6, and r7 is independently selected from the group consisting of 1, 2, 3, 4, and 5;

each occurrence of r4 is selected from the group consisting of 1, 2, and 3; and each occurrence of r5 is selected from the group consisting of 1, 2, 3, and 4.

2. The compound of claim 1, wherein BINDER is selected from the group consisting of:

(Ia)

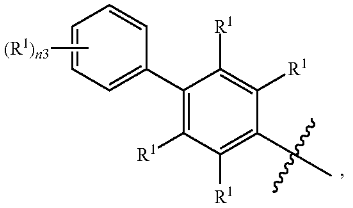

(Ib)

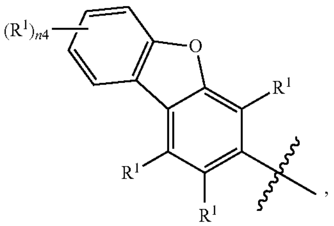

(Ic)

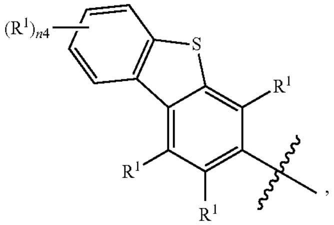

(Id)

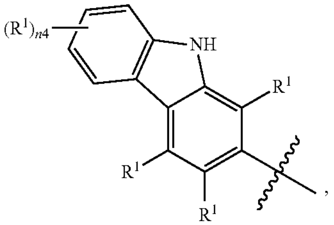

-continued (Ie)

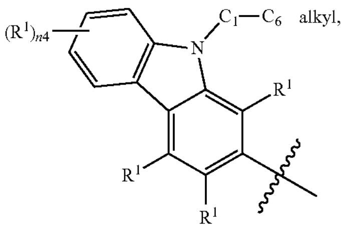

and (If)

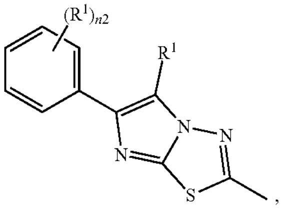

wherein:

n3 is selected from the group consisting of 0, 1, 2, 3, 4, and 5; and n4 is selected from the group consisting of 0, 1, 2, 3, and 4.

3. The compound of claim 1, wherein L is

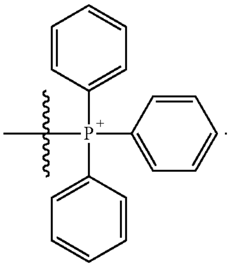

4. The compound of claim 1, wherein L is

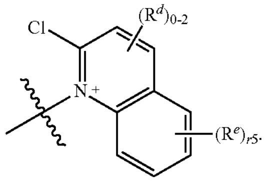

5. The compound of claim 1, wherein L is

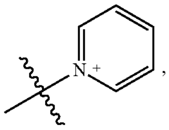

,

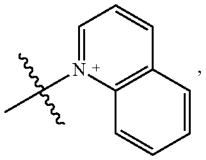

, or

-continued
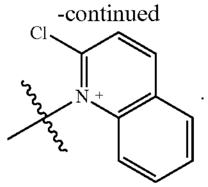
6. The compound of claim 1, wherein L is
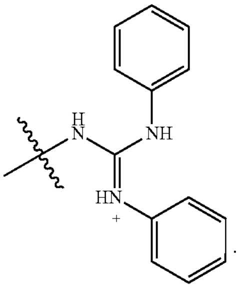 [SMILES: *N/C(=N/c1ccccc1)Nc1ccccc1]
7. A compound selected from the group consisting of:
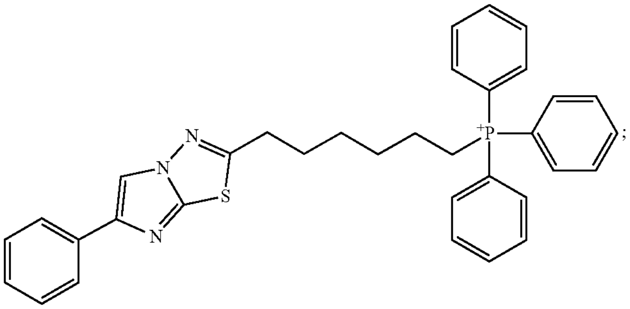
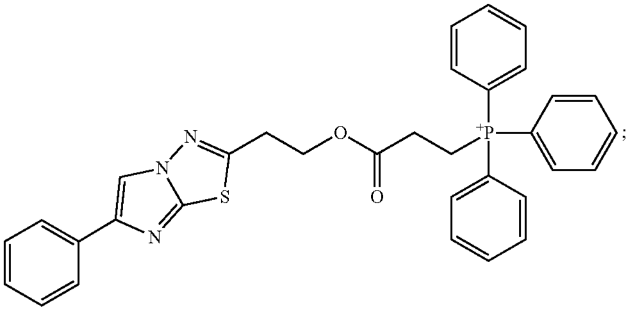
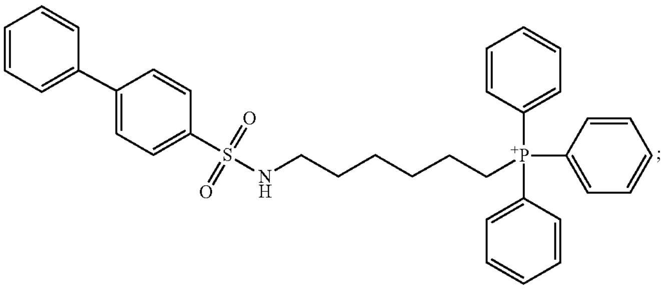

-continued
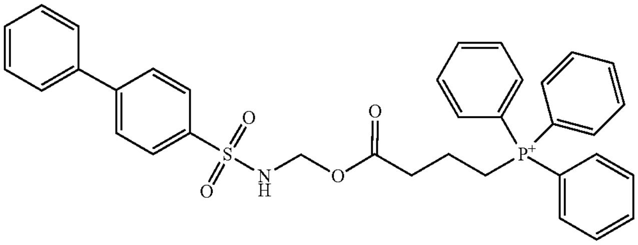
;
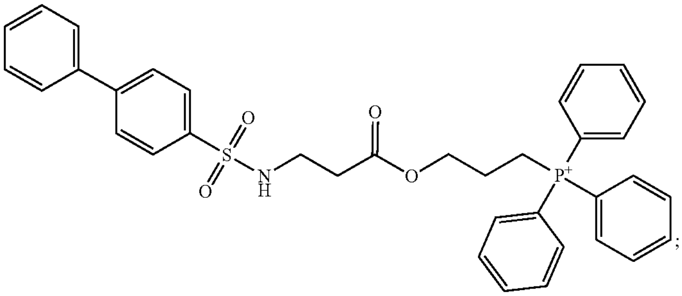
;
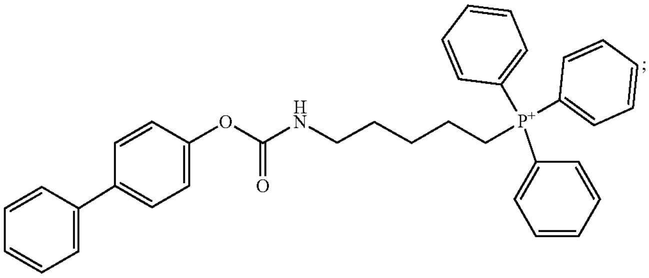
;
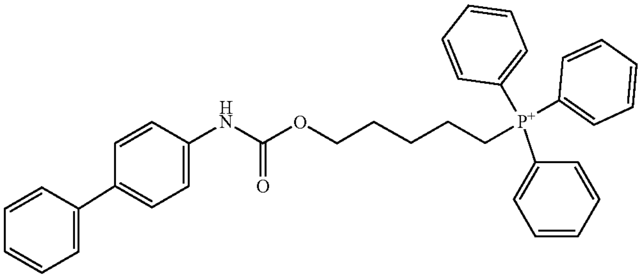
;
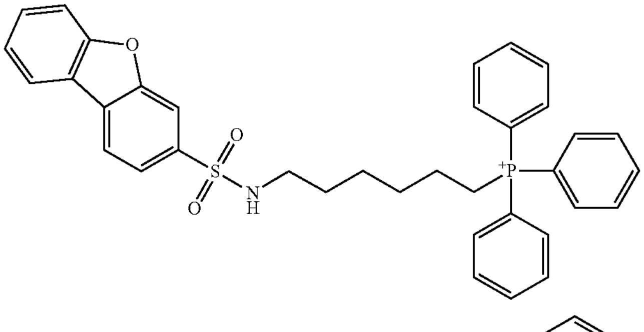
;
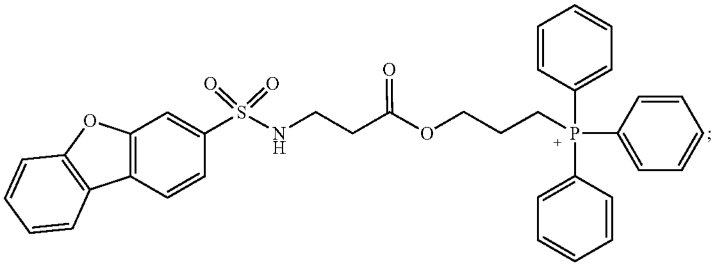
;

-continued
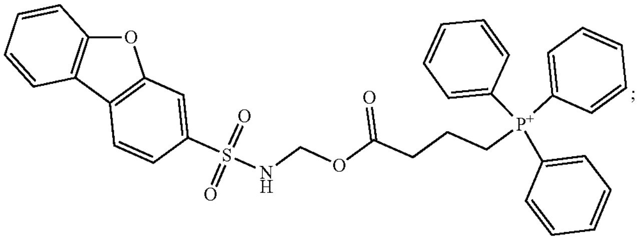
;
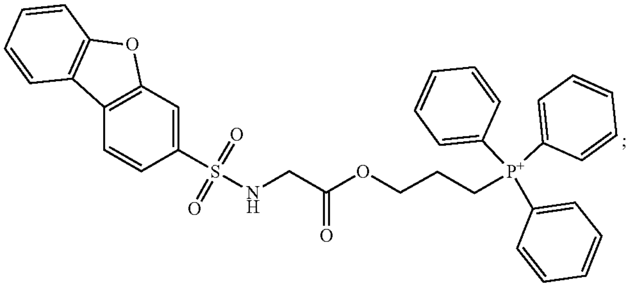
;
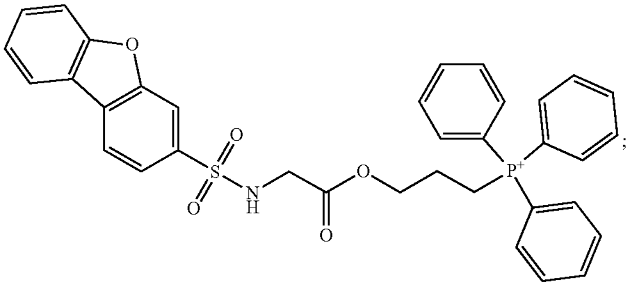
;
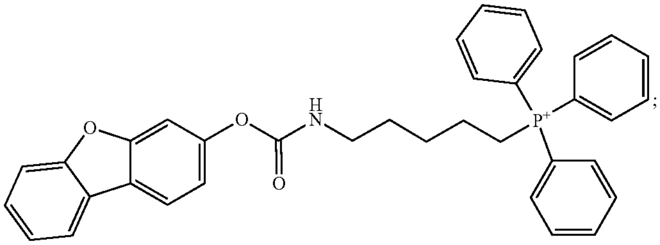
;
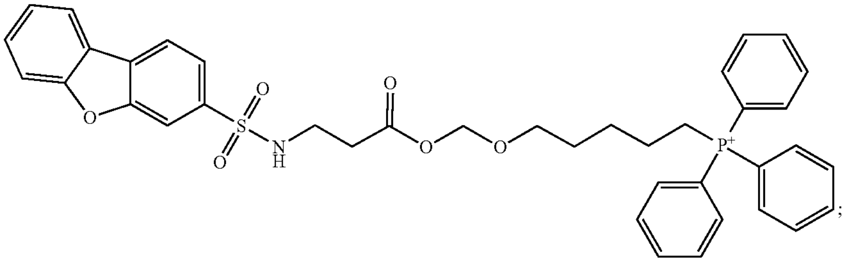
;
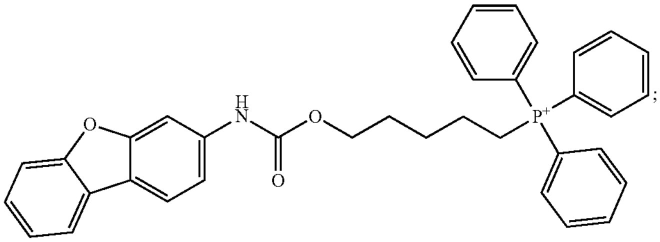
;

-continued

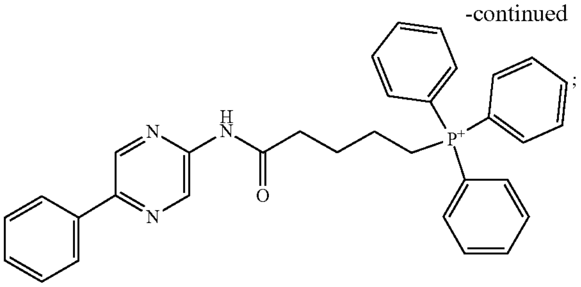

;

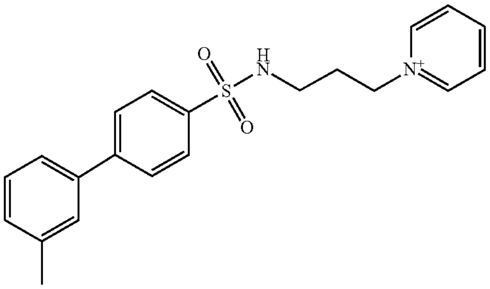

;

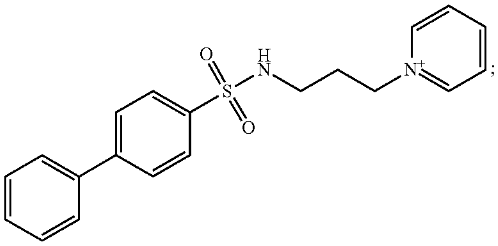

;

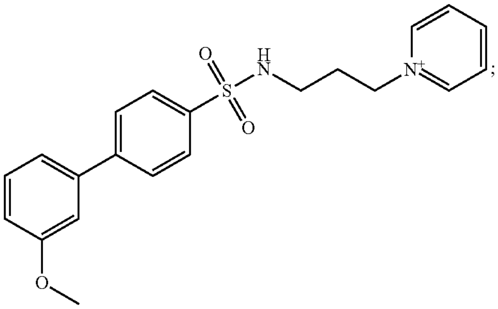

;

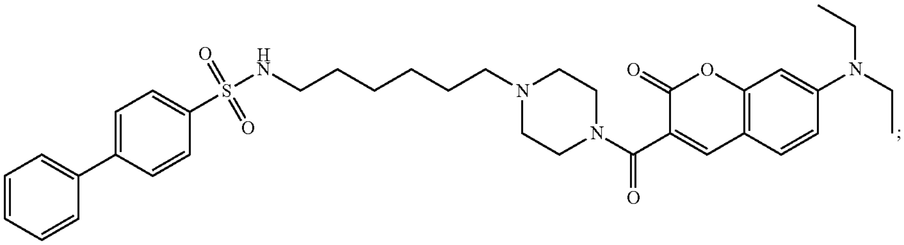

; and

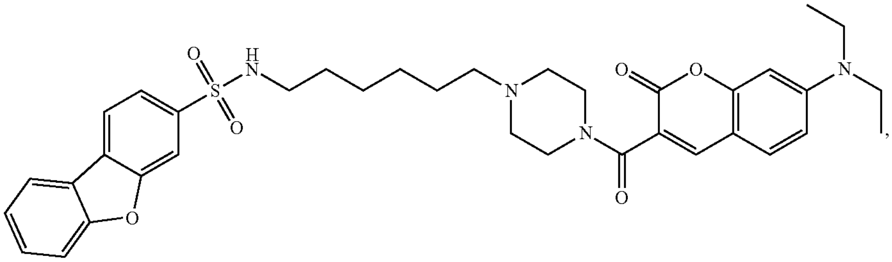

, or a salt, solvate, enantiomer, or tautomer thereof.

8. A pharmaceutical composition comprising the compound of claim 1 and at least one pharmaceutically acceptable carrier.

9. The pharmaceutical composition of claim 8, further comprising at least one additional agent that treats or ameliorates a cancer.

10. The pharmaceutical composition of claim 9, wherein the at least one additional agent comprises a MEK inhibitor, a BRAF inhibitor, or an immune checkpoint inhibitor.

11. The composition of claim 9, wherein the cancer is at least one selected from the group consisting of colorectal cancer, melanoma, drug-resistant BRAF mutant melanoma and non-small-cell lung cancer (NSCLC).

12. A method of treating or ameliorating a cancer in a subject, wherein the method comprises administering to the subject a therapeutically effective amount of the compound of claim 1.

13. A method of increasing or promoting immune cell infiltration or immune cell recruitment to a cancerous tumor in a subject, wherein the method comprises administering to the subject a therapeutically effective amount of the compound of claim 1.

14. The method of claim 12, wherein the compound is administered as a pharmaceutical composition comprising at least one pharmaceutically acceptable carrier.

15. The method of claim 12, wherein at least one of the following applies:

(a) the compound is the only therapeutically effective agent administered to the subject;

(b) the compound is the only therapeutically effective agent administered to the subject in an amount that treats or ameliorates the cancer in the subject.

16. The method of claim 12, wherein the cancer is at least one selected from the group consisting of epithelial cancer, Merkel cell carcinoma, liver cancer, cervical cancer, anal cancer, penile cancer, vulvar cancer, vaginal cancer, breast cancer, ovarian cancer, uterine cancer, skin cancer, melanoma, oral cancer, colon cancer, neck cancer, head cancer, eye cancer, Kaposi's sarcoma, leukemia, nasopharyngeal carcinoma, mesothelioma, bone cancer, brain cancer, prostate cancer, testicular cancer, pancreatic cancer, hepatocellular carcinoma, lung cancer, and lymphoma.

17. The method of claim 12, wherein the cancer is at least one selected from the group consisting of colorectal cancer, melanoma, drug-resistant BRAF mutant melanoma and non-small-cell lung cancer (NSCLC).

18. The method of claim 12, wherein at least one of the following applies:

(a) the subject is a mammal;

(b) the compound is administered by an administration route selected from the group consisting of inhalational, oral, rectal, vaginal, parenteral, intracranial, topical, transdermal, pulmonary, intranasal, buccal, ophthalmic, intrathecal, and intravenous;

(c) the subject is further administered at least one additional agent that treats or ameliorates the cancer.

19. The method of claim 18, wherein in (c) the at least one additional agent comprises a MEK inhibitor, a BRAF inhibitor, or an immune checkpoint inhibitor.

20. The method of claim 19, wherein the compound and the at least one additional agent are co-administered or co-formulated.

21. A pharmaceutical composition comprising the compound of claim 7 and at least one pharmaceutically acceptable carrier.

22. The pharmaceutical composition of claim 21, further comprising at least one additional agent that treats or ameliorates a cancer.

23. The pharmaceutical composition of claim 22, wherein the at least one additional agent comprises a MEK inhibitor, a BRAF inhibitor, or an immune checkpoint inhibitor.

* * * * *